(12) United States Patent
Hachtel et al.

(10) Patent No.: US 9,133,181 B2
(45) Date of Patent: Sep. 15, 2015

(54) SUBSTITUTED 6-(4-HYDROXY-PHENYL)-1H-PYRAZOLO[3,4-B]PYRIDINE DERIVATIVES AS KINASE INHIBITORS

(71) Applicant: SANOFI, Paris (FR)

(72) Inventors: Stephanie Hachtel, Frankfurt (DE); Christian Schoenau, Hochheim (DE); Matthias Loehn, Liederbach (DE); Oliver Plettenburg, Kelkheim (DE); Stefania Pfeiffer-Marek, Frankfurt (DE); Alexander Schiffer, Kelkheim (DE); Holger Gaul, Runkel-Hofen (DE); Aimo Kannt, Dreieich (DE); Juergen Dedio, Hofheim (DE); Angela Dudda, Hünstetten-Görsroth (DE)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 14/537,034

(22) Filed: Nov. 10, 2014

(65) Prior Publication Data

US 2015/0133432 A1    May 14, 2015

Related U.S. Application Data

(63) Continuation of application No. PCT/EP2013/058839, filed on Apr. 29, 2013.

(30) Foreign Application Priority Data

May 9, 2012  (EP) .................................. 12305513

(51) Int. Cl.
| | | |
|---|---|---|
| *C07D 401/14* | (2006.01) | |
| *A61K 31/437* | (2006.01) | |
| *C07D 417/04* | (2006.01) | |

(52) U.S. Cl.
CPC .................................. *C07D 417/04* (2013.01)

(58) Field of Classification Search
CPC ............................ C07D 401/14; A61K 31/437
USPC ......................................... 546/118; 514/303
See application file for complete search history.

(56) References Cited

U.S. PATENT DOCUMENTS

| 8,686,150 B2 | 4/2014 | Hachtel et al. |
| 8,846,712 B2 | 9/2014 | Loehn et al. |
| 2008/0182844 A1 | 7/2008 | Bjergarde et al. |
| 2012/0245170 A1 | 9/2012 | Bedjeguelal et al. |
| 2013/0150340 A1 | 6/2013 | Plettenburg et al. |

FOREIGN PATENT DOCUMENTS

| AU | 617324 | | 12/1988 |
| EP | 296110 | A2 | 12/1988 |
| EP | 0657458 | A1 | 6/1995 |
| EP | 1354882 | A1 | 10/2003 |
| WO | 95/17182 | | 6/1995 |
| WO | 00/58307 | | 10/2000 |
| WO | 02/38561 | A1 | 5/2002 |
| WO | 2005/009389 | A2 | 2/2005 |
| WO | 2005/028480 | A2 | 3/2005 |
| WO | 2005/058307 | A1 | 6/2005 |
| WO | 2008/125945 | A2 | 10/2008 |
| WO | 2008/144253 | A1 | 11/2008 |
| WO | 2010/011772 | A2 | 1/2010 |
| WO | 2010/129668 | A1 | 11/2010 |
| WO | 2011045344 | * | 4/2011 |

OTHER PUBLICATIONS

Chemical Abstract Services STN Records, Apr. 13, 2001-Apr. 17, 2011, American Chemical Society.
International Search Report as issued in PCT/EP2013/058839, mailed on Jun. 14, 2013.

* cited by examiner

*Primary Examiner* — Niloofar Rahmani
(74) *Attorney, Agent, or Firm* — Janann Y. Ali

(57) ABSTRACT

The present invention relates to pyrazolo[3,4-b]pyridine compounds of the formula I,

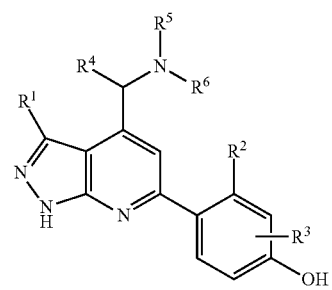

in which $R^1$, $R^2$, $R^3$, $R^4$, $R^5$ and $R^6$ are defined as indicated below. The compounds of the formula I are kinase inhibitors, and are useful for the treatment of diseases associated with diabetes and diabetic complications, such as, diabetic nephropathy, diabetic neuropathy and diabetic retinopathy, for example. The invention furthermore relates to the use of compounds of the formula I, in particular as active ingredients in pharmaceuticals, and pharmaceutical compositions comprising them.

8 Claims, No Drawings

SUBSTITUTED 6-(4-HYDROXY-PHENYL)-1H-PYRAZOLO[3,4-B]PYRIDINE DERIVATIVES AS KINASE INHIBITORS

CROSS-REFERENCE TO RELATED APPLICATIONS

This application is a continuation of International Patent Application No. PCT/EP2013/058839, filed Apr. 29, 2013, the entire contents of which are expressly incorporated herein by reference.

The present invention relates to pyrazolo[3,4-b]pyridine compounds of the formula I,

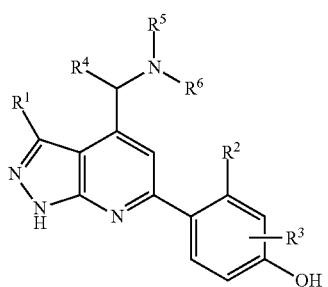

in which $R^1$, $R^2$, $R^3$, $R^4$, $R^5$ and $R^6$ are defined as indicated below. The compounds of the formula I are kinase inhibitors, and are useful for the treatment of diseases associated with diabetes and diabetic complications, e.g., diabetic nephropathy, diabetic neuropathy and diabetic retinopathy, for example. The invention furthermore relates to the use of compounds of the formula I, in particular as active ingredients in pharmaceuticals, and pharmaceutical compositions comprising them.

BACKGROUND

Protein kinase C (PKC) comprises a family of several related isoenzymes that function as serine/threonine kinases. PKC plays an important role in intercellular and intracellular signaling, gene expression, and in the control of cell differentiation and growth. Currently, at least ten isoforms of PKC are known which are different in regulation, tissue distribution, and enzymatic specificity (Newton A C. Regulation of the ABC kinases by phosphorylation: protein kinase C as a paradigm. Biochem J 2003; 370(Pt 2):361-371; Newton A C. Protein kinase C: poised to signal. Am J Physiol Endocrinol Metab 2010; 298(3):E395-E402; Nishizuka Y. Studies and prospectives of the protein kinase c family for cellular regulation. Cancer 1989; 63(10):1892-1903; Nishizuka Y. The Albert Lasker Medical Awards. The family of protein kinase C for signal transduction. JAMA 1989; 262(13):1826-1833). The PKC family of isoenzymes are grouped into three subclasses based on the domain composition of the regulatory moiety: (1) conventional PKCs (alpha, beta-II, and beta-I), (2) novel PKCs (delta, epsilon, gamma, eta and theta) and (3) atypical PKCs (zeta and iota/lambda) (Newton A C. Regulation of the ABC kinases by phosphorylation: protein kinase C as a paradigm. Biochem J 2003; 370(Pt 2):361-371; Mellor H, Parker P J. The extended protein kinase C superfamily. Biochem J 1998; 332 (Pt 2):281-292). PKC is a membrane-associated enzyme that is regulated by several distinct factors, such as membrane phospholipids, calcium, and membrane lipids, e.g. diacylglycerol (Newton A C. Regulation of the ABC kinases by phosphorylation: protein kinase C as a paradigm. Biochem J 2003; 370(Pt 2):361-371; Newton A C. Protein kinase C: poised to signal. Am J Physiol Endocrinol Metab 2010; 298(3):E395-E402; Mellor H, Parker P J. The extended protein kinase C superfamily. Biochem J 1998; 332 (Pt 2):281-292; Kishimoto A, Kikkawa U, Ogita K, Shearman M S, Nishizuka Y. The protein kinase C family in the brain: heterogeneity and its implications. Ann N Y Acad Sci 1989; 568: 181-186; Nishizuka Y. Calcium, phospholipid turnover and transmembrane signalling. Philos Trans R Soc Lond B Biol Sci 1983; 302(1108):101-112.). All PKC isoforms have an autoinhibitory pseudosubstrate sequence that is N-terminal to the C1 domain, which functions as a diacylglycerol sensor. Atypical PKCs have a diacylglycerol non-responsive C1 domain. Conventional PKCs have a C2 domain that serves as a $Ca^{2+}$-regulated phospholipid-binding module. The C2 domain in novel PKCs binds neither $Ca^{2+}$ nor membrane phospholipids. Based on the structural differences conventional PKCs require membrane phospholipids, calcium and diacylglycerol for complete activation. Novel PKCs do not require calcium but diacylglycerol for activation. The zeta and iota/lambda forms of PKC are independent of both calcium and diacylglycerol for their activation (Newton A C. Regulation of the ABC kinases by phosphorylation: protein kinase C as a paradigm. Biochem J 2003; 370(Pt 2):361-371; Newton A C. Lipid activation of protein kinases. J Lipid Res 2009; 50 Suppl:S266-S271). PKC is involved in the regulation of smooth muscle contractility. Upon stimulation PKC phosphorylates the regulatory myosin light chain ($MLC_{20}$) and inhibits the myosin associated phosphatase (MYPT). Phosphorylation of $MLC_{20}$ and inhibition of MYPT leads to an increased activity of the acto-myosin complex and to vasoconstriction in different vascular beds, e.g. resistance-sized, retinal, cerebral, coronary, conduit arteries and veins (Merkel L A, Rivera L M, Colussi D J, Perrone M H. Protein kinase C and vascular smooth muscle contractility: effects of inhibitors and down-regulation. J Pharmacol Exp Ther 1991; 257(1): 134-140; Sehic E, Malik K U. Influence of protein kinase C activators on vascular tone and adrenergic neuroeffector events in the isolated rat kidney. J Pharmacol Exp Ther 1989; 251(2):634-639.).

Overexpressed or overactivated PKC detrimentally affects heart function. Upon activation PKC affects the intracellular calcium homeostasis which results in reduced myocardial contractility and relaxation of the myocardium. Overall this effect leads to myocardial contractile insufficiency (Connelly K A, Kelly D J, Zhang Y, Prior D L, Advani A, Cox A J, That K, Krum H, Gilbert R E. Inhibition of protein kinase C-beta by ruboxistaurin preserves cardiac function and reduces extracellular matrix production in diabetic cardiomyopathy. Circ Heart Fail 2009; 2(2):129-137). Moreover, activated PKC mediates organ damage during end-organ injuries, e.g. during ischemia in heart (Connelly K A, Kelly D J, Zhang Y, Prior D L, Advani A, Cox A J, That K, Krum H, Gilbert R E. Inhibition of protein kinase C-beta by ruboxistaurin preserves cardiac function and reduces extracellular matrix production in diabetic cardiomyopathy. Circ Heart Fail 2009; 2(2):129-137; Hambleton M, Hahn H, Pleger S T, Kuhn M C, Klevitsky R, Carr A N, Kimball T F, Hewett T E, Dorn G W, Koch W J, Molkentin J D. Pharmacological—and gene therapy-based inhibition of protein kinase Calpha/beta enhances cardiac contractility and attenuates heart failure. Circulation 2006; 114(6): 574-582) or kidney (Tuttle K R. Protein kinase C-beta inhibition for diabetic kidney disease. Diabetes Res Clin Pract 2008; 82 Suppl 1:S70-S74; Anderson P W, McGill J B, Tuttle K R. Protein kinase C beta inhibition: the promise for treatment of diabetic nephropathy. Curr Opin Nephrol Hypertens 2007; 16(5):397-402). PKC and especially the PKC-beta II isoform is overexpressed or overactivated in diabetes in various different types of tissue and exerts its deleterious effect to the cells, tissues and end-organs, e.g. kidney (Tuttle K R. Protein kinase C-beta inhibition for diabetic kidney disease. Diabetes Res Clin Pract 2008; 82 Suppl 1:S70-S74; Anderson P W, McGill J B, Tuttle K R. Protein kinase C beta inhibition: the promise for treatment of diabetic nephropathy. Curr Opin Nephrol Hypertens 2007; 16(5):397-402; Tuttle K R, Bakris G L, Toto R D, McGill J B, Hu K, Anderson P W. The effect of ruboxistaurin on nephropathy in type 2 diabetes. Diabetes Care 2005; 28(11):2686-2690; Kelly D J, Zhang Y, Hepper C, Gow R M, Jaworski K, Kemp B E, Wilkinson-Berka J L, Gilbert R E. Protein kinase C beta inhibition attenuates the progression of experimental diabetic nephropathy in the presence of continued hypertension. Diabetes 2003; 52(2):512-518), heart (Connelly K A, Kelly D J, Zhang Y, Prior D L, Advani A, Cox A J, That K, Krum H, Gilbert R E. Inhibition of protein kinase C-beta by ruboxistaurin preserves cardiac function and reduces extracellular matrix production in diabetic cardiomyopathy. Circ Heart Fail 2009; 2(2):129-137; Guo M, Wu M H, Korompai F, Yuan S Y. Upregulation of PKC genes and isozymes in cardiovascular tissues during early stages of experimental diabetes. Physiol Genomics 2003; 12(2):139-146), or in tissues like the retina (Aiello L P, Clermont A, Arora V, Davis M D, Sheetz M J, Bursell S E. Inhibition of PKC beta by oral administration of ruboxistaurin is well tolerated and ameliorates diabetes-induced retinal hemodynamic abnormalities in patients. Invest Ophthalmol V is Sci 2006; 47(1):86-92; Aiello L P. The potential role of PKC beta in diabetic retinopathy and macular edema. Surv Ophthalmol 2002; 47 Suppl 2:S263-S269; Kimura M, Ishizawa M, Miura A, Itaya S, Kanoh Y, Yasuda K, Uno Y, Morita H, Ishizuka T. Platelet protein kinase C isoform content in type 2 diabetes complicated with retinopathy and nephropathy. Platelets 2001; 12(3):138-143) or neuronal tissue (Krishnan S T, Rayman G. New treatments for diabetic neuropathy: symptomatic treatments. Curr Diab Rep 2003; 3(6):459-467; Kim H, Sasaki T, Maeda K, Koya D, Kashiwagi A, Yasuda H. Protein kinase Cbeta selective inhibitor LY333531 attenuates diabetic hyperalgesia through ameliorating cGMP level of dorsal root ganglion neurons. Diabetes 2003; 52(8):2102-2109; Cotter M A, Jack A M, Cameron N E. Effects of the protein kinase C beta inhibitor LY333531 on neural and vascular function in rats with streptozotocin-induced diabetes. Clin Sci (Lond) 2002; 103(3):311-321; Nakamura J, Kato K, Hamada Y, Nakayama M, Chaya S, Nakashima E, Naruse K, Kasuya Y, Mizubayashi R, Miwa K, Yasuda Y, Kamiya H, Ienaga K, Sakakibara F, Koh N, Hotta N. A protein kinase C-beta-selective inhibitor ameliorates neural dysfunction in streptozotocin-induced diabetic rats. Diabetes 1999; 48(10):2090-2095) or in platelets (Assert R, Scherk G, Bumbure A, Pirags V, Schatz H, Pfeiffer A F. Regulation of protein kinase C by short term hyperglycaemia in human platelets in vivo and in vitro. Diabetologia 2001; 44(2):188-195; Bynagari-Settipalli Y S, Chari R, Kilpatrick L, Kunapuli S P. Protein kinase C—possible therapeutic target to treat cardiovascular diseases. Cardiovasc Hematol Disord Drug Targets 2010; 10(4):292-308; Kimura M, Ishizawa M, Miura A, Itaya S, Kanoh Y, Yasuda K, Uno Y, Morita H, Ishizuka T. Platelet protein kinase C isoform content in type 2 diabetes complicated with retinopathy and nephropathy. Platelets 2001; 12(3):138-143; Oskarsson H J, Hofineyer T G, Coppey L, Yorek M A. Effect of protein kinase C and phospholipase A2 inhibitors on the impaired ability of human diabetic platelets to cause vasodilation. Br J Pharmacol 1999; 127(4):903-908) or induces endothelial dysfunction (Chiasson V L, Quinn M A, Young K J, Mitchell B M. Protein kinase Cbetall-mediated phosphorylation of endothelial nitric oxide synthase threonine 495 mediates the endothelial dysfunction induced by FK506 (tacrolimus). J Pharmacol Exp Ther 2011; 337(3):718-723; Xu Y, Wang S, Feng L, Zhu Q, Xiang P, He B. Blockade of PKC-beta protects HUVEC from advanced glycation end products induced inflammation. Int Immunopharmacol 2010; 10(12):1552-1559; Geraldes P, King G L. Activation of protein kinase C isoforms and its impact on diabetic complications. Circ Res 2010; 106(8):1319-1331; Nacci C, Tarquinio M, Montagnani M. Molecular and clinical aspects of endothelial dysfunction in diabetes. Intern Emerg Med 2009; 4(2):107-116). Furthermore, it has been suggested that PKC signalling is involved in tumour formation (Gonelli A, Mischiati C, Guerrini R, Voltan R, Salvadori S, Zauli G. Perspectives of protein kinase C(PKC) inhibitors as anticancer agents. Mini Rev Med Chem 2009; 9(4):498-509; Ali A S, Ali S, El-Rayes B F, Philip P A, Sarkar F H. Exploitation of protein kinase C: a useful target for cancer therapy. Cancer Treat Rev 2009; 35(1):1-8), e.g. in hematological tumours (Mischiati C, Melloni E, Corallini F, Milani D, Bergamini C, Vaccarezza M. Potential role of PKC inhibitors in the treatment of hematological malignancies. Curr Pharm Des 2008; 14(21):2075-2084; Cheson B D, Zwiebel J A, Dancey J, Murgo A. Novel therapeutic agents for the treatment of myelodysplastic syndromes. Semin Oncol 2000; 27(5):560-577; Deng X, Kornblau S M, Ruvolo P P, May W S, Jr. Regulation of Bcl2 phosphorylation and potential significance for leukemic cell chemoresistance. J Natl Cancer Inst Monogr 2001; (28):30-37), in glioma formation (Baltuch G H, Dooley N P, Villemure J G, Yong V W. Protein kinase C and growth regulation of malignant gliomas. Can J Neurol Sci 1995; 22(4):264-271; Blobe G C, Obeid L M, Hannun Y A. Regulation of protein kinase C and role in cancer biology. Cancer Metastasis Rev 1994; 13(3-4):411-431; Bredel M, Pollack I F. The role of protein kinase C(PKC) in the evolution and proliferation of malignant gliomas, and the application of PKC inhibition as a novel approach to anti-glioma therapy. Acta Neurochir (Wien)) 1997; 139(11):1000-1013), in gastric and intestinal cancer (Atten M J, Godoy-Romero E, Attar B M, Milson T, Zopel M, Holian O. Resveratrol regulates cellular PKC alpha and delta to inhibit growth and induce apoptosis in gastric cancer cells. Invest New Drugs 2005; 23(2):111-119; Fahrmann M. Targeting protein kinase C (PKC) in physiology and cancer of the gastric cell system. Curr Med Chem 2008; 15(12):1175-1191), in skin cancer (Birt D F, Yaktine A, Duysen E. Glucocorticoid mediation of dietary energy restriction inhibition of mouse skin carcinogenesis. J Nutr 1999; 129 (2S Suppl):571S-574S; Birt D F, Przybyszewski J, Wang W, Stewart J, Liu Y. Identification of molecular targets for dietary energy restriction prevention of skin carcinogenesis: an idea cultivated by Edward Bresnick. J Cell Biochem 2004; 91(2):258-264), lung cancer (Herbst R S, Oh Y, Wagle A, Lahn M. Enzastaurin, a protein kinase Cbeta-selective inhibitor, and its potential application as an anticancer agent in lung cancer. Clin Cancer Res 2007; 13(15 Pt 2):s4641-s4646; Herbst R S. Targeted therapy in non-small-cell lung cancer. Oncology (Williston Park) 2002; 16(9 Suppl 9):19-24) and others. PKC is an important signal transducer of events in autoimmune responses, e.g. in T-cell (Birchall A M, Bishop J, Bradshaw D, Cline A, Coffey J, Elliott L H, Gibson V M, Greenham A, Hallam T J, Harris W. Ro 32-0432, a selective and orally active inhibitor of protein kinase C prevents T-cell activation. J Pharmacol Exp Ther 1994; 268 (2):922-929; Isakov N, Altman A. Protein kinase C(theta) in T cell activation. Annu Rev Immunol 2002; 20:761-794) or B-cell (Shinohara H, Kurosaki T. Comprehending the complex connection between PKCbeta, TAK1, and IKK in BCR signaling. Immunol Rev 2009; 232(1):300-318; Venkataraman C, Chen X C, Na S, Lee L, Neote K, Tan S L. Selective role of PKCbeta enzymatic function in regulating cell survival mediated by B cell antigen receptor cross-linking. Immunol Lett 2006; 105(1):83-89) linked autoimmune signalling, and in inflammatory processes.

The above mentioned effects of the PKC-mediated signalling leads to induction or promotion of the progression of asthma (Boschelli D H. Small molecule inhibitors of PKC-Theta as potential antiinflammatory therapeutics. Curr Top Med Chem 2009; 9(7):640-654), chronic obstructive pulmonary disease (Mercer B A, D'Armiento J M. Emerging role of MAP kinase pathways as therapeutic targets in COPD. Int J Chron Obstruct Pulmon Dis 2006; 1(2):137-150; Adcock I M, Chung K F, Caramori G, Ito K. Kinase inhibitors and airway inflammation. Eur J Pharmacol 2006; 533(1-3):118-132; Dempsey E C, Cool C D, Littler C M. Lung disease and PKCs. Pharmacol Res 2007; 55(6):545-559; Ishii M, Kurachi Y. Muscarinic acetylcholine receptors. Curr Pharm Des 2006; 12(28):3573-3581; Medina-Tato D A, Watson M L, Ward S G. Leukocyte navigation mechanisms as targets in airway diseases. Drug Discov Today 2006; 11(19-20):866-879), pulmonary hypertension (Agbani E O, Coats P, Mills A, Wadsworth R M. Peroxynitrite stimulates pulmonary artery endothelial and smooth muscle cell proliferation: involvement of ERK and PKC. Pulm Pharmacol Ther 2011; 24(1): 100-109; Littler C M, Wehling C A, Wick M J, Fagan K A, Cool C D, Messing R O, Dempsey E C. Divergent contractile and structural responses of the murine PKC-epsilon null pulmonary circulation to chronic hypoxia. Am J Physiol Lung Cell Mol Physiol 2005; 289(6):L1083-L1093), retinopathy, like retinal ischemia and neovascularization (Galvez M I. Protein kinase C inhibitors in the treatment of diabetic retinopathy. Review. Curr Pharm Biotechnol 2011; 12(3):386-391; Schwartz S G, Flynn H W, Jr., Aiello L P. Ruboxistaurin mesilate hydrate for diabetic retinopathy. Drugs Today (Barc) 2009; 45(4):269-274), nephropathy, including hypertension-induced (Kelly D J, Edgley A J, Zhang Y, That K, Tan S M, Cox A J, Advani A, Connelly K A, Whiteside C I, Gilbert R E. Protein kinase C-beta inhibition attenuates the progression of nephropathy in non-diabetic kidney disease. Nephrol Dial Transplant 2009; 24(6):1782-1790; Hayashi K, Wakino S, Ozawa Y, Homma K, Kanda T, Okubo K, Takamatsu I, Tatematsu S, Kumagai H, Saruta T. Role of protein kinase C in Ca channel blocker-induced renal arteriolar dilation in spontaneously hypertensive rats—studies in the isolated perfused hydronephrotic kidney. Keio J Med 2005; 54(2):102-108; Kelly D J, Zhang Y, Hepper C, Gow R M, Jaworski K, Kemp B E, Wilkinson-Berka J L, Gilbert R E. Protein kinase C beta inhibition attenuates the progression of experimental diabetic nephropathy in the presence of continued hypertension. Diabetes 2003; 52(2):512-518), non-hypertension-induced, and diabetic nephropathies (Danis R P, Sheetz M J. Ruboxistaurin: PKC-beta inhibition for complications of diabetes. Expert Opin Pharmacother 2009; 10(17):2913-2925; Tuttle K R. Protein kinase C-beta inhibition for diabetic kidney disease. Diabetes Res Clin Pract 2008; 82 Suppl 1:S70-S74), renal failure (Danis R P, Sheetz M J. Ruboxistaurin: PKC-beta inhibition for complications of diabetes. Expert Opin Pharmacother 2009; 10(17):2913-2925; Yamagishi S, Fukami K, Ueda S, Okuda S. Molecular mechanisms of diabetic nephropathy and its therapeutic intervention. Curr Drug Targets 2007; 8(8):952-959) and myocardial infarction (Bynagari-Settipalli Y S, Chari R, Kilpatrick L, Kunapuli S P. Protein kinase C—possible therapeutic target to treat cardiovascular diseases. Cardiovasc Hematol Disord Drug Targets 2010; 10(4):292-308; Rohilla A, Singh G, Singh M, Bala kP. Possible involvement of PKC-delta in the abrogated cardioprotective potential of ischemic preconditioning in hyperhomocysteinemic rat hearts. Biomed Pharmacother 2010; 64(3):195-202; Liu Q, Chen X, Macdonnell S M, Kranias E G, Lorenz J N, Leitges M, Houser S R, Molkentin J D. Protein kinase C{alpha}, but not PKC{beta} or PKC {gamma}, regulates contractility and heart failure susceptibility: implications for ruboxistaurin as a novel therapeutic approach. Circ Res 2009; 105(2):194-200; Yonezawa T, Kurata R, Kimura M, Inoko H. PKC delta and epsilon in drug targeting and therapeutics. Recent Pat DNA Gene Seq 2009; 3(2):96-101) cardiac hypertrophy and failure (Ferreira J C, Brum P C, Mochly-Rosen D. betaIIPKC and epsilonPKC isozymes as potential pharmacological targets in cardiac hypertrophy and heart failure. J Mol Cell Cardiol 2010; Palaniyandi S S, Sun L, Ferreira J C, Mochly-Rosen D. Protein kinase C in heart failure: a therapeutic target? Cardiovasc Res 2009; 82(2): 229-239), coronary heart disease, artherosclerosis, restenosis (Ding R Q, Tsao J, Chai H, Mochly-Rosen D, Zhou W. Therapeutic potential for protein kinase C inhibitor in vascular restenosis. J Cardiovasc Pharmacol Ther 2011; 16(2):160-167; Schleicher E, Friess U. Oxidative stress, AGE, and atherosclerosis. Kidney Int Suppl 2007; (106):517-526), diabetes, diabetic complications, glucose utilization and metabolic syndrome (Bynagari-Settipalli Y S, Chari R, Kilpatrick L, Kunapuli S P. Protein kinase C—possible therapeutic target to treat cardiovascular diseases. Cardiovasc Hematol Disord Drug Targets 2010; 10(4):292-308; Geraldes P, King G L. Activation of protein kinase C isoforms and its impact on diabetic complications. Circ Res 2010; 106(8):1319-1331; Danis R P, Sheetz MJ. Ruboxistaurin: PKC-beta inhibition for complications of diabetes. Expert Opin Pharmacother 2009; 10(17):2913-2925), immune diseases (Baier G, Wagner J. PKC inhibitors: potential in T cell-dependent immune diseases. Curr Opin Cell Biol 2009; 21(2):262-267; Mecklenbrauker I, Saijo K, Zheng N Y, Leitges M, Tarakhovsky A. Protein kinase Cdelta controls self-antigen-induced B-cell tolerance. Nature 2002; 416(6883):860-865; Wilkinson S E, Hallam T J. Protein kinase C: is its pivotal role in cellular activation over-stated? Trends Pharmacol Sci 1994; 15(2):53-57; Costello R, Mawas C, Olive D. Differential immunosuppressive effects of metabolic inhibitors on T-lymphocyte activation. Eur Cytokine Netw 1993; 4(2):139-146), like psoriasis (Sommerer C, Zeier M. AEB071—a promising immunosuppressive agent. Clin Transplant 2009; 23 Suppl 21:15-18; Rasmussen H H, Celis J E. Evidence for an altered protein kinase C(PKC) signaling pathway in psoriasis. J Invest Dermatol 1993; 101(4):560-566; Fisher G J, Tavakkol A, Leach K, Burns D, Basta P, Loomis C, Griffiths C E, Cooper K D, Reynolds N J, Elder J T. Differential expression of protein kinase C isoenzymes in normal and psoriatic adult human skin: reduced expression of protein kinase C-beta II in psoriasis. J Invest Dermatol 1993; 101(4):553-559), rheumatoid arthritis (Healy A M, Izmailova E, Fitzgerald M, Walker R, Hattersley M, Silva M, Siebert E, Terkelsen J, Picarella D, Pickard M D, LeClair B, Chandra S, Jaffee B. PKC-theta-deficient mice are protected from Th1-dependent antigen-induced arthritis. J Immunol 2006; 177(3):1886-1893; Ji J D, Tassiulas I, Park-Min K H, Aydin A, Mecklenbrauker I, Tarakhovsky A, Pricop L, Salmon J E, Ivashkiv L B. Inhibition of interleukin 10 signaling after Fc receptor ligation and during rheumatoid arthritis. J Exp Med 2003; 197(11):1573-1583; Kehlen A, Thiele K, Riemann D, Langner J. Expression, modulation and signalling of IL-17 receptor in fibroblast-like synoviocytes of patients with rheumatoid arthritis. Clin Exp Immunol 2002; 127(3):539-546), or other autoimmune disorders (Zanin-Zhorov A, Dustin M L, Blazar B R. PKC-theta function at the immunological synapse: prospects for therapeutic targeting. Trends Immunol 2011; 32(8):358-363), central nervous system disorders (Liang J, Takeuchi H, Jin S, Noda M, Li H, Doi Y, Kawanokuchi J, Sonobe Y, Mizuno T, Suzumura A. Glutamate induces neurotrophic factor production from microglia via protein kinase C pathway. Brain Res 2010; 1322:8-23; Bastianetto S, Zheng W H, Quirion R. Neuroprotective abilities of resveratrol and other red wine constituents against nitric oxide-related toxicity in cultured hippocampal neurons. Br J Pharmacol 2000; 131(4):711-720), cerebral ischemia or cerebral vasospasm (Bu X, Zhang N, Yang X, Liu Y, Du J, Liang J, Xu Q, Li J. Proteomic analysis of cPKCbetaII-interacting proteins involved in HPC-induced neuroprotection against cerebral ischemia of mice. J Neurochem 2011; 117(2):346-356), neuropathies and pain, e.g. neuropathic pain (Nakajima A, Tsuboi Y, Suzuki I, Honda K, Shinoda M, Kondo M, Matsuura S, Shibuta K, Yasuda M, Shimizu N, Iwata K. PKC-gamma in Vc and C1/C2 is involved in trigeminal neuropathic pain. J Dent Res 2011; 90(6):777-781; Malmberg A B, Chen C, Tonegawa S, Basbaum A I. Preserved acute pain and reduced neuropathic pain in mice lacking PKCgamma. Science 1997; 278(5336):279-283), cancer development and progression, neoplasia where inhibition of protein kinase C has been shown to inhibit tumor cell growth and metastasis (Kim J, Thorne S H, Sun L, Huang B, Mochly-Rosen D. Sustained inhibition of PKCalpha reduces intravasation and lung seeding during mammary tumor metastasis in an in vivo mouse model. Oncogene 2011; 30(3):323-333; Spindler K L, Lindebjerg J, Lahn M, Kjaer-Frifeldt S, Jakobsen A. Protein kinase C-beta II (PKC-beta II) expression in patients with colorectal cancer. Int J Colorectal Dis 2009; 24(6):641-645; Guo K, Li Y, Kang X, Sun L, Cui J, Gao D, Liu Y. Role of PKCbeta in hepatocellular carcinoma cells migration and invasion in vitro: a potential therapeutic target. Clin Exp Metastasis 2009; 26(3):189-195), angiogenesis (Nakamura S, Chikaraishi Y, Tsuruma K, Shimazawa M, Hara H. Ruboxistaurin, a PKCbeta inhibitor, inhibits retinal neovascularization via suppression of phosphorylation of ERK½ and Akt. Exp Eye Res 2010; 90(1):137-145; Ali A S, Ali S, El-Rayes B F, Philip P A, Sarkar F H. Exploitation of protein kinase C: a useful target for cancer therapy. Cancer Treat Rev 2009; 35(1):1-8; Tekle C, Giovannetti E, Sigmond J, Graff J R, Smid K, Peters G J. Molecular pathways involved in the synergistic interaction of the PKC beta inhibitor enzastaurin with the antifolate pemetrexed in non-small cell lung cancer cells. Br J Cancer 2008; 99(5):750-759; Mischiati C, Melloni E, Corallini F, Milani D, Bergamini C, Vaccarezza M. Potential role of PKC inhibitors in the treatment of hematological malignancies. Curr Pharm Des 2008; 14(21):2075-2084), platelet disorders leading to thrombosis (Gilio K, Harper M T, Cosemans J M, Konopatskaya O, Munnix I C, Prinzen L, Leitges M, Liu Q, Molkentin J D, Heemskerk J W, Poole A W. Functional divergence of platelet protein kinase C(PKC) isoforms in thrombus formation on collagen. J Biol Chem 2010; 285(30):23410-23419; Chari R, Getz T, Nagy B, Jr., Bhavaraju K, Mao Y, Bynagari Y S, Murugappan S, Nakayama K, Kunapuli S P. Protein kinase C[delta] differentially regulates platelet functional responses. Arterioscler Thromb Vasc Biol 2009; 29(5):699-705; Nagy B, Jr., Bhavaraju K, Getz T, Bynagari Y S, Kim S, Kunapuli S P. Impaired activation of platelets lacking protein kinase C-theta isoform. Blood 2009; 113(11):2557-2567; Harper M T, Poole A W. Isoform-specific functions of protein kinase C: the platelet paradigm. Biochem Soc Trans 2007; 35(Pt 5):1005-1008; Strehl A, Munnix I C, Kuijpers M J, van der Meijden P E, Cosemans J M, Feijge M A, Nieswandt B, Heemskerk J W. Dual role of platelet protein kinase C in thrombus formation: stimulation of pro-aggregatory and suppression of procoagulant activity in platelets. J Biol Chem 2007; 282(10):7046-7055; London F S. The protein kinase C inhibitor RO318220 potentiates thrombin-stimulated platelet-supported prothrombinase activity. Blood 2003; 102(7):2472-2481; Wheeler-Jones C P, Patel Y, Kakkar V V, Krishnamurthi S. Translocation of protein kinase C(PKC) in stimulated platelets: a role for aggregation in PKC degradation. Br J Pharmacol 1989; 98 Suppl: 845P), and leukocyte aggregation (Hu H, Zhang W, Li N. Glycoprotein IIb/IIIa inhibition attenuates platelet-activating factor-induced platelet activation by reducing protein kinase C activity. J Thromb Haemost 2003; 1(8):1805-1812; Kotovuori A, Pessa-Morikawa T, Kotovuori P, Nortamo P, Gahmberg C G. ICAM-2 and a peptide from its binding domain are efficient activators of leukocyte adhesion and integrin affinity. J Immunol 1999; 162(11):6613-6620; Lorenz H M, Lagoo A S, Hardy K J. The cell and molecular basis of leukocyte common antigen (CD45)-triggered, lymphocyte function-associated antigen-1-/intercellular adhesion molecule-1-dependent, leukocyte adhesion. Blood 1994; 83(7):1862-1870).

Until now, mainly staurosporine derivatives have been described as PKC inhibitors in the prior art, for example Ruboxistaurin (e.g. EP 657458), Enzastaurin (e.g. WO 9517182), Midostaurin (e.g. EP 296110) or Sotrastaurin (e.g. WO 2002038561). Only very few PKCβ inhibitors, which are not derived from staurosporine have been described, such as 3-amido-pyrrolo[3,4-c]pyrazole-5(1H, 4H,6H)carbaldehydes in WO 2008125945. However, there continues to be a need for further effective low molecular weight PKCβ inhibitors, in particular in view of safety and selectivity. The present invention satisfies this need by providing the pyrazolo[3,4-b]pyridine compounds of the formula I.

Pyrazolo[3,4-b]pyridine derivatives which are useful for pharmaceutical applications, have already been disclosed, for example in WO 2005028480 (Neurogen Corp. and Aventis Pharmaceuticals Inc.), in WO 2005009389 (Exelixis Inc.) or in WO 2000058307 (Neurogen Corp.). 6-(4-Hydroxy-phenyl)-1H-pyrazolo[3,4-b]pyridine-4-carboxylic acid amide derivatives are described in EPI 1306228.5 and EPI 1306377.0 (Sanofi). However, there continues to be a need for compounds with an improved profile in terms of metabolic stability and permeability. The present invention satisfies this need by providing the pyrazolo[3,4-b]pyridine compounds of the formula I.

DETAILED DESCRIPTION

Accordingly, a subject of the present invention is a compound of the formula I

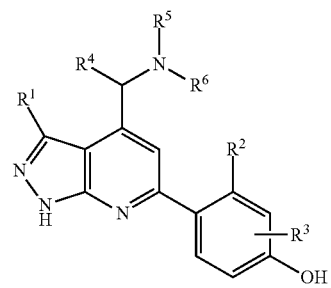

wherein
$R^1$ is $(C_1-C_4)$-alkyl, $CF_3$, cyclopropyl or cyclobutyl;
$R^2$ is H, halogen, methyl or $CF_3$;
$R^3$ is H, halogen, methyl or $CF_3$;
$R^4$ is H, $(C_1-C_4)$-alkyl or $CF_3$;
$R^5$ is H or $(C_1-C_4)$-alkyl;
$R^6$ is a 4- to 8-membered monocyclic heterocycle comprising a ring nitrogen, which is unsubstituted or mono- or disubstituted by $(C_1-C_4)$-alkyl, wherein alkyl is unsubstituted or one to threefold substituted by F; or
$R^5$ and $R^6$ together with the N-atom carrying them denote
a) a 1,4-piperazinyl of the formula

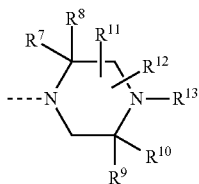

wherein
$R^7$ is H, $(C_1-C_4)$-alkyl, cyclopropyl, cyclobutyl or phenyl, wherein alkyl is unsubstituted or one to threefold substituted by F, wherein phenyl is unsubstituted or mono- or disubstituted by halogen, $CF_3$, $(C_1-C_4)$-alkyl, $O-CF_3$ or $O-(C_1-C_4)$-alkyl;
$R^8$ is H or $(C_1-C_4)$-alkyl;
or
$R^7$ and $R^8$ together with the carbon atom carrying them denote $(C_3-C_6)$-cycloalkyl;
$R^9$ is H, $(C_1-C_4)$-alkyl, cyclopropyl, cyclobutyl or phenyl, wherein alkyl is unsubstituted or one to threefold substituted by F, wherein phenyl is unsubstituted or mono- or disubstituted by halogen, $CF_3$, $(C_1-C_4)$-alkyl, $O-CF_3$ or $O-(C_1-C_4)$-alkyl;
$R^{10}$ is H or $(C_1-C_4)$-alkyl;
or
$R^9$ and $R^{10}$ together with the carbon atom carrying them denote $(C_3-C_6)$-cycloalkyl;
$R^{11}$ is H or $(C_1-C_4)$-alkyl;
$R^{12}$ is H or $(C_1-C_4)$-alkyl;
$R^{13}$ is
  i) H;
  ii) $(C_1-C_4)$-alkyl, which is unsubstituted or one to two-fold substituted by
    a. $CF_3$,
    b. OH,
    c. $O-(C_1-C_4)$-alkyl,
    d. phenyl,
    e. thienyl
    f. pyridyl,
    g. tetrahydrofuranyl,
    h. tetrahydropyranyl,
    i. 2,2'-dimethyl-1,3-dioxolanyl,
    j. $C(O)-O-(C_1-C_4)$-alkyl,
    k. $NH-(C_1-C_4)$-alkyl,
    l. $N((C_1-C_4)$-alkyl$)_2$;
  iii) $C(O)-((C1-C4)$-alkyl which is unsubstituted or monosubstituted by
    a. OH,
    b. $O-CF_3$,
    c. $O-(C_1-C_4)$-alkyl,
  iv) C(O)-tetrahydrofuranyl,
  v) C(O)-tetrahydropyranyl,
  vi) $C(O)-NH-(C_1-C_4)$-alkyl,
  vii) $C(O)-N((C_1-C_4)$-alkyl$)_2$,
  viii) $C(O)-NH-(C_1-C_4)$-alkylene-$COO(C_1-C_4)$-alkyl;
b) a morpholinyl of the formula

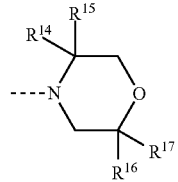

wherein
$R^{14}$ is H, $(C_1-C_4)$-alkyl, cyclopropyl, cyclobutyl or phenyl, wherein alkyl is unsubstituted or one to threefold substituted by F, wherein phenyl is unsubstituted or mono- or disubstituted by halogen, $CF_3$, $(C_1-C_4)$-alkyl, $O-CF_3$ or $O-(C_1-C_4)$-alkyl;
$R^{15}$ is H or $(C_1-C_4)$-alkyl;
or
$R^{14}$ and $R^{15}$ together with the carbon atom carrying them denote $(C_3-C_6)$-cycloalkyl;
$R^{16}$ is H, $(C_1-C_4)$-alkyl, cyclopropyl, cyclobutyl or phenyl, wherein alkyl is unsubstituted or one to threefold substituted by F, wherein phenyl is unsubstituted or mono- or disubstituted by halogen, $CF_3$, $(C_1-C_4)$-alkyl, $O-CF_3$ or $O-(C_1-C_4)$-alkyl;
$R^{17}$ is H or $(C_1-C_4)$-alkyl;
or
$R^{16}$ and $R^{17}$ together with the carbon atom carrying them denote $(C_3-C_6)$-cycloalkyl;
c) a ring A of the formula

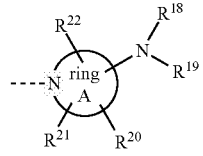

comprising one nitrogen and 3 to 6 carbon ring atoms, wherein the substituent $NR^{18}R^{19}$ is not in an adjacent position to the ring nitrogen atom and
$R^{18}$ is H, $(C_1-C_4)$-alkyl or $C(O)-(C_1-C_4)$-alkylene-$O-(C_1-C_4)$-alkyl;
$R^{19}$ is H or $(C_1-C_4)$-alkyl;
$R^{20}$ is H or $(C_1-C_4)$-alkyl;
$R^{21}$ is H or $(C_1-C_4)$-alkyl;
$R^{22}$ is H or $(C_1-C_4)$-alkyl;
d) a 1,4-diazepin of the formula

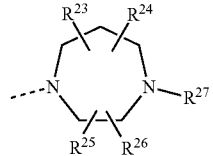

wherein
$R^{23}$ is H, $(C_1-C_4)$-alkyl, cyclopropyl, cyclobutyl or phenyl, wherein alkyl is unsubstituted or one to threefold substituted by F, wherein phenyl is unsubstituted or mono- or disubstituted by halogen, $CF_3$, $(C_1-C_4)$-alkyl, $O-CF_3$ or $O-(C_1-C_4)$-alkyl;

$R^{24}$ is H or $(C_1-C_4)$-alkyl;
or
$R^{23}$ and $R^{24}$ together with the carbon atom carrying them denote $(C_3-C_6)$-cycloalkyl;
$R^{25}$ is H, $(C_1-C_4)$-alkyl, cyclopropyl, cyclobutyl or phenyl, wherein alkyl is unsubstituted or one to threefold substituted by F, wherein phenyl is unsubstituted or mono- or disubstituted by halogen, $CF_3$, $(C_1-C_4)$-alkyl, $O-CF_3$ or $O-(C_1-C_4)$-alkyl;
$R^{26}$ is H or $(C_1-C_4)$-alkyl;
or
$R^{25}$ and $R^{26}$ together with the carbon atom carrying them denote $(C_3-C_6)$-cycloalkyl;
$R^{27}$ is
  i) H;
  ii) $(C_1-C_4)$-alkyl, which is unsubstituted or one to two-fold substituted by
    a. $CF_3$,
    b. OH,
    c. $O-(C_1-C_4)$-alkyl;
    d. pyridyl,
    e. tetrahydrofuranyl,
    f. tetrahydropyranyl,
    g. 2,2'-dimethyl-1,3-dioxolanyl,
    h. $C(O)-O-(C_1-C_4)$-alkyl;
    i. $NH-(C_1-C_4)$-alkyl;
  iii) $C(O)-(C_1-C_4)$-alkyl which is unsubstituted or mono-substituted by
    a. OH,
    b. $O-(C1-C4)$-alkyl;
  iv) C(O)-tetrahydrofuranyl;
  v) $C(O)-NH-(C_1-C_4)$-alkyl;
  vi) $C(O)-NH-(C_1-C_4)$-alkylen-$COO(C_1-C_4)$-alkyl;
in any of its stereoisomeric forms, or a mixture of stereoisomeric forms in any ratio, or a physiologically acceptable salt thereof, or a physiologically acceptable solvate of any of them.

In another group of embodiments
$R^1$ is $(C_1-C_4)$-alkyl or cyclopropyl;
$R^2$ is H, F or Cl;
$R^3$ is H or F;
$R^4$ is H or $(C_1-C_4)$-alkyl;
$R^5$ is H or methyl; and
$R^6$ is 3-azetidinyl, 3-pyrrolidinyl, 3-piperidinyl, 4-piperidinyl, 3-azepanyl, and 4-azepanyl, which is unsubstituted or mono- or disubstituted by methyl or ethyl;
or
$R^5$ and $R^6$ together with the N-atom carrying them denote
  a) a 1,4-piperazinyl of the formula

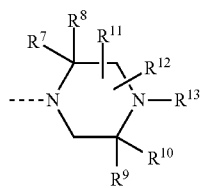

wherein
$R^7$ is H, methyl, ethyl, isopropyl, cyclopropyl, $CF_3$ or $CH_2CF_3$ or phenyl, wherein phenyl is unsubstituted or mono- or disubstituted by F, $CF_3$ or isopropyl;

$R^8$ is H, methyl or ethyl;
or
$R^7$ and $R^8$ together with the carbon atom carrying them denote $(C_3-C_5)$-cycloalkyl;
$R^9$ is H, $(C_1-C_4)$-alkyl, cyclopropyl or phenyl, wherein alkyl is unsubstituted or one to threefold substituted by F;
$R^{10}$ is H or $(C_1-C_4)$-alkyl;
or
$R^9$ and $R^{10}$ together with the carbon atom carrying them denote cyclopentyl;
$R^{11}$ is H or $(C_1-C_4)$-alkyl;
$R^{12}$ is H;
$R^{13}$ is
H, methyl,
$(CH_2)_2-CF_3$,
$(CH_2)_2-OH$,
$CH_2-CH(OH)-CH_2-OH$,
$(CH_2)_2-O-CH_3$,
$(CH_2)_3-O-CH_3$,
$CH_2$-pyrid-3-yl,
$CH_2$-tetrahydrofuran-2-yl,
$CH_2$-tetrahydropyran-4-yl,
$(CH_2)_2$-tetrahydropyran-4-yl,
$CH_2$-2,2'-dimethyl-1,3-dioxolanyl,
$CH_2-C(O)-O-CH_3$,
$(CH_2)_2-NH-CH_3$,
$C(O)CH_3$,
$C(O)-CH_2OH$,
$C(O)-CH_2OCH_3$,
$C(O)-CH_2CH_2OCH_3$,
C(O)-tetrahydrofuran-2-yl,
$C(O)-NH-C_2H_5$ or
$C(O)-NH-CH_2-COOCH_3$;
  b) a morpholinyl of the formula

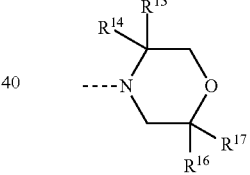

wherein
$R^{14}$, $R^{15}$, $R^{16}$ and $R^{17}$ are independently of one another H or $(C_1-C_4)$-alkyl;
  c) a ring A of the formula

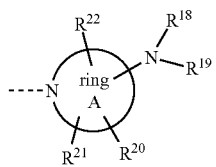

comprising one nitrogen and 4 to 5 carbon ring atoms, wherein the substituent $NR^{18}R^{19}$ is not in an adjacent position to the ring nitrogen atom
and
$R^{18}$ is H, $(C_1-C_4)$-alkyl or $C(O)-CH_2-O-CH_3$;
$R^{19}$ is H;
$R^{20}$ is H or $(C_1-C_4)$-alkyl;
$R^{21}$ is H;
$R^{22}$ is H;

d) a 1,4-diazepin of the formula

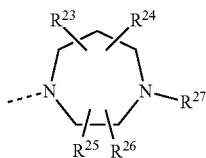

wherein
$R^{23}$ is H or $(C_1\text{-}C_4)$-alkyl;
$R^{24}$ is H;
$R^{25}$ is H;
$R^{26}$ is H;
$R^{27}$ is H, C(O)—CH$_2$—$(C_1\text{-}C_4)$-alkyl or C(O)—NH—$(C_1\text{-}C_4)$-alkyl.

In another group of embodiments
$R^1$ is methyl, ethyl or cyclopropyl.
In another group of embodiments
$R^1$ is methyl.
In another group of embodiments
$R^2$ is H, F or Cl and
$R^3$ is H, F or Cl.
In another group of embodiments
$R^2$ is H, F or Cl and
$R^3$ is H or F.
In another group of embodiments
$R^2$ is H, F or Cl and
$R^3$ is H
or
$R^2$ is H and
$R^3$ is F.
In another group of embodiments
$R^2$ is H or F and
$R^3$ is H.
In another group of embodiments
$R^2$ is H and
$R^3$ is H
or
$R^2$ is F and
$R^3$ is H.
In another group of embodiments
$R^3$ is in position 2 of the phenolic ring, which means ortho to the phenolic OH groups.
In another group of embodiments
$R^4$ is H or methyl.
In another group of embodiments
$R^4$ is H.
In another group of embodiments
$R^1$ is methyl;
$R^2$ is H, F or Cl;
$R^3$ is H or F;
$R^4$ is H or methyl.
In another group of embodiments
$R^1$ is methyl;
$R^2$ is H or F;
$R^3$ is H;
$R^4$ is H.
In another group of embodiments
$R^1$ is methyl;
$R^2$ is H;
$R^3$ is H;
$R^4$ is H.

In another group of embodiments
$R^1$ is methyl;
$R^2$ is F;
$R^3$ is H;
$R^4$ is H.
In another group of embodiments
$R^5$ is H or methyl; and
$R^6$ is 3-azetidinyl, 3-pyrrolidinyl, 3-piperidinyl, 4-piperidinyl, 3-azepanyl, and 4-azepanyl, which are unsubstituted or mono- or disubstituted by methyl or ethyl.
In another group of embodiments
$R^5$ is H and
$R^6$ is 3-piperidinyl or 4-piperidinyl, which are mono- or disubstituted by methyl and ethyl;
or
$R^5$ is methyl and
$R^6$ is 3-pyrrolidinyl.
In another group of embodiments
$R^5$ and $R^6$ together with the N-atom carrying them denote
e) a 1,4-piperazinyl of the formula

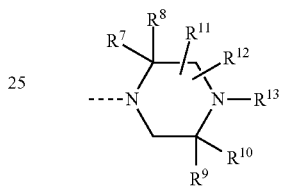

wherein
$R^7$ is H, methyl, ethyl, isopropyl, cyclopropyl, CF$_3$ or CH$_2$CF$_3$ or phenyl, wherein phenyl is unsubstituted or mono- or disubstituted by F, CF$_3$ or isopropyl;
$R^8$ is H, methyl or ethyl;
or
$R^7$ and $R^8$ together with the carbon atom carrying them denote $(C_3\text{-}C_5)$-cycloalkyl;
$R^9$ is H, $(C_1\text{-}C_4)$-alkyl, cyclopropyl or phenyl, wherein alkyl is unsubstituted or one to threefold substituted by F;
$R^{10}$ is H or $(C_1\text{-}C_4)$-alkyl;
or
$R^9$ and $R^{10}$ together with the carbon atom carrying them denote cyclopentyl;
$R^{11}$ is H or $(C_1\text{-}C_4)$-alkyl;
$R^{12}$ is H;
$R^{13}$ is
H, methyl,
(CH$_2$)$_2$—CF$_3$,
(CH$_2$)$_2$—OH,
CH$_2$—CH(OH)—CH$_2$—OH,
(CH$_2$)$_2$—O—CH$_3$
(CH$_2$)$_3$—O—CH$_3$,
CH$_2$-pyrid-3-yl,
CH$_2$-tetrahydrofuran-2-yl,
CH$_2$-tetrahydropyran-4-yl,
(CH$_2$)$_2$-tetrahydropyran-4-yl,
CH$_2$-2,2'-dimethyl-1,3-dioxolanyl,
CH$_2$—C(O)—O—CH$_3$,
(CH$_2$)$_2$—NH—CH$_3$,
C(O)CH$_3$,
C(O)—CH$_2$OH,
C(O)—CH$_2$OCH$_3$,
C(O)—CH$_2$CH$_2$OCH$_3$,
C(O)-tetrahydrofuran-2-yl,
C(O)—NH—C$_2$H$_5$ or
C(O)—NH—CH$_2$—COOCH$_3$.

In another group of embodiments
R$^5$ and R$^6$ together with the N-atom carrying them denote a 1,4-piperazinyl of the formula

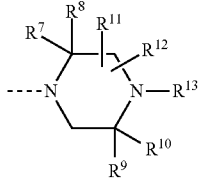

wherein
R$^7$ is H, methyl, ethyl, isopropyl, cyclopropyl, CF$_3$ or CH$_2$CF$_3$ or phenyl, wherein phenyl is unsubstituted or mono- or disubstituted by F, CF$_3$ or isopropyl;
R$^8$ is H, methyl or ethyl;
or
R$^7$ and R$^8$ together with the carbon atom carrying them denote (C$_3$-C$_5$)-cycloalkyl;
R$^9$ is H, (C$_1$-C$_4$)-alkyl, cyclopropyl or phenyl, wherein alkyl is unsubstituted or one to threefold substituted by F;
R$^{10}$ is H or (C$_1$-C$_4$)-alkyl;
or
R$^9$ and R$^{10}$ together with the carbon atom carrying them denote cyclopentyl;
R$^{11}$ is H or (C$_1$-C$_4$)-alkyl;
R$^{12}$ is H;
R$^{13}$ is
H, methyl,
(CH$_2$)$_2$—CF$_3$,
(CH$_2$)$_2$—OH,
CH$_2$—CH(OH)—CH$_2$—OH,
(CH$_2$)$_2$—O—CH$_3$,
(CH$_2$)$_3$—O—CH$_3$,
CH$_2$-pyrid-3-yl,
CH$_2$-tetrahydrofuran-2-yl,
CH$_2$-tetrahydropyran-4-yl,
(CH$_2$)$_2$-tetrahydropyran-4-yl,
CH$_2$-2,2'-dimethyl-1,3-dioxolanyl,
CH$_2$—C(O)—O—CH$_3$,
(CH$_2$)$_2$—NH—CH$_3$,
C(O)CH$_3$,
C(O)—CH$_2$OH,
C(O)—CH$_2$OCH$_3$,
C(O)—CH$_2$CH$_2$OCH$_3$,
C(O)-tetrahydrofuran-2-yl,
C(O)—NH—C$_2$H$_5$ or
C(O)—NH—CH$_2$—COOCH$_3$;
with the proviso that at least 3 radicals selected from the group consisting of R$^7$ to R$^{13}$ are H.

In another group of embodiments
R$^5$ and R$^6$ together with the N-atom carrying them denote a 1,4-piperazinyl of the formula

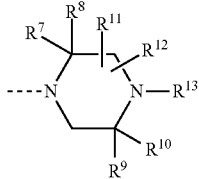

wherein
R$^7$ is H, methyl, ethyl, isopropyl, cyclopropyl, CF$_3$ or CH$_2$CF$_3$ or phenyl, wherein phenyl is unsubstituted or mono- or disubstituted by F, CF$_3$ or isopropyl;
R$^8$ is H, methyl or ethyl;
or
R$^7$ and R$^8$ together with the carbon atom carrying them denote (C$_3$-C$_5$)-cycloalkyl;
R$^9$ is H, (C$_1$-C$_4$)-alkyl, cyclopropyl or phenyl, wherein alkyl is unsubstituted or one to threefold substituted by F;
R$^{10}$ is H or (C$_1$-C$_4$)-alkyl;
or
R$^9$ and R$^{10}$ together with the carbon atom carrying them denote cyclopentyl;
R$^{11}$ is H or (C$_1$-C$_4$)-alkyl;
R$^{12}$ is H;
R$^{13}$ is
H, methyl,
(CH$_2$)$_2$—CF$_3$,
(CH$_2$)$_2$—OH,
CH$_2$—CH(OH)—CH$_2$—OH,
(CH$_2$)$_2$—O—CH$_3$,
(CH$_2$)$_3$—O—CH$_3$,
CH$_2$-pyrid-3-yl,
CH$_2$-tetrahydrofuran-2-yl,
CH$_2$-tetrahydropyran-4-yl,
(CH$_2$)$_2$-tetrahydropyran-4-yl,
CH$_2$-2,2'-dimethyl-1,3-dioxolanyl,
CH$_2$—C(O)—O—CH$_3$,
(CH$_2$)$_2$—NH—CH$_3$,
C(O)CH$_3$,
C(O)—CH$_2$OH,
C(O)—CH$_2$OCH$_3$,
C(O)—CH$_2$CH$_2$OCH$_3$,
C(O)-tetrahydrofuran-2-yl,
C(O)—NH—C$_2$H$_5$ or
C(O)—NH—CH$_2$—COOCH$_3$;
with the proviso that at least 2 radicals selected from the group consisting of R$^7$ to R$^{13}$ are H.

In another group of embodiments
R$^5$ and R$^6$ together with the N-atom carrying them denote a 1,4-piperazinyl of the formula

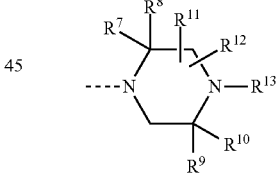

wherein
R$^7$ is H, methyl, ethyl, isopropyl, cyclopropyl, CF$_3$ or CH$_2$CF$_3$ or phenyl, wherein phenyl is unsubstituted or mono- or disubstituted by F, CF$_3$ or isopropyl;
R$^8$ is H, methyl or ethyl;
or
R$^7$ and R$^8$ together with the carbon atom carrying them denote (C$_3$-C$_5$)-cycloalkyl;
R$^9$ is H, (C$_1$-C$_4$)-alkyl, cyclopropyl or phenyl, wherein alkyl is unsubstituted or one to threefold substituted by F;
R$^{10}$ is H or (C$_1$-C$_4$)-alkyl;
R$^9$ and R$^{10}$ together with the carbon atom carrying them denote cyclopentyl;
R$^{11}$ is H or (C$_1$-C$_4$)-alkyl;
R$^{12}$ is H;
R$^{13}$ is H;
with the proviso that at least 1 radical selected from the group consisting of R$^7$ to R$^{11}$ are H.

In another group of embodiments
R$^5$ and R$^6$ together with the N-atom carrying them denote a 1,4-piperazinyl of the formula

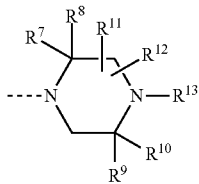

wherein
R$^7$ is H, methyl, ethyl, isopropyl, cyclopropyl, CF$_3$ or CH$_2$CF$_3$ or phenyl, wherein phenyl is unsubstituted or mono- or disubstituted by F, CF$_3$ or isopropyl;
R$^8$ is H, methyl or ethyl;
or
R$^7$ and R$^8$ together with the carbon atom carrying them denote (C$_3$-C$_5$)-cycloalkyl;
R$^9$ is H, methyl, ethyl, isopropyl, cyclopropyl, CH$_2$CF$_3$ or phenyl;
R$^{10}$ is H, methyl or ethyl;
or
R$^9$ and R$^{10}$ together with the carbon atom carrying them denote cyclopentyl;
R$^{11}$ is H or methyl;
R$^{12}$ is H;
R$^{13}$ is H.

In another group of embodiments
R$^5$ and R$^6$ together with the N-atom carrying them denote a 1,4-piperazinyl of the formula

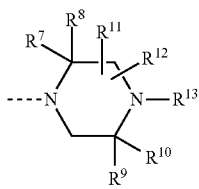

wherein
R$^7$ to R$^{10}$ and R$^{13}$ are as defined above,
R$^{11}$ is in position 3 and
R$^{12}$ is H.

In another group of embodiments
R$^5$ and R$^6$ together with the N-atom carrying them denote a 1,4-piperazinyl of the formula

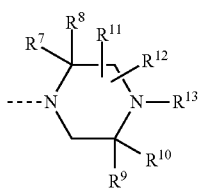

wherein
R$^7$ to R$^{10}$ and R$^{13}$ are as defined above,
R$^{11}$ is H and
R$^{12}$ is H.

In another group of embodiments
R$^5$ and R$^6$ together with the N-atom carrying them denote a 1,4-piperazinyl of the formula

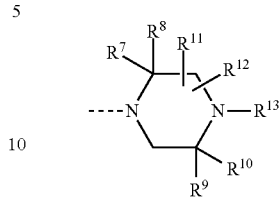

wherein
R$^7$ to R$^{10}$ are as defined above,
R$^{11}$ is H,
R$^{12}$ is H and
R$^{13}$ is H.

In another group of embodiments
R$^5$ and R$^6$ together with the N-atom carrying them denote a 1,4-piperazinyl of the formula

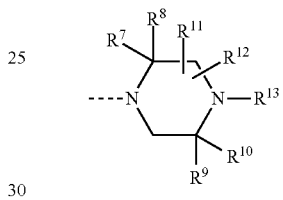

wherein
R$^7$ to R$^{12}$ are as defined above,
R$^{13}$ is
H or methyl,
(CH$_2$)$_2$—CF$_3$,
(CH$_2$)$_2$—OH,
CH$_2$—CH(OH)—CH$_2$—OH,
(CH$_2$)$_2$—O—CH$_3$,
(CH$_2$)$_3$—O—CH$_3$,
CH$_2$-pyrid-3-yl,
CH$_2$-tetrahydrofuran-2-yl,
CH$_2$-tetrahydropyran-4-yl,
(CH$_2$)$_2$-tetrahydropyran-4-yl,
CH$_2$-2,2'-dimethyl-1,3-dioxolanyl,
CH$_2$—C(O)—O—CH$_3$,
(CH$_2$)$_2$—NH—CH$_3$,
C(O)CH$_3$,
C(O)—CH$_2$OH,
C(O)—CH$_2$OCH$_3$,
C(O)—CH$_2$CH$_2$OCH$_3$,
C(O)-tetrahydrofuran-2-yl,
C(O)—NH—C$_2$H$_5$ or
C(O)—NH—CH$_2$—COOCH$_3$.

In another group of embodiments
R$^5$ and R$^6$ together with the N-atom carrying them denote a 1,4-piperazinyl of the formula

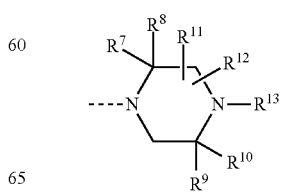

wherein
R$^7$ to R$^{10}$ are independently of one another H or methyl,
R$^{11}$ is H,
R$^{12}$ is H,
R$^{13}$ is
H, methyl,
(CH$_2$)$_2$—CF$_3$,
(CH$_2$)$_2$—OH,
CH$_2$—CH(OH)—CH$_2$—OH,
(CH$_2$)$_2$—O—CH$_3$,
(CH$_2$)$_3$—O—CH$_3$,
CH$_2$-pyrid-3-yl,
CH$_2$-tetrahydrofuran-2-yl,
CH$_2$-tetrahydropyran-4-yl,
(CH$_2$)$_2$-tetrahydropyran-4-yl,
CH$_2$-2,2'-dimethyl-1,3-dioxolanyl,
CH$_2$—C(O)—O—CH$_3$,
(CH$_2$)$_2$—NH—CH$_3$,
C(O)CH$_3$,
C(O)—CH$_2$OH,
C(O)—CH$_2$OCH$_3$,
C(O)—CH$_2$CH$_2$OCH$_3$,
C(O)-tetrahydrofuran-2-yl,
C(O)—NH—C$_2$H$_5$ or
C(O)—NH—CH$_2$—COOCH$_3$.

In another group of embodiments
R$^5$ and R$^6$ together with the N-atom carrying them denote a 1,4-piperazinyl of the formula

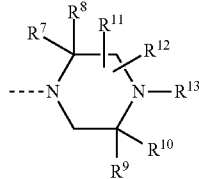

wherein
R$^7$ to R$^{10}$ are independently of one another H or methyl,
R$^{11}$ is H,
R$^{12}$ is H,
R$^{13}$ is
H, methyl,
(CH$_2$)$_2$—CF$_3$,
(CH$_2$)$_2$—OH,
CH$_2$—CH(OH)—CH$_2$—OH,
(CH$_2$)$_2$—O—CH$_3$,
(CH$_2$)$_3$—O—CH$_3$,
CH$_2$-tetrahydrofuran-2-yl,
CH$_2$-tetrahydropyran-4-yl,
(CH$_2$)$_2$-tetrahydropyran-4-yl or
CH$_2$—C(O)—O—CH$_3$.

In another group of embodiments
R$^5$ and R$^6$ together with the N-atom carrying them denote a morpholinyl of the formula

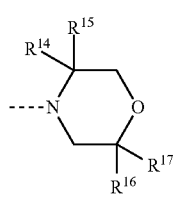

wherein
R$^{14}$, R$^{15}$, R$^{16}$ and R$^{17}$ are independently of one another H or (C$_1$-C$_4$)-alkyl;

In another group of embodiments
R$^5$ and R$^6$ together with the N-atom carrying them denote a morpholinyl of the formula

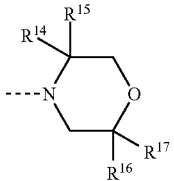

wherein
R$^{14}$ is methyl;
R$^{15}$ is methyl;
R$^{16}$ is methyl;
R$^{17}$ is methyl.

In another group of embodiments
R$^5$ and R$^6$ together with the N-atom carrying them denote a ring A of the formula

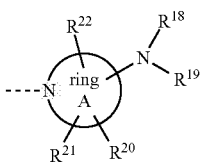

comprising one nitrogen and 4 to 5 carbon ring atoms, wherein the substituent NR$^{18}$R$^{19}$ is not in an adjacent position to the nitrogen ring atom and
R$^{18}$ is H, (C$_1$-C$_4$)-alkyl or C(O)—CH$_2$—O—CH$_3$;
R$^{19}$ is H;
R$^{20}$ is H or C$_1$-C$_4$)-alkyl;
R$^{21}$ is H;
R$^{22}$ is H.

In another group of embodiments
R$^5$ and R$^6$ together with the N-atom carrying them denote a ring A of the formula

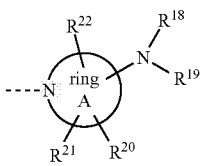

comprising one nitrogen and 4 to 5 carbon ring atoms, wherein the substituent NR$^{18}$R$^{19}$ is not in an adjacent position to the ring nitrogen atom and
R$^{18}$ is H, methyl or C(O)—CH$_2$—O—CH$_3$;
R$^{19}$ is H;
R$^{20}$ is H or methyl;
R$^{21}$ is H;
R$^{22}$ is H.

In another group of embodiments
R$^5$ and R$^6$ together with the N-atom carrying them denote a ring A of the formula

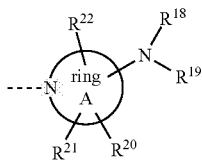

comprising one nitrogen and 4 or 5 carbon ring atoms, wherein the substituent NR$^{18}$R$^{19}$ is in position 3 and R$^{18}$ to R$^{22}$ are as defined above.

In another group of embodiments
R$^5$ and R$^6$ together with the N-atom carrying them denote a ring A of the formula

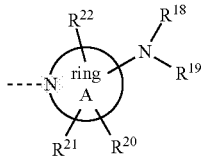

comprising one nitrogen and 4 carbon ring atoms, wherein the substituent NR$^{18}$R$^{19}$ is in position 3 and
R$^{18}$ is methyl;
R$^{19}$ is H;
R$^{20}$ is H;
R$^{21}$ is H;
R$^{22}$ is H.

In another group of embodiments
R$^5$ and R$^6$ together with the N-atom carrying them denote a ring A of the formula

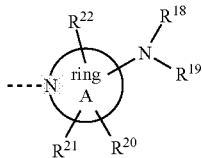

comprising one nitrogen and 5 carbon ring atoms, wherein the substituent NR$^{18}$R$^{19}$ and R$^{20}$ are in position 3 and
R$^{18}$ is H or C(O)—CH$_2$—O—CH$_3$;
R$^{19}$ is H;
R$^{20}$ is methyl;
R$^{21}$ is H;
R$^{22}$ is H.

In another group of embodiments
R$^5$ and R$^6$ together with the N-atom carrying them denote a 1,4-diazepin of the formula

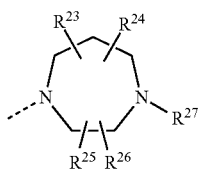

wherein
R$^{23}$ is H, (C$_1$-C$_4$)-alkyl;
R$^{24}$ is H;
R$^{25}$ is H;
R$^{26}$ is H;
R$^{27}$ is H, C(O)—CH$_2$—(C$_1$-C$_4$)-alkyl or C(O)—NH—(C$_1$-C$_4$)-alkyl.

In another group of embodiments
R$^5$ and R$^6$ together with the N-atom carrying them denote a 1,4-diazepin of the formula

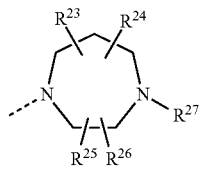

wherein
R$^{23}$ is H or methyl;
R$^{24}$ is H or methyl;
R$^{25}$ is H or methyl;
R$^{26}$ is H or methyl;
R$^{27}$ is H, C(O)—CH$_2$—OCH$_3$, or C(O)—NH—(C$_2$H$_5$).

In another group of embodiments
R$^5$ and R$^6$ together with the N-atom carrying them denote a 1,4-diazepin of the formula

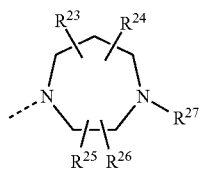

wherein
R$^{23}$ is H or methyl;
R$^{24}$ is H;
R$^{25}$ is H;
R$^{26}$ is H;
R$^{27}$ is H, C(O)—CH$_2$—OCH$_3$, or C(O)—NH—(C$_2$H$_5$).

In another group of embodiments
R$^5$ and R$^6$ together with the N-atom carrying them denote a 1,4-diazepin of the formula

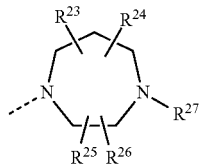

wherein
R$^{23}$ is in position 3 and
R$^{23}$ to R$^{27}$ are as defined above.

In another group of embodiments
R$^1$ is (C$_1$-C$_4$)-alkyl, CF$_3$ or cyclopropyl;
R$^2$ is H, halogen, methyl or CF$_3$;
R$^3$ is H, halogen, methyl or CF$_3$;

$R^4$ is H, $(C_1-C_4)$-alkyl or $CF_3$; and
$R^5$ and $R^6$ together with the N-atom carrying them denote a 1,4-piperazinyl of the formula

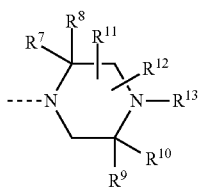

wherein
$R^7$ is H, $(C_1-C_4)$-alkyl, cyclopropyl, $CF_3$ or $CH_2CF_3$ or phenyl, wherein phenyl is unsubstituted or mono- or disubstituted by F, $CF_3$ or isopropyl;
$R^8$ is H or $(C_1-C_4)$-alkyl;
or
$R^7$ and $R^8$ together with the carbon atom carrying them denote $(C_3-C_5)$-cycloalkyl;
$R^9$ is H, $(C_1-C_4)$-alkyl, cyclopropyl or phenyl, wherein alkyl is unsubstituted or one to threefold substituted by F;
$R^{10}$ is H or $(C_1-C_4)$-alkyl;
$R^9$ and $R^{10}$ together with the carbon atom carrying them denote cyclopentyl;
$R^{11}$ is H or $(C_1-C_4)$-alkyl;
$R^{12}$ is H;
$R^{13}$ is
H, methyl,
$(CH_2)_2$—$CF_3$,
$(CH_2)_2$—OH,
$CH_2$—CH(OH)—$CH_2$—OH,
$(CH_2)_2$—O—$CH_3$,
$(CH_2)_3$—O—$CH_3$,
$CH_2$-pyrid-3-yl,
$CH_2$-tetrahydrofuran-2-yl,
$CH_2$-tetrahydropyran-4-yl,
$(CH_2)_2$-tetrahydropyran-4-yl,
$CH_2$-2,2'-dimethyl-1,3-dioxolanyl,
$CH_2$—C(O)—O—$CH_3$,
$(CH_2)_2$—NH—$CH_3$,
C(O)$CH_3$,
C(O)—$CH_2$OH,
C(O)—$CH_2$O$CH_3$,
C(O)—$CH_2$ $CH_2$O$CH_3$,
C(O)-tetrahydrofuran-2-yl,
C(O)—NH—$C_2H_5$ or
C(O)—NH—$CH_2$—COO$CH_3$.

In another group of embodiments
$R^1$ is methyl, ethyl or cyclopropyl;
$R^2$ is H, F or Cl;
$R^3$ is H or F;
$R^4$ is H or methyl;
$R^5$ is H or methyl;
$R^6$ is 3-azetidinyl, 3-pyrrolidinyl, 3-piperidinyl, 4-piperidinyl, 3-azepanyl, and 4-azepanyl, which is unsubstituted or mono- or disubstituted by methyl or ethyl; or $R^5$ and $R^6$ together with the N-atom carrying them denote a 1,4-piperazinyl of the formula

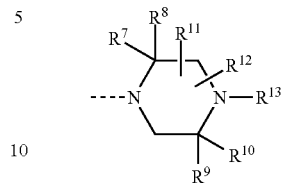

wherein
$R^7$ is H, methyl, ethyl, isopropyl, cyclopropyl, $CF_3$ or $CH_2CF_3$ or phenyl, wherein phenyl is unsubstituted or mono- or disubstituted by F, $CF_3$ or isopropyl;
$R^8$ is H, methyl or ethyl;
or
$R^7$ and $R^8$ together with the carbon atom carrying them denote $(C_3-C_5)$-cycloalkyl;
$R^9$ is H, $(C_1-C_4)$-alkyl, cyclopropyl or phenyl, wherein alkyl is unsubstituted or one to threefold substituted by F;
$R^{10}$ is H or $(C_1-C_4)$-alkyl;
$R^9$ and $R^{10}$ together with the carbon atom carrying them denote cyclopentyl;
$R^{11}$ is H or $(C_1-C_4)$-alkyl;
$R^{12}$ is H;
$R^{13}$ is
H, methyl,
$(CH_2)_2$—$CF_3$,
$(CH_2)_2$—OH,
$CH_2$—CH(OH)—$CH_2$—OH,
$(CH_2)_2$—O—$CH_3$,
$(CH_2)_3$—O—$CH_3$,
$CH_2$-pyrid-3-yl,
$CH_2$-tetrahydrofuran-2-yl,
$CH_2$-tetrahydropyran-4-yl,
$(CH_2)_2$-tetrahydropyran-4-yl,
$CH_2$-2,2'-dimethyl-1,3-dioxolanyl,
$CH_2$—C(O)—O—$CH_3$,
$(CH_2)_2$—NH—$CH_3$,
C(O)$CH_3$,
C(O)—$CH_2$OH,
C(O)—$CH_2$O$CH_3$,
C(O)—$CH_2$ $CH_2$O$CH_3$,
C(O)-tetrahydrofuran-2-yl,
C(O)—NH—$C_2H_5$ or
C(O)—NH—$CH_2$—COO$CH_3$;
or
$R^5$ and $R^6$ together with the N-atom carrying them denote a morpholinyl of the formula

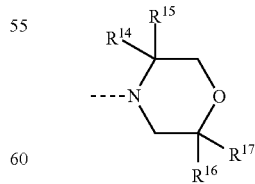

wherein
$R^{14}$ is methyl;
$R^{15}$ is methyl;
$R^{16}$ is methyl;
$R^{17}$ is methyl; or R⁵ and R⁶ together with the N-atom carrying them denote a ring A of the formula

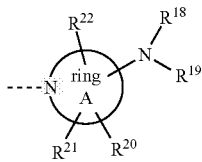

comprising one nitrogen and 4 to 5 carbon ring atoms, wherein the substituent NR¹⁸R¹⁹ is not in an adjacent position to the ring nitrogen atom and
R¹⁸ is H, methyl or C(O)—CH₂—O—CH₃;
R¹⁹ is H;
R²⁰ is H or methyl;
R²¹ is H;
R²² is H; or
R⁵ and R⁶ together with the N-atom carrying them denote a 1,4-diazepin of the formula

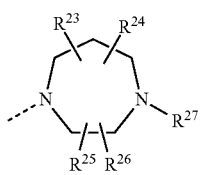

wherein
R²³ is H or methyl;
R²⁴ is H;
R²⁵ is H;
R²⁶ is H;
R²⁷ is H, C(O)—CH₂—OCH₃ or C(O)—NH—(C₂H₅).

In another group of embodiments
R¹ is methyl;
R² is H or F;
R³ is H;
R⁴ is H;
R⁵ is H;
R⁶ is 3-azetidinyl, 3-pyrrolidinyl, 3-piperidinyl, 4-piperidinyl, 3-azepanyl, and 4-azepanyl, which is unsubstituted or mono- or disubstituted by methyl or ethyl;
or
R⁵ and R⁶ together with the N-atom carrying them denote a 1,4-piperazinyl of the formula

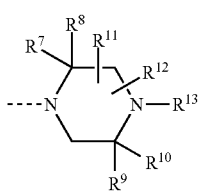

wherein
R⁷ is H, methyl, ethyl, isopropyl, cyclopropyl, CF₃ or CH₂CF₃ or phenyl, wherein phenyl is unsubstituted or mono- or disubstituted by F, CF₃ or isopropyl;

R⁸ is H, methyl or ethyl;
or
R⁷ and R⁸ together with the carbon atom carrying them denote (C₃-C₅)-cycloalkyl;
R⁹ is H, (C₁-C₄)-alkyl, cyclopropyl or phenyl, wherein alkyl is unsubstituted or one to threefold substituted by F;
R¹⁰ is H or (C₁-C₄)-alkyl;
or
R⁹ and R¹⁰ together with the carbon atom carrying them denote cyclopentyl;
R¹¹ is H or (C₁-C₄)-alkyl;
R¹² is H;
R¹³ is
H, methyl,
(CH₂)₂—CF₃,
(CH₂)₂—OH,
CH₂—CH(OH)—CH₂—OH,
(CH₂)₂—O—CH₃,
(CH₂)₃—O—CH₃,
CH₂-pyrid-3-yl,
CH₂-tetrahydrofuran-2-yl,
CH₂-tetrahydropyran-4-yl,
(CH₂)₂-tetrahydropyran-4-yl,
CH₂-2,2'-dimethyl-1,3-dioxolanyl,
CH₂—C(O)—O—CH₃,
(CH₂)₂—NH—CH₃,
C(O)CH₃,
C(O)—CH₂OH,
C(O)—CH₂OCH₃,
C(O)—CH₂CH₂OCH₃,
C(O)-tetrahydrofuran-2-yl,
C(O)—NH—C₂H₅ or
C(O)—NH—CH₂—COOCH₃;
with the proviso that at least 2 radicals selected from the group consisting of R⁷ to R¹³ are H;
or
R⁵ and R⁶ together with the N-atom carrying them denote a ring A of the formula

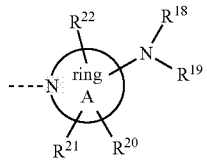

comprising one nitrogen and 4 to 5 carbon ring atoms, wherein the substituent NR¹⁸R¹⁹ is not in an adjacent position to the ring nitrogen atom and
R¹⁸ is H, methyl or C(O)—CH₂—O—CH₃;
R¹⁹ is H;
R²⁰ is H or methyl;
R²¹ is H;
R²² is H;
or
R⁵ and R⁶ together with the N-atom carrying them denote a 1,4-diazepin of the formula

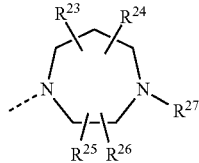

wherein
R²³ is H or methyl;
R²⁴ is H;
R²⁵ is H;
R²⁶ is H;
R²⁷ is H, C(O)—CH₂—OCH₃ or C(O)—NH—(C₂H₅).
In another group of embodiments
R¹ is (C₁-C₄)-alkyl or cyclopropyl;
R² is H, F or Cl;
R³ is H or F;
R⁴ is H or (C₁-C₄)-alkyl;
R⁵ is H or methyl; and
R⁶ is 3-azetidinyl, 3-pyrrolidinyl, 3-piperidinyl, 4-piperidinyl, 3-azepanyl, and 4-azepanyl, which is unsubstituted or mono- or disubstituted by methyl or ethyl.
or
R⁵ and R⁶ together with the N-atom carrying them denote
a 1,4-piperazinyl of the formula

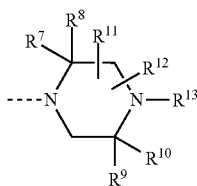

wherein
R⁷ is H, methyl, ethyl, isopropyl, cyclopropyl, CF₃ or CH₂CF₃ or phenyl, wherein phenyl is unsubstituted or mono- or disubstituted by F, CF₃ or isopropyl;
R⁸ is H, methyl or ethyl;
or
R⁷ and R⁸ together with the carbon atom carrying them denote (C₃-C₅)-cycloalkyl;
R⁹ is H, (C₁-C₄)-alkyl, cyclopropyl or phenyl, wherein alkyl is unsubstituted or one to threefold substituted by F;
R¹⁰ is H or (C₁-C₄)-alkyl; or
R⁹ and R¹⁰ together with the carbon atom carrying them denote cyclopentyl;
R¹¹ is H or (C₁-C₄)-alkyl;
R¹² is H;
R¹³ is
H, methyl,
(CH₂)₂—CF₃,
(CH₂)₂—OH,
CH₂—CH(OH)—CH₂—OH,
(CH₂)₂—O—CH₃,
(CH₂)₃—O—CH₃,
CH₂-tetrahydrofuran-2-yl,
CH₂-tetrahydropyran-4-yl,
(CH₂)₂-tetrahydropyran-4-yl or
CH₂—C(O)—O—CH₃.
In another embodiment compounds of the formula I are encompassed selected from the group consisting of
1  3-Fluoro-4-[3-methyl-4-(2-phenyl-piperazin-1-ylmethyl)-1H-pyrazolo[3,4-b]pyridin-6-yl]-phenol
2  3-Fluoro-4-{4-[2-(4-isopropyl-phenyl)-piperazin-1-ylmethyl]-3-methyl-1H-pyrazolo[3,4-b]pyridin-6-yl}-phenol
3  3-Fluoro-4-{3-methyl-4-[2-(4-trifluoromethyl-phenyl)-piperazin-1-ylmethyl]-1H-pyrazolo[3,4-b]pyridin-6-yl}-phenol
4  3-Fluoro-4-{4-[2-(4-fluoro-phenyl)-piperazin-1-ylmethyl]-3-methyl-1H-pyrazolo[3,4-b]pyridin-6-yl}-phenol
5  3-Fluoro-4-[3-methyl-4-(2-trifluoromethyl-piperazin-1-ylmethyl)-1H-pyrazolo[3,4-b]pyridin-6-yl]-phenol
6  3-Fluoro-4-{4-[2-(3-fluoro-phenyl)-piperazin-1-ylmethyl]-3-methyl-1H-pyrazolo[3,4-b]pyridin-6-yl}-phenol
7  4-[4-(6,9-Diaza-spiro[4.5]dec-6-ylmethyl)-3-methyl-1H-pyrazolo[3,4-b]pyridin-6-yl]-3-fluoro-phenol
8  3-Fluoro-4-{3-methyl-4-[2-(3-trifluoromethyl-phenyl)-piperazin-1-ylmethyl]-1H-pyrazolo[3,4-b]pyridin-6-yl}-phenol
9  4-{4-[2-(3,5-Difluoro-phenyl)-piperazin-1-ylmethyl]-3-methyl-1H-pyrazolo[3,4-b]pyridin-6-yl}-3-fluoro-phenol
10  3-Fluoro-4-{4-[2-(2-fluoro-phenyl)-piperazin-1-ylmethyl]-3-methyl-1H-pyrazolo[3,4-b]pyridin-6-yl}-phenol
11  3-Fluoro-4-[3-methyl-4-(2,2,5-trimethyl-piperazin-1-ylmethyl)-1H-pyrazolo[3,4-b]pyridin-6-yl]-phenol
12  3-Fluoro-4-[3-methyl-4-(2-methyl-2-phenyl-piperazin-1-ylmethyl)-1H-pyrazolo[3,4-b]pyridin-6-yl]-phenol
13  3-Fluoro-4-(3-methyl-4-piperazin-1-ylmethyl-1H-pyrazolo[3,4-b]pyridin-6-yl)-phenol
14  4-[4-(4,7-Diaza-spiro[2.5]oct-4-ylmethyl)-3-methyl-1H-pyrazolo[3,4-b]pyridin-6-yl]-3-fluoro-phenol
15  4-[4-(8,8-Dimethyl-6,9-diaza-spiro[4.5]dec-6-ylmethyl)-3-methyl-1H-pyrazolo[3,4-b]pyridin-6-yl]-3-fluoro-phenol
16  3-Fluoro-4-[3-methyl-4-(8-methyl-6,9-diaza-spiro[4.5]dec-6-ylmethyl)-1H-pyrazolo[3,4-b]pyridin-6-yl]-phenol
17  4-[4-(5,8-Diaza-spiro[3.5]non-5-ylmethyl)-3-methyl-1H-pyrazolo[3,4-b]pyridin-6-yl]-3-fluoro-phenol
18  4-[4-(2,2-Diethyl-piperazin-1-ylmethyl)-3-methyl-1H-pyrazolo[3,4-b]pyridin-6-yl]-3-fluoro-phenol
19  3-Fluoro-4-[3-methyl-4-(5-methyl-2-trifluoromethyl-piperazin-1-ylmethyl)-1H-pyrazolo[3,4-b]pyridin-6-yl]-phenol
20  3-Fluoro-4-[4-(5-isopropyl-2,2-dimethyl-piperazin-1-ylmethyl)-3-methyl-1H-pyrazolo[3,4-b]pyridin-6-yl]-phenol
21  4-[4-(5-Ethyl-2,2,5-trimethyl-piperazin-1-ylmethyl)-3-methyl-1H-pyrazolo[3,4-b]pyridin-6-yl]-3-fluoro-phenol
22  4-[4-(5,5-Diethyl-2,2-dimethyl-piperazin-1-ylmethyl)-3-methyl-1H-pyrazolo[3,4-b]pyridin-6-yl]-3-fluoro-phenol
23  4-[4-(5-Cyclopropyl-2,2,5-trimethyl-piperazin-1-ylmethyl)-3-methyl-1H-pyrazolo[3,4-b]pyridin-6-yl]-3-fluoro-phenol
24  4-[4-(3-Amino-3-methyl-piperidin-1-ylmethyl)-3-methyl-1H-pyrazolo[3,4-b]pyridin-6-yl]-3-fluoro-phenol
25  3-Fluoro-4-[3-methyl-4-(3-methyl-[1,4]diazepan-1-ylmethyl)-1H-pyrazolo[3,4-b]pyridin-6-yl]-phenol
26  4-[4-(2,2-Dimethyl-piperazin-1-ylmethyl)-3-methyl-1H-pyrazolo[3,4-b]pyridin-6-yl]-3-fluoro-phenol
27  4-[4-((2S,5R)-2,5-Dimethyl-piperazin-1-ylmethyl)-3-methyl-1H-pyrazolo[3,4-b]pyridin-6-yl]-3-fluoro-phenol
28  3-Fluoro-4-[3-methyl-4-(2,2,5,5-tetramethyl-piperazin-1-ylmethyl)-1H-pyrazolo[3,4-b]pyridin-6-yl]-phenol
29  3-Fluoro-4-[3-methyl-4-(trans-2-methyl-5-phenyl-piperazin-1-ylmethyl)-1H-pyrazolo[3,4-b]pyridin-6-yl]-phenol
30  4-[4-((2S,5R)-5-Ethyl-2-methyl-piperazin-1-ylmethyl)-3-methyl-1H-pyrazolo[3,4-b]pyridin-6-yl]-3-fluoro-phenol
31  4-[4-(2-Ethyl-2,5,5-trimethyl-piperazin-1-ylmethyl)-3-methyl-1H-pyrazolo[3,4-b]pyridin-6-yl]-3-fluoro-phenol
32  4-[4-(2,2-Diethyl-5,5-dimethyl-piperazin-1-ylmethyl)-3-methyl-1H-pyrazolo[3,4-b]pyridin-6-yl]-3-fluoro-phenol
33  4-[3-Methyl-4-(8-methyl-6,9-diaza-spiro[4.5]dec-9-ylmethyl)-1H-pyrazolo[3,4-b]pyridin-6-yl]-phenol
34  4-[4-(2-Cyclopropyl-2,5,5-trimethyl-piperazin-1-ylmethyl)-3-methyl-1H-pyrazolo[3,4-b]pyridin-6-yl]-3-fluoro-phenol 35  3-Fluoro-4-[3-methyl-4-(8-methyl-6,9-diaza-spiro[4.5]dec-9-ylmethyl)-1H-pyrazolo[3,4-b]pyridin-6-yl]-phenol
36  4-[4-(8,8-Dimethyl-6,9-diaza-spiro[4.5]dec-9-ylmethyl)-3-methyl-1H-pyrazolo[3,4-b]pyridin-6-yl]-3-fluoro-phenol
37  3-Fluoro-4-[4-(2-isopropyl-5,5-dimethyl-piperazin-1-ylmethyl)-3-methyl-1H-pyrazolo[3,4-b]pyridin-6-yl]-phenol
38  3-Fluoro-4-[3-methyl-4-(2,5,5-trimethyl-piperazin-1-ylmethyl)-1H-pyrazolo[3,4-b]pyridin-6-yl]-phenol
39  4-[4-(2-Ethyl-5,5-dimethyl-piperazin-1-ylmethyl)-3-methyl-1H-pyrazolo[3,4-b]pyridin-6-yl]-3-fluoro-phenol
40  4-[4-(4,7-Diaza-spiro[2.5]oct-4-ylmethyl)-3-methyl-1H-pyrazolo[3,4-b]pyridin-6-yl]-phenol
41  4-[3-Methyl-4-(2-phenyl-piperazin-1-ylmethyl)-1H-pyrazolo[3,4-b]pyridin-6-yl]-phenol
42  4-{4-[2-(4-Fluoro-phenyl)-piperazin-1-ylmethyl]-3-methyl-1H-pyrazolo[3,4-b]pyridin-6-yl}-phenol
43  4-[3-Methyl-4-(trans-5-methyl-2-phenyl-piperazin-1-ylmethyl)-1H-pyrazolo[3,4-b]pyridin-6-yl]-phenol
44  4-{3-Methyl-4-[2-(4-trifluoromethyl-phenyl)-piperazin-1-ylmethyl]-1H-pyrazolo[3,4-b]pyridin-6-yl}-phenol
45  4-{4-[2-(4-Isopropyl-phenyl)-piperazin-1-ylmethyl]-3-methyl-1H-pyrazolo[3,4-b]pyridin-6-yl}-phenol
46  4-{4-[(3-Ethyl-piperidin-3-ylamino)-methyl]-3-methyl-1H-pyrazolo[3,4-b]pyridin-6-yl}-phenol
47  4-[4-(6,9-Diaza-spiro[4.5]dec-6-ylmethyl)-3-methyl-1H-pyrazolo[3,4-b]pyridin-6-yl]-phenol
48  4-[3-Methyl-4-(2,2,5-trimethyl-piperazin-1-ylmethyl)-1H-pyrazolo[3,4-b]pyridin-6-yl]-phenol
49  4-[3-Methyl-4-(2,2,5,5-tetramethyl-piperazin-1-ylmethyl)-1H-pyrazolo[3,4-b]pyridin-6-yl]-phenol
50  4-[4-(2-Ethyl-2,5,5-trimethyl-piperazin-1-ylmethyl)-3-methyl-1H-pyrazolo[3,4-b]pyridin-6-yl]-phenol
51  4-[4-(2,2-Diethyl-5,5-dimethyl-piperazin-1-ylmethyl)-3-methyl-1H-pyrazolo[3,4-b]pyridin-6-yl]-phenol
52  4-[3-Methyl-4-(2,5,5-trimethyl-piperazin-1-ylmethyl)-1H-pyrazolo[3,4-b]pyridin-6-yl]-phenol
53  4-[4-(2-Ethyl-5,5-dimethyl-piperazin-1-ylmethyl)-3-methyl-1H-pyrazolo[3,4-b]pyridin-6-yl]-phenol
54  4-[4-((2S,5R)-2,5-Dimethyl-piperazin-1-ylmethyl)-3-methyl-1H-pyrazolo[3,4-b]pyridin-6-yl]-phenol
55  4-[4-(3,3-Dimethyl-piperazin-1-ylmethyl)-3-methyl-1H-pyrazolo[3,4-b]pyridin-6-yl]-3-fluoro-phenol
56  3-Fluoro-4-[3-methyl-4-(2,2,5,5-tetramethyl-morpholin-4-ylmethyl)-1H-pyrazolo[3,4-b]pyridin-6-yl]-phenol
57  4-[4-(5-Ethyl-2,2,5-trimethyl-piperazin-1-ylmethyl)-3-methyl-1H-pyrazolo[3,4-b]pyridin-6-yl]-phenol
58  4-[4-(5,5-Diethyl-2,2-dimethyl-piperazin-1-ylmethyl)-3-methyl-1H-pyrazolo[3,4-b]pyridin-6-yl]-2-fluoro-phenol
59  3-Chloro-4-[4-(5,5-diethyl-2,2-dimethyl-piperazin-1-ylmethyl)-3-methyl-1H-pyrazolo[3,4-b]pyridin-6-yl]-phenol
60  4-{4-[(3,3-Dimethyl-piperidin-4-ylamino)-methyl]-3-methyl-1H-pyrazolo[3,4-b]pyridin-6-yl}-phenol
61  4-[3-Methyl-4-(2,2,5-trimethyl-4-pyridin-3-ylmethyl-piperazin-1-ylmethyl)-1H-pyrazolo[3,4-b]pyridin-6-yl]-phenol
62  4-{3-Methyl-4-[2,2,5-trimethyl-4-(tetrahydro-furan-2-ylmethyl)-piperazin-1-ylmethyl]-1H-pyrazolo[3,4-b]pyridin-6-yl}-phenol
63  4-{4-[4-(2-Methoxy-ethyl)-2,2,5-trimethyl-piperazin-1-ylmethyl]-3-methyl-1H-pyrazolo[3,4-b]pyridin-6-yl}-phenol
64  4-{4-[4-(3-Methoxy-propyl)-2,2,5-trimethyl-piperazin-1-ylmethyl]-3-methyl-1H-pyrazolo[3,4-b]pyridin-6-yl}-phenol
65  3-Fluoro-4-{3-methyl-4-[2,2,5,5-tetramethyl-4-(3,3,3-trifluoro-propyl)-piperazin-1-ylmethyl]-1H-pyrazolo[3,4-b]pyridin-6-yl}-phenol
66  3-Fluoro-4-[3-methyl-4-(2,2,4,5,5-pentamethyl-piperazin-1-ylmethyl)-1H-pyrazolo[3,4-b]pyridin-6-yl]-phenol
67  3-Fluoro-4-{4-[4-(3-methoxy-propyl)-2,2,5,5-tetramethyl-piperazin-1-ylmethyl]-3-methyl-1H-pyrazolo[3,4-b]pyridin-6-yl}-phenol
68  3-Fluoro-4-(3-methyl-4-{2,2,5,5-tetramethyl-4-[2-(tetrahydro-pyran-4-yl)-ethyl]-piperazin-1-ylmethyl}-1H-pyrazolo[3,4-b]pyridin-6-yl)-phenol
69  4-{4-[4-((S)-2,2-Dimethyl-[1,3]dioxolan-4-ylmethyl)-2,2,5,5-tetramethyl-piperazin-1-ylmethyl]-3-methyl-1H-pyrazolo[3,4-b]pyridin-6-yl}-3-fluoro-phenol
70  3-Fluoro-4-{3-methyl-4-[2,2,5,5-tetramethyl-4-(tetrahydro-pyran-4-ylmethyl)-piperazin-1-ylmethyl]-1H-pyrazolo[3,4-b]pyridin-6-yl}-phenol
71  3-Fluoro-4-[3-methyl-4-(6,8,8-trimethyl-6,9-diaza-spiro[4.5]dec-9-ylmethyl)-1H-pyrazolo[3,4-b]pyridin-6-yl]-phenol
72  3-Fluoro-4-{4-[4-(2-hydroxy-ethyl)-2,2,5,5-tetramethyl-piperazin-1-ylmethyl]-3-methyl-1H-pyrazolo[3,4-b]pyridin-6-yl}-phenol
73  (S)-3-{4-[6-(2-Fluoro-4-hydroxy-phenyl)-3-methyl-1H-pyrazolo[3,4-b]pyridin-4-ylmethyl]-2,2,5,5-tetramethyl-piperazin-1-yl}-propane-1,2-diol
74  {4-[6-(2-Fluoro-4-hydroxy-phenyl)-3-methyl-1H-pyrazolo[3,4-b]pyridin-4-ylmethyl]-2,2,5,5-tetramethyl-piperazin-1-yl}acetic acid methyl ester
75  1-{4-[6-(2-Fluoro-4-hydroxy-phenyl)-3-methyl-1H-pyrazolo[3,4-b]pyridin-4-ylmethyl]-2,2,5,5-tetramethyl-piperazin-1-yl}-2-methoxy-ethanone
76  1-{4-[6-(2-Fluoro-4-hydroxy-phenyl)-3-methyl-1H-pyrazolo[3,4-b]pyridin-4-ylmethyl]-2,2,5,5-tetramethyl-piperazin-1-yl}-3-methoxy-propan-1-one
77  {4-[6-(2-Fluoro-4-hydroxy-phenyl)-3-methyl-1H-pyrazolo[3,4-b]pyridin-4-ylmethyl]-2,2,5,5-tetramethyl-piperazin-1-yl}-(tetrahydro-furan-3-yl)-methanone
78  1-{4-[6-(2-Fluoro-4-hydroxy-phenyl)-3-methyl-1H-pyrazolo[3,4-b]pyridin-4-ylmethyl]-2,2,5,5-tetramethyl-piperazin-1-yl}ethanone
79  1-{4-[6-(2-Fluoro-4-hydroxy-phenyl)-3-methyl-1H-pyrazolo[3,4-b]pyridin-4-ylmethyl]-2-methyl-[1,4]diazepan-1-yl}-2-methoxy-ethanone
80  1-{4-[6-(2-Fluoro-4-hydroxy-phenyl)-3-methyl-1H-pyrazolo[3,4-b]pyridin-4-ylmethyl]-2,2,5,5-tetramethyl-piperazin-1-yl}-2-hydroxy-ethanone
81  N-{1-[6-(2-Fluoro-4-hydroxy-phenyl)-3-methyl-1H-pyrazolo[3,4-b]pyridin-4-ylmethyl]-3-methyl-piperidin-3-yl}-2-methoxy-acetamide
82  1-{9-[6-(4-Hydroxy-phenyl)-3-methyl-1H-pyrazolo[3,4-b]pyridin-4-ylmethyl]-8-methyl-6,9-diaza-spiro[4.5]dec-6-yl}-2-methoxy-ethanone
83  4-{3-Methyl-4-[2,2,5,5-tetramethyl-4-(3,3,3-trifluoro-propyl)-piperazin-1-ylmethyl]-1H-pyrazolo[3,4-b]pyridin-6-yl}-phenol
84  4-[3-Methyl-4-(2,2,4,5,5-pentamethyl-piperazin-1-ylmethyl)-1H-pyrazolo[3,4-b]pyridin-6-yl]-phenol
85  4-{3-Methyl-4-[2,2,5,5-tetramethyl-4-(2-methylamino-ethyl)-piperazin-1-ylmethyl]-1H-pyrazolo[3,4-b]pyridin-6-yl}-phenol
86  {4-[6-(4-Hydroxy-phenyl)-3-methyl-1H-pyrazolo[3,4-b]pyridin-4-ylmethyl]-2,2,5,5-tetramethyl-piperazin-1-yl}-acetic acid methyl ester 87 ({4-[6-(4-Hydroxy-phenyl)-3-methyl-1H-pyrazolo[3,4-b]pyridin-4-ylmethyl]-2,2,5,5-tetramethyl-piperazine-1-carbonyl}-amino)-acetic acid methyl ester
88 4-[6-(4-Hydroxy-phenyl)-3-methyl-1H-pyrazolo[3,4-b]pyridin-4-ylmethyl]-2,2,5,5-tetramethyl-piperazine-1-carboxylic acid ethylamide
89 4-[6-(2-Fluoro-4-hydroxy-phenyl)-3-methyl-1H-pyrazolo[3,4-b]pyridin-4-ylmethyl]-2-methyl-[1,4]diazepane-1-carboxylic acid ethylamide
90 1-{4-[6-(2-Fluoro-4-hydroxy-phenyl)-3-methyl-1H-pyrazolo[3,4-b]pyridin-4-ylmethyl]-2,2,5,5-tetramethyl-piperazin-1-yl}-2-methoxy-ethanone
91 4-{3-Methyl-4-[(R)-3-(2,2,2-trifluoro-ethyl)-piperazin-1-ylmethyl]-1H-pyrazolo[3,4-b]pyridin-6-yl}-phenol
92 4-{3-Methyl-4-[(R)-2-(2,2,2-trifluoro-ethyl)-piperazin-1-ylmethyl]-1H-pyrazolo[3,4-b]pyridin-6-yl}-phenol
93 4-[3-Methyl-4-(3-methylamino-pyrrolidin-1-ylmethyl)-1H-pyrazolo[3,4-b]pyridin-6-yl]-phenol
94 4-{3-Methyl-4-[(methyl-pyrrolidin-3-yl-amino)-methyl]-1H-pyrazolo[3,4-b]pyridin-6-yl}-phenol
95 4-(3-Cyclopropyl-4-piperazin-1-ylmethyl-1H-pyrazolo[3,4-b]pyridin-6-yl)-phenol
96 4-(3-Ethyl-4-piperazin-1-ylmethyl-1H-pyrazolo[3,4-b]pyridin-6-yl)-phenol
97 3-Fluoro-4-[3-methyl-4-(1-piperazin-1-yl-ethyl)-1H-pyrazolo[3,4-b]pyridin-6-yl]-phenol
98 4-{4-[14(3S,5R)-3,5-Dimethyl-piperazin-1-yl)-ethyl]-3-methyl-1H-pyrazolo[3,4-b]pyridin-6-yl}-3-fluoro-phenol
99 3-Fluoro-4-[3-methyl-4-((2S,5R)-2-methyl-5-phenyl-piperazin-1-ylmethyl)-1H-pyrazolo[3,4-b]pyridin-6-yl]-phenol
100 3-Fluoro-4-[3-methyl-4-((2R,5S)-2-methyl-5-phenyl-piperazin-1-ylmethyl)-1H-pyrazolo[3,4-b]pyridin-6-yl]-phenol
101 3-Fluoro-4-{4-[(S)-2-(4-isopropyl-phenyl)-piperazin-1-ylmethyl]-3-methyl-1H-pyrazolo[3,4-b]pyridin-6-yl}-phenol
102 3-Fluoro-4-{4-[(R)-2-(4-isopropyl-phenyl)-piperazin-1-ylmethyl]-3-methyl-1H-pyrazolo[3,4-b]pyridin-6-yl}-phenol
103 3-Fluoro-4-{3-methyl-4-[(S)-2-(4-trifluoromethyl-phenyl)-piperazin-1-ylmethyl]-1H-pyrazolo[3,4-b]pyridin-6-yl}-phenol
104 3-Fluoro-4-{3-methyl-4-[(R)-2-(4-trifluoromethyl-phenyl)-piperazin-1-ylmethyl]-1H-pyrazolo[3,4-b]pyridin-6-yl}-phenol
105 3-Fluoro-4-{4-[(S)-2-(4-fluoro-phenyl)-piperazin-1-ylmethyl]-3-methyl-1H-pyrazolo[3,4-b]pyridin-6-yl}-phenol
106 3-Fluoro-4-{4-[(R)-2-(4-fluoro-phenyl)-piperazin-1-ylmethyl]-3-methyl-1H-pyrazolo[3,4-b]pyridin-6-yl}-phenol
107 3-Fluoro-4-[3-methyl-4-((R)-2-trifluoromethyl-piperazin-1-ylmethyl)-1H-pyrazolo[3,4-b]pyridin-6-yl]-phenol
108 3-Fluoro-4-[3-methyl-4-((S)-2-trifluoromethyl-piperazin-1-ylmethyl)-1H-pyrazolo[3,4-b]pyridin-6-yl]-phenol
109 3-Fluoro-4-[3-methyl-4-((S)-2-phenyl-piperazin-1-ylmethyl)-1H-pyrazolo[3,4-b]pyridin-6-yl]-phenol
110 3-Fluoro-4-[3-methyl-4-((R)-2-phenyl-piperazin-1-ylmethyl)-1H-pyrazolo[3,4-b]pyridin-6-yl]-phenol
111 4-[3-Methyl-4-((2S,5R)-5-methyl-2-phenyl-piperazin-1-ylmethyl)-1H-pyrazolo[3,4-b]pyridin-6-yl]-phenol
112 4-[3-Methyl-4-((2R,5S)-5-methyl-2-phenyl-piperazin-1-ylmethyl)-1H-pyrazolo[3,4-b]pyridin-6-yl]-phenol
113 4-{3-Methyl-4-[(S)-2-(4-trifluoromethyl-phenyl)-piperazin-1-ylmethyl]-1H-pyrazolo[3,4-b]pyridin-6-yl}-phenol
114 4-{3-Methyl-4-[(R)-2-(4-trifluoromethyl-phenyl)-piperazin-1-ylmethyl]-1H-pyrazolo[3,4-b]pyridin-6-yl}-phenol
115 3-Fluoro-4-[3-methyl-4-((S)-2,2,5-trimethyl-piperazin-1-ylmethyl)-1H-pyrazolo[3,4-b]pyridin-6-yl]-phenol
116 3-Fluoro-4-[3-methyl-4-((R)-2,2,5-trimethyl-piperazin-1-ylmethyl)-1H-pyrazolo[3,4-b]pyridin-6-yl]-phenol
117 3-Fluoro-4-[3-methyl-4-((S)-2-methyl-2-phenyl-piperazin-1-ylmethyl)-1H-pyrazolo[3,4-b]pyridin-6-yl]-phenol
118 3-Fluoro-4-[3-methyl-4-((R)-2-methyl-2-phenyl-piperazin-1-ylmethyl)-1H-pyrazolo[3,4-b]pyridin-6-yl]-phenol
119 3-Fluoro-4-{4-[(S)-2-(3-fluoro-phenyl)-piperazin-1-ylmethyl]-3-methyl-1H-pyrazolo[3,4-b]pyridin-6-yl}-phenol
120 3-Fluoro-4-{4-[(R)-2-(3-fluoro-phenyl)-piperazin-1-ylmethyl]-3-methyl-1H-pyrazolo[3,4-b]pyridin-6-yl}-phenol
121 4-[4-((R)-2-Ethyl-2,5,5-trimethyl-piperazin-1-ylmethyl)-3-methyl-1H-pyrazolo[3,4-b]pyridin-6-yl]-3-fluoro-phenol
122 4-[4-((S)-2-Ethyl-2,5,5-trimethyl-piperazin-1-ylmethyl)-3-methyl-1H-pyrazolo[3,4-b]pyridin-6-yl]-3-fluoro-phenol
123 3-Fluoro-4-[3-methyl-4-((R)-2,5,5-trimethyl-piperazin-1-ylmethyl)-1H-pyrazolo[3,4-b]pyridin-6-yl]-phenol
124 3-Fluoro-4-[3-methyl-4-((S)-2,5,5-trimethyl-piperazin-1-ylmethyl)-1H-pyrazolo[3,4-b]pyridin-6-yl]-phenol
125 4-[4-((S)-2-Cyclopropyl-2,5,5-trimethyl-piperazin-1-ylmethyl)-3-methyl-1H-pyrazolo[3,4-b]pyridin-6-yl]-3-fluoro-phenol
126 4-[4-((R)-2-Cyclopropyl-2,5,5-trimethyl-piperazin-1-ylmethyl)-3-methyl-1H-pyrazolo[3,4-b]pyridin-6-yl]-3-fluoro-phenol
127 3-Fluoro-4-[3-methyl-4-((S)-8-methyl-6,9-diaza-spiro[4.5]dec-6-ylmethyl)-1H-pyrazolo[3,4-b]pyridin-6-yl]-phenol
128 3-Fluoro-4-[3-methyl-4-((R)-8-methyl-6,9-diaza-spiro[4.5]dec-6-ylmethyl)-1H-pyrazolo[3,4-b]pyridin-6-yl]-phenol
129 3-Fluoro-4-[4-((S)-5-isopropyl-2,2-dimethyl-piperazin-1-ylmethyl)-3-methyl-1H-pyrazolo[3,4-b]pyridin-6-yl]-phenol
130 3-Fluoro-4-[4-((R)-5-isopropyl-2,2-dimethyl-piperazin-1-ylmethyl)-3-methyl-1H-pyrazolo[3,4-b]pyridin-6-yl]-phenol
131 4-[3-Methyl-4-((S)-2,2,5-trimethyl-piperazin-1-ylmethyl)-1H-pyrazolo[3,4-b]pyridin-6-yl]-phenol
132 4-[3-Methyl-4-((R)-2,2,5-trimethyl-piperazin-1-ylmethyl)-1H-pyrazolo[3,4-b]pyridin-6-yl]-phenol
133 3-Fluoro-4-[4-((S)-2-isopropyl-5,5-dimethyl-piperazin-1-ylmethyl)-3-methyl-1H-pyrazolo[3,4-b]pyridin-6-yl]-phenol
134 3-Fluoro-4-[4-((R)-2-isopropyl-5,5-dimethyl-piperazin-1-ylmethyl)-3-methyl-1H-pyrazolo[3,4-b]pyridin-6-yl]-phenol
135 4-[4-((R)-5-Ethyl-2,2,5-trimethyl-piperazin-1-ylmethyl)-3-methyl-1H-pyrazolo[3,4-b]pyridin-6-yl]-3-fluoro-phenol
136 4-[4-((S)-5-Ethyl-2,2,5-trimethyl-piperazin-1-ylmethyl)-3-methyl-1H-pyrazolo[3,4-b]pyridin-6-yl]-3-fluoro-phenol 137 3-Fluoro-4-[3-methyl-4-((S)-8-methyl-6,9-diaza-spiro[4.5]dec-9-ylmethyl)-1H-pyrazolo[3,4-b]pyridin-6-yl]-phenol
138 3-Fluoro-4-[3-methyl-4-((R)-8-methyl-6,9-diaza-spiro[4.5]dec-9-ylmethyl)-1H-pyrazolo[3,4-b]pyridin-6-yl]-phenol
139 4-[3-Methyl-4-((S)-2,5,5-trimethyl-piperazin-1-ylmethyl)-1H-pyrazolo[3,4-b]pyridin-6-yl]-phenol
140 4-[3-Methyl-4-((R)-2,5,5-tri methyl-piperazin-1-ylmethyl)-1H-pyrazolo[3,4-b]pyridin-6-yl]-phenol
141 4-[4-((R)-2-Ethyl-2,5,5-trimethyl-piperazin-1-ylmethyl)-3-methyl-1H-pyrazolo[3,4-b]pyridin-6-yl]-phenol
142 4-[4-((S)-2-Ethyl-2,5,5-trimethyl-piperazin-1-ylmethyl)-3-methyl-1H-pyrazolo[3,4-b]pyridin-6-yl]-phenol
143 4-[4-((S)-2-Ethyl-5,5-dimethyl-piperazin-1-ylmethyl)-3-methyl-1H-pyrazolo[3,4-b]pyridin-6-yl]-3-fluoro-phenol
144 4-[4-((R)-2-Ethyl-5,5-dimethyl-piperazin-1-ylmethyl)-3-methyl-1H-pyrazolo[3,4-b]pyridin-6-yl]-3-fluoro-phenol
145 4-[4-((S)-2-Ethyl-5,5-dimethyl-piperazin-1-ylmethyl)-3-methyl-1H-pyrazolo[3,4-b]pyridin-6-yl]-phenol
146 4-[4-((R)-2-Ethyl-5,5-dimethyl-piperazin-1-ylmethyl)-3-methyl-1H-pyrazolo[3,4-b]pyridin-6-yl]-phenol
147 4-[4-((S)-3-Amino-3-methyl-piperidin-1-ylmethyl)-3-methyl-1H-pyrazolo[3,4-b]pyridin-6-yl]-3-fluoro-phenol
148 4-[4-((R)-3-Amino-3-methyl-piperidin-1-ylmethyl)-3-methyl-1H-pyrazolo[3,4-b]pyridin-6-yl]-3-fluoro-phenol
149 4-[4-((R)-5-Cyclopropyl-2,2,5-trimethyl-piperazin-1-ylmethyl)-3-methyl-1H-pyrazolo[3,4-b]pyridin-6-yl]-3-fluoro-phenol
150 4-[4-((S)-5-Cyclopropyl-2,2,5-trimethyl-piperazin-1-ylmethyl)-3-methyl-1H-pyrazolo[3,4-b]pyridin-6-yl]-3-fluoro-phenol
151 3-Fluoro-4-[3-methyl-4-((2R,5S)-5-methyl-2-trifluoromethyl-piperazin-1-ylmethyl)-1H-pyrazolo[3,4-b]pyridin-6-yl]-phenol
152 3-Fluoro-4-[3-methyl-4-((2R,5R)-5-methyl-2-trifluoromethyl-piperazin-1-ylmethyl)-1H-pyrazolo[3,4-b]pyridin-6-yl]-phenol
153 3-Fluoro-4-[3-methyl-4-((2S,5R)-5-methyl-2-trifluoromethyl-piperazin-1-ylmethyl)-1H-pyrazolo[3,4-b]pyridin-6-yl]-phenol
154 3-Fluoro-4-[3-methyl-4-((2S,5S)-5-methyl-2-trifluoromethyl-piperazin-1-ylmethyl)-1H-pyrazolo[3,4-b]pyridin-6-yl]-phenol.

In another embodiment compounds of the formula I are encompassed selected from the group consisting of
4 3-Fluoro-4-{4-[2-(4-fluoro-phenyl)-piperazin-1-ylmethyl]-3-methyl-1H-pyrazolo[3,4-b]pyridin-6-yl}-phenol
5 3-Fluoro-4-[3-methyl-4-(2-trifluoromethyl-piperazin-1-ylmethyl)-1H-pyrazolo[3,4-b]pyridin-6-yl]-phenol
6 3-Fluoro-4-{4-[2-(3-fluoro-phenyl)-piperazin-1-ylmethyl]-3-methyl-1H-pyrazolo[3,4-b]pyridin-6-yl}-phenol
7 4-[4-(6,9-Diaza-spiro[4.5]dec-6-ylmethyl)-3-methyl-1H-pyrazolo[3,4-b]pyridin-6-yl]-3-fluoro-phenol
11 3-Fluoro-4-[3-methyl-4-(2,2,5-trimethyl-piperazin-1-ylmethyl)-1H-pyrazolo[3,4-b]pyridin-6-yl]-phenol
13 3-Fluoro-4-(3-methyl-4-piperazin-1-ylmethyl-1H-pyrazolo[3,4-b]pyridin-6-yl)-phenol
14 4-[4-(4,7-Diaza-spiro[2.5]oct-4-ylmethyl)-3-methyl-1H-pyrazolo[3,4-b]pyridin-6-yl]-3-fluoro-phenol
15 4-[4-(8,8-Dimethyl-6,9-diaza-spiro[4.5]dec-6-ylmethyl)-3-methyl-1H-pyrazolo[3,4-b]pyridin-6-yl]-3-fluoro-phenol
16 3-Fluoro-4-[3-methyl-4-(8-methyl-6,9-diaza-spiro[4.5]dec-6-ylmethyl)-1H-pyrazolo[3,4-b]pyridin-6-yl]-phenol
17 4-[4-(5,8-Diaza-spiro[3.5]non-5-ylmethyl)-3-methyl-1H-pyrazolo[3,4-b]pyridin-6-yl]-3-fluoro-phenol
18 4-[4-(2,2-Diethyl-piperazin-1-ylmethyl)-3-methyl-1H-pyrazolo[3,4-b]pyridin-6-yl]-3-fluoro-phenol
19 3-Fluoro-4-[3-methyl-4-(5-methyl-2-trifluoromethyl-piperazin-1-ylmethyl)-1H-pyrazolo[3,4-b]pyridin-6-yl]-phenol
20 3-Fluoro-4-[4-(5-isopropyl-2,2-dimethyl-piperazin-1-ylmethyl)-3-methyl-1H-pyrazolo[3,4-b]pyridin-6-yl]-phenol
21 4-[4-(5-Ethyl-2,2,5-trimethyl-piperazin-1-ylmethyl)-3-methyl-1H-pyrazolo[3,4-b]pyridin-6-yl]-3-fluoro-phenol
22 4-[4-(5,5-Diethyl-2,2-dimethyl-piperazin-1-ylmethyl)-3-methyl-1H-pyrazolo[3,4-b]pyridin-6-yl]-3-fluoro-phenol
23 4-[4-(5-Cyclopropyl-2,2,5-trimethyl-piperazin-1-ylmethyl)-3-methyl-1H-pyrazolo[3,4-b]pyridin-6-yl]-3-fluoro-phenol
26 4-[4-(2,2-Dimethyl-piperazin-1-ylmethyl)-3-methyl-1H-pyrazolo[3,4-b]pyridin-6-yl]-3-fluoro-phenol
27 4-[4-((2S,5R)-2,5-Dimethyl-piperazin-1-ylmethyl)-3-methyl-1H-pyrazolo[3,4-b]pyridin-6-yl]-3-fluoro-phenol
28 3-Fluoro-4-[3-methyl-4-(2,2,5,5-tetramethyl-piperazin-1-ylmethyl)-1H-pyrazolo[3,4-b]pyridin-6-yl]-phenol
30 4-[4-((2S,5R)-5-Ethyl-2-methyl-piperazin-1-ylmethyl)-3-methyl-1H-pyrazolo[3,4-b]pyridin-6-yl]-3-fluoro-phenol
31 4-[4-(2-Ethyl-2,5,5-trimethyl-piperazin-1-ylmethyl)-3-methyl-1H-pyrazolo[3,4-b]pyridin-6-yl]-3-fluoro-phenol
32 4-[4-(2,2-Diethyl-5,5-dimethyl-piperazin-1-ylmethyl)-3-methyl-1H-pyrazolo[3,4-b]pyridin-6-yl]-3-fluoro-phenol
34 4-[4-(2-Cyclopropyl-2,5,5-trimethyl-piperazin-1-ylmethyl)-3-methyl-1H-pyrazolo[3,4-b]pyridin-6-yl]-3-fluoro-phenol
37 3-Fluoro-4-[4-(2-isopropyl-5,5-dimethyl-piperazin-1-ylmethyl)-3-methyl-1H-pyrazolo[3,4-b]pyridin-6-yl]-phenol
38 3-Fluoro-4-[3-methyl-4-(2,5,5-trimethyl-piperazin-1-ylmethyl)-1H-pyrazolo[3,4-b]pyridin-6-yl]-phenol
39 4-[4-(2-Ethyl-5,5-dimethyl-piperazin-1-ylmethyl)-3-methyl-1H-pyrazolo[3,4-b]pyridin-6-yl]-3-fluoro-phenol
40 4-[4-(4,7-Diaza-spiro[2.5]oct-4-ylmethyl)-3-methyl-1H-pyrazolo[3,4-b]pyridin-6-yl]-phenol
42 4-{4-[2-(4-Fluoro-phenyl)-piperazin-1-ylmethyl]-3-methyl-1H-pyrazolo[3,4-b]pyridin-6-yl}-phenol
47 4-[4-(6,9-Diaza-spiro[4.5]dec-6-ylmethyl)-3-methyl-1H-pyrazolo[3,4-b]pyridin-6-yl]-phenol
48 4-[3-Methyl-4-(2,2,5-trimethyl-piperazin-1-ylmethyl)-1H-pyrazolo[3,4-b]pyridin-6-yl]-phenol
49 4-[3-Methyl-4-(2,2,5,5-tetramethyl-piperazin-1-ylmethyl)-1H-pyrazolo[3,4-b]pyridin-6-yl]-phenol
50 4-[4-(2-Ethyl-2,5,5-trimethyl-piperazin-1-ylmethyl)-3-methyl-1H-pyrazolo[3,4-b]pyridin-6-yl]-phenol
51 4-[4-(2,2-Diethyl-5,5-dimethyl-piperazin-1-ylmethyl)-3-methyl-1H-pyrazolo[3,4-b]pyridin-6-yl]-phenol
52 4-[3-Methyl-4-(2,5,5-trimethyl-piperazin-1-ylmethyl)-1H-pyrazolo[3,4-b]pyridin-6-yl]-phenol
53 4-[4-(2-Ethyl-5,5-dimethyl-piperazin-1-ylmethyl)-3-methyl-1H-pyrazolo[3,4-b]pyridin-6-yl]-phenol
54 4-[4-((2S,5R)-2,5-Dimethyl-piperazin-1-ylmethyl)-3-methyl-1H-pyrazolo[3,4-b]pyridin-6-yl]-phenol
55 4-[4-(3,3-Dimethyl-piperazin-1-ylmethyl)-3-methyl-1H-pyrazolo[3,4-b]pyridin-6-yl]-3-fluoro-phenol
57 4-[4-(5-Ethyl-2,2,5-trimethyl-piperazin-1-ylmethyl)-3-methyl-1H-pyrazolo[3,4-b]pyridin-6-yl]-phenol
58 4-[4-(5,5-Diethyl-2,2-dimethyl-piperazin-1-ylmethyl)-3-methyl-1H-pyrazolo[3,4-b]pyridin-6-yl]-2-fluoro-phenol 59 3-Chloro-4-[4-(5,5-diethyl-2,2-dimethyl-piperazin-1-ylmethyl)-3-methyl-1H-pyrazolo[3,4-b]pyridin-6-yl]-phenol 62 4-{3-M ethyl-4-[2,2,5-trimethyl-4-(tetrahydro-furan-2-ylmethyl)-piperazin-1-ylmethyl]-1H-pyrazolo[3,4-b]pyridin-6-yl}-phenol 63 4-{4-[4-(2-Methoxy-ethyl)-2,2,5-trimethyl-piperazin-1-yl methyl]-3-methyl-1H-pyrazolo[3,4-b]pyridin-6-yl}-phenol 64 4-{4-[4-(3-Methoxy-propyl)-2,2,5-trimethyl-piperazin-1-ylmethyl]-3-methyl-1H-pyrazolo[3,4-b]pyridin-6-yl}-phenol 65 3-Fluoro-4-{3-methyl-4-[2,2,5,5-tetramethyl-4-(3,3,3-trifluoro-propyl)-piperazin-1-ylmethyl]-1H-pyrazolo[3,4-b]pyridin-6-yl}-phenol 66 3-Fluoro-4-[3-methyl-4-(2,2,4,5,5-pentamethyl-piperazin-1-ylmethyl)-1H-pyrazolo[3,4-b]pyridin-6-yl]-phenol 67 3-Fluoro-4-{4-[4-(3-methoxy-propyl)-2,2,5,5-tetramethyl-piperazin-1-ylmethyl]-3-methyl-1H-pyrazolo[3,4-b]pyridin-6-yl}-phenol 68 3-Fluoro-4-(3-methyl-4-{2,2,5,5-tetramethyl-4-[2-(tetrahydro-pyran-4-yl)-ethyl]-piperazin-1-ylmethyl}-1H-pyrazolo[3,4-b]pyridin-6-yl)-phenol 69 4-{4-[4-((S)-2,2-Dimethyl-[1,3]dioxolan-4-ylmethyl)-2,2,5,5-tetramethyl-piperazin-1-ylmethyl]-3-methyl-1H-pyrazolo[3,4-b]pyridin-6-yl}-3-fluoro-phenol 70 3-Fluoro-4-{3-methyl-4-[2,2,5,5-tetramethyl-4-(tetrahydro-pyran-4-ylmethyl)-piperazin-1-ylmethyl]-1H-pyrazolo[3,4-b]pyridin-6-yl}-phenol 72 3-Fluoro-4-{4-[4-(2-hydroxy-ethyl)-2,2,5,5-tetramethyl-piperazin-1-ylmethyl]-3-methyl-1H-pyrazolo[3,4-b]pyridin-6-yl}-phenol 73 (S)-3-{4-[6-(2-Fluoro-4-hydroxy-phenyl)-3-methyl-1-pyrazolo[3,4-b]pyridin-4-yl methyl]-2,2,5,5-tetramethyl-piperazin-1-yl}-propane-1,2-diol 83 4-{3-M ethyl-4-[2,2,5,5-tetramethyl-4-(3,3,3-trifluoropropyl)-piperazin-1-ylmethyl]-1H-pyrazolo[3,4-b]pyridin-6-yl}-phenol 84 4-[3-Methyl-4-(2,2,4,5,5-pentamethyl-piperazin-1-ylmethyl)-1H-pyrazolo[3,4-b]pyridin-6-yl]-phenol {86 4-[6-(4-Hydroxy-phenyl)-3-methyl-1H-pyrazolo[3,4-b]pyridin-4-ylmethyl]-2,2,5,5-tetramethyl-piperazin-1-yl}-acetic acid methyl ester 91 4-{3-Methyl-4-[(R)-3-(2,2,2-trifluoro-ethyl)-piperazin-1-ylmethyl]-1H-pyrazolo[3,4-b]pyridin-6-yl}-phenol 92 4-{3-Methyl-4-[(R)-2-(2,2,2-trifluoro-ethyl)-piperazin-1-ylmethyl]-1H-pyrazolo[3,4-b]pyridin-6-yl}-phenol 97 3-Fluoro-4-[3-methyl-4-(1-piperazin-1-yl-ethyl)-1H-pyrazolo[3,4-b]pyridin-6-yl]-phenol 98 4-{4-[14(3S,5R)-3,5-Dimethyl-piperazin-1-yl)-ethyl]-3-methyl-1H-pyrazolo[3,4-b]pyridin-6-yl}-3-fluoro-phenol 105 3-Fluoro-4-{4-[(S)-2-(4-fluoro-phenyl)-piperazin-1-ylmethyl]-3-methyl-1H-pyrazolo[3,4-b]pyridin-6-yl}-phenol 106 3-Fluoro-4-{4-[(R)-2-(4-fluoro-phenyl)-piperazin-1-ylmethyl]-3-methyl-1H-pyrazolo[3,4-b]pyridin-6-yl}-phenol 107 3-Fluoro-4-[3-methyl-4-((R)-2-trifluoromethyl-piperazin-1-ylmethyl)-1H-pyrazolo[3,4-b]pyridin-6-yl]-phenol 108 3-Fluoro-4-[3-methyl-4-((S)-2-trifluoromethyl-piperazin-1-ylmethyl)-1H-pyrazolo[3,4-b]pyridin-6-yl]-phenol 115 3-Fluoro-4-[3-methyl-4-((S)-2,2,5-trimethyl-piperazin-1-ylmethyl)-1H-pyrazolo[3,4-b]pyridin-6-yl]-phenol 116 3-Fluoro-4-[3-methyl-4-((R)-2,2,5-trimethyl-piperazin-1-ylmethyl)-1H-pyrazolo[3,4-b]pyridin-6-yl]-phenol 121 4-[4-((R)-2-Ethyl-2,5,5-trimethyl-piperazin-1-ylmethyl)-3-methyl-1H-pyrazolo[3,4-b]pyridin-6-yl]-3-fluoro-phenol 122 4-[4-((S)-2-Ethyl-2,5,5-trimethyl-piperazin-1-ylmethyl)-3-methyl-1H-pyrazolo[3,4-b]pyridin-6-yl]-3-fluoro-phenol 123 3-Fluoro-4-[3-methyl-4-((R)-2,5,5-trimethyl-piperazin-1-ylmethyl)-1H-pyrazolo[3,4-b]pyridin-6-yl]-phenol 124 3-Fluoro-4-[3-methyl-4-((S)-2,5,5-trimethyl-piperazin-1-ylmethyl)-1H-pyrazolo[3,4-b]pyridin-6-yl]-phenol 125 4-[4-((S)-2-Cyclopropyl-2,5,5-trimethyl-piperazin-1-ylmethyl)-3-methyl-1H-pyrazolo[3,4-b]pyridin-6-yl]-3-fluoro-phenol 126 4-[4-((R)-2-Cyclopropyl-2,5,5-trimethyl-piperazin-1-ylmethyl)-3-methyl-1H-pyrazolo[3,4-b]pyridin-6-yl]-3-fluoro-phenol 129 3-Fluoro-4-[4-((S)-5-isopropyl-2,2-dimethyl-piperazin-1-ylmethyl)-3-methyl-1H-pyrazolo[3,4-b]pyridin-6-yl]-phenol 130 3-Fluoro-4-[4-((R)-5-isopropyl-2,2-dimethyl-piperazin-1-ylmethyl)-3-methyl-1H-pyrazolo[3,4-b]pyridin-6-yl]-phenol 131 4-[3-Methyl-4-((S)-2,2,5-trimethyl-piperazin-1-ylmethyl)-1H-pyrazolo[3,4-b]pyridin-6-yl]-phenol 132 4-[3-Methyl-44(R)-2,2,5-trimethyl-piperazin-1-ylmethyl)-1H-pyrazolo[3,4-b]pyridin-6-yl]-phenol 133 3-Fluoro-4-[4-((S)-2-isopropyl-5,5-dimethyl-piperazin-1-ylmethyl)-3-methyl-1H-pyrazolo[3,4-b]pyridin-6-yl]-phenol 134 3-Fluoro-4-[4-((R)-2-isopropyl-5,5-dimethyl-piperazin-1-ylmethyl)-3-methyl-1H-pyrazolo[3,4-b]pyridin-6-yl]-phenol 135 4-[4-((R)-5-Ethyl-2,2,5-trimethyl-piperazin-1-ylmethyl)-3-methyl-1H-pyrazolo[3,4-b]pyridin-6-yl]-3-fluoro-phenol 136 4-[4-((S)-5-Ethyl-2,2,5-trimethyl-piperazin-1-ylmethyl)-3-methyl-1H-pyrazolo[3,4-b]pyridin-6-yl]-3-fluoro-phenol 139 4-[3-Methyl-4-((S)-2,5,5-trimethyl-piperazin-1-ylmethyl)-1H-pyrazolo[3,4-b]pyridin-6-yl]-phenol 140 4-[3-Methyl-4-((R)-2,5,5-trimethyl-piperazin-1-ylmethyl)-1H-pyrazolo[3,4-b]pyridin-6-yl]-phenol 141 4-[4-((R)-2-Ethyl-2,5,5-trimethyl-piperazin-1-ylmethyl)-3-methyl-1H-pyrazolo[3,4-b]pyridin-6-yl]-phenol 142 4-[4-((S)-2-Ethyl-2,5,5-trimethyl-piperazin-1-ylmethyl)-3-methyl-1H-pyrazolo[3,4-b]pyridin-6-yl]-phenol 143 4-[4-((S)-2-Ethyl-5,5-dimethyl-piperazin-1-ylmethyl)-3-methyl-1H-pyrazolo[3,4-b]pyridin-6-yl]-3-fluoro-phenol 144 4-[4-((R)-2-Ethyl-5,5-dimethyl-piperazin-1-ylmethyl)-3-methyl-1H-pyrazolo[3,4-b]pyridin-6-yl]-3-fluoro-phenol 145 4-[4-((S)-2-Ethyl-5,5-dimethyl-piperazin-1-ylmethyl)-3-methyl-1H-pyrazolo[3,4-b]pyridin-6-yl]-phenol 146 4-[4-((R)-2-Ethyl-5,5-dimethyl-piperazin-1-ylmethyl)-3-methyl-1H-pyrazolo[3,4-b]pyridin-6-yl]-phenol 149 4-[4-((R)-5-Cyclopropyl-2,2,5-trimethyl-piperazin-1-yl methyl)-3-methyl-1H-pyrazolo[3,4-b]pyridin-6-yl]-3-fluoro-phenol 150 4-[4-((S)-5-Cyclopropyl-2,2,5-trimethyl-piperazin-1-ylmethyl)-3-methyl-1H-pyrazolo[3,4-b]pyridin-6-yl]-3-fluoro-phenol 151 3-Fluoro-4-[3-methyl-4-((2R,5S)-5-methyl-2-trifluoromethyl-piperazin-1-ylmethyl)-1H-pyrazolo[3,4-b]pyridin-6-yl]-phenol 152 3-Fluoro-4-[3-methyl-4-((2R,5R)-5-methyl-2-trifluoromethyl-piperazin-1-ylmethyl)-1H-pyrazolo[3,4-b]pyridin-6-yl]-phenol
153 3-Fluoro-4-[3-methyl-4-((2S,5R)-5-methyl-2-trifluoromethyl-piperazin-1-ylmethyl)-1H-pyrazolo[3,4-b]pyridin-6-yl]-phenol
154 3-Fluoro-4-[3-methyl-4-((2S,5S)-5-methyl-2-trifluoromethyl-piperazin-1-ylmethyl)-1H-pyrazolo[3,4-b]pyridin-6-yl]-phenol In another embodiment compounds of the formula I are encompassed selected from the group consisting of 11 3-Fluoro-4-[3-methyl-4-(2,2,5-tri methyl-piperazin-1-ylmethyl)-1H-pyrazolo[3,4-b]pyridin-6-yl]-phenol
20 3-Fluoro-4-[4-(5-isopropyl-2,2-dimethyl-piperazin-1-ylmethyl)-3-methyl-1H-pyrazolo[3,4-b]pyridin-6-yl]-phenol
21 4-[4-(5-Ethyl-2,2,5-trimethyl-piperazin-1-ylmethyl)-3-methyl-1H-pyrazolo[3,4-b]pyridin-6-yl]-3-fluoro-phenol
27 4-[4-((2S,5R)-2,5-Dimethyl-piperazin-1-ylmethyl)-3-methyl-1H-pyrazolo[3,4-b]pyridin-6-yl]-3-fluoro-phenol
28 3-Fluoro-4-[3-methyl-4-(2,2,5,5-tetramethyl-piperazin-1-ylmethyl)-1H-pyrazolo[3,4-b]pyridin-6-yl]-phenol
30 4-[4-((2S,5R)-5-Ethyl-2-methyl-piperazin-1-ylmethyl)-3-methyl-1H-pyrazolo[3,4-b]pyridin-6-yl]-3-fluoro-phenol
31 4-[4-(2-Ethyl-2,5,5-trimethyl-piperazin-1-ylmethyl)-3-methyl-1H-pyrazolo[3,4-b]pyridin-6-yl]-3-fluoro-phenol
37 3-Fluoro-4-[4-(2-isopropyl-5,5-dimethyl-piperazin-1-ylmethyl)-3-methyl-1H-pyrazolo[3,4-b]pyridin-6-yl]-phenol
38 3-Fluoro-4-[3-methyl-4-(2,5,5-trimethyl-piperazin-1-ylmethyl)-1H-pyrazolo[3,4-b]pyridin-6-yl]-phenol
39 4-[4-(2-Ethyl-5,5-dimethyl-piperazin-1-ylmethyl)-3-methyl-1H-pyrazolo[3,4-b]pyridin-6-yl]-3-fluoro-phenol
48 4-[3-Methyl-4-(2,2,5-trimethyl-piperazin-1-ylmethyl)-1H-pyrazolo[3,4-b]pyridin-6-yl]-phenol
49 4-[3-Methyl-4-(2,2,5,5-tetramethyl-piperazin-1-ylmethyl)-1H-pyrazolo[3,4-b]pyridin-6-yl]-phenol
50 4-[4-(2-Ethyl-2,5,5-trimethyl-piperazin-1-ylmethyl)-3-methyl-1H-pyrazolo[3,4-b]pyridin-6-yl]-phenol
52 4-[3-Methyl-4-(2,5,5-trimethyl-piperazin-1-ylmethyl)-1H-pyrazolo[3,4-b]pyridin-6-yl]-phenol
53 4-[4-(2-Ethyl-5,5-dimethyl-piperazin-1-ylmethyl)-3-methyl-1H-pyrazolo[3,4-b]pyridin-6-yl]-phenol
54 4-[4-((2S,5R)-2,5-Dimethyl-piperazin-1-ylmethyl)-3-methyl-1H-pyrazolo[3,4-b]pyridin-6-yl]-phenol
57 4-[4-(5-Ethyl-2,2,5-trimethyl-piperazin-1-ylmethyl)-3-methyl-1H-pyrazolo[3,4-b]pyridin-6-yl]-phenol
62 4-{3-Methyl-4-[2,2,5-trimethyl-4-(tetrahydro-furan-2-ylmethyl)-piperazin-1-ylmethyl]-1H-pyrazolo[3,4-b]pyridin-6-yl}-phenol
63 4-{4-[4-(2-Methoxy-ethyl)-2,2,5-trimethyl-piperazin-1-ylmethyl]-3-methyl-1H-pyrazolo[3,4-b]pyridin-6-yl}-phenol
64 4-{4-[4-(3-Methoxy-propyl)-2,2,5-trimethyl-piperazin-1-ylmethyl]-3-methyl-1H-pyrazolo[3,4-b]pyridin-6-yl}-phenol
65 3-Fluoro-4-{3-methyl-4-[2,2,5,5-tetramethyl-4-(3,3,3-trifluoro-propyl)-piperazin-1-ylmethyl]-1H-pyrazolo[3,4-b]pyridin-6-yl}-phenol
66 3-Fluoro-4-[3-methyl-4-(2,2,4,5,5-pentamethyl-piperazin-1-ylmethyl)-1H-pyrazolo[3,4-b]pyridin-6-yl]-phenol
67 3-Fluoro-4-{4-[4-(3-methoxy-propyl)-2,2,5,5-tetramethyl-piperazin-1-ylmethyl]-3-methyl-1H-pyrazolo[3,4-b]pyridin-6-yl}-phenol
68 3-Fluoro-4-(3-methyl-4-{2,2,5,5-tetramethyl-4-[2-(tetrahydro-pyran-4-yl)-ethyl]-piperazin-1-ylmethyl}-1H-pyrazolo[3,4-b]pyridin-6-yl)-phenol
70 3-Fluoro-4-{3-methyl-4-[2,2,5,5-tetramethyl-4-(tetrahydro-pyran-4-ylmethyl)-piperazin-1-ylmethyl]-1H-pyrazolo[3,4-b]pyridin-6-yl}-phenol
72 3-Fluoro-4-{4-[4-(2-hydroxy-ethyl)-2,2,5,5-tetramethyl-piperazin-1-ylmethyl]-3-methyl-1H-pyrazolo[3,4-b]pyridin-6-yl}-phenol
73 (S)-3-{4-[6-(2-Fluoro-4-hydroxy-phenyl)-3-methyl-1-pyrazolo[3,4-b]pyridin-4-ylmethyl]-2,2,5,5-tetramethyl-piperazin-1-yl}-propane-1,2-diol
83 4-{3-Methyl-4-[2,2,5,5-tetramethyl-4-(3,3,3-trifluoropropyl)-piperazin-1-ylmethyl]-1H-pyrazolo[3,4-b]pyridin-6-yl}-phenol
84 4-[3-Methyl-4-(2,2,4,5,5-pentamethyl-piperazin-1-ylmethyl)-1H-pyrazolo[3,4-b]pyridin-6-yl]-phenol
91 4-{3-Methyl-4-[(R)-3-(2,2,2-trifluoro-ethyl)-piperazin-1-ylmethyl]-1H-pyrazolo[3,4-b]pyridin-6-yl}-phenol
92 4-{3-Methyl-4-[(R)-2-(2,2,2-trifluoro-ethyl)-piperazin-1-ylmethyl]-1H-pyrazolo[3,4-b]pyridin-6-yl}-phenol
97 3-Fluoro-4-[3-methyl-4-(1-piperazin-1-yl-ethyl)-1H-pyrazolo[3,4-b]pyridin-6-yl]-phenol
115 3-Fluoro-4-[3-methyl-4-((S)-2,2,5-trimethyl-piperazin-1-ylmethyl)-1H-pyrazolo[3,4-b]pyridin-6-yl]-phenol
116 3-Fluoro-4-[3-methyl-4-((R)-2,2,5-trimethyl-piperazin-1-ylmethyl)-1H-pyrazolo[3,4-b]pyridin-6-yl]-phenol
121 4-[4-((R)-2-Ethyl-2,5,5-trimethyl-piperazin-1-ylmethyl)-3-methyl-1H-pyrazolo[3,4-b]pyridin-6-yl]-3-fluoro-phenol
122 4-[4-((S)-2-Ethyl-2,5,5-trimethyl-piperazin-1-ylmethyl)-3-methyl-1H-pyrazolo[3,4-b]pyridin-6-yl]-3-fluoro-phenol
123 3-Fluoro-4-[3-methyl-4-((R)-2,5,5-trimethyl-piperazin-1-ylmethyl)-1H-pyrazolo[3,4-b]pyridin-6-yl]-phenol
124 3-Fluoro-4-[3-methyl-4-((S)-2,5,5-trimethyl-piperazin-1-ylmethyl)-1H-pyrazolo[3,4-b]pyridin-6-yl]-phenol
129 3-Fluoro-4-[4-((S)-5-isopropyl-2,2-dimethyl-piperazin-1-ylmethyl)-3-methyl-1H-pyrazolo[3,4-b]pyridin-6-yl]-phenol
130 3-Fluoro-4-[4-((R)-5-isopropyl-2,2-dimethyl-piperazin-1-ylmethyl)-3-methyl-1H-pyrazolo[3,4-b]pyridin-6-yl]-phenol
131 4-[3-Methyl-4-((S)-2,2,5-trimethyl-piperazin-1-ylmethyl)-1H-pyrazolo[3,4-b]pyridin-6-yl]-phenol
132 4-[3-Methyl-4-((R)-2,2,5-trimethyl-piperazin-1-ylmethyl)-1H-pyrazolo[3,4-b]pyridin-6-yl]-phenol
133 3-Fluoro-4-[4-((S)-2-isopropyl-5,5-dimethyl-piperazin-1-ylmethyl)-3-methyl-1H-pyrazolo[3,4-b]pyridin-6-yl]-phenol
134 3-Fluoro-4-[4-((R)-2-isopropyl-5,5-dimethyl-piperazin-1-ylmethyl)-3-methyl-1H-pyrazolo[3,4-b]pyridin-6-yl]-phenol
135 4-[4-((R)-5-Ethyl-2,2,5-trimethyl-piperazin-1-ylmethyl)-3-methyl-1H-pyrazolo[3,4-b]pyridin-6-yl]-3-fluoro-phenol
136 4-[4-((S)-5-Ethyl-2,2,5-trimethyl-piperazin-1-ylmethyl)-3-methyl-1H-pyrazolo[3,4-b]pyridin-6-yl]-3-fluoro-phenol
139 4-[3-Methyl-4-((S)-2,5,5-trimethyl-piperazin-1-ylmethyl)-1H-pyrazolo[3,4-b]pyridin-6-yl]-phenol
140 4-[3-Methyl-4-((R)-2,5,5-trimethyl-piperazin-1-ylmethyl)-1H-pyrazolo[3,4-b]pyridin-6-yl]-phenol
141 4-[4-((R)-2-Ethyl-2,5,5-trimethyl-piperazin-1-ylmethyl)-3-methyl-1H-pyrazolo[3,4-b]pyridin-6-yl]-phenol
142 4-[4-((S)-2-Ethyl-2,5,5-trimethyl-piperazin-1-ylmethyl)-3-methyl-1H-pyrazolo[3,4-b]pyridin-6-yl]-phenol 143 4-[4-((S)-2-Ethyl-5,5-dimethyl-piperazin-1-ylmethyl)-3-methyl-1H-pyrazolo[3,4-b]pyridin-6-yl]-3-fluoro-phenol 144 4-[4-((R)-2-Ethyl-5,5-dimethyl-piperazin-1-ylmethyl)-3-methyl-1H-pyrazolo[3,4-b]pyridin-6-yl]-3-fluoro-phenol 145 4-[4-((S)-2-Ethyl-5,5-dimethyl-piperazin-1-ylmethyl)-3-methyl-1H-pyrazolo[3,4-b]pyridin-6-yl]-phenol 146 4-[4-((R)-2-Ethyl-5,5-dimethyl-piperazin-1-ylmethyl)-3-methyl-1H-pyrazolo[3,4-b]pyridin-6-yl]-phenol.

Structural elements such as groups, substituents, hetero ring members, numbers or other features, for example alkyl groups, groups like $R^1$, $R^2$, $R^3$ etc., which can occur several times in the compounds of the formula I, can all independently of one another have any of the indicated meanings and can in each case be identical to or different from one another. For example, the alkyl groups in a dialkylamino group can be identical or different.

As used here, the terms "including" and "comprising" are used in their open, non-limiting sense. As used herein, the terms "$(C_1-C_8)$" or "$(C_5-C_8)$" and so forth, refer to moieties having 1 to 8 or 5 to 8 carbon atoms, respectively. Within terms like "$(C_0-C_6)$-alkyl" or "$(C_0-C_6)$-alkylen" "$C_0$-alkyl" or "$(C_0)$-alkylen" refer to a bond, or in case of an unsubstituted "$(C_0)$-alkyl" it refers to a hydrogen.

The term "alkyl", as used herein, refers to saturated, monovalent hydrocarbon radicals. The term "alkenyl", as used herein, refers to monovalent hydrocarbon radicals, which contain at least one carbon-carbon double bond, wherein each double bond can have E- or Z-configuration. The term "alkinyl", as used herein, refers to monovalent hydrocarbon radicals, which contain at least one carbon-carbon triple bond. The alkyl, alkenyl and alkynyl groups can be linear, i.e. straight-chain, or branched. This also applies when they are part of other groups, for example alkyloxy groups (=alkoxy groups, O-alkylgroups), alkyloxycarbonyl groups or alkyl-substituted amino groups, or when they are substituted. Depending on the respective definition, the number of carbon atoms in an alkyl group can be 1, 2, 3, 4, 5, 6, 7 or 8, or 1, 2, 3, 4, 5 or 6, or 1, 2, 3 or 4, or 1, 2 or 3. Examples of alkyl are methyl, ethyl, propyl including n-propyl and isopropyl, butyl including n-butyl, sec-butyl, isobutyl and tert-butyl, pentyl including n-pentyl, 1-methylbutyl, isopentyl, neopentyl and tert-pentyl, hexyl including n-hexyl, 3,3-dimethylbutyl and isohexyl, heptyl and octyl. Double bonds and triple bonds in alkenyl groups and alkynyl groups can be present in any positions. In one embodiment of the invention, alkenyl groups contain one double bond and alkynyl groups contain one triple bond. In one embodiment of the invention, an alkenyl group or alkynyl group contains at least three carbon atoms and is bonded to the remainder of the molecule via a carbon atom which is not part of a double bond or triple bond. Examples of alkenyl and alkynyl are ethenyl, prop-1-enyl, prop-2-enyl (=allyl), but-2-enyl, 2-methylprop-2-enyl, 3-methylbut-2-enyl, hex-3-enyl, hex-4-enyl, prop-2-ynyl (=propargyl), but-2-ynyl, but-3-ynyl, hex-4-ynyl or hex-5-ynyl. Substituted alkyl groups, alkenyl groups and alkynyl groups can be substituted in any positions, provided that the respective compound is sufficiently stable and is suitable for the desired purpose such as use as a drug substance. The prerequisite that a specific group and a compound of the formula I are sufficiently stable and suitable for the desired purpose such as use as a drug substance, applies in general with respect to the definitions of all groups in the compounds of the formula I.

Independently of one another and independently of any other substituents, alkyl groups, divalent alkyl groups, alkenyl groups, alkynyl groups, cycloalkyl groups and heterocloalkyl groups are optionally substituted by one or more fluorine substituents which can be located in any positions, i.e., the said groups can be unsubstituted by fluorine substituents or substituted by fluorine substituents, for example by 1, 2, 3, 4, 5, 6, 7, 8, 9, 10, 11, 12 or 13, or by 1, 2, 3, 4, 5, 6, 7, 8 or 9, or by 1, 2, 3, 4, 5, 6 or 7, or by 1, 2, 3, 4 or 5, or by 1, 2 or 3, or by 1 or 2, fluorine substituents. Examples of fluorine-substituted said groups are trifluoromethyl, 2-fluoroethyl, 2,2,2-trifluoroethyl, pentafluoroethyl, 3,3,3-trifluoropropyl, 2,2,3,3,3-pentafluoropropyl, 4,4,4-trifluorobutyl, heptafluoroisopropyl, —CHF—, —CF$_2$—, —CF$_2$—CH$_2$—, —CH$_2$—CF$_2$—, —CF$_2$—CF$_2$—, —CF(CH$_3$)—, —C(CF$_3$)$_2$—, —C(CH$_3$)$_2$—CF$_2$—, —CF$_2$—C(CH$_3$)$_2$—, 1-fluoro-cyclopropyl, 2,2-difluorocyclopropyl, 3,3-difluorocyclobutyl, 1-fluorocyclohexyl, 4,4-difluorocyclohexyl, 3,3,4,4,5,5-hexafluorocyclohexyl. Examples of alkyloxy groups in which the alkyl moiety is fluorine-substituted, are trifluoromethoxy, 2,2,2-trifluoro-ethoxy, pentafluoroethoxy and 3,3,3-trifluoropropoxy.

The term "alkanediyl" or "alkylene"", as used herein, refers to saturated, divalent hydrocarbon radicals. The term "alkenediyl", as used herein, refers to divalent hydrocarbon radicals, which contain at least one carbon-carbon double bond, wherein each double bond can have E- or Z-configuration. The term "alkindiyl", as used herein, refers to divalent hydrocarbon radicals, which contain at least one carbon-carbon triple bond. As far as applicable, the preceding explanations regarding alkyl, alkenyl and alkinyl groups apply correspondingly to alkanediyl, alkendiyl and alkindiyl groups, which thus can likewise be linear and branched. Examples of divalent alkyl groups are —CH$_2$— (=methylene), —CH$_2$—CH$_2$—, —CH$_2$—CH$_2$—CH$_2$—, —CH$_2$—CH$_2$—CH$_2$—CH$_2$—, —CH(CH$_3$)—, —C(CH$_3$)$_2$—, —CH(CH$_3$)—CH$_2$—, —CH$_2$—CH(CH$_3$)—, —C(CH$_3$)$_2$—CH$_2$—, —CH$_2$—C(CH$_3$)$_2$—.

The term "cycloalkyl", as used herein, unless otherwise indicated, refers to a monovalent radical of a saturated or partially saturated hydrocarbon ring system, which can be monocyclic, bicyclic or tricyclic, i.e. which can contain one, two or three rings. The bicyclic or tricyclic ring system can be a fused ring system, in which two adjacent rings share two adjacent carbon atoms. The bicyclic or tricyclic ring system can be a spiro ring system or a di-spiro-ringsystem, in which two adjacent rings share a single carbon atom. The tricyclic ring system can also be a bicyclic spiro ring system, to which another ring is fused, that means that the latter ring and the ring in the spiro ring system, to which it is attached, share two adjacent carbon atoms; herein the latter ring can be an aromatic, saturated or partially saturated ring. The bicyclic or tricyclic system can also be a non-fused or bridged ring system, in which two adjacent rings share two non-adjacent carbon atoms. The bicyclic or tricyclic ring can be attached by any ring atom except a spiro- or a bridgehead atom.

In a monocyclic cycloalkyl group the number of ring carbon atoms can be 3, 4, 5, 6, 7 or 8. In one embodiment of the invention, the number of ring carbon atoms in a cycloalkyl group, independently of the number of ring carbon atoms in any other cycloalkyl group, is 3, 4, 5 or 6, in another embodiment 3, 4 or 5, in another embodiment 3 or 4, in another embodiment 3, in another embodiment 5, 6 or 7, in another embodiment 5 or 6, in another embodiment 6 or 7, in another embodiment 5, in another embodiment 6. Examples of cycloalkyl groups are cyclopropyl, cyclobutyl, cyclopentyl, cyclohexyl, cycloheptyl and cyclooctyl.

In a bicyclic cycloalkyl group the number of ring carbon atoms can be 6, 7, 8, 9, 10, 11 or 12. In one embodiment of the invention, the number of ring carbon atoms in a bicyclic cycloalkyl group can be 7, 8, 9, 10 or 11, in another embodiment 8, 9 or 10. In a tricyclic cycloalkyl group the number of ring carbon atoms can be 7, 8, 9, 10, 11, 12, 13, 14 or 15. In one embodiment of the invention, the number of ring carbon atoms in a tricyclic cycloalkyl group can be 10, 11 or 12.

Exemplary bicyclic or tricyclic fused ring cycloalkyls are derived from, but not limited to, the following ring systems: bicyclo[3.1.0]hexane, bicyclo[4.1.0]heptane, bicycle-[5.1.0]octane, bicyclo[3.2.0]heptane, bicyclo[4.2.0]octane, octahydro-pentalene, octahydro-indene, decahydro-azulene, decahydro-naphthalene, decahydro-benzocycloheptene, dodecahydro-heptalene, 1,2,3,3a,4,6a-hexahydro-pentalene, 1,2,3,4-tetrahydro-pentalene, 2,3,3a,4,5,7a-hexahydro-1H-indene, 2,3,3a,4,7,7a-hexahydro-1H-indene, 3a,4,5,6,7,7a-hexahydro-1H-indene, 4,5,6,7-tetrahydro-1H-indene, indane, 1,2,3,4,4a,5,6,8a-octahydro-naphthalene, 1,2,3,4,4a,5,8,8a-octahydro-naphthalene, 1,2,4a,5,8,8a-hexahydro-naphthalene, 1,4,4a,5,8,8a-hexahydro-naphthalene, 1,2,3,4-tetrahydro-naphthalene, 2,3,4,4a,5,6,9,9a-octahydro-1H-benzocycloheptene, 2,3,4,4a,5,9a-hexahydro-1H-benzocycloheptene, 4,4a,5,6,7,8,9,9a-octahydro-1H-benzocycloheptene, 6,7,8,9-tetrahydro-5H-benzocycloheptene, 1,2,3,4,5,5a,6,7,8,10a-decahydro-heptalene, dodecahydro-as-indacene and 2,3,3a,4,9,9a-hexahydro-1H-cyclopenta[b]naphthalene:

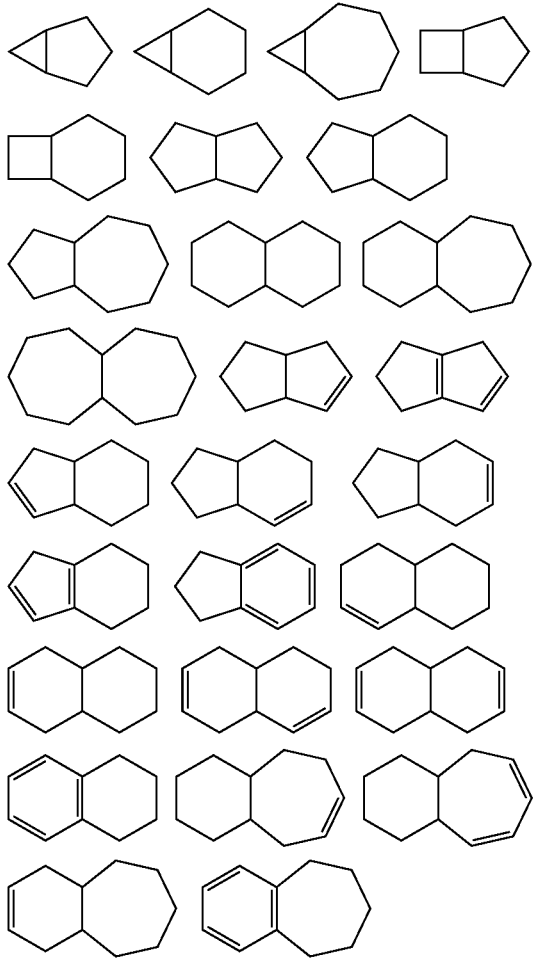

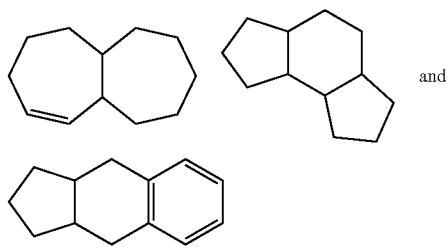

Exemplary bicyclic or tricyclic spiro ring cycloalkyls are derived from, but not limited to, the following ring systems: spiro[2.4]heptane, spiro[2.5]octane, spiro[2.6]nonane, spiro[3.3]heptane, spiro[3.4]octane, spiro[3.5]nonane, spiro[3.6]decane, spiro[4.4]nonane, spiro[4.5]decane, spiro[4.6]undecane, spiro[5.5]undecane, spiro[5.6]dodecane, spiro[6.6]tridecane, dispiro[2.2.4.2]dodecane, dispiro[2.2.3.2]undecane, dispiro-[2.1.4.2]undecane and spiro[5.5]undec-2-ene:

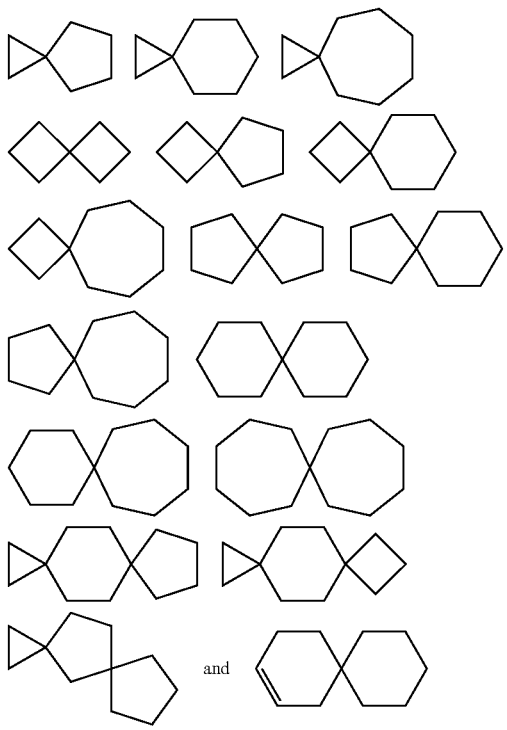

Exemplary cycloalkyls, in which a ring is fused to one ring of a bicyclic spiro system, are derived from, but not limited to, the following ring systems:

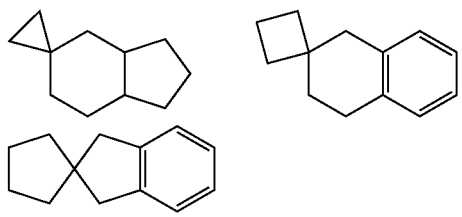

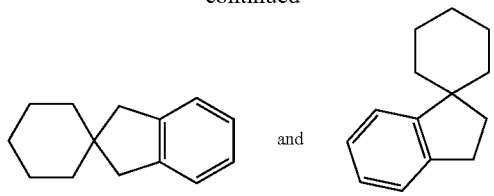

Exemplary non-fused or bridged bicyclic or tricyclic ring cycloalkyls are derived from, but not limited to, the following ring systems: bicyclo[2.2.1]heptane, bicyclo[2.2.2]octane, bicyclo[3.2.1]octane, bicyclo[3.2.2]nonane and adamantane.

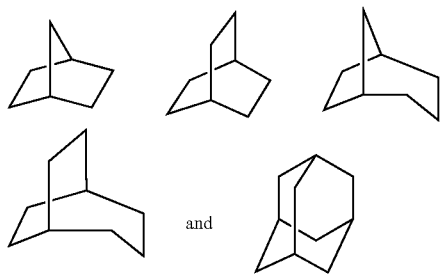

The term "heterocycloalkyl" or "heterocyclyl", as used herein, unless otherwise indicated, refers to a cycloalkyl as defined above, in which 1, 2, 3 or 4 carbon atoms are replaced by nitrogen, oxygen or sulfur atoms, provided that a spiro atom is always a carbon atom and a bridgehead atom is either a carbon or a nitrogen atom and provided that the heterocycloalkyl system is stable and suitable as a subgroup for the desired purpose of the compound of the formula I such as use as a drug substance. Depending on the definition of the respective heterocyclic group, in one embodiment of the invention the number of ring heteroatoms which can be present in a heterocyclic group, independently of the number of ring heteroatoms in any other heterocyclic group, is 1, 2, 3 or 4, in another embodiment 1, 2 or 3, in another embodiment 1 or 2, in another embodiment 2, in another embodiment 1, wherein the ring heteroatoms can be identical or different. The heterocycloalkyl group can be attached by any ring carbon atom or saturated ring nitrogen atom, with the exeption of spiro- or bridgehead atoms. A ring sulfur atom in a heterocycloalkyl group can carry zero, one or two oxo groups, it is a non-oxidized sulfur atom S in case it does not carry any oxo group, or it is an S(O) group (=sulfoxide group, S-oxide group) in case it carries one oxo group, or it is an S(O)$_2$ group (=sulfone group, S,S-dioxide group) in case it carries two oxo groups.

Exemplary monocyclic heterocycloalkyls are derived from, but not limited to, the following ring systems: aziridine, oxirane, azetidine, oxetane, pyrrolidine, tetrahydrofurane, tetrahydrothiophene, 4,5-dihydrothiazole, piperidine, piperazine, morpholine, thiomorpholine, tetrahydropyran, 1,4-dioxane, 1,4-oxathiane, 1,2,3,6-tetrahydropyridine, azepane, 2,3,4,7-tetrahydro-1H-azepine, 2,7-dihydro-1H-azepine, 1,4-diazepane, 1,4-oxazepane, 1,4-thiazepane and 1,4-dioxepane:

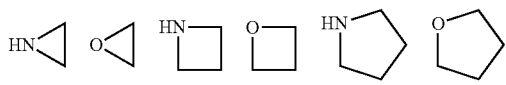

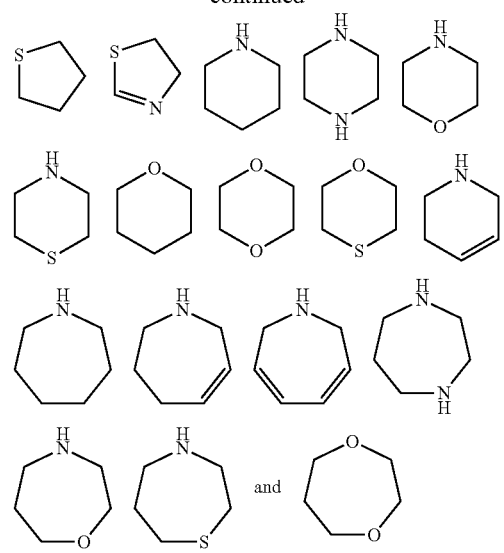

In one embodiment monocyclic heterocycloalkyls are derived from azetidine, pyrrolidine, piperidine, piperazine, morpholine or 1,4-diazepane:

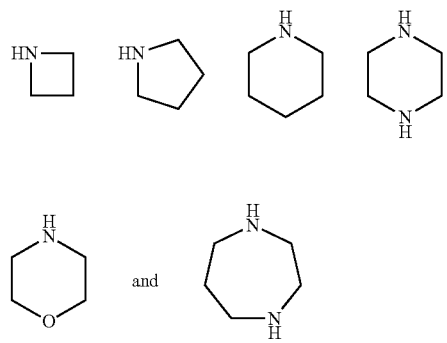

Exemplary bicyclic fused ring heterocycloalkyls are derived from, but not limited to, the following ring systems: 3-aza-bicyclo[3.1.0]hexane, 2-aza-bicyclo[4.1.0]heptane, 2-oxa-5-aza-bicyclo[5.1.0]octane, 3-aza-bicyclo[3.2.0]heptane, 2-aza-bicyclo[4.2.0]octane, octahydro-pyrrolo[3,4-c]pyrrole, octahydro-pyrrolo[3,4-b]pyrrole, octahydro-pyrrolo[3,4-b]pyridine, octahydro-thieno[3,4-b]pyrazine, octahydro-furo[3,4-b]pyridine, octahydro-cyclopenta[1,4]oxazine, octahydro-pyrrolo[1,2-a]pyrimidine, octahydro-pyrrolo[1,2-a]pyrazine, octahydro-cyclopenta[e][1,4]oxazepine, decahydro-quinoxaline, decahydro-[1,6]naphthyridine, octahydro-benzo[1,4]oxazine, octahydro-benzo-[1,4]thiazine, octahydro-pyrido[1,2-a]pyrazine, octahydro-pyrano[3,2-b]pyridine, decahydro-1-oxa-9-aza-benzocycloheptene, 1,2,3,3a,6,6a-hexahydro-cyclopenta[b]pyrrole, 5,6-dihydro-4H-cyclopenta[b]thiophene, 2,3,4,4a,7,7a-hexahydro-1H-[2]pyrindine, 2,4a,5,6,7,7a-hexahydro-1H-[1]pyrindine, 2,3,3a,4,7,7a-hexahydro-1H-indole, 1,2,3,4-tetrahydro-quinoxaline, 4,5,6,7-tetrahydro-benzofuran, benzo[1,3]dioxole, 3,4,4a,7,8,8a-hexahydro-2H-benzo[1,4]oxazine, 1,2,3,4,4a,5,8,8a-octahydro-quinoxaline, 4a,5,8,8a-tetrahydro-2H-thiopyrano[3,2-b]pyridine and 1,2,3,4-tetrahydro-[1,5]naphthyridine:

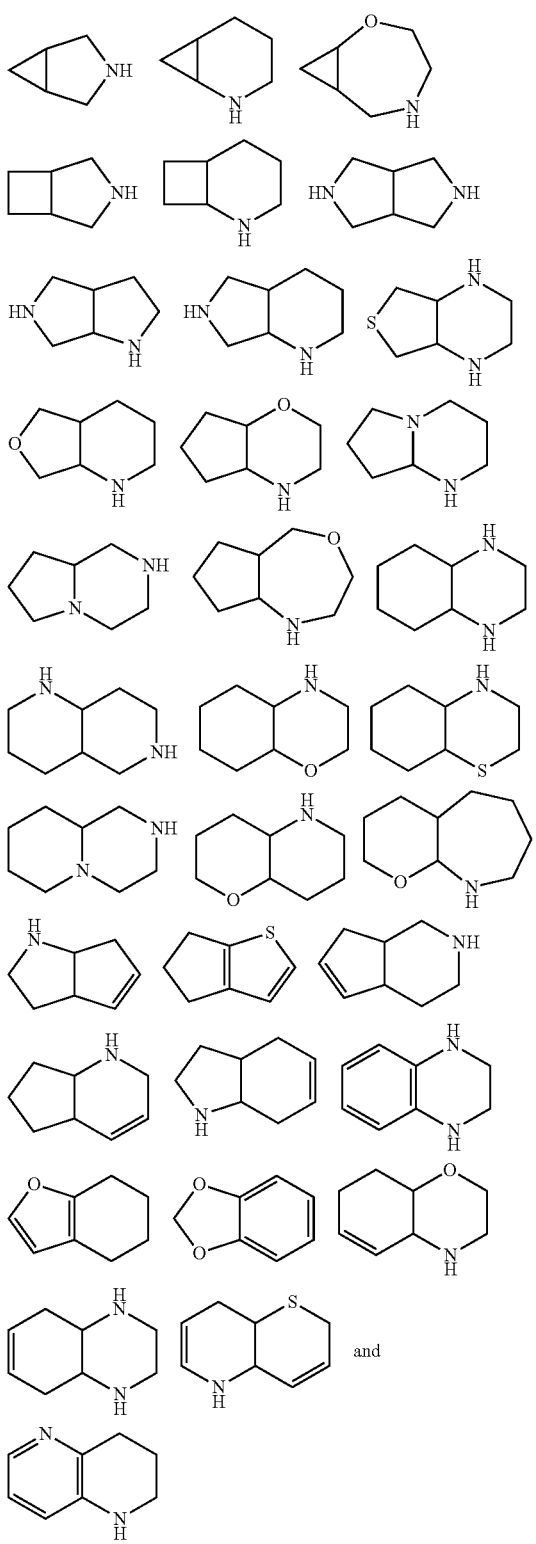

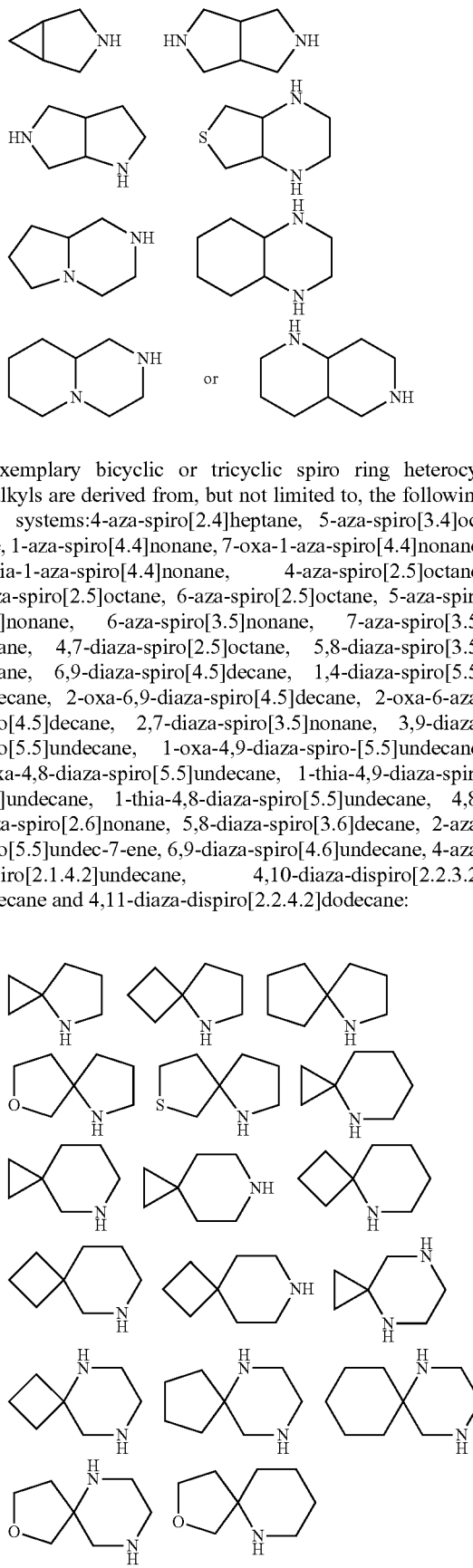

In one embodiment bicyclic fused ring heterocycloalkyls are derived from 3-aza-bicyclo[3.1.0]hexane, octahydro-pyrrolo[3,4-c]pyrrole, octahydro-pyrrolo[3,4-b]pyrrole, octahydro-thieno[3,4-b]pyrazine, octahydro-pyrrolo[1,2-a]pyrazine, decahydro-quinoxaline, octahydro-pyrido[1,2-a]pyrazine or decahydro-[1,6]naphthyridine:

Exemplary bicyclic or tricyclic spiro ring heterocycloalkyls are derived from, but not limited to, the following ring systems: 4-aza-spiro[2.4]heptane, 5-aza-spiro[3.4]octane, 1-aza-spiro[4.4]nonane, 7-oxa-1-aza-spiro[4.4]nonane, 7-thia-1-aza-spiro[4.4]nonane, 4-aza-spiro[2.5]octane, 5-aza-spiro[2.5]octane, 6-aza-spiro[2.5]octane, 5-aza-spiro[3.5]nonane, 6-aza-spiro[3.5]nonane, 7-aza-spiro[3.5]nonane, 4,7-diaza-spiro[2.5]octane, 5,8-diaza-spiro[3.5]nonane, 6,9-diaza-spiro[4.5]decane, 1,4-diaza-spiro[5.5]undecane, 2-oxa-6,9-diaza-spiro[4.5]decane, 2-oxa-6-aza-spiro[4.5]decane, 2,7-diaza-spiro[3.5]nonane, 3,9-diaza-spiro[5.5]undecane, 1-oxa-4,9-diaza-spiro-[5.5]undecane, 1-oxa-4,8-diaza-spiro[5.5]undecane, 1-thia-4,9-diaza-spiro[5.5]undecane, 1-thia-4,8-diaza-spiro[5.5]undecane, 4,8-diaza-spiro[2.6]nonane, 5,8-diaza-spiro[3.6]decane, 2-aza-spiro[5.5]undec-7-ene, 6,9-diaza-spiro[4.6]undecane, 4-aza-dispiro[2.1.4.2]undecane, 4,10-diaza-dispiro[2.2.3.2]undecane and 4,11-diaza-dispiro[2.2.4.2]dodecane:

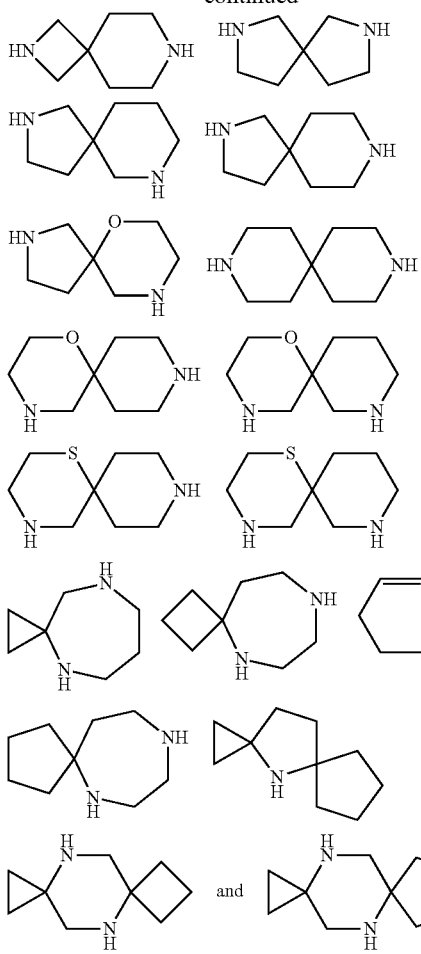

In one embodiment bicyclic or tricyclic spiro ring heterocycloalkyls are derived from 4,7-diaza-spiro[2.5]octane, 6-aza-spiro[3.5]nonane, 5,8-diaza-spiro[3.5]nonane, 6,9-diaza-spiro[4.5]decane, 2,7-diaza-spiro[3.5]nonane, 2,7-diaza-spiro[4.4]nonane, 2,7-diaza-spiro[4.5]decane, 2,8-diaza-spiro[4.5]decane, 6-oxa-2,9-diaza-spiro[4.5]decane, 3,9-diaza-spiro[5.5]undecane, 1-oxa-4,9-diaza-spiro[5.5]undecane or 1-oxa-4,8-diaza-spiro[5.5]undecane:

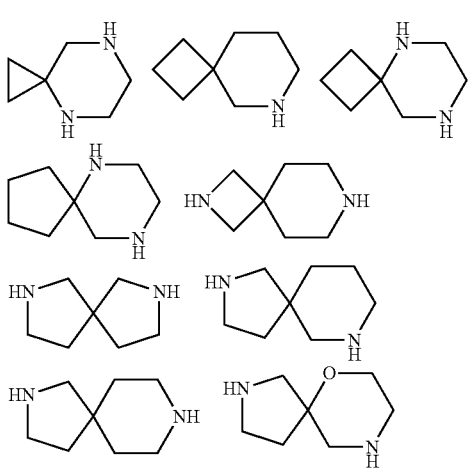

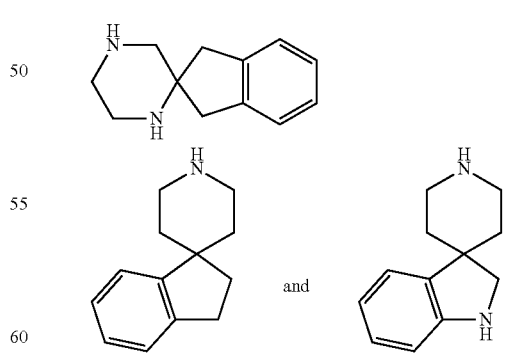

Exemplary heterocycloalkyls, in which a ring is fused to one ring of a bicyclic spiro system, are derived from, but not limited to, the following ring systems: octahydro-spiro[cyclopentane-1,2'(3'H)-quinoxalin], 1',4'-dihydro-spiro[cyclopentane-1,2'(3'H)-quinoxalin], 1',2',4,5-tetrahydro-spiro[furan-3(2H), 3'-[3H]indol], 1,3-dihydro-spiro[indene-2,2'-piperazine], 2,3-dihydro-spiro[1H-indene-1,4'-piperidin] and 1,2-dihydro-5-spiro[3H-indole-3,4'-piperidin]:

In one embodiment heterocycloalkyls, in which a ring is fused to one ring of a bicyclic spiro system, are derived from 3-dihydro-spiro[indene-2,2'-piperazine], 2,3-dihydro-spiro[1H-indene-1,4'-piperidin] or 1,2-dihydro-5-spiro[3H-indole-3,4'-piperidin]:

Exemplary non-fused or bridged bicyclic or tricyclic ring heterocycloalkyls are derived from, but not limited to, the following ring systems: 2-aza-bicyclo[2.2.1]heptane, 1-aza-bicyclo[2.2.2]octane, 8-aza-bicyclo[3.2.1]octane, 3-aza-bicyclo[3.2.1]octane, 9-aza-bicyclo[3.3.1]nonane, 2,5-diazabicyclo[2.2.1]heptane, 2,5-diaza-bicyclo[2.2.2]octane, 3,8-diaza-bicyclo[3.2.1]octane and 3,7-diaza-bicyclo[3.3.1]nonane:

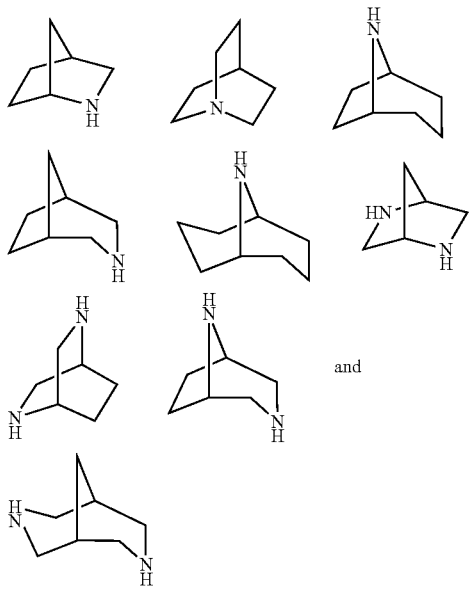

and

The term "aryl", as used herein, refers to a radical derived from an aromatic hydrocarbon by removal of one hydrogen, such as phenyl or naphthyl (=naphthalenyl).

The term "heteroaryl" or "hetaryl" as used herein, refers to a radical derived from an aromatic mono- or bicyclic ring system, in which 1, 2, 3, 4 or 5 carbon atoms are replaced by heteroatoms. The ring heteroatoms are generally chosen from N, O and S, wherein N includes ring nitrogen atoms which carry a hydrogen atom or a substituent as well as ring nitrogen atoms which do not carry a hydrogen atom or a substituent. Ring heteroatoms can be located in any position, provided that the heterocyclic system is stable and suitable as a subgroup for the desired purpose of the compound of the formula I such as use as a drug substance. Heteroaryl radicals are derived from 5-membered or 6-membered monocyclic rings or 8-membered, 9-membered or 10-membered bicyclic rings, in another embodiment 5-membered or 6-membered monocyclic rings or 9-membered or 10-membered bicyclic rings, in another embodiment 5-membered or 6-membered monocyclic rings.

Exemplary heteroaryl systems are derived from, but not limited to, the following ring systems: pyrrole, furan, thiophene, imidazole, pyrazole, oxazole (=[1,3]oxazole), isoxazole (=[1,2]oxazole), thiazole (=[1,3]thiazole), isothiazole (=[1,2]thiazole), [1,2,3]triazole, [1,2,4]triazole, [1,2,4]oxadiazole, [1,3,4]oxadiazole, [1,2,4]thiadiazole, [1,3,4]thiadiazole, tetrazole, pyridine, pyridazine, pyrimidine, pyrazine, [1,2,3]triazine, [1,2,4]triazine, [1,3,5]triazine, indole, isoindole, benzofuran, benzothiophene[1,3]benzoxazole, [1,3]benzothiazole, benzoimidazole, indazole, quinoline, isoquinoline, cinnoline, quinazoline, quinoxaline, phthalazine, different naphthyridines, e.g. [1,8]naphthyridine, different thienopyridines, e.g. thieno[2,3-b]pyridine and purine:

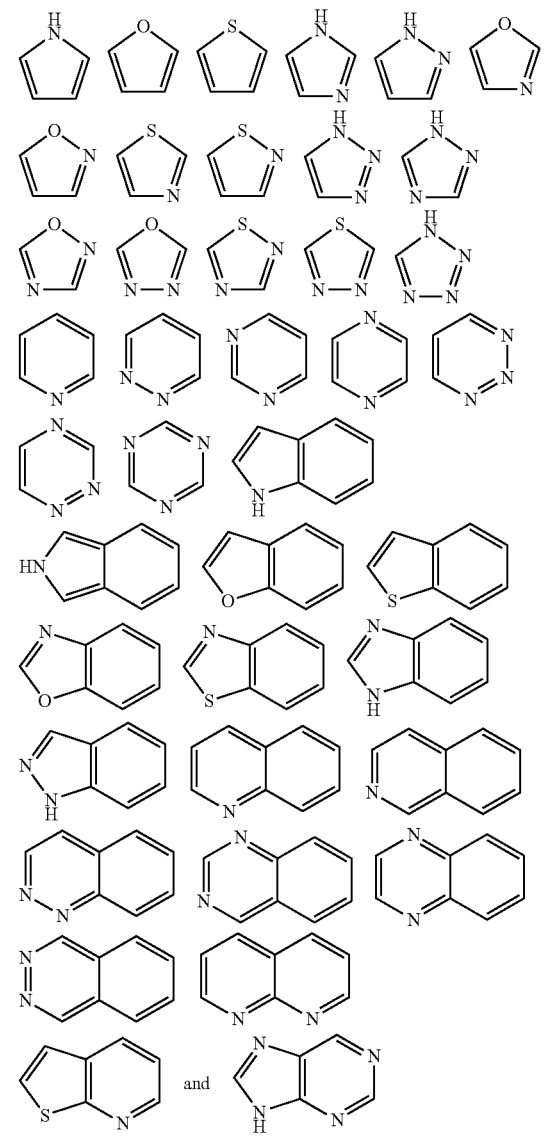

and

Groups like phenyl, naphthyl (=naphthalenyl) and residues of aromatic heterocycles which are optionally substituted by one or more substituents, can be unsubstituted or substituted, for example by 1, 2, 3, 4 or 5, or by 1, 2, 3 or 4, or by 1, 2 or 3, or by 1 or 2, or by 1, identical or different substituents which can be located in any positions. Aromatic nitrogen heterocycles which in the parent ring system carry a hydrogen atom on a ring nitrogen atom in a 5-membered ring, such as a pyrrole, imidazole, indole or benzoimidazole ring, for example, can be substituted on ring carbon atoms and/or on such ring nitrogen atoms. In one embodiment of the invention, substituents on such ring nitrogen atoms are chosen from (C1-C4)-alkyl groups, i.e. such ring nitrogen atoms in aromatic heterocycles carry a hydrogen atom or a (C1-C4)-alkyl substituent. When it is stated with respect to ring nitrogen atoms in aromatic heterocycles and any other heterocycles that they can carry a hydrogen atom or a substituent, such ring nitrogen atoms either carry a hydrogen atom or a substituent or they do not carry a hydrogen atom or substituent. Ring nitrogen atoms which carry a hydrogen atom or a substituent, occur in a nitrogen-containing aromatic 5-membered ring as is present in pyrrole, imidazole, indole or benzoimidazole, for example, and in a non-aromatic ring including a saturated ring. Ring nitrogen atoms which do not carry a hydrogen atom or a substituent unless they are present in positively charged form, including any further ring nitrogen atoms in addition to ring nitrogen atoms which carry a hydrogen atom or a substituent, occur in an aromatic ring as is present in thiazole, imidazole, pyridine or benzoimidazole, for example, and in a non-aromatic ring in which they are part of a double bond, and they occur as ring nitrogen atoms via which a ring is bonded. Suitable ring nitrogen atoms in aromatic heterocycles in the compounds of the formula I, such as the ring nitrogen atom in a pyridine ring or a quinoline ring, can in general also be present as N-oxide or as quaternary salt, for example as N—(C1-C4)-alkyl salt such as N-methyl salt, wherein in one embodiment of the invention the counter anion in such quaternary salt is a physiologically acceptable anion which is derived from an acid that forms a physiologically acceptable salt.

In monosubstituted phenyl groups, the substituent can be located in the 2-position, the 3-position or the 4-position. In disubstituted phenyl groups, the substituents can be located in 2,3-position, 2,4-position, 2,5-position, 2,6-position, 3,4-position or 3,5-position. In trisubstituted phenyl groups, the substituents can be located in 2,3,4-position, 2,3,5-position, 2,3,6-position, 2,4,5-position, 2,4,6-position or 3,4,5-position. Naphthyl can be 1-naphthyl (=naphthalen-1-yl) or 2-naphthyl (=naphthalen-2-yl). In monosubstituted 1-naphthyl groups, the substituent can be located in the 2-, 3-, 4-, 5-, 6-, 7- or 8-position. In monosubstituted 2-naphthyl groups, the substituent can be located in the 1-, 3-, 4-, 5-, 6-, 7- or 8-position. In disubstituted naphthyl groups, the substituents can likewise be located in any positions both in the ring via which the naphthyl group is bonded and/or in the other ring.

Ring heteroatoms can be located in any positions, provided that the heterocyclic system is known in the art and is stable and suitable as a subgroup for the desired purpose of the compound of the formula I such as use as a drug substance. In one embodiment of the invention, two ring oxygen atoms cannot be present in adjacent ring positions of any heterocycle, in another embodiment two ring heteroatoms chosen from oxygen and sulfur cannot be present in adjacent ring positions of any heterocycle. Substituents on heterocyclic groups can be located in any positions. For example, in a pyridin-2-yl group substituents can be located in the 3-position and/or 4-position and/or 5-position and/or 6-position, in a pyridin-3-yl group substituent can be located in the 2-position and/or 4-position and/or 5-position and/or 6-position, in a pyridin-4-yl group substituents can be located in the 2-position and/or 3-position and/or 5-position and/or 6-position.

The following illustrates the position of residues within formula I

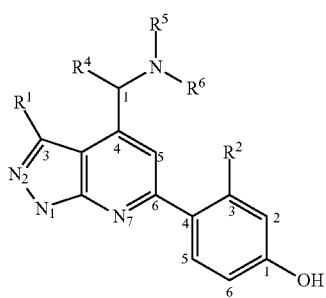

I

If $R^5$ and $R^6$ together with the nitrogen atom to which they are attached to form a heterocycle the position of the nitrogen atom to which they are attached to is the 1 position.

Halogen is fluorine, chlorine, bromine or iodine. In one embodiment of the invention, any halogen in a compound of the formula I is independently of any other halogen chosen from fluorine, chlorine and bromine, in another embodiment from fluorine and chlorine, and in yet another embodiment it is fluorine.

When an oxo group is bonded to a carbon atom, it replaces two hydrogen atoms on a carbon atom of the parent system. Thus, if a $CH_2$ group in a chain or a ring is substituted by oxo, i.e. by a doubly bonded oxygen atom, it becomes a CO group. Evidently, an oxo group cannot occur as a substituent on a carbon atom in an aromatic ring such as in a phenyl group, for example. When a ring sulfur atom in a heterocyclic group can carry one or two oxo groups, it is a non-oxidized sulfur atom S in case it does not carry any oxo group, or it is an S(O) group (=sulfoxide group, S-oxide group) in case it carries one oxo group, or it is an $S(O)_2$ group (=sulfone group, S,S-dioxide group) in case it carries two oxo groups.

The present invention includes all stereoisomeric forms of the compounds of the formula I and their salts and solvates. With respect to each chiral center, independently of any other chiral center, the compounds of the formula I can be present in S configuration or substantially S configuration, or in R configuration or substantially R configuration, or as a mixture of the S isomer and the R isomer in any ratio. The invention includes all possible enantiomers and diastereomers and mixtures of two or more stereoisomers, for example mixtures of enantiomers and/or diastereomers, in all ratios. Thus, compounds according to the invention which can exist as enantiomers can be present in enantiomerically pure form, both as levorotatory and as dextrorotatory antipodes, and in the form of mixtures of the two enantiomers in all ratios including racemates. In the case of a E/Z isomerism, or cis/trans isomerism, for example on double bonds or rings such as cycloalkyl rings, the invention includes both the E form and Z form, or the cis form and the trans form, as well as mixtures of these forms in all ratios. In one embodiment of the invention, a compound which can occur in two or more stereoisomeric forms is a pure, or substantially pure, individual stereoisomer. The preparation of individual stereoisomers can be carried out, for example, by separation of a mixture of isomers by customary methods, for example by chromatography or crystallization, by the use of stereochemically uniform starting materials in the synthesis, or by stereoselective synthesis. Optionally, a derivatization can be carried out before a separation of stereoisomers. The separation of a mixture of stereoisomers can be carried out at the stage of the compound of the formula I or at the stage of a starting material or an intermediate during the synthesis. The present invention also includes all tautomeric forms of the compounds of the formula I and their salts and solvates.

In case the compounds of the formula I contain one or more acidic and/or basic groups, i.e. salt-forming groups, the invention also includes their corresponding physiologically or toxicologically acceptable salts, i.e. non-toxic salts, in particular their pharmaceutically acceptable salts.

The present invention furthermore includes all solvates of compounds of the formula I, for example hydrates or adducts with alcohols such as $(C_1-C_4)$-alkanols, active metabolites of the compounds of the formula I, and also prodrugs and derivatives of the compounds of the formula I which in vitro may not necessarily exhibit pharmacological activity but which in vivo are converted into pharmacologically active compounds, for example esters or amides of carboxylic acid groups.

The compounds of the present invention, PKC inhibitors, can be widely combined with other pharmacologically active compounds, e.g., with all antihypertensives and nephroprotectives, mentioned in the Rote Liste 2011, antidiabetics mentioned in the Rote Liste 2011, chapter 12; all weight-reducing agents/appetite suppressants mentioned in the Rote Liste 2011, chapter 1; all diuretics mentioned in the Rote Liste 2011, chapter 36; all lipid-lowering agents mentioned in the Rote Liste 2011, chapter 58. They can be combined with the inventive compound of the formula I, especially for a synergistic improvement in action. The active ingredient combination can be administered either by separate administration of the active ingredients to the patient or in the form of combination products in which a plurality of active ingredients are present in one pharmaceutical preparation. When the active ingredients are administered by separate administration of the active ingredients, this can be done simultaneously or successively. Most of the active ingredients mentioned hereinafter are disclosed in the USP Dictionary of USAN and International Drug Names, US Pharmacopeia, Rockville 2006.

Antidiabetics include insulin and insulin derivatives, for example Lantus® (see www.lantus.com) or HMR 1964 or Levemir® (insulin detemir), Humalog® (Insulin Lispro), insulin degludec, insulin aspart, polyethylene glycosidized (PEGylated) Insulin Lispro as described in WO2009152128, Humulin®, VIAject™, SuliXen®, VIAject™ or those as described in WO2005005477 (Novo Nordisk), fast-acting insulins (see U.S. Pat. No. 6,221,633), inhalable insulins, for example Exubera®, Nasulin™, or oral insulins, for example IN-105 (Nobex) or Oral-lyn™ (Generex Biotechnology), or Technosphere® insulin (MannKind) or Cobalamin™ oral insulin or ORMD-0801 or insulins or insulin precursors as described in WO2007128815, WO2007128817, WO2008034881, WO2008049711, WO2008145721, WO2009034117, WO2009060071, WO2009133099 or insulins which can be administered transdermally; additionally included are also those insulin derivatives which are bonded to albumin by a bifunctional linker, as described, for example, in WO2009121884;

GLP-1 derivatives and GLP-1 agonists, for example exenatide or specific formulations thereof, as described, for example, in WO2008061355, WO2009080024, WO2009080032, liraglutide, taspoglutide (R-1583), albiglutide, lixisenatide or those which have been disclosed in WO 98/08871, WO2005027978, WO2006037811, WO2006037810 by Novo Nordisk NS, in WO 01/04156 by Zealand or in WO 00/34331 by Beaufour-Ipsen, pramlintide acetate (Symlin; Amylin Pharmaceuticals), inhalable GLP-1 (MKC-253 from MannKind) AVE-0010, BIM-51077 (R-1583, ITM-077), PC-DAC:exendin-4 (an exendin-4 analog which is bonded covalently to recombinant human albumin), biotinylated exendin (WO2009107900), a specific formulation of exendin-4 as described in US2009238879, CVX-73, CVX-98 and CVx-96 (GLP-1 analogs which are bonded covalently to a monoclonal antibody which has specific binding sites for the GLP-1 peptide), CNTO-736 (a GLP-1 analog which is bonded to a domain which includes the Fc portion of an antibody), PGC-GLP-1 (GLP-1 bonded to a nanocarrier), agonists or modulators, as described, for example, in D. Chen et al., Proc. Natl. Acad. Sci. USA 104 (2007) 943, those as described in WO2006124529, WO2007124461, WO2008062457, WO2008082274, WO2008101017, WO2008081418, WO2008112939, WO2008112941, WO2008113601, WO2008116294, WO2008116648, WO2008119238, WO2008148839, US2008299096, WO2008152403, WO2009030738, WO2009030771, WO2009030774, WO2009035540, WO2009058734, WO2009111700, WO2009125424, WO2009129696, WO2009149148, peptides, for example obinepitide (TM-30338), orally active GLP-1 analogs (e.g. NN9924 from Novo Nordisk), amylin receptor agonists, as described, for example, in WO2007104789, WO2009034119, analogs of the human GLP-1, as described in WO2007120899, WO2008022015, WO2008056726, chimeric pegylated peptides containing both GLP-1 and glucagon residues, as described, for example, in WO2008101017, WO2009155257, WO2009155258, glycosylated GLP-1 derivatives as described in WO2009153960, and orally active hypoglycemic ingredients.

Antidiabetics also include gastrin analogs, for example TT-223.

Antidiabetics additionally include poly- or monoclonal antibodies directed, for example, against interleukin 1 beta (IL-113), for example XOMA-052.

Antidiabetics additionally include peptides which can bind to the human pro-islet peptide (HIP) receptor, as described, for example, in WO2009049222.

Antidiabetics also include agonists of the glucose-dependent insulinotropic polypeptide (GIP) receptor, as described, for example, in WO2006121860.

Antidiabetics also include the glucose-dependent insulinotropic polypeptide (GIP), and also analogous compounds, as described, for example, in WO2008021560, WO2010016935, WO2010016936, WO2010016938, WO2010016940, WO2010016944.

Additionally included are analogs and theivatives of human pancreatic polypeptide, as described, for example, in WO2009007714.

Antidiabetics additionally include encapsulated insulin-producing porcine cells, for example DiabeCell®.

Antidiabetics also include analogs and theivatives of fibroblast growth factor 21 (FGF-21), as described, for example, in WO2009149171, WO2010006214.

The orally active hypoglycemic ingredients preferably include sulfonylureas,
biguanidines,
meglitinides,
oxadiazolidinediones,
thiazolidinediones,
PPAR and RXR modulators,
glucosidase inhibitors,
inhibitors of glycogen phosphorylase,
glucagon receptor antagonists,
glucokinase activators,
inhibitors of fructose 1,6-bisphosphatase,
modulators of glucose transporter 4 (GLUT4),
inhibitors of glutamine:fructose-6-phosphate amidotransferase (GFAT),
GLP-1 agonists,
potassium channel openers, for example pinacidil, cromakalim, diazoxide, diazoxide choline salt, or those as described in R. D. Carr et al., Diabetes 52, 2003, 2513.2518, in J. B. Hansen et al., Current Medicinal Chemistry 11, 2004, 1595-1615, in T. M. Tagmose et al., J. Med. Chem. 47, 2004, 3202-3211 or in M. J. Coghlan et al., J. Med. Chem. 44, 2001, 1627-1653, or those which have been disclosed in WO 97/26265 and WO 99/03861 by Novo Nordisk A/S,
active ingredients which act on the ATP-dependent potassium channel of the beta cells,
inhibitors of dipeptidyl peptidase-IV (DPP-IV),
insulin sensitizers,
inhibitors of liver enzymes involved in stimulating gluconeogenesis and/or glycogenolysis, modulators of glucose uptake, of glucose transport and of glucose reabsorption,
modulators of sodium-dependent glucose transporter 1 or 2 (SGLT1, SGLT2),
inhibitors of 11-beta-hydroxysteroid dehydrogenase-1 (11β-HSD1),
inhibitors of protein tyrosine phosphatase-1B (PTP-1B),
nicotinic acid receptor agonists,
inhibitors of hormone-sensitive or endothelial lipases,
inhibitors of acetyl-CoA carboxylase (ACC1 and/or ACC2) or
inhibitors of GSK-3 beta.

Also included are compounds which modify the lipid metabolism, such as active antihyperlipidemic ingredients and active antilipidemic ingredients,
HMG-CoA reductase inhibitors,
farnesoid X receptor (FXR) modulators,
fibrates,
cholesterol reabsorption inhibitors,
CETP inhibitors,
bile acid absorption inhibitors,
MTP inhibitors,
estrogen receptor gamma agonists (ERR γ agonists),
sigma-1 receptor antagonists,
antagonists of the somatostatin 5 receptor (SST5 receptor);
compounds which reduce food intake, and
compounds which increase thermogenesis.

In one embodiment of the invention, the compound of the formula I is administered in combination with insulin.

In another embodiment of the invention, the compound of the formula I is administered in combination with an insulin sensitizer, for example PN-2034 or ISIS-113715.

In one embodiment, the compound of the formula I is administered in combination with an active ingredient which acts on the ATP-dependent potassium channel of the beta cells, for example sulfonylureas, for example tolbutamide, glibenclamide, glipizide, gliclazide or glimepiride, or those formulations as described, for example, in EP2103302.

In one embodiment, the compound of the formula I is administered in combination with a tablet which comprises both glimepiride, which is released rapidly, and metformin, which is released over a longer period (as described, for example, in US2007264331, WO2008050987, WO2008062273).

In one embodiment, the compound of the formula I is administered in combination with a biguanide, for example metformin or one of its salts.

In a further embodiment, the compound of the formula I is administered in combination with a guanidine, for example benzylguanidine or one of its salts, or those guanidines as described in WO2009087395.

In another embodiment, the compound of the formula I is administered in combination with a meglitinide, for example repaglinide, nateglinide or mitiglinide.

In a further embodiment, the compound of the formula I is administered with a combination of mitiglinide with a glitazone, e.g. pioglitazone hydrochloride.

In a further embodiment, the compound of the formula I is administered with a combination of mitiglinide with an alpha-glucosidase inhibitor.

In a further embodiment, the compound of the formula I is administered in combination with antidiabetic compounds, as described in WO2007095462, WO2007101060, WO2007105650.

In a further embodiment, the compound of the formula I is administered in combination with antihypoglycemic compounds, as described in WO2007137008, WO2008020607.

In one embodiment, the compound of the formula I is administered in combination with a thiazolidinedione, for example troglitazone, ciglitazone, pioglitazone, rosiglitazone or the compounds disclosed in WO 97/41097 by Dr. Reddy's Research Foundation, especially 5-[[4-[(3,4-dihydro-3-methyl-4-oxo-2-quinazolinylmethoxy]phenyl]methyl]-2,4-thiazolidinedione.

In one embodiment of the invention, the compound of the formula I is administered in combination with a PPAR gamma agonist, for example rosiglitazone, pioglitazone, JTT-501, GI 262570, R-483, CS-011 (rivoglitazone), DRL-17564, DRF-2593 (balaglitazone), INT-131, T-2384, or those as described in WO2005086904, WO2007060992, WO2007100027, WO2007103252, WO2007122970, WO2007138485, WO2008006319, WO2008006969, WO2008010238, WO2008017398, WO2008028188, WO2008066356, WO2008084303, WO2008089461-WO2008089464, WO2008093639, WO2008096769, WO2008096820, WO2008096829, US2008194617, WO2008099944, WO2008108602, WO2008109334, WO2008110062, WO2008126731, WO2008126732, WO2008137105, WO2009005672, WO2009038681, WO2009046606, WO2009080821, WO2009083526, WO2009102226, WO2009128558, WO2009139340.

In one embodiment of the invention, the compound of the formula I is administered in combination with Competact™, a solid combination of pioglitazone hydrochloride with metformin hydrochloride.

In one embodiment of the invention, the compound of the formula I is administered in combination with Tandemact™, a solid combination of pioglitazone with glimepiride.

In a further embodiment of the invention, the compound of the formula I is administered in combination with a solid combination of pioglitazone hydrochloride with an angiotensin II agonist, for example TAK-536.

In one embodiment of the invention, the compound of the formula I is administered in combination with a PPAR alpha agonist or mixed PPAR alpha/PPAR delta agonist, for example GW9578, GW-590735, K-111, LY-674, KRP-101, DRF-10945, LY-518674, CP-900691, BMS-687453, BMS-711939, or those as described in WO2001040207, WO2002096894, WO2005097076, WO2007056771, WO2007087448, WO2007089667, WO2007089557, WO2007102515, WO2007103252, JP2007246474, WO2007118963, WO2007118964, WO2007126043, WO2008006043, WO2008006044, WO2008012470, WO2008035359, WO2008087365, WO2008087366, WO2008087367, WO2008117982, JP2009023975, WO2009033561, WO2009047240, WO2009072581, WO2009080248, WO2009080242, WO2009149819, WO2009149820, WO2009147121, WO2009153496, WO2010008299, WO2010014771.

In one embodiment of the invention, the compound of the formula I is administered in combination with a mixed PPAR alpha/gamma agonist, for example naveglitazar, aleglitazar, LY-510929, ONO-5129, E-3030, AVE 8042, AVE 8134, AVE 0847, AVE 0897, CKD-501 (lobeglitazone sulfate), MBX-213, KY-201, BMS-759509, or as described in WO 00/64888, WO 00/64876, WO03/020269, WO2004024726, WO2007099553, US2007276041, WO2007085135, WO2007085136, WO2007141423, WO2008016175, WO2008053331, WO2008109697, WO2008109700, WO2008108735, WO2009026657, WO2009026658, WO2009149819, WO2009149820 or in J.P. Berger et al., TRENDS in Pharmacological Sciences 28(5), 244-251, 2005.

In one embodiment of the invention, the compound of the formula I is administered in combination with a PPAR delta agonist, for example GW-501516, or as described in WO2006059744, WO2006084176, WO2006029699, WO2007039172-WO2007039178, WO2007071766, WO2007101864, US2007244094, WO2007119887, WO2007141423, US2008004281, WO2008016175, WO2008066356, WO2008071311, WO2008084962, US2008176861, WO2009012650, US2009137671, WO2009080223, WO2009149819, WO2009149820, WO2010000353.

In one embodiment of the invention, the compound of the formula I is administered in combination with a pan-SP-PARM (selective PPAR modulator alpha, gamma, delta), for example GFT-505, indeglitazar, or those as described in WO2008035359, WO2009072581.

In one embodiment, the compound of the formula I is administered in combination with metaglidasen or with MBX-2044 or other partial PPAR gamma agonists/antagonists.

In one embodiment, the compound of the formula I is administered in combination with an α-glucosidase inhibitor, for example miglitol or acarbose, or those as described, for example, in WO2007114532, WO2007140230, US2007287674, US2008103201, WO2008065796, WO2008082017, US2009076129.

In one embodiment, the compound of the formula I is administered in combination with an inhibitor of glycogen phosphorylase, for example PSN-357 or FR-258900, or those as described in WO2003084922, WO2004007455, WO2005073229-31, WO2005067932, WO2008062739, WO2008099000, WO2008113760, WO2009016118, WO2009016119, WO2009030715, WO2009045830, WO2009045831, WO2009127723.

In another embodiment, the compound of the formula I is administered in combination with an inhibitor of the interaction of liver glycogen phosphorylase with the protein PPP1R3 (GL subunit of glycogen-associated protein phosphatase 1 (PP1)), as described, for example, in WO2009030715.

In one embodiment, the compound of the formula I is administered in combination with glucagon receptor antagonists, for example A-770077 or NNC-25-2504 or as described in WO2004100875, WO2005065680, WO2006086488, WO2007047177, WO2007106181, WO2007111864, WO2007120270, WO2007120284, WO2007123581, WO2007136577, WO2008042223, WO2008098244, WO2009057784, WO2009058662, WO2009058734, WO2009110520, WO2009120530, WO2009140342, WO2010019828.

In a further embodiment, the compound of the formula I is administered in combination with an antisense compound, e.g. ISIS-325568, which inhibits the production of the glucagon receptor.

In one embodiment, the compound of the formula I is administered in combination with activators of glucokinase, for example LY-2121260 (WO2004063179), PSN-105, PSN-110, GKA-50, or those as described, for example, in WO2004072031, WO2004072066, WO2005080360, WO2005044801, WO2006016194, WO2006058923, WO2006112549, WO2006125972, WO2007017549, WO2007017649, WO2007007910, WO2007007040-42, WO2007006760-61, WO2007006814, WO2007007886, WO2007028135, WO2007031739, WO2007041365, WO2007041366, WO2007037534, WO2007043628, WO2007053345, WO2007051846, WO2007051845, WO2007053765, WO2007051847, WO2007061923, WO2007075847, WO2007089512, WO2007104034, WO2007117381, WO2007122482, WO2007125103, WO2007125105, US2007281942, WO2008005914, WO2008005964, WO2008043701, WO2008044777, WO2008047821, US2008096877, WO2008050117, WO2008050101, WO2008059625, US2008146625, WO2008078674, WO2008079787, WO2008084043, WO2008084044, WO2008084872, WO2008089892, WO2008091770, WO2008075073, WO2008084043, WO2008084044, WO2008084872, WO2008084873, WO2008089892, WO2008091770, JP2008189659, WO2008104994, WO2008111473, WO2008116107, WO2008118718, WO2008120754, US2008280875, WO2008136428, WO2008136444, WO2008149382, WO2008154563, WO2008156174, WO2008156757, US2009030046, WO2009018065, WO2009023718, WO2009039944, WO2009042435, WO2009046784, WO2009046802, WO2009047798, WO2009063821, WO2009081782, WO2009082152, WO2009083553, WO2009091014, US2009181981, WO2009092432, WO2009099080, WO2009106203, WO2009106209, WO2009109270, WO2009125873, WO2009127544, WO2009127546, WO2009128481, WO2009133687, WO2009140624, WO2010013161, WO2010015849, WO2010018800.

In one embodiment, the compound of the formula I is administered in combination with an inhibitor of gluconeogenesis, as described, for example, in FR-225654, WO2008053446.

In one embodiment, the compound of the formula I is administered in combination with inhibitors of fructose 1,6-bisphosphatase (FBPase), for example MB-07729, CS-917 (MB-06322) or MB-07803, or those as described in WO2006023515, WO2006104030, WO2007014619, WO2007137962, WO2008019309, WO2008037628, WO2009012039, EP2058308, WO2009068467, WO2009068468.

In one embodiment, the compound of the formula I is administered in combination with modulators of glucose transporter 4 (GLUT4), for example KST-48 (D.-O. Lee et al.: Arzneim.-Forsch. Drug Res. 54 (12), 835 (2004)).

In one embodiment, the compound of the formula I is administered in combination with inhibitors of glutamine:fructose-6-phosphate amidotransferase (GFAT), as described, for example, in WO2004101528.

In one embodiment, the compound of the formula I is administered in combination with inhibitors of dipeptidyl peptidase-IV (DPP-IV), for example vildagliptin (LAF-237), sitagliptin (MK-0431), sitagliptin phosphate, saxagliptin (BMS-477118), GSK-823093, PSN-9301, SYR-322, SYR-619, TA-6666, TS-021, GRC-8200 (melogliptin), GW-825964X, KRP-104, DP-893, ABT-341, ABT-279 or another salt thereof, S-40010, S-40755, PF-00734200, BI-1356, PHX-1149, DSP-7238, alogliptin benzoate, linagliptin, melogliptin, carmegliptin, or those compounds as described in WO2003074500, WO2003106456, WO2004037169, WO200450658, WO2005037828, WO2005058901, WO2005012312, WO2005/012308, WO2006039325, WO2006058064, WO2006015691, WO2006015701, WO2006015699, WO2006015700, WO2006018117, WO2006099943, WO2006099941, JP2006160733, WO2006071752, WO2006065826, WO2006078676, WO2006073167, WO2006068163, WO2006085685, WO2006090915, WO2006104356, WO2006127530, WO2006111261, US2006890898, US2006803357, US2006303661, WO2007015767 (LY-2463665), WO2007024993, WO2007029086, WO2007063928, WO2007070434, WO2007071738, WO2007071576, WO2007077508, WO2007087231, WO2007097931, WO2007099385, WO2007100374, WO2007112347, WO2007112669, WO2007113226, WO2007113634, WO2007115821, WO2007116092, US2007259900, EP1852108, US2007270492, WO2007126745, WO2007136603, WO2007142253, WO2007148185, WO2008017670, US2008051452, WO2008027273, WO2008028662, WO2008029217, JP2008031064, JP2008063256, WO2008033851, WO2008040974, WO2008040995, WO2008060488, WO2008064107, WO2008066070, WO2008077597, JP2008156318, WO2008087560, WO2008089636, WO2008093960, WO2008096841, WO2008101953, WO2008118848, WO2008119005, WO2008119208, WO2008120813, WO2008121506, WO2008130151, WO2008131149, WO2009003681, WO2009014676, WO2009025784, WO2009027276, WO2009037719, WO2009068531, WO2009070314, WO2009065298, WO2009082134, WO2009082881, WO2009084497, WO2009093269, WO2009099171, WO2009099172, WO2009111239, WO2009113423, WO2009116067, US2009247532, WO2010000469, WO2010015664.

In one embodiment, the compound of the formula I is administered in combination with Janumet™, a solid combination of sitagliptin phosphate with metformin hydrochloride.

In one embodiment, the compound of the formula I is administered in combination with Eucreas®, a solid combination of vildagliptin with metformin hydrochloride.

In a further embodiment, the compound of the formula I is administered in combination with a solid combination of alogliptin benzoate with pioglitazone.

In one embodiment, the compound of the formula I is administered in combination with a solid combination of a salt of sitagliptin with metformin hydrochloride.

In one embodiment, the compound of the formula I is administered in combination with a combination of a DPP-IV inhibitor with omega-3 fatty acids or omega-3 fatty acid esters, as described, for example, in WO2007128801.

In one embodiment, the compound of the formula I is administered in combination with a combination of a DPP-IV inhibitor with metformin hydrochloride, as described, for example, in WO2009121945.

In one embodiment, the compound of the formula I is administered in combination with a combination of a DPP-IV inhibitor with a GPR-119 agonist, as described, for example, in WO2009123992.

In one embodiment, the compound of the formula I is administered in combination with a combination of a DPP-IV inhibitor with miglitol, as described, for example, in WO2009139362.

In one embodiment, the compound of the formula I is administered in combination with a solid combination of a salt of sitagliptin with metformin hydrochloride.

In one embodiment, the compound of the formula I is administered in combination with a solid combination of alopliptin benzoate with pioglitazone hydrochloride.

In one embodiment, the compound of the formula I is administered in combination with a substance which enhances insulin secretion, for example KCP-265 (WO2003097064), or those as described in WO2007026761, WO2008045484, US2008194617, WO2009109259, WO2009109341.

In one embodiment, the compound of the formula I is administered in combination with agonists of the glucose-dependent insulinotropic receptor (GDIR), for example APD-668.

In one embodiment of the invention, the compound of the formula I is administered in combination with an ATP citrate lyase inhibitor, for example SB-204990.

In one embodiment, the compound of the formula I is administered in combination with modulators of the sodium-dependent glucose transporter 1 and/or 2 (SGLT1, SGLT2), for example KGA-2727, T-1095, SGL-0010, AVE 2268, SAR 7226, SGL-5083, SGL-5085, SGL-5094, ISIS-388626, sergliflozin, dapagliflozin or remogliflozin etabonate, canagliflozin, or as described, for example, in WO2004007517, WO200452903, WO200452902, PCT/EP2005/005959, WO2005085237, JP2004359630, WO2005121161, WO2006018150, WO2006035796, WO2006062224, WO2006058597, WO2006073197, WO2006080577, WO2006087997, WO2006108842, WO2007000445, WO2007014895, WO2007080170, WO2007093610, WO2007126117, WO2007128480, WO2007129668, US2007275907, WO2007136116, WO2007143316, WO2007147478, WO2008001864, WO2008002824, WO2008013277, WO2008013280, WO2008013321, WO2008013322, WO2008016132, WO2008020011, JP2008031161, WO2008034859, WO2008042688, WO2008044762, WO2008046497, WO2008049923, WO2008055870, WO2008055940, WO2008069327, WO2008070609, WO2008071288, WO2008072726, WO2008083200, WO2008090209, WO2008090210, WO2008101586, WO2008101939, WO2008116179, WO2008116195, US2008242596, US2008287529, WO2009026537, WO2009049731, WO2009076550, WO2009084531, WO2009096503, WO2009100936, WO2009121939, WO2009124638, WO2009128421, WO2009135673, WO2010009197, WO2010018435, WO2010018438 or by A. L. Handlon in Expert Opin. Ther. Patents (2005) 15(11), 1531-1540.

In a further embodiment of the invention, the compound of the formula I is administered in combination with a solid combination of an SGLT inhibitor with a DPP-IV inhibitor, as described in WO2009091082.

In one embodiment, the compound of the formula I is administered in combination with a stimulator of glucose transport, as described, for example, in WO2008136392, WO2008136393.

In one embodiment, the compound of the formula I is administered in combination with inhibitors of 11-beta-hydroxysteroid dehydrogenase 1 (11β-HSD1), for example BVT-2733, JNJ-25918646, INCB-13739, INCB-20817, D10-92 ((−)-ketoconazole) or those as described, for example, in WO200190090-94, WO200343999, WO2004112782, WO200344000, WO200344009, WO2004112779, WO2004113310, WO2004103980, WO2004112784, WO2003065983, WO2003104207, WO2003104208, WO2004106294, WO2004011410, WO2004033427, WO2004041264, WO2004037251, WO2004056744, WO2004058730, WO2004065351, WO2004089367, WO2004089380, WO2004089470-71, WO2004089896, WO2005016877, WO2005063247, WO2005097759, WO2006010546, WO2006012227, WO2006012173, WO2006017542, WO2006034804, WO2006040329, WO2006051662, WO2006048750, WO2006049952, WO2006048331, WO2006050908, WO2006024627, WO2006040329, WO2006066109, WO2006074244, WO2006078006, WO2006106423, WO2006132436, WO2006134481, WO2006134467, WO2006135795, WO2006136502, WO2006138508, WO2006138695, WO2006133926, WO2007003521, WO2007007688, US2007066584, WO2007029021, WO2007047625, WO2007051811, WO2007051810, WO2007057768, WO2007058346, WO2007061661, WO2007068330, WO2007070506, WO2007087150, WO2007092435, WO2007089683, WO2007101270, WO2007105753, WO2007107470, WO2007107550, WO2007111921, US2007207985, US2007208001, WO2007115935, WO2007118185, WO2007122411, WO2007124329, WO2007124337, WO2007124254, WO2007127688, WO2007127693, WO2007127704, WO2007127726, WO2007127763, WO2007127765, WO2007127901, US2007270424, JP2007291075, WO2007130898, WO2007135427, WO2007139992, WO2007144394, WO2007145834. WO2007145835, WO2007146761, WO2008000950, WO2008000951, WO2008003611, WO2008005910, WO2008006702, WO2008006703, WO2008011453, WO2008012532, WO2008024497, WO2008024892, WO2008032164, WO2008034032, WO2008043544, WO2008044656, WO2008046758, WO2008052638, WO2008053194, WO2008071169, WO2008074384, WO2008076336, WO2008076862, WO2008078725, WO2008087654, WO2008088540, WO2008099145, WO2008101885, WO2008101886, WO2008101907, WO2008101914, WO2008106128, WO2008110196, WO2008119017, WO2008120655, WO2008127924, WO2008130951, WO2008134221, WO2008142859, WO2008142986, WO2008157752, WO2009001817, WO2009010416, WO2009017664, WO2009020140, WO2009023180, WO2009023181, WO2009023664, WO2009026422, WO2009038064, WO2009045753, WO2009056881, WO2009059666, WO2009061498, WO2009063061, WO2009070497, WO2009074789, WO2009075835, WO2009088997, WO2009090239, WO2009094169, WO2009098501, WO2009100872, WO2009102428, WO2009102460, WO2009102761, WO2009106817, WO2009108332, WO2009112691, WO2009112845, WO2009114173, WO2009117109, US2009264401, WO2009118473, WO2009131669, WO2009132986, WO2009134384, WO2009134387, WO2009134392, WO2009134400, WO2009135581, WO2009138386, WO2010006940, WO2010010157, WO2010010174, WO2010011917.

In one embodiment, the compound of the formula I is administered in combination with inhibitors of protein tyrosine phosphatase-1B (PTP-1B), as described, for example, in WO200119830-31, WO200117516, WO2004506446, WO2005012295, WO2005116003, WO2005116003, WO2006007959, DE 10 2004 060542.4, WO2007009911, WO2007028145, WO2007067612-615, WO2007081755, WO2007115058, US2008004325, WO2008033455, WO2008033931, WO2008033932, WO2008033934, WO2008089581, WO2008148744, WO2009032321, WO2009109999, WO2009109998.

In a further embodiment, the compound of the formula I is administered in combination with stimulators of tyrosine kinase B (Trk-B), as described, for example, in WO2010014613.

In a further embodiment, the compound of the formula I is administered in combination with beta 3 agonists (also called beta-3 adrenoceptor agonists), as described, for example, in Physiol. Behav. 2004 Sep. 15; 82(2-3):489-96, J Clin Invest (1998) 101: 2387-93, Curr. Pharma. Des. 2001 September; 7(14):1433-49, Bioorganic & Medicinal Chemistry Letters volume 14, number 13, Jul. 5, 2004, pages 3525-3529 (BMS-201620).

In one embodiment of the invention, the compound of the formula I is administered in combination with an agonist of GPR109A (HM74A receptor agonists; NAR agonists (nicotinic acid receptor agonists)), for example nicotinic acid or extended release niacin in conjunction with MK-0524A (laropiprant) or MK-0524, or those compounds as described in WO2004041274, WO2006045565, WO2006045564, WO2006069242, WO2006085108, WO2006085112, WO2006085113, WO2006124490, WO2006113150, WO2007002557, WO2007017261, WO2007017262, WO2007017265, WO2007015744, WO2007027532, WO2007092364, WO2007120575, WO2007134986, WO2007150025, WO2007150026, WO2008016968, WO2008051403, WO2008086949, WO2008091338, WO2008097535, WO2008099448, US2008234277, WO2008127591.

In another embodiment of the invention, the compound of the formula I is administered in combination with a solid combination of niacin with simvastatin.

In another embodiment of the invention, the compound of the formula I is administered in combination with nicotinic acid or "extended release niacin" in conjunction with MK-0524A (laropiprant).

In a further embodiment of the invention, the compound of the formula I is administered in combination with nicotinic acid or "extended release niacin" in conjunction with MK-0524A (laropiprant) and with simvastatin.

In one embodiment of the invention, the compound of the formula I is administered in combination with nicotinic acid or another nicotinic acid receptor agonist and a prostaglandin DP receptor antagonist, for example those as described in WO2008039882.

In another embodiment of the invention, the compound of the formula I is administered in combination with a solid combination of niacin with meloxicam, as described, for example, in WO2009149056.

In another embodiment of the invention, the compound of the formula I is administered in combination with an agonist of GPR116, as described, for example, in WO2006067531, WO2006067532.

In one embodiment, the compound of the formula I is administered in combination with modulators of GPR40, as described, for example, in WO2007013689, WO2007033002, WO2007106469, US2007265332, WO2007123225, WO2007131619, WO2007131620, WO2007131621, US2007265332, WO2007131622, WO2007136572, WO2008001931, WO2008030520, WO2008030618, WO2008054674, WO2008054675, WO2008066097, US2008176912, WO2008130514, WO2009038204, WO2009039942, WO2009039943, WO2009048527, WO2009054479, WO2009058237, WO2009111056, WO2010012650.

In one embodiment, the compound of the formula I is administered in combination with modulators of GPR119 (G-protein-coupled glucose-dependent insulinotropic receptor), for example PSN-119-1, PSN-821, PSN-119-2, MBX-2982 or those as described, for example, in WO2004065380, WO2005061489 (PSN-632408), WO2006083491, WO2007003960-62 and WO2007003964, WO2007035355, WO2007116229, WO2007116230, WO2008005569, WO2008005576, WO2008008887, WO2008008895, WO2008025798, WO2008025799, WO2008025800, WO2008070692, WO2008076243, WO200807692, WO2008081204, WO2008081205, WO2008081206, WO2008081207, WO2008081208, WO2008083238, WO2008085316, WO2008109702, WO2008130581, WO2008130584, WO2008130615, WO2008137435, WO2008137436, WO2009012275, WO2009012277, WO2009014910, WO2009034388, WO2009038974, WO2009050522, WO2009050523, WO2009055331, WO2009105715, WO2009105717, WO2009105722, WO2009106561, WO2009106565, WO2009117421, WO2009125434, WO2009126535, WO2009129036, US2009286812, WO2009143049, WO2009150144, WO2010001166, WO2010004343, WO2010004344, WO2010004345, WO2010004346, WO2010004347, WO2010004348, WO2010008739, WO2010006191, WO2010009183, WO2010009195, WO2010009207, WO2010009208, WO2010014593.

In a further embodiment, the compound of the formula I is administered in combination with modulators of GPR120, as described, for example, in EP1688138, WO2008066131, WO2008066131, WO2008103500, WO2008103501, WO2008139879, WO2009038204, WO2009147990, WO2010008831.

In another embodiment, the compound of the formula I is administered in combination with antagonists of GPR105, as described, for example, in WO2009000087, WO2009070873.

In a further embodiment, the compound of the formula I is administered in combination with agonists of GPR43, for example ESN-282.

In one embodiment, the compound of the formula I is administered in combination with inhibitors of hormone-sensitive lipase (HSL) and/or phospholipases, as described, for example, in WO2005073199, WO2006074957, WO2006087309, WO2006111321, WO2007042178, WO2007119837, WO2008122352, WO2008122357, WO2009009287.

In one embodiment, the compound of the formula I is administered in combination with inhibitors of endothelial lipase, as described, for example, in WO2007110216.

In one embodiment, the compound of the formula I is administered in combination with a phospholipase A2 inhibitor, for example darapladib or A-002, or those as described in WO2008048866, WO20080488867, US2009062369.

In one embodiment, the compound of the formula I is administered in combination with myricitrin, a lipase inhibitor (WO2007119827).

In one embodiment, the compound of the formula I is administered in combination with an inhibitor of glycogen synthase kinase-3 beta (GSK-3 beta), as described, for example, in US2005222220, WO2005085230, WO2005111018, WO2003078403, WO2004022544, WO2003106410, WO2005058908, US2005038023, WO2005009997, US2005026984, WO2005000836, WO2004106343, EP1460075, WO2004014910, WO2003076442, WO2005087727, WO2004046117, WO2007073117, WO2007083978, WO2007120102, WO2007122634, WO2007125109, WO2007125110, US2007281949, WO2008002244, WO2008002245, WO2008016123, WO2008023239, WO2008044700, WO2008056266, WO2008057940, WO2008077138, EP1939191, EP1939192, WO2008078196, WO2008094992, WO2008112642, WO2008112651, WO2008113469, WO2008121063, WO2008121064, EP-1992620, EP-1992621, EP1992624, EP-1992625, WO2008130312, WO2009007029, EP2020232, WO2009017452, WO2009035634, WO2009035684, WO2009038385, WO2009095787, WO2009095788, WO2009095789, WO2009095792, WO2009145814, US2009291982, WO2009154697, WO2009156857, WO2009156859, WO2009156860, WO2009156861, WO2009156863, WO2009156864, WO2009156865, WO2010013168, WO2010014794.

In one embodiment, the compound of the formula I is administered in combination with an inhibitor of phosphoenolpyruvate carboxykinase (PEPCK), for example those as described in WO2004074288.

In one embodiment, the compound of the formula I is administered in combination with an inhibitor of phosphoinositide kinase-3 (PI3K), for example those as described in WO2008027584, WO2008070150, WO2008125833, WO2008125835, WO2008125839, WO2009010530, WO2009026345, WO2009071888, WO2009071890, WO2009071895.

In one embodiment, the compound of the formula I is administered in combination with an inhibitor of serum/glucocorticoid-regulated kinase (SGK), as described, for example, in WO2006072354, WO2007093264, WO2008009335, WO2008086854, WO2008138448.

In one embodiment, the compound of the formula I is administered in combination with a modulator of the glucocorticoid receptor, as described, for example, in WO2008057855, WO2008057856, WO2008057857, WO2008057859, WO2008057862, WO2008059867, WO2008059866, WO2008059865, WO2008070507, WO2008124665, WO2008124745, WO2008146871, WO2009015067, WO2009040288, WO2009069736, WO2009149139.

In one embodiment, the compound of the formula I is administered in combination with a modulator of the mineralocorticoid receptor (MR), for example drospirenone, or those as described in WO2008104306, WO2008119918.

In one embodiment, the compound of the formula I is administered in combination with an inhibitor of protein kinase C beta (PKC beta), for example ruboxistaurin, or those as described in WO2008096260, WO2008125945.

In one embodiment, the compound of the formula I is administered in combination with an inhibitor of protein kinase D, for example doxazosin (WO2008088006).

In a further embodiment, the compound of the formula I is administered in combination with an activator/modulator of the AMP-activated protein kinase (AMPK), as described, for example, in WO2007062568, WO2008006432, WO2008016278, WO2008016730, WO2008020607, WO2008083124, WO2008136642, WO2009019445, WO2009019446, WO2009019600, WO2009028891, WO2009065131, WO2009076631, WO2009079921, WO2009100130, WO2009124636, WO2009135580, WO2009152909.

In one embodiment, the compound of the formula I is administered in combination with an inhibitor of ceramide kinase, as described, for example, in WO2007112914, WO2007149865.

In a further embodiment, the compound of the formula I is administered in combination with an inhibitor of MAPK-interacting kinase 1 or 2 (MNK1 or 2), as described, for example, in WO2007104053, WO2007115822, WO2008008547, WO2008075741.

In one embodiment, the compound of the formula I is administered in combination with inhibitors of "I-kappaB kinase" (IKK inhibitors), as described, for example, in WO2001000610, WO2001030774, WO2004022057, WO2004022553, WO2005097129, WO2005113544, US2007244140, WO2008099072, WO2008099073, WO2008099073, WO2008099074, WO2008099075, WO2009056693, WO2009075277, WO2009089042, WO2009120801.

In another embodiment, the compound of the formula I is administered in combination with inhibitors of NF-kappaB (NFKB) activation, for example salsalate.

In a further embodiment, the compound of the formula I is administered in combination with inhibitors of ASK-1 (apoptosis signal-regulating kinase 1), as described, for example, in WO2008016131, WO2009123986.

In one embodiment of the invention, the compound of the formula I is administered in combination with an HMG-CoA reductase inhibitor such as simvastatin, fluvastatin, pravastatin, lovastatin, atorvastatin, cerivastatin, rosuvastatin, pitavastatin, L-659699, BMS-644950, NCX-6560, or those as described in US2007249583, WO2008083551, WO2009054682.

In a further embodiment of the invention, the compound of the formula I is administered in combination with a farnesoid X receptor (FXR) modulator, for example WAY-362450 or those as described in WO2003099821, WO2005056554, WO2007052843, WO2007070796, WO2007092751, JP2007230909, WO2007095174, WO2007140174, WO2007140183, WO2008000643, WO2008002573, WO2008025539, WO2008025540, JP2008214222, JP2008273847, WO2008157270, US2008299118, US2008300235, WO2009005998, WO2009012125, WO2009027264, WO2009062874, US2009131409, US2009137554, US2009163552, WO2009127321, EP2128158.

In another embodiment of the invention, the compound of the formula I is administered in combination with a ligand of the liver X receptor (LXR), as described, for example, in WO2007092965, WO2008041003, WO2008049047, WO2008065754, WO2008073825, US2008242677, WO2009020683, US2009030082, WO2009021868, US2009069373, WO2009024550, WO2009040289, WO2009086123, WO2009086129, WO2009086130, WO2009086138, WO2009107387, US2009247587, WO2009133692, WO2008138438, WO2009144961, WO2009150109.

In one embodiment of the invention, the compound of the formula I is administered in combination with a fibrate, for example fenofibrate, clofibrate, bezafibrate, or those as described in WO2008093655.

In one embodiment of the invention, the compound of the formula I is administered in combination with fibrates, for example the choline salt of fenofibrate (SLV-348; Trilipix™).

In one embodiment of the invention, the compound of the formula I is administered in combination with fibrates, for example the choline salt of fenofibrate (Trilipix™) and an HMG-CoA reductase inhibitor, for example rosuvastatin.

In a further embodiment of the invention, the compound of the formula I is administered in combination with bezafibrate and diflunisal.

In a further embodiment of the invention, the compound of the formula I is administered in combination with a solid combination of fenofibrate or a salt thereof with simvastatin, rosuvastatin, fluvastatin, lovastatin, cerivastatin, pravastatin, pitavastatin or atorvastatin.

In a further embodiment of the invention, the compound of the formula I is administered in combination with Synordia (R), a solid combination of fenofibrate with metformin.

In another embodiment of the invention, the compound of the formula I is administered in combination with a solid combination of metformin with an MTP inhibitor, as described in WO2009090210.

In one embodiment of the invention, the compound of the formula I is administered in combination with a cholesterol reabsorption inhibitor, for example ezetimibe, tiqueside, pamaqueside, FM-VP4 (sitostanol/campesterol ascorbyl phosphate; Forbes Medi-Tech, WO2005042692, WO2005005453), MD-0727 (Microbia Inc., WO2005021497, WO2005021495) or with compounds as described in WO2002066464, WO2005000353 (Kotobuki Pharmaceutical Co. Ltd.) or WO2005044256 or WO2005062824 (Merck & Co.) or WO2005061451 and WO2005061452 (AstraZeneca AB) and WO2006017257 (Phenomix) or WO2005033100 (Lipideon Biotechnology AG), or as described in WO2002050060, WO2002050068, WO2004000803, WO2004000804, WO2004000805, WO2004087655, WO2004097655, WO2005047248, WO2006086562, WO2006102674, WO2006116499, WO2006121861, WO2006122186, WO2006122216, WO2006127893, WO2006137794, WO2006137796, WO2006137782, WO2006137793, WO2006137797, WO2006137795, WO2006137792, WO2006138163, WO2007059871, US2007232688, WO2007126358, WO2008033431, WO2008033465, WO2008052658, WO2008057336, WO2008085300, WO2008104875, US2008280836, WO2008108486.

In one embodiment of the invention, the compound of the formula I is administered in combination with an NPC1 L1 antagonist, for example those as described in WO2008033464, WO2008033465.

In one embodiment of the invention, the compound of the formula I is administered in combination with Vytorin™, a solid combination of ezetimibe with simvastatin.

In one embodiment of the invention, the compound of the formula I is administered in combination with a solid combination of ezetimibe with atorvastatin.

In one embodiment of the invention, the compound of the formula I is administered in combination with a solid combination of ezetimibe with fenofibrate.

In one embodiment of the invention, the further active ingredient is a diphenylazetidinone derivative, as described, for example, in U.S. Pat. No. 6,992,067 or U.S. Pat. No. 7,205,290.

In a further embodiment of the invention, the further active ingredient is a diphenylazetidinone derivative, as described, for example, in U.S. Pat. No. 6,992,067 or U.S. Pat. No. 7,205,290, combined with a statin, for example simvastatin, fluvastatin, pravastatin, lovastatin, cerivastatin, atorvastatin, pitavastatin or rosuvastatin.

In one embodiment of the invention, the compound of the formula I is administered in combination with a solid combination of lapaquistat, a squalene synthase inhibitor, with atorvastatin.

In a further embodiment of the invention, the compound of the formula I is administered in combination with a conjugate consisting of the HMG-CoA reductase inhibitor atorvastatin with the renin inhibitor aliskiren (WO2009090158).

In one embodiment of the invention, the compound of the formula I is administered in combination with a CETP inhibitor, for example torcetrapib, anacetrapib or JTT-705 (dalcetrapib), or those as described in WO2006002342, WO2006010422, WO2006012093, WO2006073973, WO2006072362, WO2007088996, WO2007088999, US2007185058, US2007185113, US2007185154, US2007185182, WO2006097169, WO2007041494, WO2007090752, WO2007107243, WO2007120621, US2007265252, US2007265304, WO2007128568, WO2007132906, WO2008006257, WO2008009435, WO2008018529, WO2008058961, WO2008058967, WO2008059513, WO2008070496, WO2008115442, WO2008111604, WO2008129951, WO2008141077, US2009118287, WO2009062371, WO2009071509.

In one embodiment of the invention, the compound of the formula I is administered in combination with bile acid reabsorption inhibitors (inhibitors of the intestinal bile acid transporter (IBAT)) (see, for example, U.S. Pat. No. 6,245,744, U.S. Pat. No. 6,221,897 or WO00/61568), for example HMR 1741, or those as described in DE 10 2005 033099.1 and DE 10 2005 033100.9, DE 10 2006 053635, DE 10 2006 053637, WO2007009655-56, WO2008058628, WO2008058629, WO2008058630, WO2008058631.

In one embodiment, the compound of the formula I is administered in combination with agonists of GPBAR1 (G-protein-coupled bile acid receptor 1; TGR5), for example INT-777 or those as described, for example, in US20060199795, WO2007110237, WO2007127505, WO2008009407, WO2008067219, WO2008067222, FR2908310, WO2008091540, WO2008097976, US2009054304, WO2009026241, WO2009146772, WO2010014739, WO2010014836.

In one embodiment, the compound of the formula I is administered in combination with modulators of histone deacetylase, for example ursodeoxycholic acid, as described in WO2009011420.

In one embodiment, the compound of the formula I is administered in combination with inhibitors/modulators of the TRPM5 channel (TRP cation channel M5), as described, for example, in WO2008097504, WO2009038722.

In one embodiment, the compound of the formula I is administered in combination with inhibitors/modulators of the TRPA1 channel (TRP cation channel A1), as described, for example, in US2009176883, WO2009089083, WO2009144548.

In one embodiment, the compound of the formula I is administered in combination with inhibitors/modulators of the TRPV3 channel (TRP cation channel V3), as described, for example, in WO2009084034, WO2009130560.

In one embodiment of the invention, the compound of the formula I is administered in combination with a polymeric bile acid adsorber, for example cholestyramine, colesevelam hydrochloride.

In one embodiment of the invention, the compound of the formula I is administered in combination with colesevelam hydrochloride and metformin or a sulfonylurea or insulin.

In one embodiment of the invention, the compound of the formula I is administered in combination with tocotrienol and insulin or an insulin derivative.

In one embodiment of the invention, the compound of the formula I is administered in combination with a chewing gum comprising phytosterols (Reductol™)

In one embodiment of the invention, the compound of the formula I is administered in combination with an inhibitor of the microsomal triglyceride transfer protein (MTP inhibitor), for example implitapide, BMS-201038, R-103757, AS-1552133, SLx-4090, AEGR-733, JTT-130, or those as described in WO2005085226, WO2005121091, WO2006010423, WO2006113910, WO2007143164, WO2008049806, WO2008049808, WO2008090198, WO2008100423, WO2009014674.

In a further embodiment of the invention, the compound of the formula I is administered in combination with a combination of a cholesterol absorption inhibitor, for example ezetimibe, and an inhibitor of the triglyceride transfer protein (MTP inhibitor), for example implitapide, as described in WO2008030382 or in WO2008079398.

In one embodiment of the invention, the compound of the formula I is administered in combination with an active antihypertriglyceridemic ingredient, for example those as described in WO2008032980.

In another embodiment of the invention, the compound of the formula I is administered in combination with an antagonist of the somatostatin 5 receptor (SST5 receptor), for example those as described in WO2006094682.

In one embodiment of the invention, the compound of the formula I is administered in combination with an ACAT inhibitor, for example avasimibe, SMP-797 or KY-382, or those as described in WO2008087029, WO2008087030, WO2008095189, WO2009030746, WO2009030747, WO2009030750, WO2009030752, WO2009070130, WO2009081957, WO2009081957.

In a further embodiment of the invention, the compound of the formula I is administered in combination with an inhibitor of liver carnitine palmitoyltransferase-1 (L-CPT1), as described, for example, in WO2007063012, WO2007096251 (ST-3473), WO2008015081, US2008103182, WO2008074692, WO2008145596, WO2009019199, WO2009156479, WO2010008473.

In another embodiment of the invention, the compound of the formula I is administered in combination with an inhibitor of carnitin O-palmitoyltransferase II (CPT2), as described, for example, in US2009270500, US2009270505, WO2009132978, WO2009132979.

In a further embodiment of the invention, the compound of the formula I is administered in combination with a modulator of serine palmitoyltransferase (SPT), as described, for example, in WO2008031032, WO2008046071, WO2008083280, WO2008084300.

In one embodiment of the invention, the compound of the formula I is administered in combination with a squalene synthetase inhibitor, for example BMS-188494, TAK-475 (lapaquistat acetate), or as described in WO2005077907, JP2007022943, WO2008003424, WO2008132846, WO2008133288, WO2009136396.

In one embodiment of the invention, the compound of the formula I is administered in combination with ISIS-301012 (mipomersen), an antisense oligonucleotide which is capable of regulating the apolipoprotein B gene.

In one embodiment of the invention, the compound of the formula I is administered in combination with apolipoprotein (ApoB) SNALP, a therapeutic product which comprises an siRNA (directed against the ApoB gene).

In one embodiment of the invention, the compound of the formula I is administered in combination with a stimulator of the ApoA-1 gene, as described, for example, in WO2008092231.

In one embodiment of the invention, the compound of the formula I is administered in combination with a modulator of the synthesis of apolipoprotein C-III, for example ISIS-APOCIIIRx.

In one embodiment of the invention, the compound of the formula I is administered in combination with an LDL receptor inducer (see U.S. Pat. No. 6,342,512), for example HMR1171, HMR1586, or those as described in WO2005097738, WO2008020607.

In another embodiment of the invention, the compound of the formula I is administered in combination with an HDL cholesterol-elevating agent, for example those as described in WO2008040651, WO2008099278, WO2009071099, WO2009086096, US2009247550.

In one embodiment of the invention, the compound of the formula I is administered in combination with an ABCA1 expression enhancer, as described, for example, in WO2006072393, WO2008062830, WO2009100326.

In one embodiment of the invention, the compound of the formula I is administered in combination with a lipoprotein lipase modulator, for example ibrolipim (NO-1886).

In one embodiment of the invention, the compound of the formula I is administered in combination with a lipoprotein (a) antagonist, for example gemcabene (CI-1027).

In one embodiment of the invention, the compound of the formula I is administered in combination with a lipase inhibitor, for example orlistat or cetilistat (ATL-962).

In one embodiment of the invention, the compound of the formula I is administered in combination with an adenosine A1 receptor agonist (adenosine A1 R), for example CVT-3619 or those as described, for example, in EP1258247, EP1375508, WO2008028590, WO2008077050, WO2009050199, WO2009080197, WO2009100827, WO2009112155.

In one embodiment of the invention, the compound of the formula I is administered in combination with an adenosine A2B receptor agonist (adenosine A2B R), for example ATL-801.

In another embodiment of the invention, the compound of the formula I is administered in combination with a modulator of adenosine A2A and/or adenosine A3 receptors, as described, for example, in WO2007111954, WO2007121918, WO2007121921, WO2007121923, WO2008070661, WO2009010871.

In a further embodiment of the invention, the compound of the formula I is administered in combination with a ligand of the adenosine A1/A2B receptors, as described, for example, in WO2008064788, WO2008064789, WO2009080198, WO2009100827, WO2009143992.

In one embodiment of the invention, the compound of the formula I is administered in combination with an adenosine A2B receptor antagonist (adenosine A2B R), as described in US2007270433, WO2008027585, WO2008080461, WO2009037463, WO2009037467, WO2009037468, WO2009118759.

In one embodiment, the compound of the formula I is administered in combination with inhibitors of acetyl-CoA carboxylase (ACC1 and/or ACC2), for example those as described in WO199946262, WO200372197, WO2003072197, WO2005044814, WO2005108370, JP2006131559, WO2007011809, WO2007011811, WO2007013691, WO2007095601-603, WO2007119833, WO2008065508, WO2008069500, WO2008070609, WO2008072850, WO2008079610, WO2008088688, WO2008088689, WO2008088692, US2008171761, WO2008090944, JP2008179621, US2008200461, WO2008102749, WO2008103382, WO2008121592, WO2009082346, US2009253725, JP2009196966, WO2009144554, WO2009144555, WO2010003624, WO2010002010.

In another embodiment, the compound of the formula I is administered in combination with modulators of microsomal acyl-CoA:glycerol-3-phosphate acyltransferase 3 (GPAT3, described in WO2007100789) or with modulators of microsomal acyl-CoA:glycerol-3-phosphate acyltransferase 4 (GPAT4, described in WO2007100833) or with modulators of mitochondrial glycerol-3-phosphate O-acyltransferase, described in WO2010005922.

In a further embodiment, the compound of the formula I is administered in combination with modulators of xanthine oxidoreductase (XOR).

In another embodiment, the compound of the formula I is administered in combination with inhibitors of soluble epoxide hydrolase (sEH), as described, for example, in WO2008051873, WO2008051875, WO2008073623, WO2008094869, WO2008112022, WO2009011872, WO2009049154, WO2009049157, WO2009049165, WO2009073772, WO2009097476, WO2009111207, WO2009129508, WO2009151800.

In a further embodiment, the compound of the formula I is administered in combination with CART modulators (see "Cocaine-amphetamine-regulated transcript influences energy metabolism, anxiety and gastric emptying in mice" Asakawa, A. et al.: Hormone and Metabolic Research (2001), 33(9), 554-558);

NPY antagonists, for example 4-[(4-aminoquinazolin-2-ylamino)methyl]-cyclohexylmethylnaphthalene-1-sulfonamide hydrochloride (CGP 71683A) or velneperit or those as described in WO2009110510;

NPY-5 receptor antagonists/receptor modulators, such as L-152804 or the compound "NPY-5-BY" from Banyu, or as described, for example, in WO2006001318, WO2007103295, WO2007125952, WO2008026563, WO2008026564, WO2008052769, WO2008092887, WO2008092888, WO2008092891, WO2008129007, WO2008134228, WO2009054434, WO2009095377, WO2009131096;

NPY-4 receptor antagonists, as described, for example, in WO2007038942;

NPY-2 receptor antagonists/modulators, as described, for example, in WO2007038943, WO2009006185, US2009099199, US2009099243, US2009099244, WO2009079593, WO2009079597;

peptide YY 3-36 (PYY3-36) or analogous compounds, for example CJC-1682 (PYY3-36 conjugated with human serum albumin via Cys34) or CJC-1643 (derivative of PYY3-36, which is conjugated in vivo to serum albumin), or those as described in WO2005080424, WO2006095166, WO2008003947, WO2009080608;

NPY-2 receptor agonists, as described, for example, in WO2009080608;

derivatives of the peptide obestatin, as described by WO2006096847;

CB1R (cannabinoid receptor 1) antagonists/inverse agonists, for example rimonabant, surinabant (SR147778), SLV-319 (ibipinabant), AVE-1625, taranabant (MK-0364) or salts thereof, otenabant (CP-945,598), rosonabant, V-24343 or those compounds as described in, for example, EP 0656354, WO 00/15609, WO2001/64632-64634, WO 02/076949, WO2005080345, WO2005080328, WO2005080343, WO2005075450, WO2005080357, WO200170700, WO2003026647-48, WO200302776, WO2003040107, WO2003007887, WO2003027069, U.S. Pat. No. 6,509,367, WO200132663, WO2003086288, WO2003087037, WO2004048317, WO2004058145, WO2003084930, WO2003084943, WO2004058744, WO2004013120, WO2004029204, WO2004035566, WO2004058249, WO2004058255, WO2004058727, WO2004069838, US20040214837, US20040214855, US20040214856, WO2004096209, WO2004096763, WO2004096794, WO2005000809, WO2004099157, US20040266845, WO2004110453, WO2004108728, WO2004000817, WO2005000820, US20050009870, WO200500974, WO2004111033-34, WO200411038-39, WO2005016286, WO2005007111, WO2005007628, US20050054679, WO2005027837, WO2005028456, WO2005063761-62, WO2005061509, WO2005077897, WO2006018662, WO2006047516, WO2006060461, WO2006067428, WO2006067443, WO2006087480, WO2006087476, WO2006100208, WO2006106054, WO2006111849, WO2006113704, WO2007009705, WO2007017124, WO2007017126, WO2007018459, WO2007018460, WO2007016460, WO2007020502, WO2007026215, WO2007028849, WO2007031720, WO2007031721, WO2007036945, WO2007038045, WO2007039740, US20070015810, WO2007046548, WO2007047737, WO2007057687, WO2007062193, WO2007064272, WO2007079681, WO2007084319, WO2007084450, WO2007086080, EP1816125, US2007213302, WO2007095513, WO2007096764, US2007254863, WO2007119001, WO2007120454, WO2007121687, WO2007123949, US2007259934, WO2007131219, WO2007133820, WO2007136571, WO2007136607, WO2007136571, U.S. Pat. No. 7,297,710, WO2007138050, WO2007139464, WO2007140385, WO2007140439, WO2007146761, WO2007148061, WO2007148062, US2007293509, WO2008004698, WO2008017381, US2008021031, WO2008024284, WO2008031734, WO2008032164, WO2008034032, WO2008035356, WO2008036021, WO2008036022, WO2008039023, WO2998043544, WO2008044111, WO2008048648, EP1921072-A1, WO2008053341, WO2008056377, WO2008059207, WO2008059335, WO2008062424, WO2008068423, WO2008068424, WO2008070305, WO2008070306, WO2008074816, WO2008074982, WO2008075012, WO2008075013, WO2008075019, WO2008075118, WO2008076754, WO2008081009, WO2008084057, EP1944295, US2008090809, US2008090810, WO2008092816, WO2008094473, WO2008094476, WO2008099076, WO2008099139, WO2008101995, US2008207704, WO2008107179, WO2008109027, WO2008112674, WO2008115705, WO2008118414, WO2008119999, WO200812000, WO2008121257, WO2008127585, WO2008129157, WO2008130616, WO2008134300, US2008262066, US2008287505, WO2009005645, WO2009005646, WO2009005671, WO2009023292, WO2009023653, WO2009024819, WO2009033125, EP2042175, WO2009053548WO2009053553, WO2009054923, WO2009054929, WO2009059264, WO2009073138, WO2009074782, WO2009075691, WO2009078498, WO2009087285, WO2009074782, WO2009097590, WO2009097995, WO2009097996, WO2009097998, WO2009097999, WO2009098000, WO2009106708, US2009239909, WO2009118473, US2009264436, US2009264476, WO2009130234, WO2009131814, WO2009131815, US2009286758, WO2009141532, WO2009141533, WO2009153569, WO2010003760, WO2010012437, WO2010019762;

cannabinoid receptor 1/cannabinoid receptor 2 (CB1/CB2) modulating compounds, for example delta-9-tetrahydrocannabivarin, or those as described, for example, in WO2007001939, WO2007044215, WO2007047737, WO2007095513, WO2007096764, WO2007112399, WO2007112402, WO2008122618, WO2009007697, WO2009012227, WO2009087564, WO2009093018, WO2009095752, WO2009120660, WO2010012964;

cannabinoid receptor 2 (CB2) modulating compounds, for example those as described, for example, in WO2008063625, WO2008157500, WO2009004171, WO2009032754, WO2009055357, WO2009061652, WO2009063495, WO2009067613, WO2009114566;

modulators of FAAH (fatty acid amide hydrolase), as described, for example, in WO2007140005, WO2008019357, WO2008021625, WO2008023720, WO2008030532, WO2008129129, WO2008145839, WO2008145843, WO2008147553, WO2008153752, WO2009011904, WO2009048101, WO2009084970, WO2009105220, WO2009109504, WO2009109743, WO2009117444, WO2009127944, WO2009138416, WO2009151991, WO2009152025, WO2009154785, WO2010005572, WO2010017079;

inhibitors of fatty acid synthase (FAS), as described, for example, in WO2008057585, WO2008059214, WO2008075064, WO2008075070, WO2008075077, WO2009079860;

inhibitors of LCE (long chain fatty acid elongase)/long chain fatty acid CoA ligase, as described, for example, in WO2008120653, WO2009038021, WO2009044788, WO2009081789, WO2009099086;

vanilloid-1 receptor modulators (modulators of TRPV1), as described, for example, in WO2007091948, WO2007129188, WO2007133637, WO2008007780, WO2008010061, WO2008007211, WO2008010061, WO2008015335, WO2008018827, WO2008024433, WO2008024438, WO2008032204, WO2008050199, WO2008059339, WO2008059370, WO2008066664, WO2008075150, WO2008090382, WO2008090434, WO2008093024, WO2008107543, WO2008107544, WO2008110863, WO2008125295, WO2008125296, WO2008125337, WO2008125342, WO2008132600, WO2008133973, WO2009010529, WO2009010824, WO2009016241, WO2009023539, WO2009038812, WO2009050348, WO2009055629, WO2009055749, WO2009064449, WO2009081222, WO2009089057, WO2009109710WO2009112677, WO2009112678, WO2009112679, WO2009121036, WO2009124551, WO2009136625, WO2010002209;

modulators, ligands, antagonists or inverse agonists of the opioid receptors, for example GSK-982 or those as described, for example, in WO2007047397, WO2008021849, WO2008021851, WO2008032156, WO2008059335, WO2008125348, WO2008125349, WO2008142454, WO2009030962, WO2009103552, WO2009115257;

modulators of the "orphan opioid (ORL-1) receptor", as described, for example, in US2008249122, WO2008089201;

agonists of the prostaglandin receptor, for example bimatoprost or those compounds as described in WO2007111806;

MC4 receptor agonists (melanocortin-4 receptor agonists, MC4R agonists, for example N-[2-(3a-benzyl-2-methyl-3-oxo-2,3,3a,4,6,7-hexahydropyrazolo[4,3-c]pyridin-5-yl)-1-(4-chlorophenyl)-2-oxoethyl]-1-amino-1,2,3,4-tetrahydronaphthalene-2-carboxamide; (WO 01/91752)) or LB53280, LB53279, LB53278 or THIQ, MB243, RY764, CHIR-785, PT-141, MK-0493, or those as described in WO2005060985, WO2005009950, WO2004087159, WO2004078717, WO2004078716, WO2004024720, US20050124652, WO2005051391, WO2004112793, WOUS20050222014, US20050176728, US20050164914, US20050124636, US20050130988, US20040167201, WO2004005324, WO2004037797, WO2004089307, WO2005042516, WO2005040109, WO2005030797, US20040224901, WO200501921, WO200509184, WO2005000339, EP1460069, WO2005047253, WO2005047251, WO2005118573, EPI 538159, WO2004072076, WO2004072077, WO2006021655-57, WO2007009894, WO2007015162, WO2007041061, WO2007041052, JP2007131570, EP-1842846, WO2007096186, WO2007096763, WO2007141343, WO2008007930, WO2008017852, WO2008039418, WO2008087186, WO2008087187, WO2008087189, WO2008087186WO2008087190, WO2008090357, WO2008142319, WO2009015867, WO2009061411, US2009076029, US2009131465, WO2009071101, US2009305960, WO2009144432, WO2009151383, WO2010015972;

MC4 receptor modulators (melanocortin-4 receptor modulators), as described, for example, in WO2009010299, WO2009074157;

orexin receptor 1 antagonists (OX1R antagonists), orexin receptor 2 antagonists (OX2R antagonists) or mixed OX1R/OX2R antagonists (e.g. 1-(2-methylbenzoxazol-6-yl)-3-[1,5] naphthyridin-4-ylurea hydrochloride (SB-334867-A), or those as described, for example, in WO200196302, WO200185693, WO2004085403, WO2005075458, WO2006067224, WO2007085718, WO2007088276, WO2007116374, WO2007122591, WO2007126934, WO2007126935, WO2008008517, WO2008008518, WO2008008551, WO2008020405, WO2008026149, WO2008038251, US2008132490, WO2008065626, WO2008078291, WO2008087611, WO2008081399, WO2008108991, WO2008107335, US2008249125, WO2008147518, WO2008150364, WO2009003993, WO2009003997, WO2009011775, WO2009016087, WO2009020642, WO2009058238, US2009186920, US2009203736, WO2009092642, WO2009100994, WO2009104155, WO2009124956, WO2009133522, WO2009156951, WO2010017260);

histamine H3 receptor antagonists/inverse agonists (e.g. 3-cyclohexyl-1-(4,4-dimethyl-1,4,6,7-tetrahydroimidazo[4,5-c]pyridin-5-yl)propan-1-one oxalic acid salt (WO 00/63208), or those as described in WO200064884, WO2005082893, WO2005123716, US2005171181 (e.g. PF-00389027), WO2006107661, WO2007003804, WO2007016496, WO2007020213, WO2007049798, WO2007055418, WO2007057329, WO2007062999, WO2007065820, WO2007068620, WO2007068641, WO2007075629, WO2007080140, WO2007082840, WO2007088450, WO2007088462, WO2007094962, WO2007099423, WO2007100990, WO2007105053, WO2007106349, WO2007110364, WO2007115938, WO2007131907, WO2007133561, US2007270440, WO2007135111, WO2007137955, US2007281923, WO2007137968, WO2007138431, WO2007146122, WO2008005338, WO2008012010, WO2008015125, WO2008045371, EPI 757594, WO2008068173, WO2008068174, US20080171753, WO2008072703, WO2008072724, US2008188484, US2008188486, US2008188487, WO2008109333, WO2008109336, WO2008126886, WO2008154126, WO2008151957, US2008318952, WO2009003003, WO2009013195, WO2009036132, WO2009039431, WO2009045313, WO2009058300, WO2009063953, WO2009067401, WO2009067405, WO2009067406, US2009163464, WO2009100120, WO2009105206, WO2009121812, WO2009126782, WO2010011653, WO2010011657);

histamine H1/histamine H3 modulators, for example betahistine or its dihydrochloride;

modulators of the histamine H3 transporter or of the histamine H3/serotonin transporter, as described, for example, in WO2008002816, WO2008002817, WO2008002818, WO2008002820;

modulators of vesicular monoamine transporter 2 (VMAT2), as described, for example, in WO2009126305;

histamine H4 modulators, as described, for example, in WO2007117399, US2009156613;

CRF antagonists (e.g. [2-methyl-9-(2,4,6-trimethylphenyl)-9H-1,3,9-triazafluoren-4-yl]dipropylamine (WO 00/66585) or those CRF1 antagonists as described in WO2007105113, WO2007133756, WO2008036541, WO2008036579, WO2008083070, WO2010015628, WO2010015655);

CRF BP antagonists (e.g. urocortin);

urocortin agonists;

modulators of the beta-3 adrenoceptor, for example 1-(4-chloro-3-methanesulfonylmethylphenyl)-2-[2-(2,3-dimethyl-1H-indol-6-yloxy)ethylamino]ethanol hydrochloride (WO 01/83451) or solabegron (GW-427353) or N-5984 (KRP-204), or those as described in JP2006111553, WO2002038543, WO2002038544, WO2007048840-843, WO2008015558, EP1947103, WO2008132162;

MSH (melanocyte-stimulating hormone) agonists;

MCH (melanine-concentrating hormone) receptor antagonists (for example NBI-845, A-761, A-665798, A-798, ATC-0175, T-226296, T-71 (AMG-071, AMG-076), GW-856464, NGD-4715, ATC-0453, ATC-0759, GW-803430, or those compounds as described in WO2005085200, WO2005019240, WO2004011438, WO2004012648, WO2003015769, WO2004072025, WO2005070898, WO2005070925, WO2004039780, WO2004092181, WO2003033476, WO2002006245, WO2002089729, WO2002002744, WO2003004027, FR2868780, WO2006010446, WO2006038680, WO2006044293, WO2006044174, JP2006176443, WO2006018280, WO2006018279, WO2006118320, WO2006130075, WO2007018248, WO2007012661, WO2007029847, WO2007024004, WO2007039462, WO2007042660, WO2007042668, WO2007042669, US2007093508, US2007093509, WO2007048802, JP2007091649, WO2007092416; WO2007093363-366, WO2007114902, WO2007114916, WO2007141200, WO2007142217, US2007299062, WO2007146758, WO2007146759, WO2008001160, WO2008016811, WO2008020799, WO2008022979, WO2008038692, WO2008041090, WO2008044632, WO2008047544, WO2008061109, WO2008065021, WO2008068265, WO2008071646, WO2008076562, JP2008088120, WO2008086404, WO2008086409, US2008269110, WO2008140239, WO2009021740, US2009011994, US2009082359, WO2009041567, WO2009076387, WO2009089482, WO2009103478, WO2009119726, WO2009120655, WO2009123194, WO2009137270, WO2009146365, WO2009154132);

CCK-A (CCK-1) modulators (for example {2-[4-(4-chloro-2,5-dimethoxyphenyl)-5-(2-cyclohexylethyl)-thiazol-2-ylcarbamoyl]-5,7-dimethylindol-1-yl}acetic acid trifluoroacetic acid salt (WO 99/15525) or SR-146131 (WO 0244150) or SSR-125180) or those as described in WO2005116034, WO2007120655, WO2007120688, WO2007120718, WO2008091631;

serotonin reuptake inhibitors (e.g. dexfenfluramine), or those as described in WO2007148341, WO2008034142, WO2008081477, WO2008120761, WO2008141081, WO2008141082, WO2008145135, WO2008150848, WO2009043834, WO2009077858;

mixed serotonin/dopamine reuptake inhibitors (e.g. bupropion), or those as described in WO2008063673, or solid combinations of bupropion with naltrexone or bupropion with zonisamide;

mixed reuptake inhibitors, for example DOV-21947 or those as described in WO2009016214, WO2009016215, WO2009077584, WO2009098208, WO2009098209, WO2009106769, WO2009109517, WO2009109518, WO2009109519, WO2009109608, WO2009145357, WO2009149258;

mixed serotoninergic and noradrenergic compounds (e.g. WO 00/71549);

5-HT receptor agonists, for example 1-(3-ethylbenzofuran-7-yl)piperazine oxalic acid salt (WO 01/09111);

mixed dopamine/norepinephrine/acetylcholine reuptake inhibitors (e.g. tesofensine), or those as described, for example, in WO2006085118, WO2008150480;

dopamine antagonists, as described, for example, in WO2008079838, WO2008079839, WO2008079847, WO2008079848;

norepinephrine reuptake inhibitors, as described, for example, in US2008076724, WO2009062318;

5-HT1A receptor modulators, as described, for example, in WO2009006227, WO2009137679, WO2009137732;

5-HT2A receptor antagonists, as described, for example, in WO2007138343;

5-HT2C receptor agonists (for example lorcaserine hydrochloride (APD-356) or BVT-933, or those as described in WO200077010, WO200077001-02, WO2005019180, WO2003064423, WO200242304, WO2005035533, WO2005082859, WO2006004937, US2006025601, WO2006028961, WO2006077025, WO2006103511, WO2007028132, WO2007084622, US2007249709; WO2007132841, WO2007140213, WO2008007661, WO2008007664, WO2008009125, WO2008010073, WO2008108445, WO2009063991, WO2009063992, WO2009063993, WO2009079765);

5-HT6 receptor modulators, for example E-6837, BVT-74316, PF-3246799 or PRX-07034, or those as described, for example, in WO2005058858, WO2007054257, WO2007107373, WO2007108569, WO2007108742-744, WO2008003703, WO2008027073, WO2008034815, WO2008054288, EPI 947085, WO2008084491, WO2008084492, WO2008092665, WO2008092666, WO2008101247, WO2008110598, WO2008116831, WO2008116833, WO2008117169, WO2008136017, WO2008147812, EP2036888, WO2009013010, WO2009034581, WO2009053997, WO2009056632, WO2009073118, WO2009115515, WO2009135925, WO2009135927, WO2010000456, WO2010012806, EP2145887;

agonists of estrogen receptor gamma (ERRγ agonists), as described, for example, in WO2007131005, WO2008052709;

agonists of estrogen receptor alpha (ERRα/ERR1 agonists), as described, for example, in WO2008109727;

agonists of estrogen receptor beta (ERRβ agonists), as described, for example, in WO2009055734, WO2009100335, WO2009127686;

sigma-1 receptor antagonists, as described, for example, in WO2007098953, WO2007098961, WO2008015266, WO2008055932, WO2008055933, WO2009071657;

muscarin 3 receptor (M3R) antagonists, as described, for example, in WO2007110782, WO2008041184;

bombesin receptor agonists (BRS-3 agonists), as described, for example, in WO2008051404, WO2008051405, WO2008051406, WO2008073311;

galanin receptor antagonists;

growth hormone (e.g. human growth hormone or AOD-9604);

growth hormone releasing compounds (tert-butyl 6-benzyloxy-1-(2-diisopropylaminoethylcarbamoyl)-3,4-dihydro-1H-isoquinoline-2-carboxylate (WO 01/85695));

growth hormone secretagogue receptor antagonists (ghrelin antagonists), for example A-778193, or those as described in WO2005030734, WO2007127457, WO2008008286, WO2009056707;

growth hormone secretagogue receptor modulators (ghrelin modulators), for example JMV-2959, JMV-3002, JMV-2810, JMV-2951, or those as described in WO2006012577 (e.g. YIL-781 or YIL-870), WO2007079239, WO2008092681, WO2008145749, WO2008148853, WO2008148854, WO2008148856, WO2009047558, WO2009071283, WO2009115503;

TRH agonists (see, for example, EP 0 462 884);

decoupling protein 2 or 3 modulators (as described, for example, in WO2009128583);

chemical decouplers (e.g. WO2008059023, WO2008059024, WO2008059025, WO2008059026);

leptin receptor agonists (see, for example, Lee, Daniel W.; Leinung, Matthew C.; Rozhayskaya-Arena, Marina; Grasso, Patricia. Leptin agonists as a potential approach to the treatment of obesity. Drugs of the Future (2001), 26(9), 873-881);

leptin receptor modulators, as described, for example, in WO2009019427, WO2009071658, WO2009071668, WO2009071677, WO2009071678, WO2009147211, WO2009147216, WO2009147219, WO2009147221;

DA agonists (bromocriptin, bromocriptin mesylate, doprexin) or those as described in US2009143390;

lipase/amylase inhibitors (e.g. WO 00/40569, WO2008107184, WO2009049428, WO2009125819);

inhibitors of diacylglycerol O-acyltransferases (DGATs), for example BAY-74-4113, or as described, for example, in US2004/0224997, WO2004094618, WO200058491, WO2005044250, WO2005072740, JP2005206492, WO2005013907, WO2006004200, WO2006019020, WO2006064189, WO2006082952, WO2006120125, WO2006113919, WO2006134317, WO2007016538, WO2007060140, JP2007131584, WO2007071966, WO2007126957, WO2007137103, WO2007137107, WO2007138304, WO2007138311, WO2007141502, WO2007141517, WO2007141538, WO2007141545, WO2007144571, WO2008011130, WO2008011131, WO2008039007, WO2008048991, WO2008067257, WO2008099221, WO2008129319, WO2008141976, WO2008148840, WO2008148849, WO2008148851, WO2008148868, WO2009011285, WO2009016462, WO2009024821, US2009076275, WO2009040410, WO2009071483, WO2009081195, WO2009119534, WO2009126624, WO2009126861, WO2010007046, WO2010017040;

inhibitors of monoacylglycerol acyltransferase (2-acylglycerol O-acyltransferase; MGAT), as described, for example, in WO2008038768;

inhibitors of fatty acid synthase (FAS), for example C75, or those as described in WO2004005277, WO2008006113;

inhibitors of stearoyl-CoA delta9 desaturase (SCD1), as described, for example, in WO2007009236, WO2007044085, WO2007046867, WO2007046868, WO20070501124, WO2007056846, WO2007071023, WO2007130075, WO2007134457, WO2007136746, WO2007143597, WO2007143823, WO2007143824, WO2008003753, WO2008017161, WO2008024390, WO2008029266, WO2008036715, WO2008043087, WO2008044767, WO2008046226, WO2008056687, WO2008062276, WO2008064474, WO2008074824, WO2008074832, WO2008074833, WO2008074834, WO2008074835, WO2008089580, WO2008096746, WO2008104524, WO2008116898, US2008249100, WO2008120744, WO2008120759, WO2008123469, WO2008127349, WO2008128335, WO2008135141, WO2008139845, WO2008141455, US20080255130, US2008255161, WO2008141455, WO2009010560, WO2009016216, WO2009022573, WO2009024287, JP2009019013, WO2009037542, WO2009056556, WO2009060053, WO2009060054, WO2009070533, WO2009073973, WO2009103739, WO2009117659, WO2009117676, US2009253693, US2009253738, WO2009124259, WO2009126123, WO2009126527, WO2009129625, WO2009137201, WO2009150196, WO2009156484, WO2010006962, WO2010007482;

inhibitors of fatty acid desaturase 1 (delta5 desaturase), as described, for example, in WO2008089310;

inhibitors of monoglyceride lipase (MGL), as described in WO2008145842;

hypoglycemic/hypertriglyceridemic indoline compounds, as described in WO2008039087, WO2009051119;

inhibitors of "adipocyte fatty acid-binding protein aP2", for example BMS-309403 or those as described in WO2009028248;

activators of adiponectin secretion, as described, for example, in WO2006082978, WO2008105533, WO2008136173;

promoters of adiponectin production, as described, for example, in WO2007125946, WO2008038712;

modified adiponectins, as described, for example, in WO2008121009;

oxyntomodulin or analogs thereof (for example, TKS-1225);

oleoyl-estrone or agonists or partial agonists of the thyroid hormone receptor (thyroid hormone receptor agonists), for example: KB-2115 (eprotirome), QRX-431 (sobetirome) or DITPA, or those as described in WO20058279, WO200172692, WO200194293, WO2003084915, WO2004018421, WO2005092316, WO2007003419, WO2007009913, WO2007039125, WO2007110225, WO2007110226, WO2007128492, WO2007132475, WO2007134864, WO2008001959, WO2008106213, JP2009155261;

or agonists of the thyroid hormone receptor beta (TR-beta), for example MB-07811 or MB-07344, or those as described in WO2008062469.

In one embodiment of the invention, the compound of the formula I is administered in combination with a combination of eprotirome with ezetimibe.

In one embodiment of the invention, the compound of the formula I is administered in combination with an inhibitor of site-1 protease (S1P), for example PF-429242.

In a further embodiment of the invention, the compound of the formula I is administered in combination with a modulator of the "trace amine associated receptor 1" (TAAR1), as described, for example, in US2008146523, WO2008092785.

In one embodiment of the invention, the compound of the formula I is administered in combination with an inhibitor of growth factor receptor bound protein 2 (GRB2), as described, for example, in WO2008067270.

In a further embodiment of the invention, the compound of the formula I is administered in combination with an RNAi (siRNA) therapeutic agent directed against PCSK9 (proprotein convertase subtilisin/kexin type 9).

In one embodiment, the compound of the formula I is administered in combination with Omacor® or Lovaza™ (omega-3 fatty acid ester; highly concentrated ethyl ester of eicosapentaenoic acid and of docosahexaenoic acid).

In one embodiment, the compound of the formula I is administered in combination with lycopene.

In one embodiment of the invention, the compound of the formula I is administered in combination with an antioxidant, for example OPC-14117, AGI-1067 (succinobucol), probucol, tocopherol, ascorbic acid,␤-carotene or selenium, or those as described in WO2009135918.

In one embodiment of the invention, the compound of the formula I is administered in combination with a vitamin, for example vitamin B6 or vitamin B12.

In one embodiment, the compound of the formula I is administered in combination with more than one of the aforementioned compounds, for example in combination with a sulfonylurea and metformin, a sulfonylurea and acarbose, repaglinide and metformin (PrandiMet™), insulin and a sulfonylurea, insulin and metformin, insulin and troglitazone, insulin and lovastatin, etc.

In a further embodiment, the compound of the formula I is administered in combination with an activator of soluble guanylate cyclase (sGC), as described, for example, in WO2009032249.

In another embodiment, the compound of the formula I is administered in combination with an inhibitor of carboanhydrase type 2 (carbonic anhydrase type 2), for example those as described in WO2007065948, WO2009050252.

In another embodiment, the compound of the formula I is administered in combination with topiramat or a derivative thereof, as described in WO2008027557, US2009304789.

In a further embodiment, the compound of the formula I is administered in combination with a solid combination of topiramat with phentermin (Qnexa™)

In a further embodiment, the compound of the formula I is administered in combination with an antisense compound, e.g. ISIS-377131, which inhibits the production of the glucocorticoid receptor.

In another embodiment, the compound of the formula I is administered in combination with an aldosterone synthase inhibitor and an antagonist of the glucocorticoid receptor, a cortisol synthesis inhibitor and/or an antagonist of the corticotropin releasing factor, as described, for example, in EP1 886695, WO2008119744.

In one embodiment, the compound of the formula I is administered in combination with an agonist of the RUP3 receptor, as described, for example, in WO2007035355, WO2008005576.

In another embodiment, the compound of the formula I is administered in combination with an activator of the gene which codes for ataxia telangiectasia mutated (ATM) protein kinase, for example chloroquine.

In one embodiment, the compound of the formula I is administered in combination with a tau protein kinase 1 inhibitor (TPK1 inhibitor), as described, for example, in WO2007119463, WO2009035159, WO2009035162.

In one embodiment, the compound of the formula I is administered in combination with a "c-Jun N-terminal kinase" inhibitor (JNK inhibitor), for example B1-78D3 or those as described, for example, in WO2007125405, WO2008028860, WO2008118626.

In one embodiment, the compound of the formula I is administered in combination with an endothelin A receptor antagonist, for example avosentan (SPP-301).

In one embodiment, the compound of the formula I is administered in combination with inhibitors of neutral endopeptidase (NEP inhibitors), as described, for example, in WO2009138122, WO2009135526.

In one embodiment, the compound of the formula I is administered in combination with modulators of the glucocorticoid receptor (GR), for example KB-3305 or those compounds as described, for example, in WO2005090336, WO2006071609, WO2006135826, WO2007105766, WO2008120661, WO2009040288, WO2009058944, WO2009108525, WO2009111214.

In one embodiment, the further active ingredient is varenicline tartrate, a partial agonist of the alpha 4-beta 2 nicotinic acetylcholine receptor.

In one embodiment, the further active ingredient is an agonist of the alpha 7-nicotinic acetylcholine receptor, as described, for example, in WO2009018551, WO2009071519, WO2009071576, WO2009071577.

In one embodiment, the further active ingredient is trodusquemine.

In one embodiment, the further active ingredient is a modulator of the enzyme SIRT1 and/or SIRT3 (an NAD$^+$-dependent protein deacetylase); this active ingredient may, for example, be resveratrol in suitable formulations, or those compounds as specified in WO2007019416 (e.g. SRT-1720), WO2008073451, WO2008156866, WO2008156869, WO2009026701, WO2009049018, WO2009058348, WO2009061453, WO2009134973, WO2009146358, WO2010003048.

In one embodiment of the invention, the further active ingredient is DM-71 (N-acetyl-L-cysteine with bethanechol).

In one embodiment, the compound of the formula I is administered in combination with antihypercholesterolemic compounds, as described, for example, in WO2004000803, WO2006000804, WO2004000805, WO2004087655, WO2005113496, WO2007059871, WO2007107587, WO2007111994, WO2008052658, WO2008106600, WO2008113796, US2008280836, WO2009113952, US2009312302

In a further embodiment, the compound of the formula I is administered in combination with inhibitors of SREBP (sterol regulatory element-binding protein), for example fatostatin, or those as described, for example, in WO2008097835.

In another embodiment, the compound of the formula I is administered in combination with a cyclic peptide agonist of the VPAC2 receptor, as described, for example, in WO2007101146, WO2007133828.

In a further embodiment, the compound of the formula I is administered in combination with an agonist of the endothelin receptor, as described, for example, in WO2007112069.

In a further embodiment, the compound of the formula I is administered in combination with AKP-020 (bis(ethylmaltolato)oxovanadium(IV)).

In another embodiment, the compound of the formula I is administered in combination with tissue-selective androgen receptor modulators (SARM), as described, for example, in WO2007099200, WO2007137874.

In a further embodiment, the compound of the formula I is administered in combination with an AGE (advanced glycation endproduct) inhibitor, as described, for example, in JP2008024673.

In one embodiment of the invention, the further active ingredient is leptin; see, for example, "Perspectives in the therapeutic use of leptin", Salvador, Javier; Gomez-Ambrosi, Javier; Fruhbeck, Gema, Expert Opinion on Pharmacotherapy (2001), 2(10), 1615-1622.

In another embodiment of the invention, the further active ingredient is metreleptin (recombinant methionyl-leptin) combined with pramlintide.

In a further embodiment of the invention, the further active ingredient is the tetrapeptide ISF-402.

In one embodiment, the further active ingredient is dexamphetamine or amphetamine.

In one embodiment, the further active ingredient is fenfluramine or dexfenfluramine.

In another embodiment, the further active ingredient is sibutramine or those derivatives as described in WO2008034142.

In one embodiment, the further active ingredient is mazindol or phentermin.

In a further embodiment, the further active ingredient is geniposidic acid (WO2007100104) or derivatives thereof (JP2008106008).

In another embodiment, the further active ingredient is a neuropeptide FF2 agonist, as described, for example, in WO2009038012.

In one embodiment, the further active ingredient is a nasal calcium channel blocker, for example diltiazem, or those as described in U.S. Pat. No. 7,138,107.

In one embodiment, the further active ingredient is an inhibitor of sodium-calcium ion exchange, for example those as described in WO2008028958, WO2008085711.

In a further embodiment, the further active ingredient is a blocker of calcium channels, for example of CaV3.2 or CaV2.2, as described in WO2008033431, WO2008033447, WO2008033356, WO2008033460, WO2008033464, WO2008033465, WO2008033468, WO2008073461.

In one embodiment, the further active ingredient is a modulator of a calcium channel, for example those as described in WO2008073934, WO2008073936, WO2009107660.

In one embodiment, the further active ingredient is an inhibitor of the calcium metabolism, for example those as described in US2009124680.

In one embodiment, the further active ingredient is a blocker of the "T-type calcium channel", as described, for example, in WO2008033431, WO2008110008, US2008280900, WO2008141446, US2009270338, WO2009146540, US2009325979, WO2009146539.

In one embodiment, the further active ingredient is an inhibitor of KCNQ potassium channel 2 or 3, for example those as described in US2008027049, US2008027090.

In one embodiment, the further active ingredient is a modulator of KCNN potassium channel 1, 2 or 3 (modulators of the SK1, SK2 and/or SK3 channel), for example those as described in US2009036475.

In one embodiment, the further active ingredient is an inhibitor of the potassium Kv1.3 ion channel, for example those as described in WO2008040057, WO2008040058, WO2008046065, WO2009043117.

In one embodiment, the further active ingredient is a potassium channel modulator, for example those as described in WO2008135447, WO2008135448, WO2008135591, WO2009099820.

In a further embodiment, the further active ingredient is a hyperpolarization-activated cyclic nucleotide-gated (HCN) potassium-sodium channel inhibitor, for example those as described in US2009069296.

In another embodiment, the further active ingredient is an inhibitor of the sodium-potassium-2 chloride (NKCCl) cotransporter, for example those as described in WO2009130735.

In another embodiment, the further active ingredient is a voltage-gated sodium channel inhibitor, for example those as described in WO2009049180, WO2009049181.

In another embodiment, the further active ingredient is a modulator of the MCP-1 receptor (monocyte chemoattractant protein-1 (MCP-1)), for example those as described in WO2008014360, WO2008014381.

In one embodiment, the further active ingredient is a modulator of somatostatin receptor 3 (SSTR3), for example those as described in WO2009011836.

In one embodiment, the further active ingredient is a modulator of somatostatin receptor 5 (SSTR5), for example those as described in WO2008019967, US2008064697, US2008249101, WO2008000692, US2008293756, WO2008148710.

In one embodiment, the further active ingredient is a modulator of somatostatin receptor 2 (SSTR2), for example those as described in WO2008051272.

In one embodiment, the further active ingredient is a compound which is capable of reducing the amount of retinol-binding protein 4 (RBP4), for example those as described in WO2009051244, WO2009145286.

In one embodiment, the further active ingredient is an erythropoietin-mimetic peptide which acts as an erythropoietin (EPO) receptor agonist. Such molecules are described, for example, in WO2008042800.

In a further embodiment, the further active ingredient is an anorectic/a hypoglycemic compound, for example those as described in WO2008035305, WO2008035306, WO2008035686.

In one embodiment, the further active ingredient is an inductor of lipoic acid synthetase, for example those as described in WO2008036966, WO2008036967.

In one embodiment, the further active ingredient is a stimulator of endothelial nitric oxide synthase (eNOS), for example those as described in WO2008058641, WO2008074413.

In one embodiment, the further active ingredient is a modulator of carbohydrate and/or lipid metabolism, for example those as described in WO2008059023, WO2008059024, WO2008059025, WO2008059026.

In a further embodiment, the further active ingredient is an angiotensin II receptor antagonist, for example those as described in WO2008062905, WO2008067378, WO2008062905.

In one embodiment, the further active ingredient is an agonist of the sphingosine 1-phosphate receptor (S1P), for example those as described in WO2008064315, WO2008074820, WO2008074821, WO2008135522, WO2009019167, WO2009043013, WO2009080663, WO2009085847, WO2009151529, WO2009151621, WO2009151626, WO2009154737.

In one embodiment, the further active ingredient is an agent which retards gastric emptying, for example 4-hydroxyisoleucine (WO2008044770).

In one embodiment, the further active ingredient is a tryptophan-5-hydroxylase inhibitor-1 (TPH1 inhibitor), which modulates gastrointestinal motility, as described, for example, in WO2009014972.

In one embodiment, the further active ingredient is a muscle-relaxing substance, as described, for example, in WO2008090200.

In a further embodiment, the further active ingredient is an inhibitor of monoamine oxidase B (MAO-B), for example those as described in WO2008092091, WO2009066152.

In a further embodiment, the further active ingredient is an inhibitor of monoamine oxidase A (MAO-A), for example those as described in WO2009030968.

In another embodiment, the further active ingredient is an inhibitor of the binding of cholesterol and/or triglycerides to the SCP-2 protein (sterol carrier protein-2), for example those as described in US2008194658.

In a further embodiment, the further active ingredient is a compound which binds to the β-subunit of the trimeric GTP-binding protein, for example those as described in WO2008126920.

In one embodiment, the further active ingredient is a urate anion exchanger inhibitor 1, as described, for example, in WO2009070740.

In one embodiment, the further active ingredient is a modulator of the ATP transporter, as described, for example, in WO2009108657.

In another embodiment, the further active ingredient is lisofylline, which prevents autoimmune damage to insulin-producing cells.

In yet another embodiment, the further active ingredient is an extract from *Bidens pilosa* with the ingredient cytopiloyne as described in EP1955701.

In one embodiment, the further active ingredient is an inhibitor of glucosylceramide synthase, as described, for example, in WO2008150486.

In a further embodiment of the invention, the further active ingredient is a glycosidase inhibitor, as described, for example, in WO2009117829, WO2009155753.

In another embodiment, the further active ingredient is an ingredient from the plant *Hoodia Gordonii*, as described in US2009042813, EP2044852.

In one embodiment, the further active ingredient is an antidiabetic, for example D-tagatose.

In one embodiment, the further active ingredient is a zinc complex of curcumin, as described in WO2009079902.

In one embodiment, the further active ingredient is an inhibitor of the "cAMP response element binding protein" (CREB), as described in WO2009143391.

In another embodiment, the further active ingredient is an antagonist of the bradykinin B1 receptor, as described in WO2009124746.

In a further embodiment, the further active ingredient is a compound which is capable of modulating diabetic peripheral neuropathy (DPN). Such modulators are, for example, FK-1706 or SB-509, or those as described in WO1989005304, WO2009092129, WO2010002956.

In one embodiment, the further active ingredient is a compound which is capable of modulating diabetic nephropathy. Such compounds are described, for example, in WO2009089545, WO2009153261.

In one embodiment, the further active ingredient is an inhibitor (e.g. an anti-CD38 antibody) of CD38, as described in US2009196825.

In one embodiment, the further active ingredient is an inhibitor of human fibroblast growth factor receptor 4 (FGFR4), as described, for example, in WO2009046141.

In a further embodiment of the invention, the further active ingredient is a compound which protects the beta cell, for example 1 4-alpha-lipolyl-andrographolide (AL-1).

In yet another embodiment of the invention, the further active ingredient is the INGAP (islet neogenesis associated protein) peptide, a peptide which reestablishes insulin production in patients with diabetes mellitus.

In one embodiment of the invention, the further active ingredient is a modulator of the CFTR (cystic fibrosis transmembrane conductance regulator), as described, for example, in US2009246137, US2009264433, US2009264441, US2009264471, US2009264481, US2009264486, WO2010019239.

In one embodiment of the invention, the further active ingredient is a compound which stimulates/modulates insulin release, for example those as described in WO2009109258, WO2009132739, US2009281057, WO2009157418.

In one embodiment of the invention, the further active ingredient is an extract from *Hippophae rhamnoides*, as described, for example, in WO2009125071.

In one embodiment of the invention, the further active ingredient is an from *Huanglien* and *Ku Ding Cha*, as described, for example, in WO2009133458.

In another embodiment, the further active ingredient is a root extract from *Cipadessa baccifera*, as described in US2009238900.

In one embodiment of the invention, the further active ingredients are borapetoside A and/or borapetoside C, which can be isolated from the plant SDH-V, a species of *Tinospora crispa*, as described, for example, in US2010016213.

In one embodiment, the compound of the formula I is administered in combination with bulking agents, preferably insoluble bulking agents (see, for example, Carob/Caromax® (Zunft H J; et al., Carob pulp preparation for treatment of hypercholesterolemia, ADVANCES IN THERAPY (2001 September-October), 18(5), 230-6). Caromax® is a carob-containing product from Nutrinova, Nutrition Specialties & Food Ingredients GmbH, Industriepark Höchst, 65926 Frankfurt/Main)). Combination with Caromax® is possible in one preparation or by separate administration of compounds of the formula I and Caromax®. Caromax® can in this connection also be administered in the form of food products such as, for example, in bakery products or muesli bars.

It will be appreciated that every suitable combination of the compounds of the invention with one or more of the aforementioned compounds and optionally one or more other pharmacologically active substances is considered to be covered within the scope of protection conferred by the present invention.

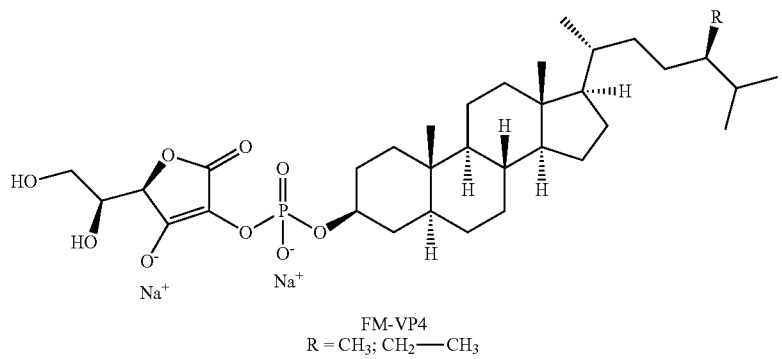

FM-VP4
R = CH$_3$; CH$_2$—CH$_3$

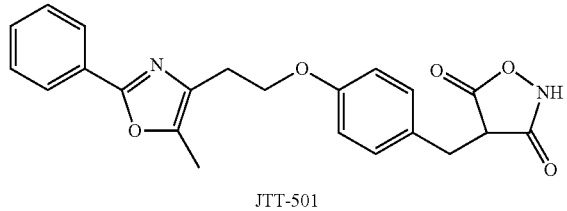

JTT-501

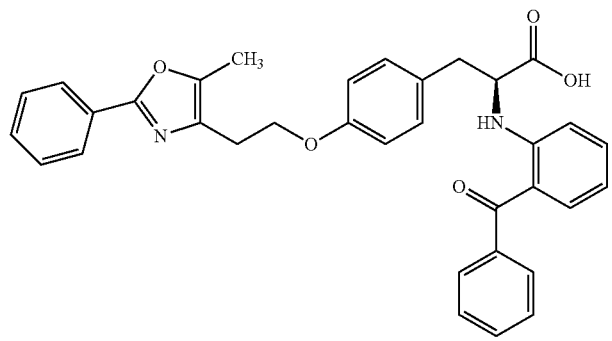

GI 262570

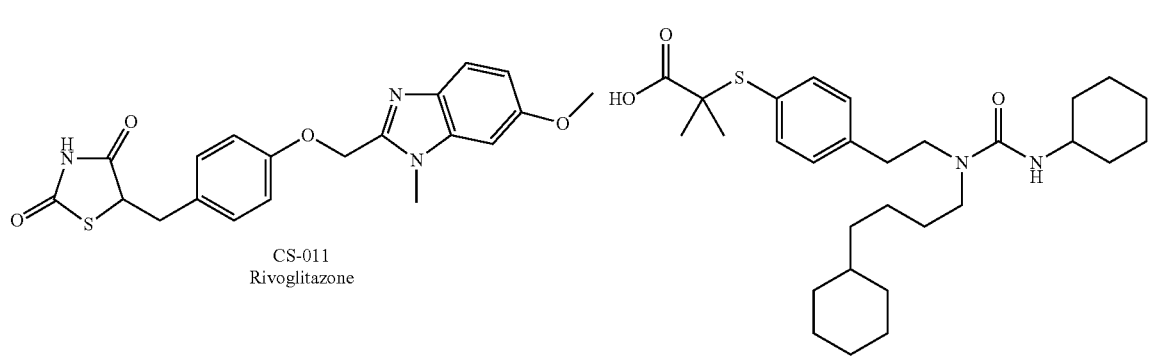

CS-011
Rivoglitazone

GW-9578

-continued
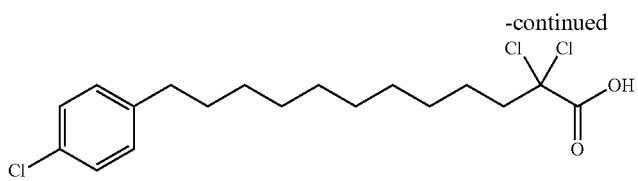
K-111
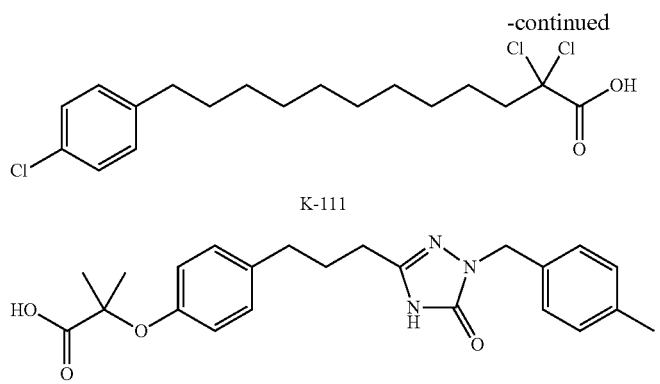
LY-518674
KRP-101
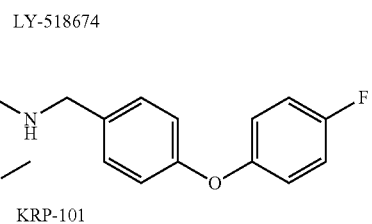
LY-510929
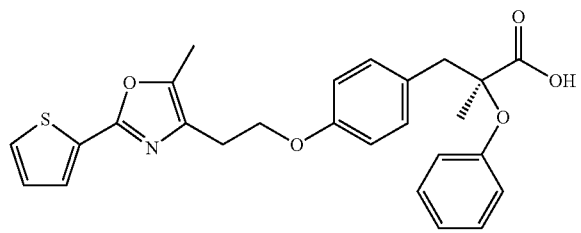
GW-501516
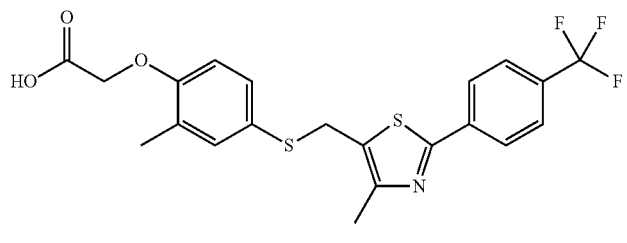
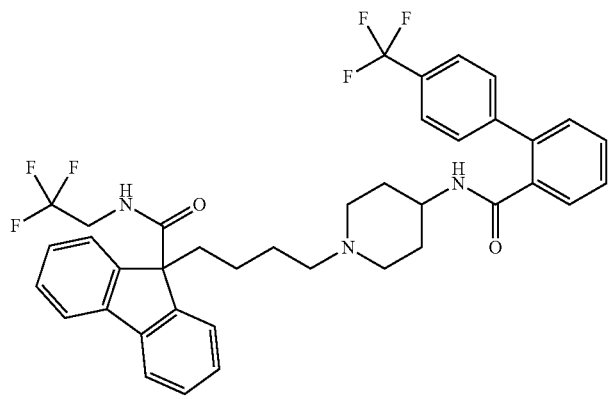
BMS-201038

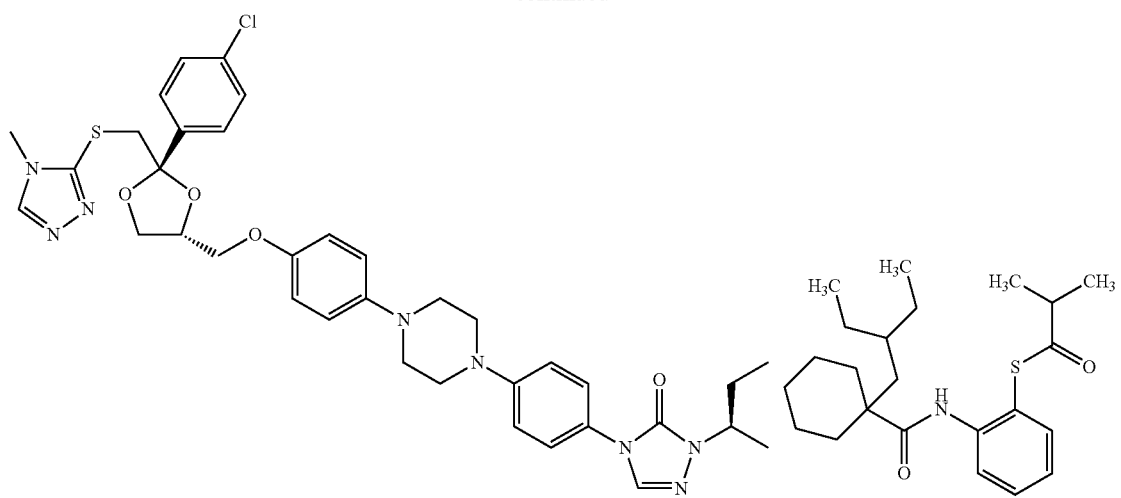
R-103757
JTT-705
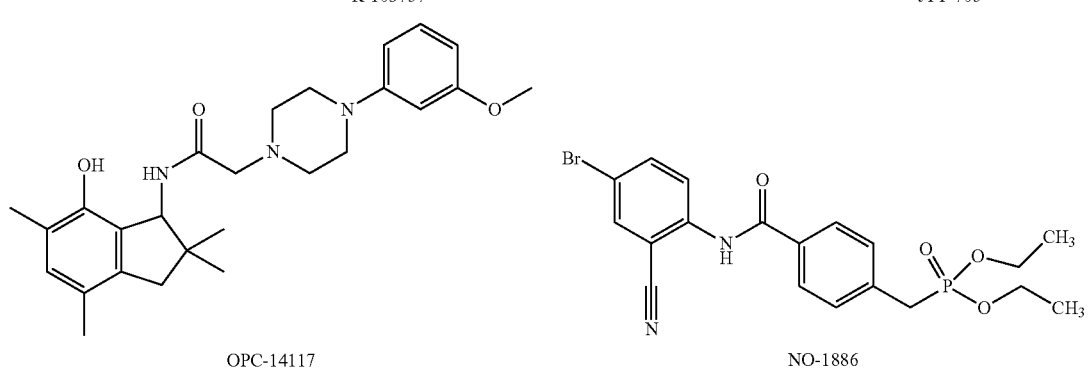
OPC-14117
NO-1886
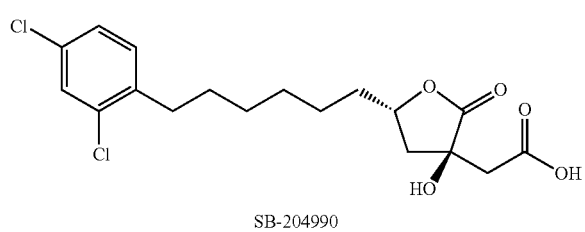
SB-204990
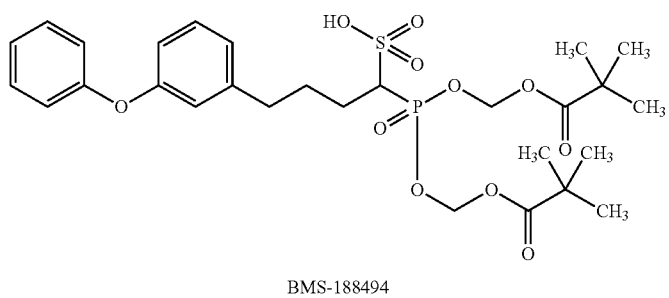
BMS-188494
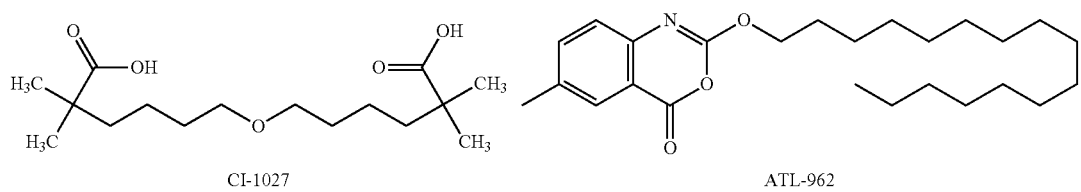
CI-1027
ATL-962

-continued
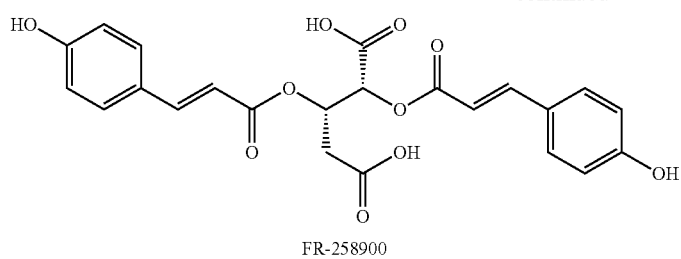
FR-258900
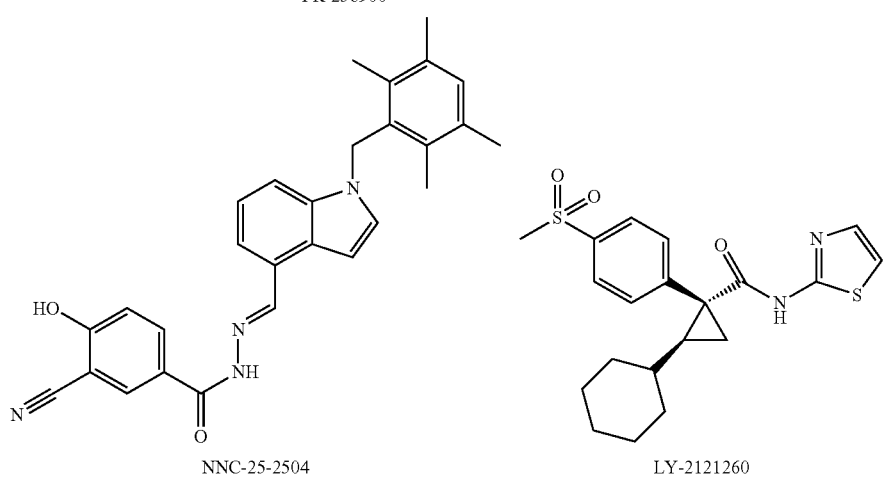
NNC-25-2504
LY-2121260
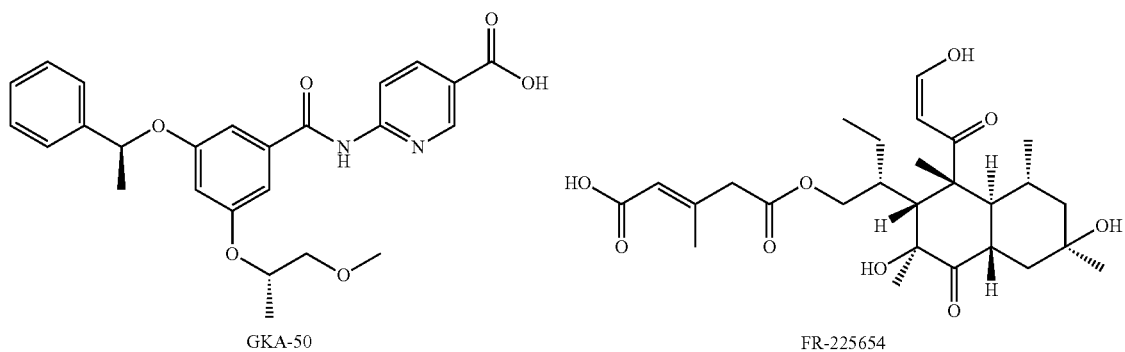
GKA-50
FR-225654
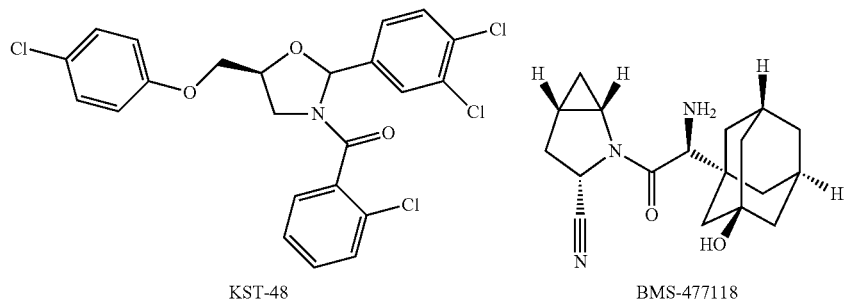
KST-48
BMS-477118
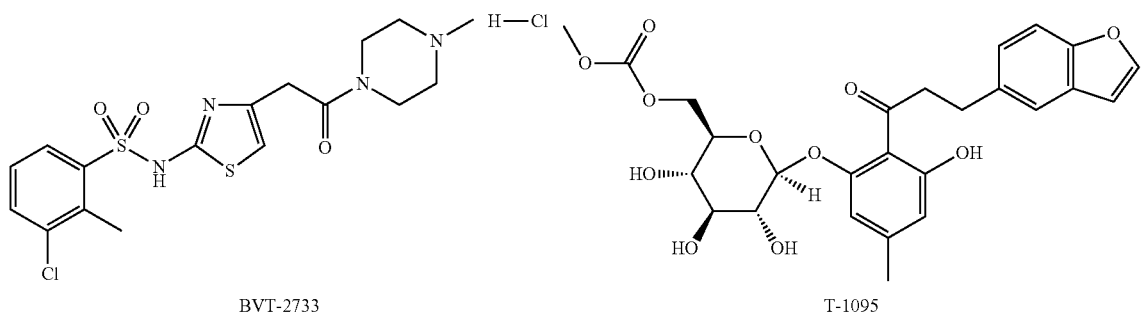
BVT-2733
T-1095

-continued
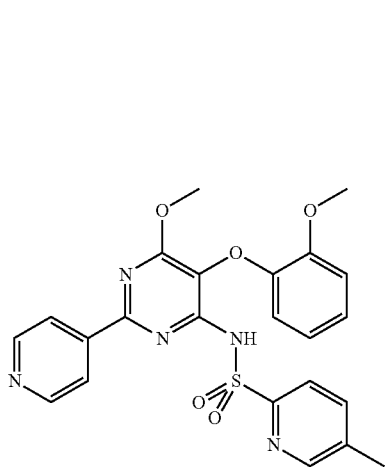
SPP-301
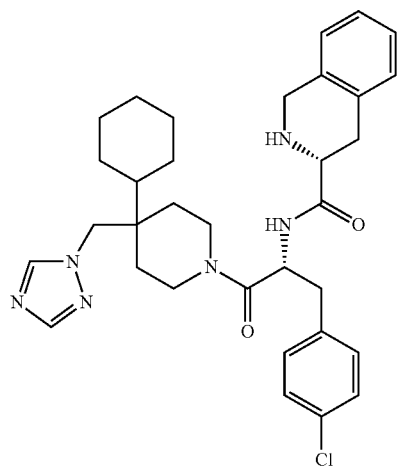
THIQ
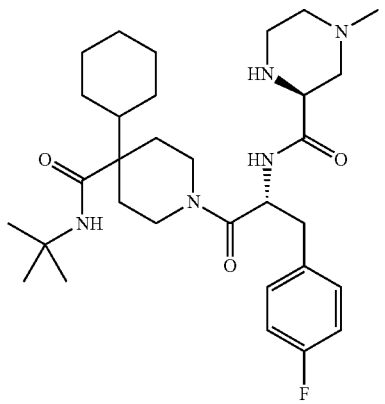
MB243
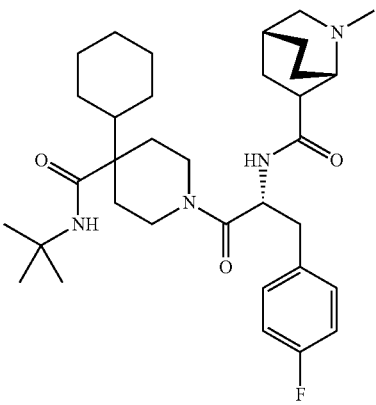
RY764
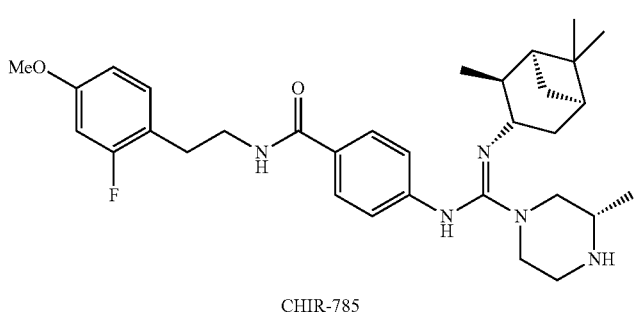
CHIR-785
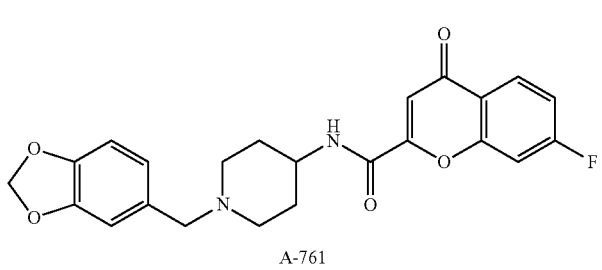
A-761
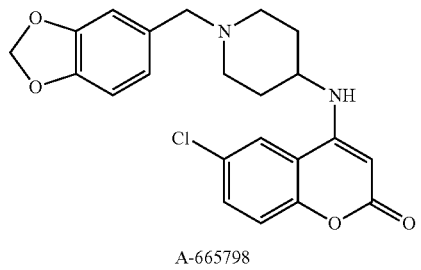
A-665798

93
94
-continued
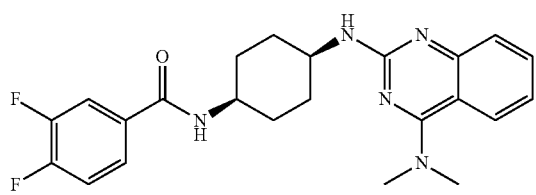
ATC-0175
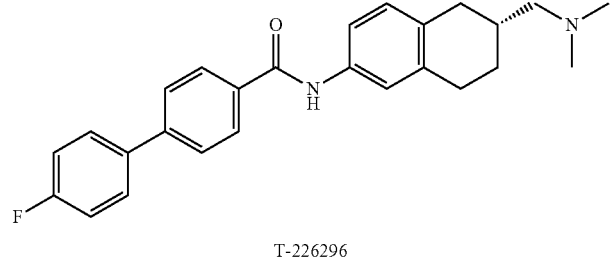
T-226296
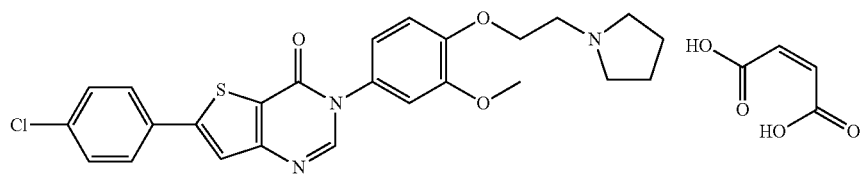
GW-803430
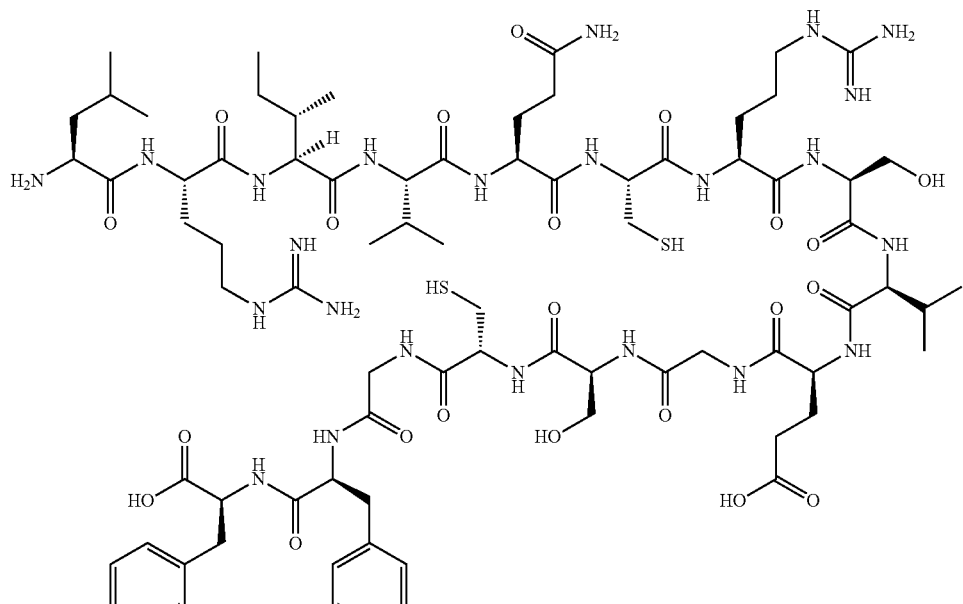
AOD-9604
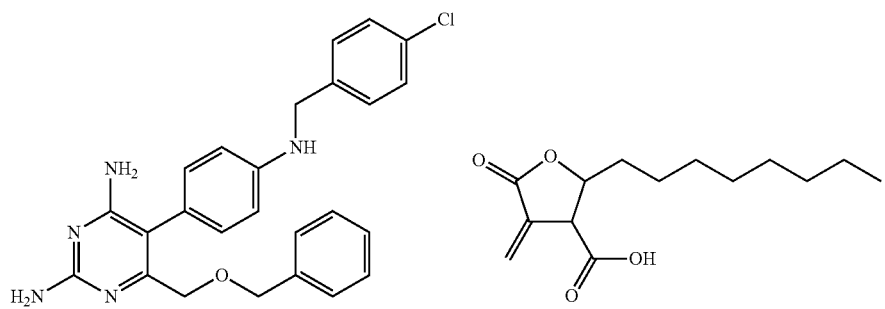
A-778193
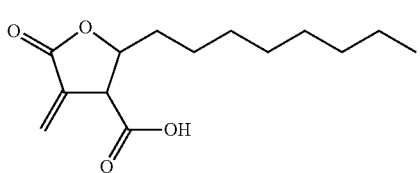
C75

-continued
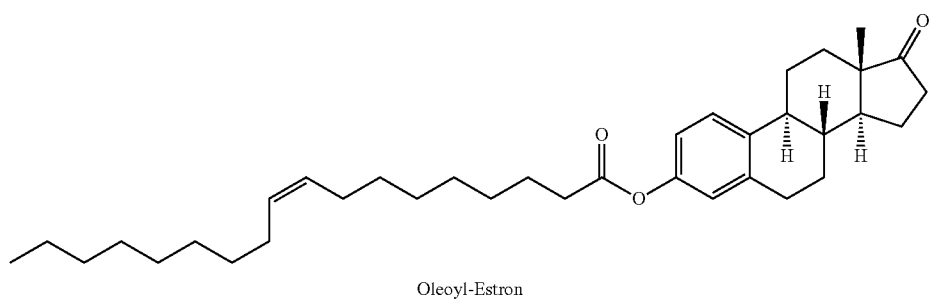
Oleoyl-Estron
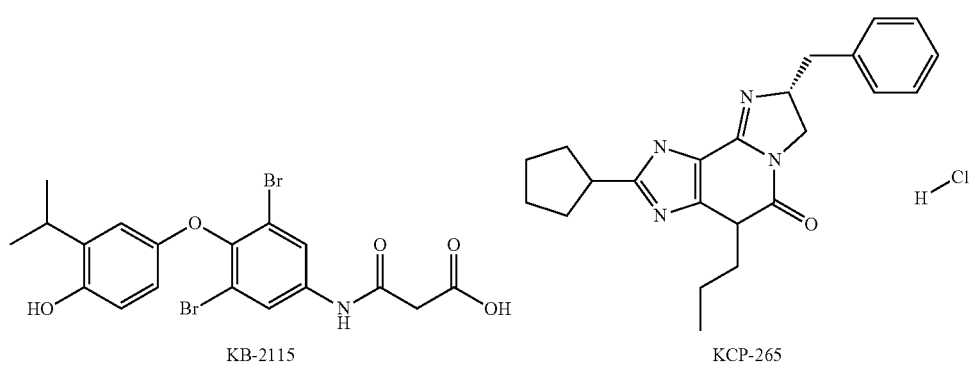
KB-2115          KCP-265
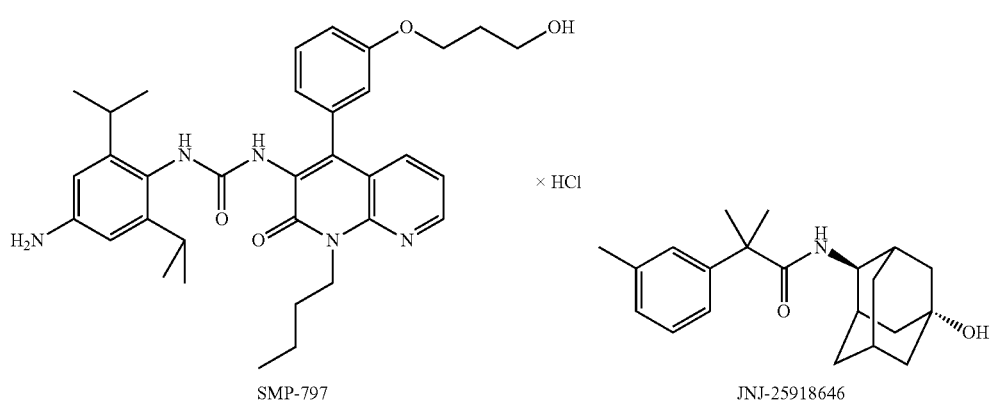
SMP-797          JNJ-25918646
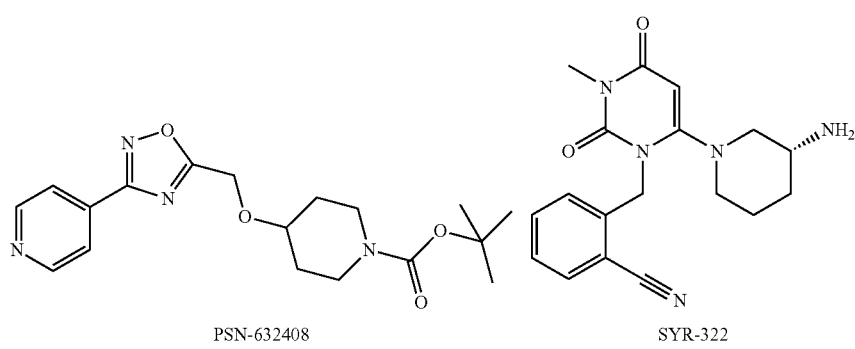
PSN-632408          SYR-322
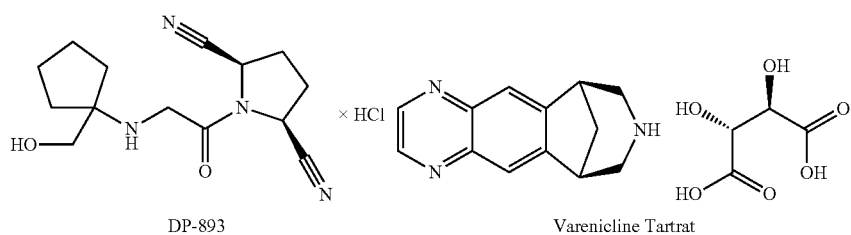
DP-893          Varenicline Tartrat -continued
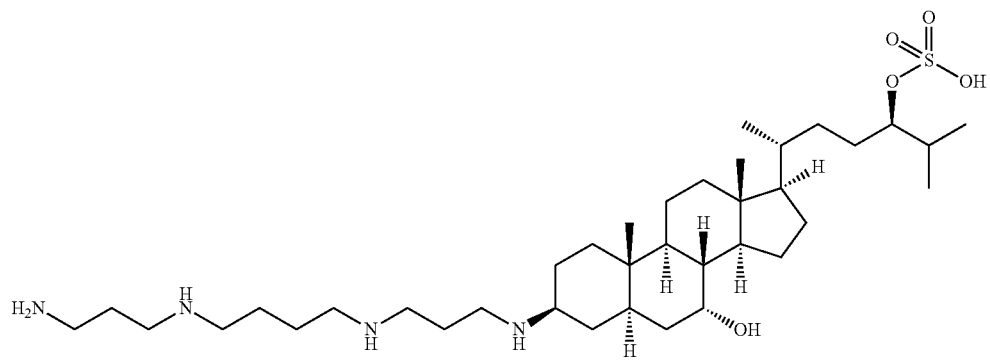
Trodusquemine
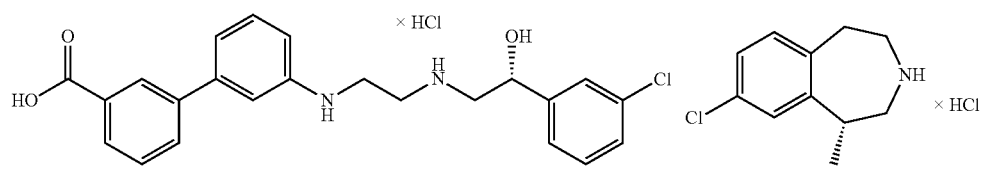
Solabegron    Lorcaserin Hydrochlorid
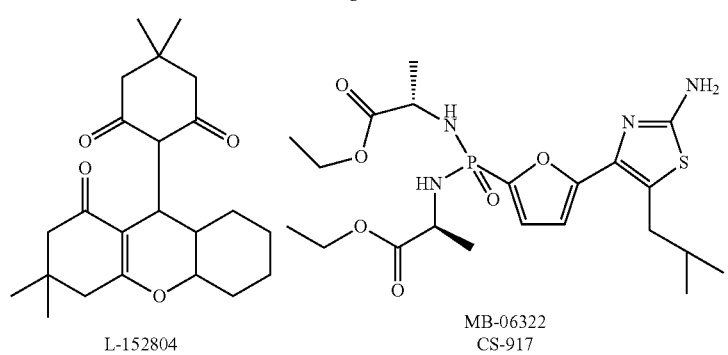
L-152804    MB-06322 CS-917
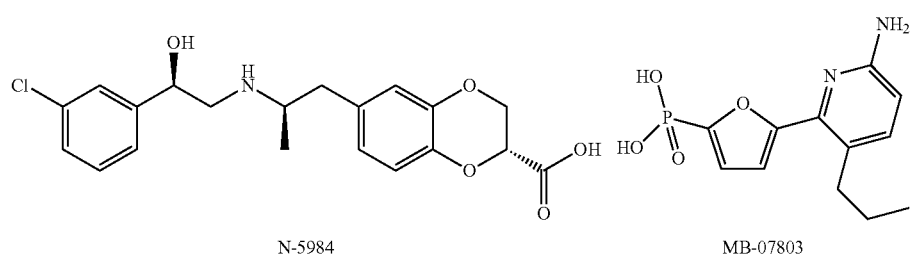
N-5984    MB-07803
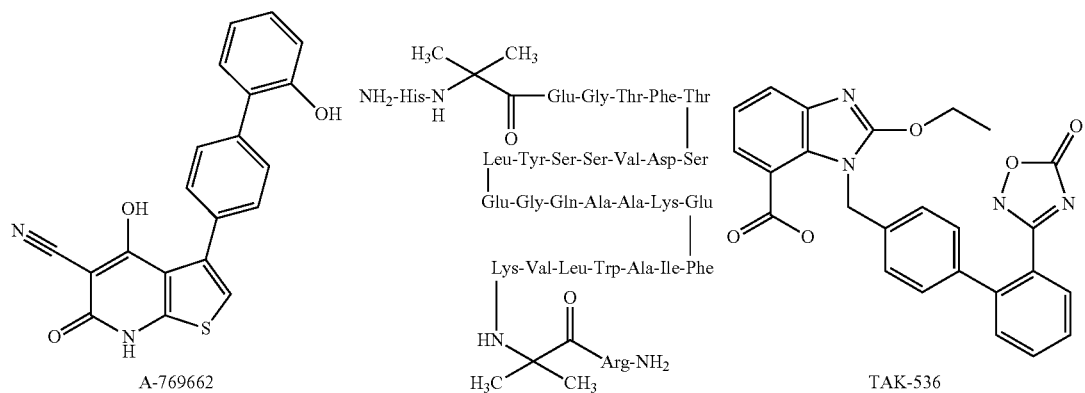
A-769662    TAK-536

-continued
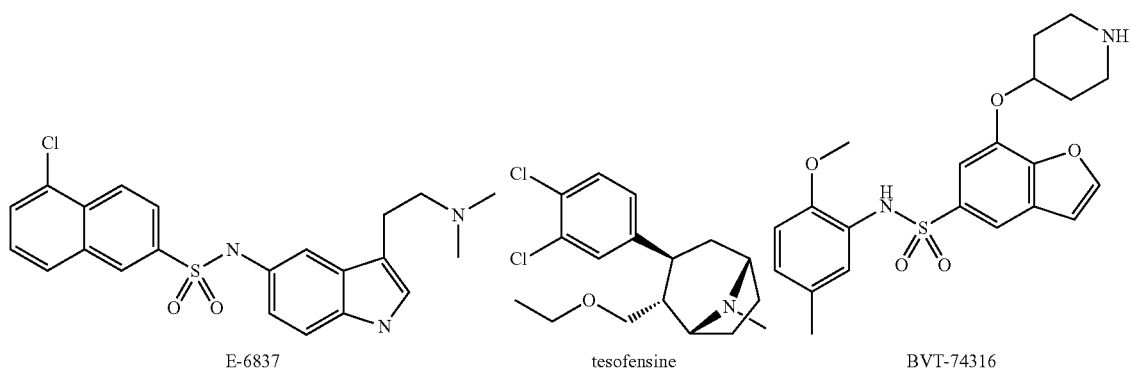
E-6837  tesofensine  BVT-74316
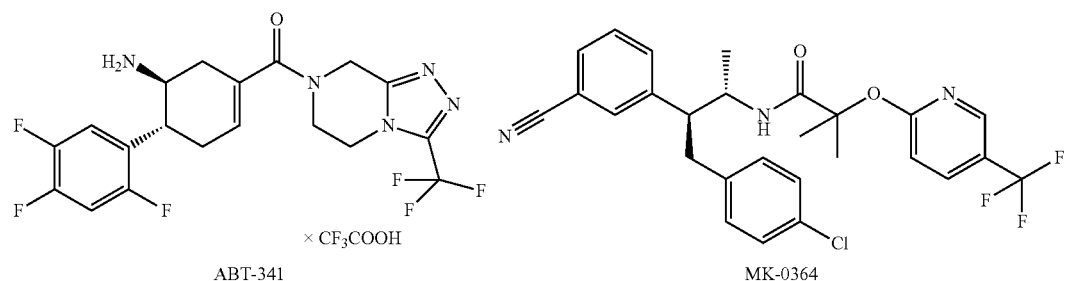
ABT-341  MK-0364
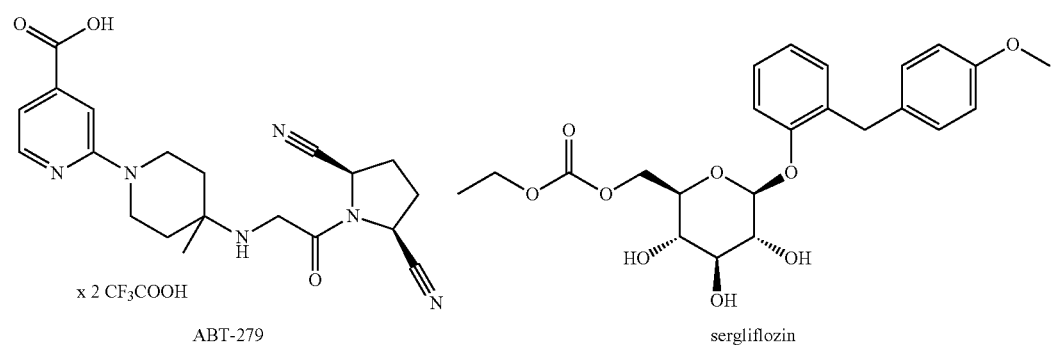
ABT-279  sergliflozin
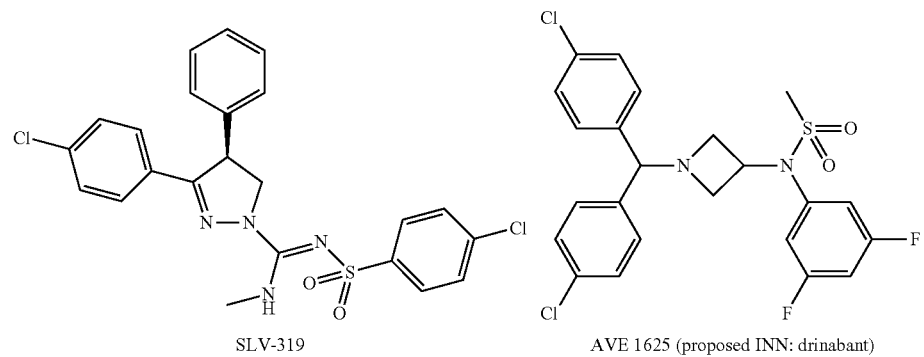
SLV-319  AVE 1625 (proposed INN: drinabant)

-continued
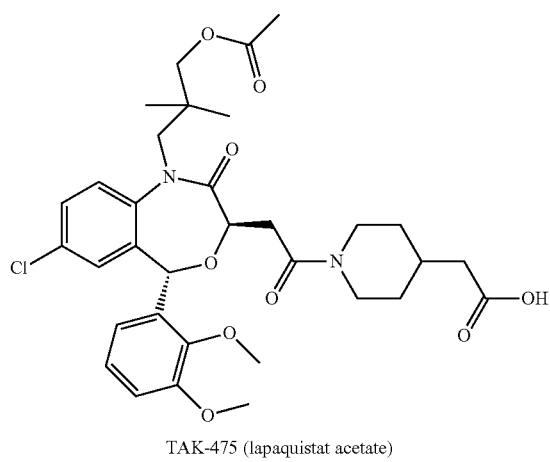
TAK-475 (lapaquistat acetate)
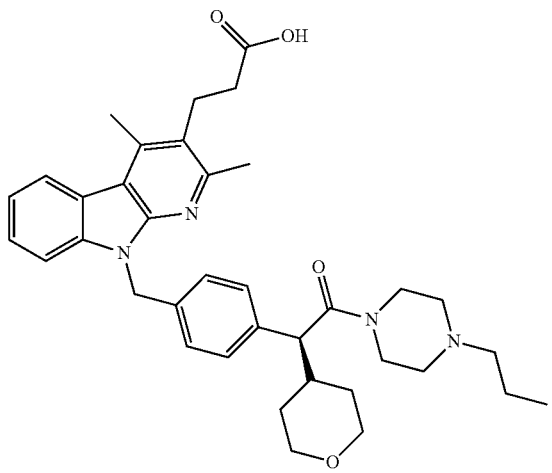
AS-1552133
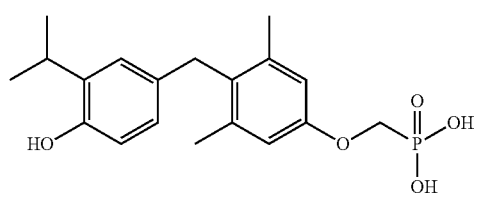
MB-07344
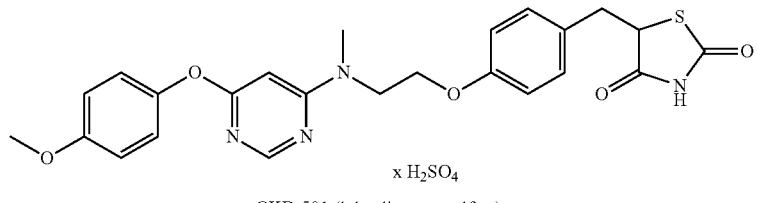
x H₂SO₄
CKD-501 (lobeglitazone sulfate)
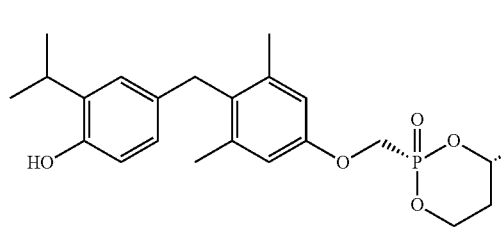
MB-07811
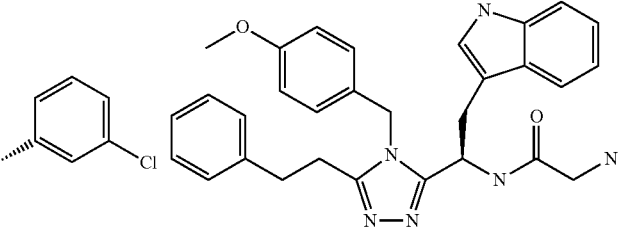
JMV-2959
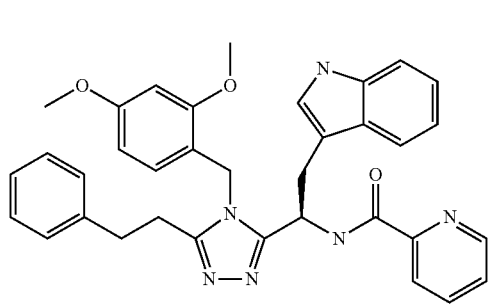
JMV-3002
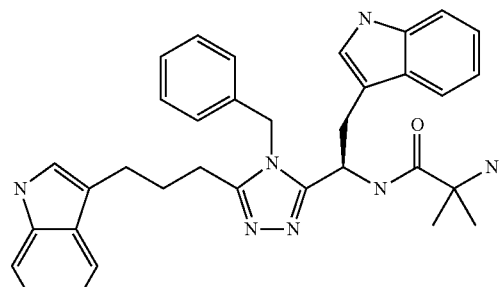
JMV-2810

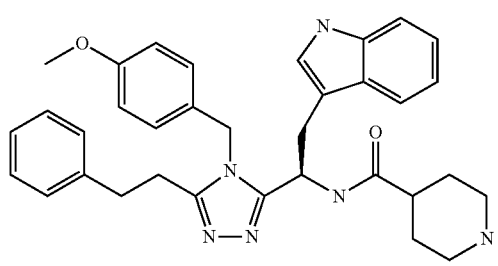
JMV-2951
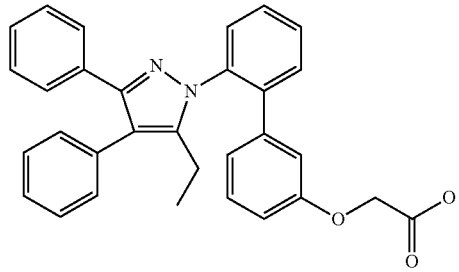
BMS-309403
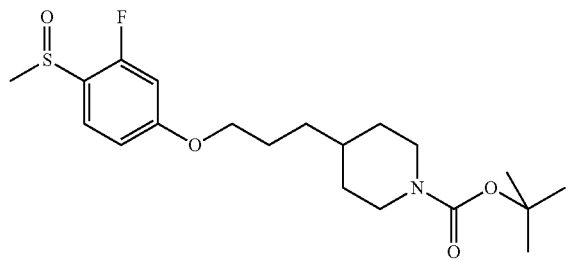
PSN-119-1
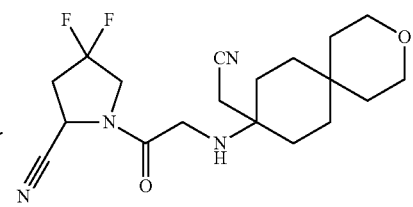
S-40755
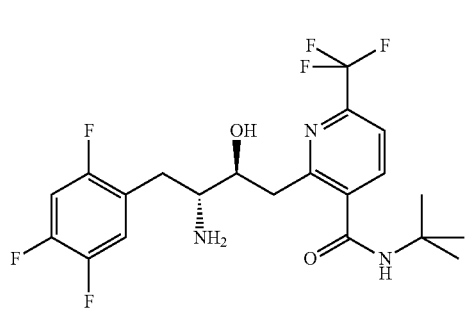
LY-2463665
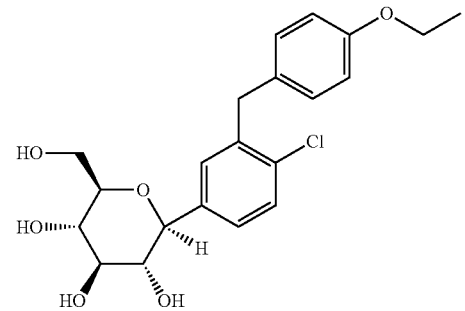
dapagliflozin, BMS-512148
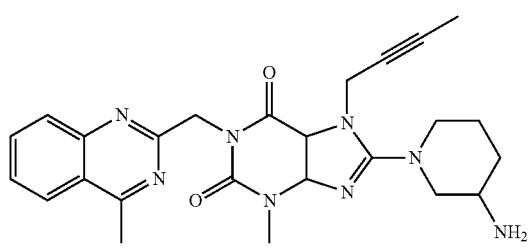
BI-1356
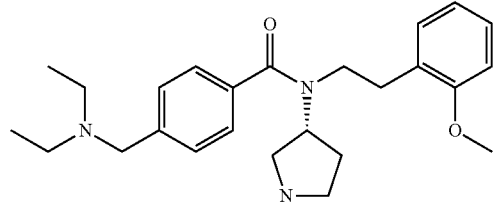
PF-429242
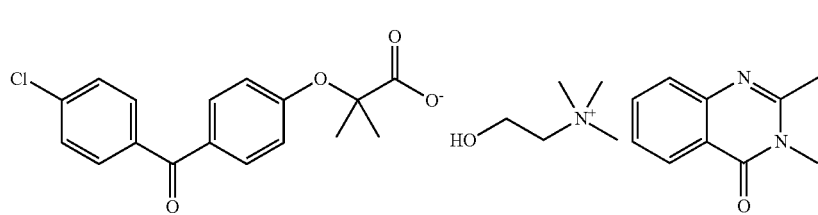
SLV-348
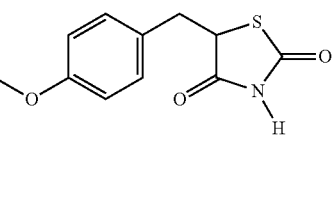
balaglitazone -continued
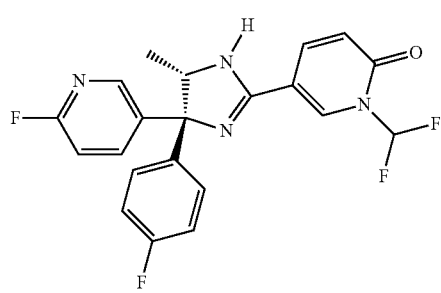
"NPY-5-BY"
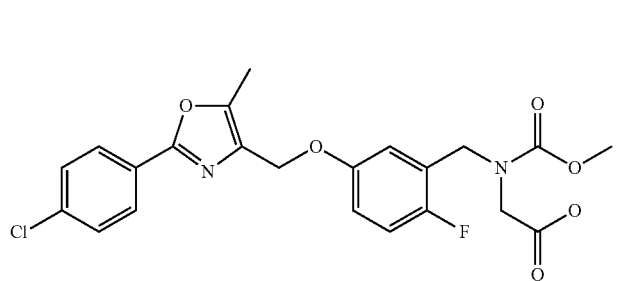
BMS-711939
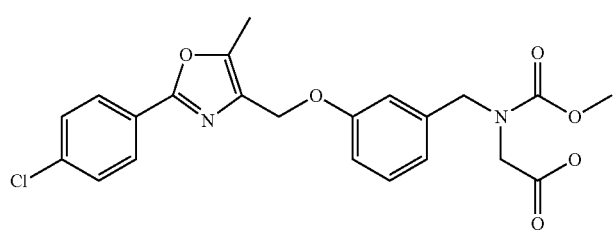
BMS-687453
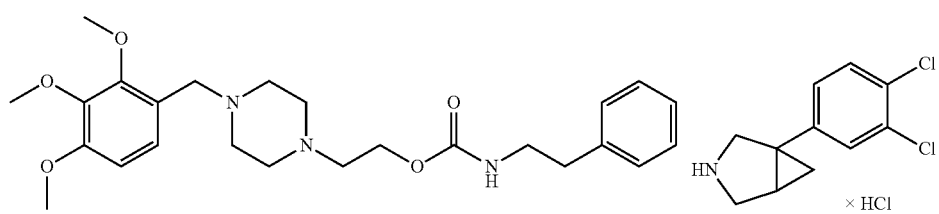
ST-3473    DOV-21947
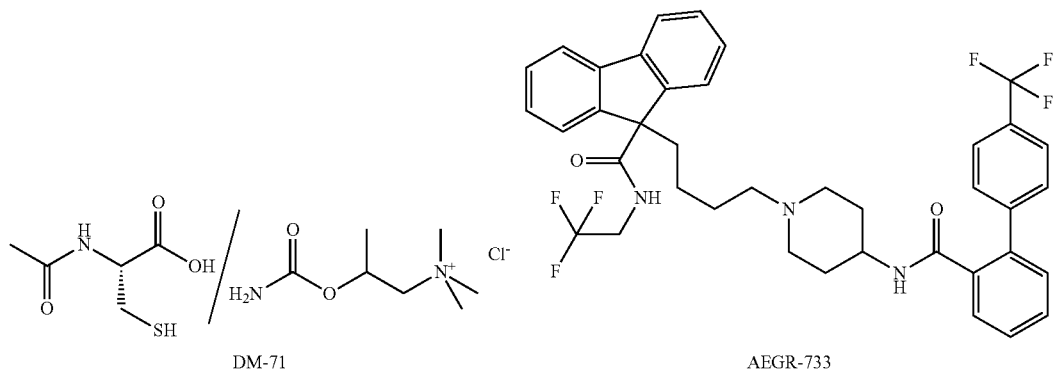
DM-71    AEGR-733
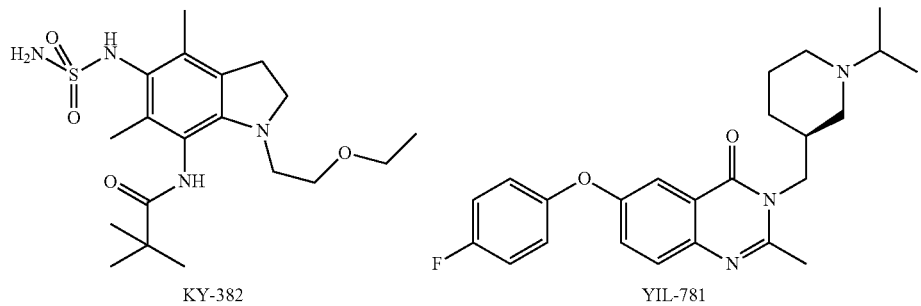
KY-382
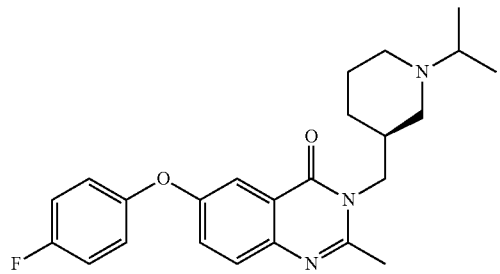
YIL-781

-continued
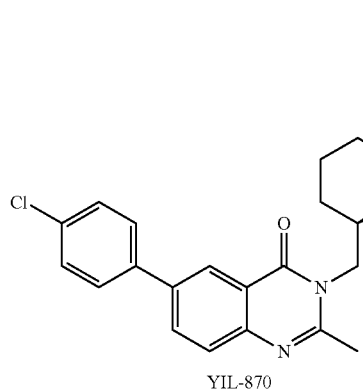
YIL-870
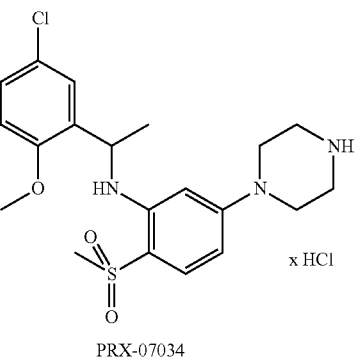
PRX-07034 x HCl
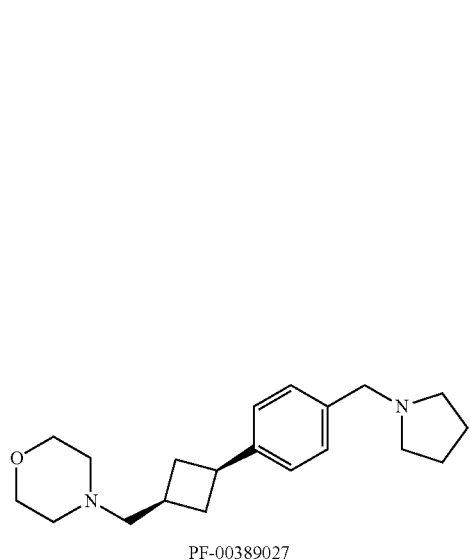
PF-00389027
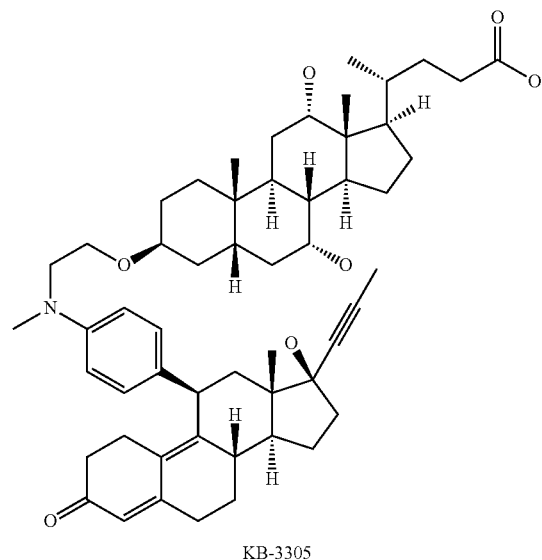
KB-3305
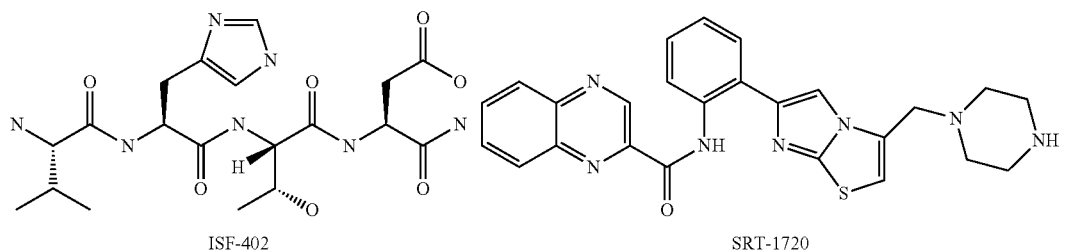
ISF-402
SRT-1720
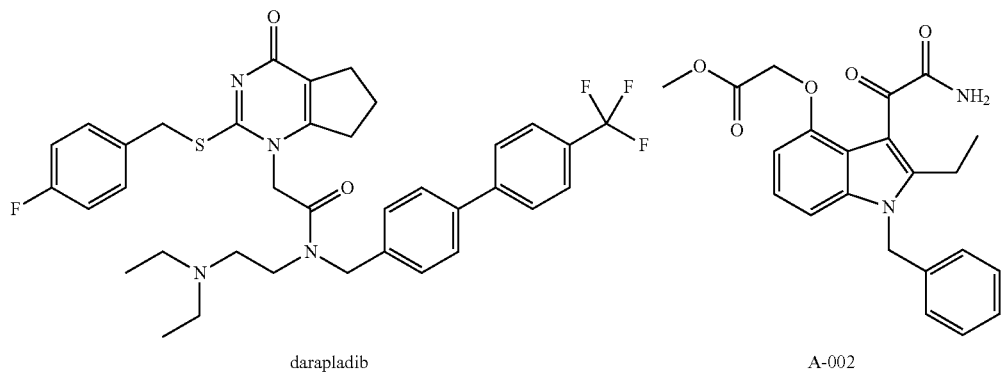
darapladib
A-002

-continued
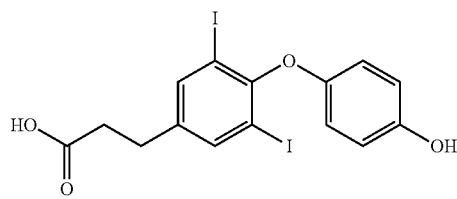
DITPA
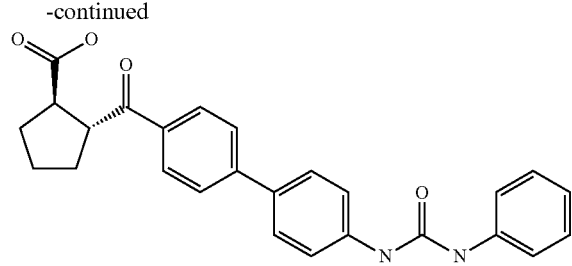
DGAT-1 inhibitor from WO2007137103
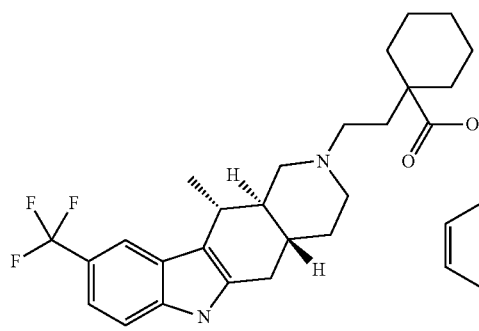
AMG-071
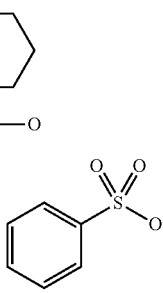
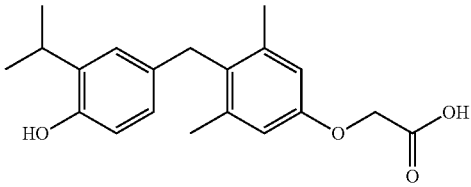
sobetirome
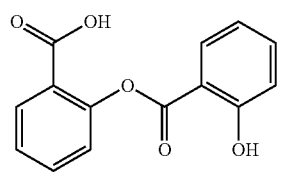
salsalate
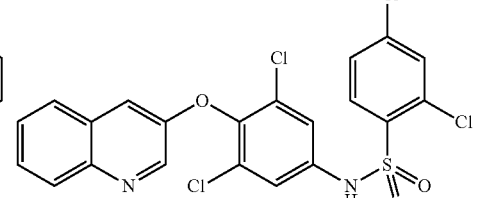
INT-131
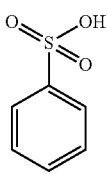
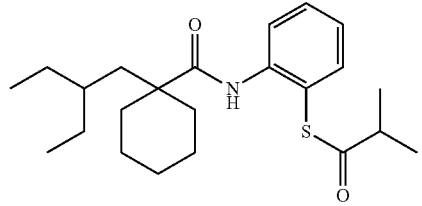
dalcetrapib
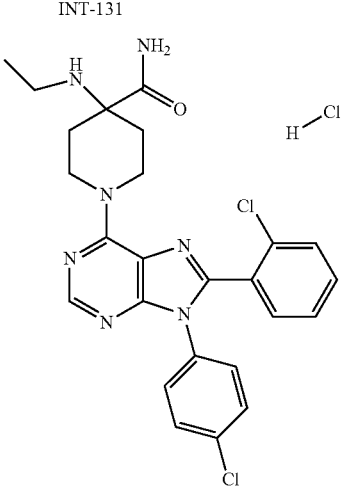
otenabant
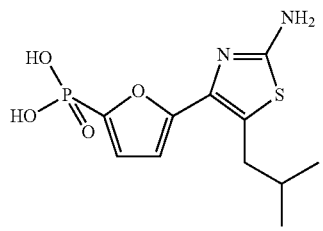
MB-07229
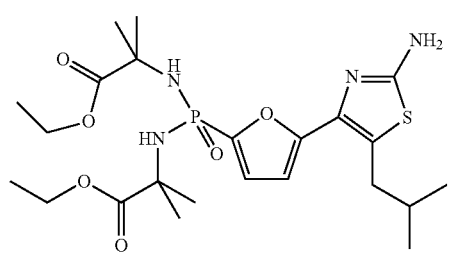
MB-07803
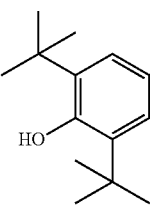
succinobucol 111
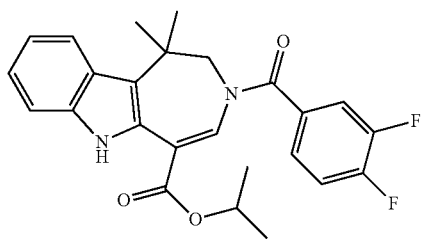
WAY-362450
-continued
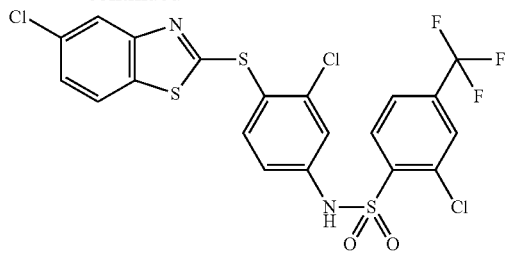
T-2384
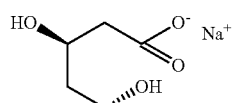
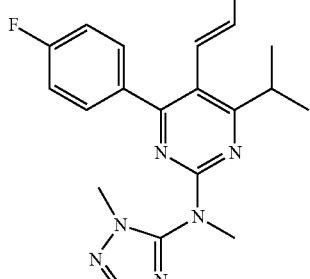
BMS-644950
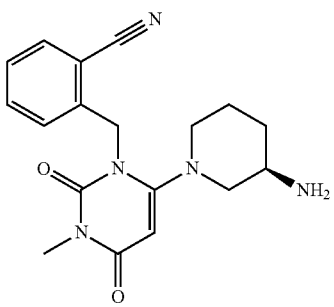
alogliptin benzoate
112
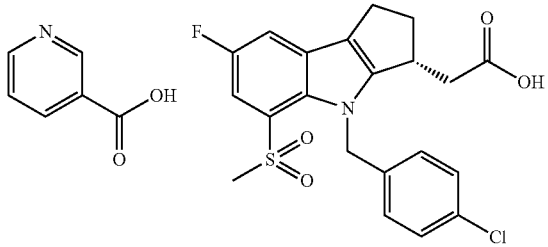
nicotinic acid/laropiprant
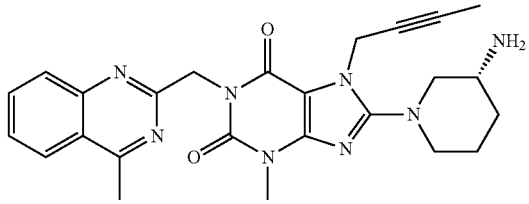
linagliptin
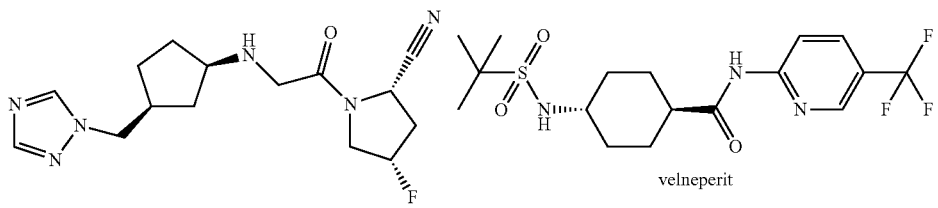
melogliptin
velneperit
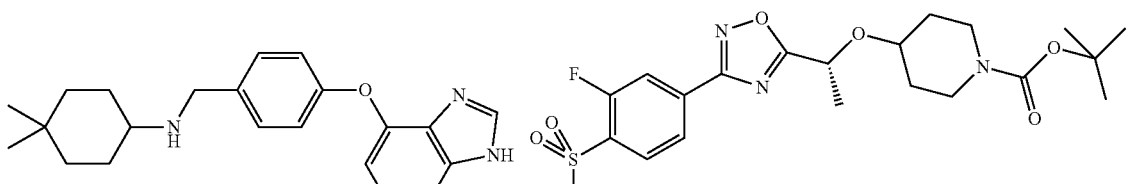
GSK-982
PSN-119-2

-continued
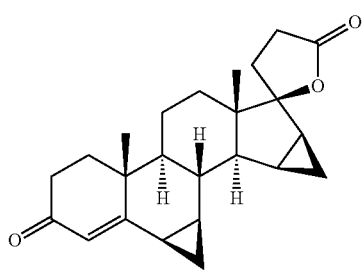
drospirenone
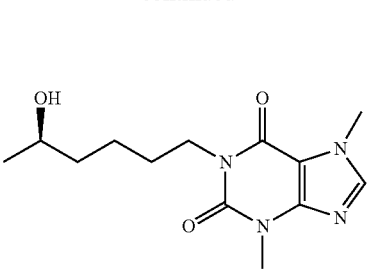
lisofylline
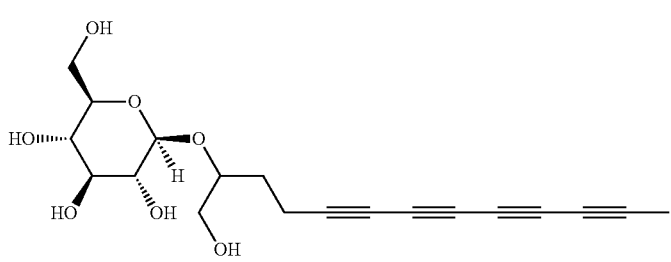
cytopiloin
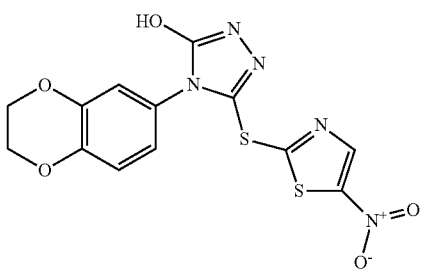
BI-78D3
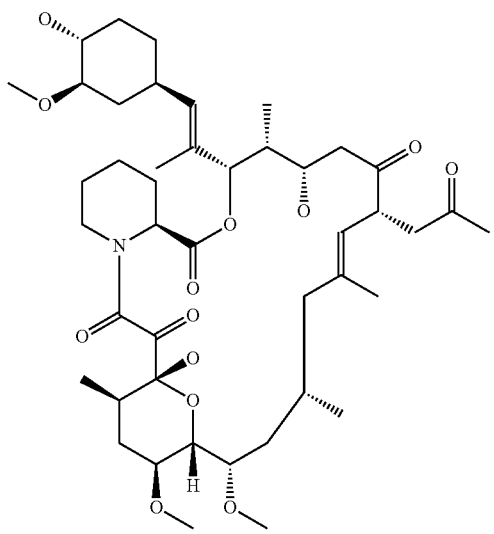
FK-1706
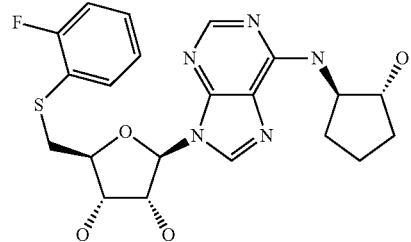
CVT-3619
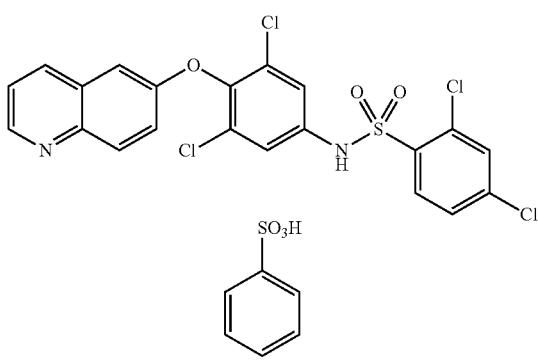
INT-131

-continued
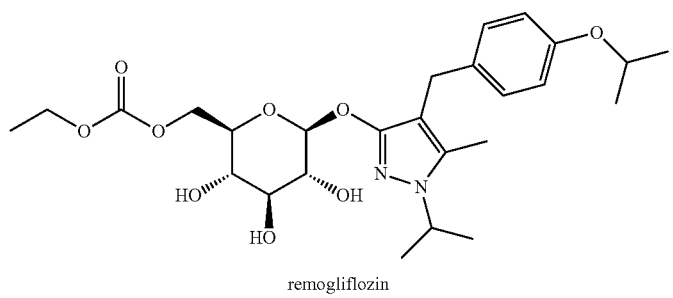
remogliflozin
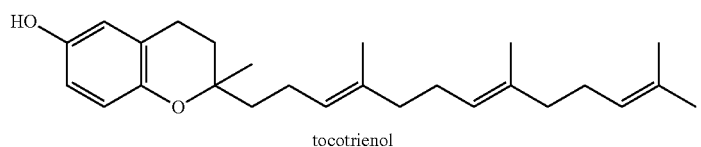
tocotrienol
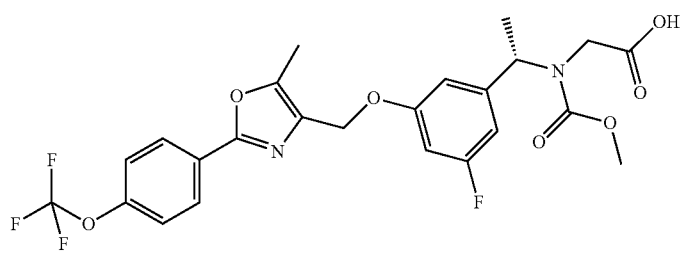
BMS-759509
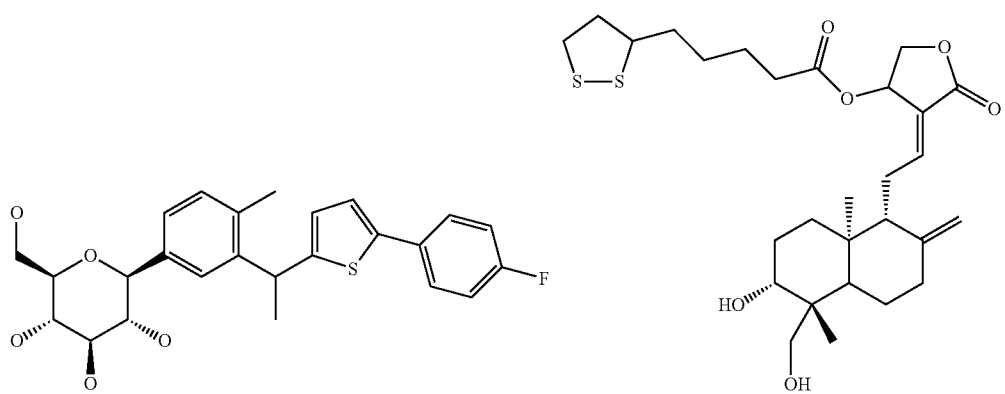
canagliflozin            14-alpha-lipolyl-andrographolide (AL-1)
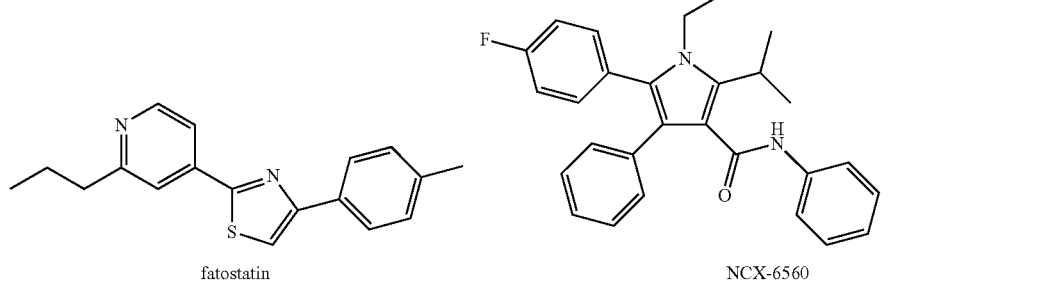
fatostatin            NCX-6560

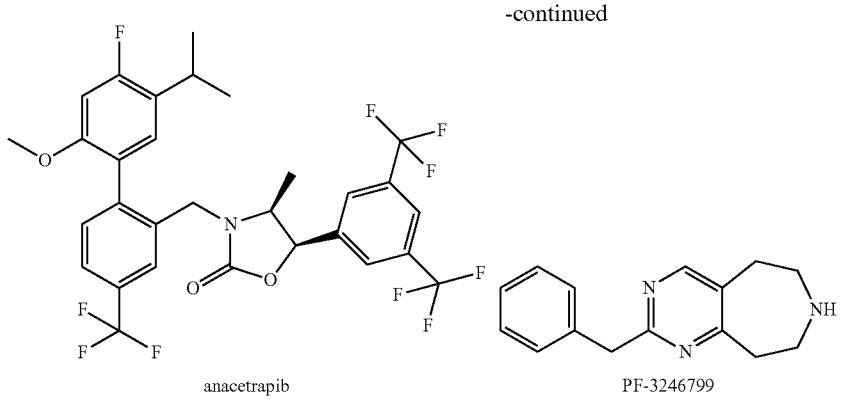

anacetrapib    PF-3246799

Also suitable are the following active ingredients for combination preparations:
all antiepileptics specified in the Rote Liste 2011, chapter 15;
all antihypertensives specified in the Rote Liste 2011, chapter 17;
all hypotonics specified in the Rote Liste 2011, chapter 19;
all anticoagulants specified in the Rote Liste 2011, chapter 20;
all arteriosclerosis drugs specified in the Rote Liste 2011, chapter 25;
all beta receptors, calcium channel blockers and inhibitors of the renin angiotensin system specified in the Rote Liste 2011, chapter 27;
all diuretics and perfusion-promoting drugs specified in the Rote Liste 2011, chapter 36 and 37;
all withdrawal drugs/drugs for the treatment of addictive disorders specified in the Rote Liste 2011, chapter 39;
all coronary drugs and gastrointestinal drugs specified in the Rote Liste 2011, chapter 55 and 60;
all migraine drugs, neuropathy preparations and Parkinson's drugs specified in the Rote Liste 2011, chapter 61, 66 and 70.

It will be appreciated that every suitable combination of the compounds of the invention with one or more of the aforementioned compounds and optionally one or more other pharmacologically active substances is considered to be covered within the scope of protection conferred by the present invention.

PKC-inhibitors can be administered to animals, in particular to mammals including humans, as pharmaceuticals by themselves, in mixtures with one another, or in the form of pharmaceutical compositions. The administration can be carried out orally, for example in the form of tablets, film-coated tablets, sugar-coated tablets, granules, hard and soft gelatin capsules, solutions including aqueous, alcoholic and oily solutions, juices, drops, syrups, emulsions or suspensions, rectally, for example in the form of suppositories, or parenterally, for example in the form of solutions for subcutaneous, intramuscular or intravenous injection or infusion, in particular aqueous solutions.

Suitable pharmaceutical compounds for oral administration may be in the form of separate units, for example capsules, cachets, lozenges or tablets, each of which contains a defined amount of the compound of formula I; as powders or granules; as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one (or more) surfactant(s)/dispersant(s) in a suitable machine. Molded tablets can be produced by molding the compound, which is in powder form and has been moistened with an inert liquid diluent, in a suitable machine.

Pharmaceutical compositions which are suitable for per-oral (sublingual) administration comprise lozenges which contain a compound of formula I with a flavoring, typically sucrose, and gum arabic or tragacanth, and pastilles which comprise the compound in an inert base such as gelatin and glycerol or sucrose and gum arabic.

Coated formulations and coated slow-release formulations, especially acid- and gastric juice-resistant formulations, also belong within the framework of the invention. Suitable coatings resistant to gastric juice comprise cellulose acetate phthalate, polyvinyl acetate phthalate, hydroxypropylmethylcellulose phthalate and anionic polymers of methacrylic acid and methyl methacrylate.

Pharmaceutical compositions suitable for rectal administration are preferably in the form of single-dose suppositories. These can be produced by mixing a compound of formula I with one or more conventional solid carriers, for example cocoa butter, and shaping resulting mixture.

Pharmaceutical compositions suitable for parenteral administration comprise preferably sterile aqueous preparations of a compound of formula I, which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions of the invention generally contain 0.1 to 5% by weight of the active compound.

Other suitable administration forms are, for example, percutaneous or topical administration, for example in the form of ointments, creams, tinctures, sprays, powders or transdermal therapeutic systems, or inhalative administration, for example in the form of nasal sprays or aerosol mixtures, or forms such as microcapsules, implants or rods.

Pharmaceutical compositions suitable for topical use on the skin are preferably in the form of ointment, cream, lotion, paste, spray, aerosol or oil. The carriers used may be petrolatum, lanolin, polyethylene glycols, alcohols and combinations of two or more of these substances. The active ingredient is generally present in a concentration of 0.1 to 15% by weight of the composition, for example 0.5 to 2%.

Transdermal administration is also possible. Pharmaceutical compositions suitable for transdermal uses may be in the form of single patches which are suitable for long-term close contact with the patient's epidermis. Such patches suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. A particular option is for the active ingredient to be released by electrotransport or iontophoresis as described, for example, in Pharmaceutical Research, 2(6): 318 (1986).

PKC inhibitors can additionally be used in systems for local drug delivery, for example in coated stents for preventing or reducing in-stent restenosis or by applying them locally by means of a catheter. The appropriate administration form depends, among others, on the disease to be treated and on its severity.

The dosing of PKC inhibitors to achieve the desirable therapeutic effect depends on a number of factors, for example the specific compound chosen, the intended use, the mode of administration and the clinical condition of the patient. The daily dose is generally in the range from 0.3 mg to 100 mg (typically from 3 mg to 50 mg) per day and per kilogram of body weight, for example 3-10 mg/kg/day. An intravenous dose may be, for example, in the range from 0.3 mg to 1.0 mg/kg, which can suitably be administered as infusion of 10 ng to 100 ng per kilogram and per minute. Suitable infusion solutions for these purposes may contain, for example, 0.1 ng to 100 mg, typically 1 ng to 100 mg, per milliliter. Single doses may contain, for example, 1 mg to 10 g of the active ingredient. Thus, ampoules for injections may contain, for example, from 1 mg to 100 mg, and orally administrable single-dose formulations, for example tablets or capsules, may contain, for example, from 1.0 to 1000 mg, typically from 10 to 600 mg. For treatment of the abovementioned conditions, the compounds of the formula I themselves may be used as the compound, but they are preferably present with a compatible carrier in the form of a pharmaceutical composition. The carrier must, of course, be acceptable in the sense that it is compatible with the other ingredients of the composition and is not harmful for the patient's health. The carrier may be a solid or a liquid or both and is preferably formulated with the compound as a single dose, for example as a tablet, which may contain 0.05% to 95% by weight of the active ingredient. Other pharmaceutically active substances may likewise be present, including other compounds of formula I. The pharmaceutical compositions of the invention can be produced by one of the known pharmaceutical methods, which essentially consist of mixing the ingredients with pharmacologically acceptable carriers and/or excipients.

The present invention provides novel and potent PKC inhibitors. The compounds of the present invention are selective to PKC over other kinases and are isozyme-selective. Selective PKC inhibitors are useful in preventing and treating diseases associated with diabetes and diabetic complications (e.g. diabetic cardiomyopathy, diabetic nephropathy, diabetic micro- and macrovascular complications, diabetic neuropathy and diabetic retinopathy, preferably diabetic nephropathy, diabetic neuropathy and diabetic retinopathy), cardiovascular diseases, diseases associated with hypertension- and non-hypertension-related and ischemic and non-ischemic end-organ damage (e.g. mycardial infarction, coronary heart disease, atherosclerosis, cardiac and renal hypertrophy, stroke), diseases associated with inflammation and fibrosis, central nervous system disorders (e.g. neuropathic pain), dermatological diseases, autoimmune diseases (e.g. psoriasis, type 1 diabetes) and cancer (e.g. hematological tumours, glioma, gastric and intestinal cancer, skin cancer and lung cancer).

Another subject of the present invention are processes for the preparation of the compounds of the formula I and their salts and solvates, by which the compounds are obtainable and which are outlined in the following.

In one process, a compound of the formula II is reacted with a compound of the formula III to give a compound of the formula IV, which is subsequently reduced to a compound of formula Ia, which can be a compound of formula I already or which can be converted into a compound of formula I,

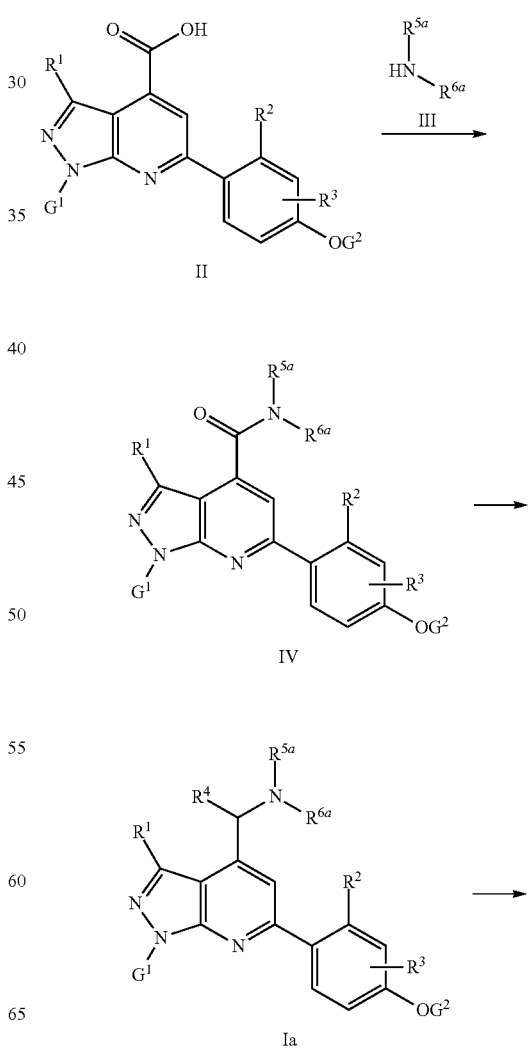

-continued

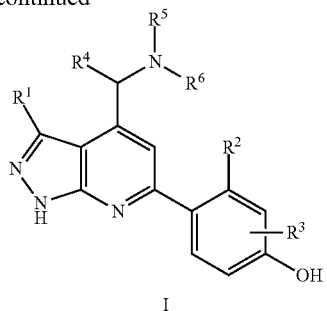

wherein the groups $R^1$, $R^2$, $R^3$, $R^5$ and $R^6$ in the compounds of the formulae Ia, II and IV are defined as in the compounds of the formula I and wherein the group $R^4$ in the compounds of formula I and Ia is defined as hydrogen. The groups $R^{5a}$ and $R^{6a}$ in the compounds of formulae Ia, III and IV are, independently of each other, either defined as the groups $R^5$ and $R^6$ in formula I, or they are precursors of the groups $R^5$ and $R^6$ in formula I, they can for example contain functional groups in protected form or functional groups which can be converted to obtain the final groups $R^5$ and $R^6$. The group $G^1$ in the compounds of formulae Ia, II and IV is defined as a hydrogen or a protecting group for a pyrazole nitrogen, such as, for example, a 2-tetrahydropyranyl-group, a benzyl group, a 4-methoxybenzyl or a 2,5-dimethoxybenzyl group. The group $G^2$ in the compounds of formulae Ia, II and IV is defined as a hydrogen or a protecting group for a phenolic hydroxyl group, such as, for example, a 2-tetrahydropyranyl-group, a methoxymethyl group, a benzyl group, a 4-methoxybenzyl or a 2,5-dimethoxybenzyl group.

The compounds of the formula II may also be present in another tautomeric form, especially for compounds, in which $G^1$ is hydrogen, for example in the form of the respective 2H-pyrazolo[3,4-b]pyridine derivatives in which the mobile hydrogen atom, which in formula II is bonded to the ring nitrogen atom in the 1-position of the pyrazolo[3,4-b]pyridine ring system, is bonded to the ring nitrogen atom in the 2-position of the pyrazolo[3,4-b]pyridine ring system. As far as applicable, it applies to all compounds occurring in the preparation of the compounds of the formula I that they can be present in any other tautomeric form than the one represented in their formulae.

The reaction of the compounds of the formulae II and III to form an amide of formula Ia is generally performed in the presence of activating agents, such as CDI, DCC, EDC, HOAt, HOBt, HATU, TOTU, TBTU, BEP or combinations thereof, and optionally an additional base, such as TEA, DIPEA or N-methylmorpholin in an appropriate inert solvent, for example a hydrocarbon or a chlorinated hydrocarbon such as benzene, toluene, chlorobenzene, dichloromethane, dichloroethane, chloroform, or an ether such as tetrahydrofurane, 1,4-dioxane, dibutylether, diisopropylether, methyl-tert-butylether, dimethoxyethane, or an ester such as ethyl acetate or ethyl butanoate or an amide such as N,N-dimethylformamide or N,N-dimethylacetamide or N-methyl-pyridone or a in mixture of solvents. The reaction temperature in this case is generally from −30° C. to 200° C., preferably from −20° C. to 80°, more preferably from 0° C. to 20° C. The reaction time is generally from 15 min to 6 days, preferably from 15 min to 16 h, depending on the composition of the mixture and the chosen temperature range. The acids of formula II can be subjected to the reaction in form of their salts, for example their sodium salts. They can also be transformed into an activated derivative prior to the coupling with the amine, for example into an acid chloride or an acid anhydride by standard transformations. The amines of formula III can be subjected to the reaction in form of their salts, for example as hydrochloride or triflate salts, in which case usually an additional equivalent of the base is added to the reaction. As far as applicable and unless otherwise indicated, it applies to all acidic or basic compounds occurring in the preparation of the compounds of the formula I that they can be present in form of their salts. In this transformation the groups $G^1$ and $G^2$ in compounds of the formula II can have any meaning given above, but preferably the group $G^1$ represents a protecting group for a pyrazole nitrogen, such as, for example, a 2-tetrahydropyranyl-group, a benzyl group, a 4-methoxybenzyl or a 2,5-dimethoxybenzyl group and the group $G^2$ represents a protecting group for a phenolic hydroxyl group, such as, for example, a 2-tetrahydropyranyl-group, a methoxymethyl group, a benzyl group, a 4-methoxybenzyl or a 2,5-dimethoxybenzyl group.

The reduction of an amide of formula IV to a compound of formula Ia, wherein $R^4$ is hydrogen, is generally performed in the presence of reducing agents, such as $BH_3$-THF, $BH_3$-DMS, lithium borohydride or sodium borohydride, lithium trialkyl borohydride, e.g. $LiBHEt_3$ or $LiBHsBu_3$, DIBAL or $LiAlH_4$ or combinations thereof, preferably $BH_3$-DMS or $LiAlH_4$, more preferably $BH_3$-DMS, and optionally an additional activating agent, such as titanium(IV)chloride, aluminium(III)chloride or TMSCl, in an appropriate inert solvent, for example a hydrocarbon or a chlorinated hydrocarbon such as benzene, toluene, chlorobenzene, dichloromethane, dichloroethane, chloroform, or an ether such as tetrahydrofurane, 1,4-dioxane, dibutylether, diisopropylether, methyl-tert-butylether, dimethoxyethane, or a in mixture of solvents, preferably in an ether, more preferably in tetrahydrofurane or 1,4-dioxane. The reaction temperature in this case is generally from −30° C. to 200° C., preferably from −20° C. to 120°, more preferably from 0° C. to 100° C. The reaction time is generally from 15 min to 6 days, preferably from 15 min to 16 h, depending on the composition of the mixture and the chosen temperature range.

A compound of the formula Ia can already be a compound of formula I, if $G^1$ and $G^2$ are both H and if $R^{5a}$ is $R^5$ and $R^{6a}$ is $R^6$. If a compound of formula Ia is not already a compound of formula I, it can be transformed into a compound of formula I in one step or in several steps depending of the meaning of the groups $G^1$, $G^2$, $R^{5a}$ and $R^{6a}$. If the groups $R^{5a}$ and/or $R^{6a}$ contain or if the groups $G^1$ and/or $G^2$ consist of protecting groups that can be cleaved by hydrogenation, e.g. a benzyl group or a 4-methoxybenzyl group, one step in the transformation of a compound of formula Ia to a compound of formula I can be a catalytic hydrogenation or a transfer hydrogenation. If the groups $R^{5a}$ and/or $R^{6a}$ contain or if the groups $G^1$ and/or $G^2$ consist of protecting groups that can be cleaved by treatment with acid, e.g. a 2-tetrahydropyranyl group, a 4-methoxy-benzyl group, a 2,4-dimethoxybenzyl group or a tert-butoxycarbonyl group, one step in the transformation of a compound of formula Ia to a compound of formula I can be an acidic deprotection. All deprotection reactions used in the above-described transformation of compounds of the formula Ia, in which the groups $R^{5a}$ and/or $R^{6a}$ contain or in which the groups $G^1$ and/or $G^2$ consist of protecting groups, to compounds of formula I are per se well known to the skilled person and can be carried out under standard conditions according to, or analogously to, procedures described in the literature, for example in P. J. Kocienski, Protecting Groups, Georg Thieme Verlag, Stuttgart, 1994 or T. W. Greene, P. G. M. Wuts, Protective Groups in Organic Synthesis, John Wiley, New York, 1999).

A transformation of a compound of formula Ia, in which the groups $R^{5a}$ and/or $R^{6a}$ are precursors to the groups $R^5$ and/or $R^6$ into a compound of formula I can also include a functionalization or modification of contained functional groups according to standard procedures, for example by esterification, amidation, hydrolysis, etherification, alkylation, acylation, sulfonylation, reduction, oxidation, conversion into salts, and others. For example, a hydroxy group, which may be obtained from a protected hydroxy group by deprotection, can be esterified to give a carboxylic acid ester or a sulfonic acid ester, or etherified. Etherifications of hydroxy groups can favorably be performed by alkylation with the respective halogen compound, for example a bromide or iodide, in the presence of a base, for example an alkaline metal carbonate such potassium carbonate or cesium carbonate in an inert solvent, for example an amide like DMF or NMP or a ketone like acetone or butan-2-one, or with the respective alcohol under the conditions of the Mitsunobu reaction referred to above. A hydroxy group can be converted into a halide by treatment with a halogenating agent. A halogen atom can be replaced with a variety of groups in a substitution reaction which may also be a transition-metal catalyzed reaction. A nitro group can be reduced to an amino group, for example by catalytic hydrogenation. An amino group, which may be obtained from a protected amino group by deprotection, can be modified under standard conditions for alkylation, for example by reaction with a halogen compound or by reductive amination of a carbonyl compound, or for acylation or sulfonylation, for example by reaction with a reactive carboxylic acid derivative, like an acid chloride or anhydride or a sulfonic acid chloride, or with a carboxylic acid in the presence of activating agents, such as CDI, DCC, EDC, HOAt, HOBt, HATU, TOTU, TBTU, BEP or combinations thereof, or for carbamoylation, for example by reaction with an isocyanate. A carboxylic ester group can be hydrolyzed under acidic or basic conditions to give a carboxylic acid. A carboxylic acid group can be activated or converted into a reactive derivative as mentioned afore and reacted with an alcohol or an amine or ammonia to give an ester or amide. A primary amide can be dehydrated to give a nitrile. A sulfur atom, for example in an alkyl-S— group or in a heterocyclic ring, can be oxidized with a peroxide like hydrogen peroxide or a peracid to give a sulfoxide moiety $S(O)$ or a sulfone moiety $S(O)_2$. A carboxylic acid group, carboxylic acid ester group and a ketone group can be reduced to an alcohol, for example by means of a complex hydride such as lithium aluminium hydride, lithium borohydride or sodium borohydride. All reactions used in the above-described syntheses of the compounds of the formula I are per se well known to the skilled person and can be carried out under standard conditions according to, or analogously to, procedures described in the literature, for example in Houben-Weyl, Methoden der Organischen Chemie (Methods of Organic Chemistry), Thieme-Verlag, Stuttgart, or Organic Reactions, John Wiley & Sons, New York.

The compounds of the formula II can be obtained by reacting an aminopyrazole compound of the formula IV with a benzaldehyde of formula V and a pyruvic acid derivative of formula VI to give a compound of formula IIa, which can be a compound of formula II already or which can be converted into a compound of formula II,

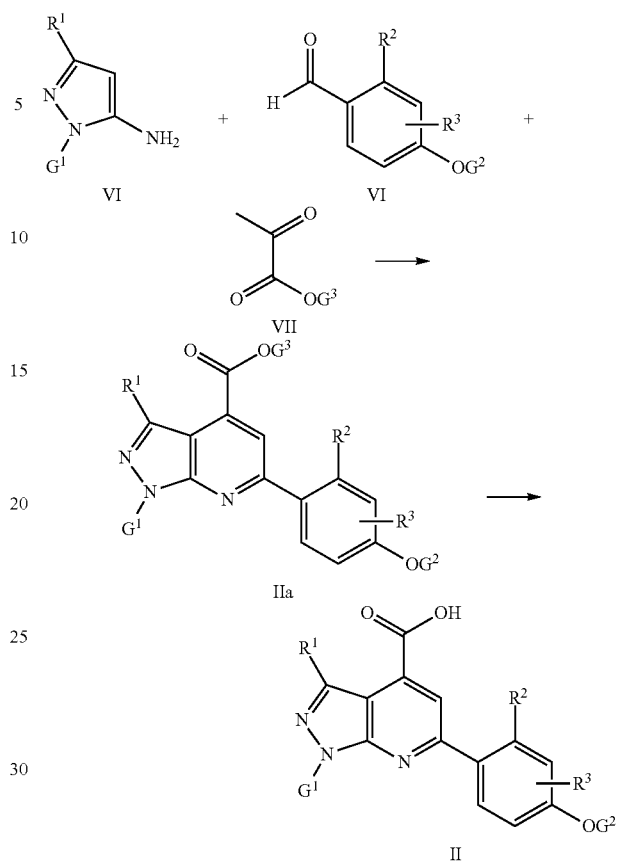

wherein the groups $R^1$, $R^2$, and $R^3$ in the compounds of the formulae II, IIa, V and VI are defined as in the compounds of the formula I. The group $G^1$ in the compounds of formulae II, IIa and V is defined as a hydrogen or a protecting group for a pyrazole nitrogen, such as, for example, a 2-tetrahydropyranyl-group, a benzyl group, a 4-methoxybenzyl or a 2,5-dimethoxybenzyl group. The group $G^2$ in the compounds of formulae II, IIa and VI is defined as a hydrogen or a protecting group for a phenolic hydroxyl group, such as, for example, a 2-tetrahydropyranyl-group, a methoxymethyl group, a benzyl group, a 4-methoxybenzyl or a 2,5-dimethoxybenzyl group. The group $G^3$ in the compounds of formulae IIa and VII is hydrogen, or a protecting group for a carboxylic acid, such as, for example methyl, ethyl, propyl, tert-butyl or benzyl, preferably methyl or ethyl.

The reaction of an aminopyrazole compound of the formula V with a benzaldehyde of formula VI and a pyruvic acid derivative of formula VII is generally performed in the presence of acids, for example acetic acid or hydrochloric acid, in an appropriate solvent, for example in an alcohol as ethanol, methanol or iso-propanol or an ether such as tetrahydrofurane, 1,4-dioxane, dibutylether, diisopropylether, methyl-tert-butyl-ether, dimethoxyethane or in water, or in mixtures thereof. The reaction temperature in this case is generally from −30° C. to 200° C., preferably from 0° C. to 150°, more preferably from 0° C. to 80° C. The reaction time is generally from 30 min to 48 h, preferably from 30 min to 6 h, depending on the composition of the mixture and the chosen temperature range. Depending on the solvents and conditions applied the preferred regionisomer of formula IIa can be easily isolated by precipitation from the reaction mixture.

A compound of the formula IIa can already be a compound of formula II, if G¹ and G² are identical in the compounds of formula IIa and II and if G³ in the compound of formula IIa is H. If a compound of formula IIa is not already a compound of formula II, it can be transformed into a compound of formula II in one step or in several steps depending of the meaning of the groups G¹, G² and G³. For example, a compound of formula IIa, in which G¹ is hydrogen, can be converted into a compound of formula IIa, in which G¹ is a protecting group for a pyrazole nitrogen, by a suitable protection reaction, e.g. by the reaction with 3,4-dihydro-2H-pyrane under acidic catalysis. Alternatively, or as an additional step, a compound of formula IIa, in which G² is hydrogen, can be converted to a compound of formula II, in which G² is a protecting group for a phenolic hydroxyl group, for example a benzyl group, by a suitable protection reaction, e.g. by the reaction with a benzyl halide such as benzyl bromide or benzyl chloride in the presence of a base such as sodium carbonate. Alternatively or as an additional step, a compound of formula IIa, in which G³ is not hydrogen, but a protecting group for a carboxylic acid, the compound of formula IIa can be reacted to a compound of formula II by a suitable deprotection reaction, e.g. a basic hydrolysis, if G3 is a methyl, ethyl or propyl residue. As it is known to the skilled person the employed protection groups should be chosen in a manner to be compatible with the desired reaction conditions for all subsequent steps. All protection and deprotection reactions used in the above-described transformation of compounds of the formula IIa to compounds of formula II are well known to the skilled person and can be carried out under standard conditions according to, or analogously to, procedures described in the literature, for example in P. J. Kocienski, Protecting Groups, Georg Thieme Verlag, Stuttgart, 1994 or T. W. Greene, P. G. M. Wuts, Protective Groups in Organic Synthesis, John Wiley, New York, 1999).

Alternatively, the compounds of the formula II can be obtained by reacting an aminopyrazole of formula V with a 2-oxo succinic acid derivative of formula VIII (or a tautomer and/or salt thereof) to a compound of formula IX, the obtained compound of formula IX is then converted into a compound of formula Xa, which is then reacted with a compound of formula XI to give a compound of formula IIa, which can be a compound of formula II already or which can be converted into a compound of formula II,

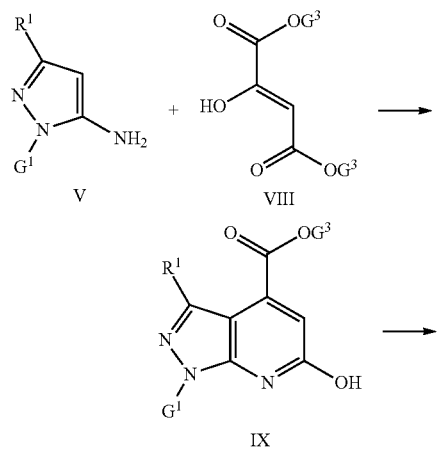

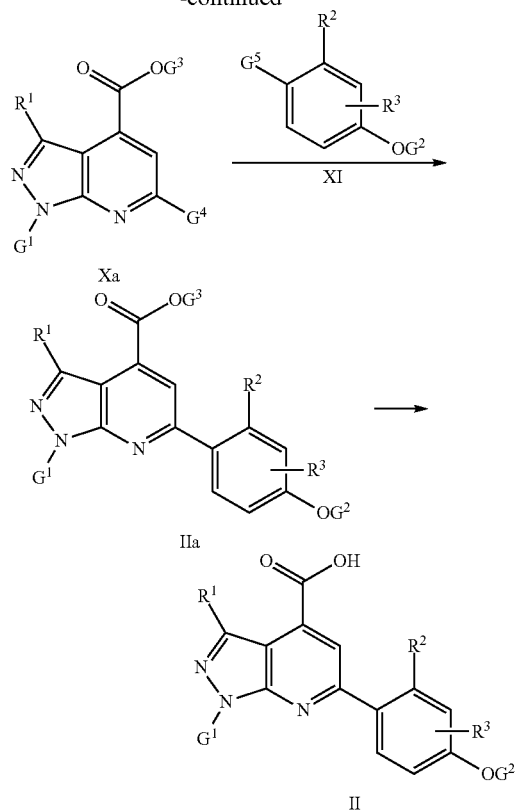

wherein the groups R¹, R² and R³ in the compounds of the formulae II, IIa, V, IXI, Xa and XI are defined as in the compounds of the formula I. The group G¹ in the compounds of formulae II, IIa, V, IX and Xa is defined as a hydrogen or a protecting group for a pyrrazole nitrogen, such as, for example, a 2-tetrahydropyranyl-group, a benzyl group, a 4-methoxybenzyl or a 2,5-dimethoxybenzyl group. The group G² in the compounds of formulae II, IIa and XI is defined as a hydrogen or a protecting group for a phenolic hydroxyl group, such as, for example, a 2-tetrahydropyranyl-group, a methoxymethyl group, a benzyl group, a 4-methoxybenzyl or a 2,5-dimethoxybenzyl group. The group G³ in the compounds of formulae IIa, VIII, IX and Xa is hydrogen or a protecting group for a carboxylic acid, such as, for example methyl, ethyl, propyl, tert-butyl or benzyl, preferably methyl or ethyl. The group G⁴ in the compounds of formula Xa is a leaving group, that can be replaced in a Suzuki-type reaction, such as a halide, e.g. a bromide or a chloride or as a sulfonate, e.g. a trifluoromethanesulfonate or methanesulfonate. The group G⁵ in the compounds of formula XI is a boronic acid or a boronic ester or cyclic boronic ester.

The reaction of an aminopyrazole of formula V with a compound of formula VIII (or a tautomer and/or salt thereof, e.g. a dialkyl oxalacetate sodium salt) to a compound of formula IX is generally carried out in the presence of an acid, such as aqueous hydrochloric acid or acetic acid or trifluoro acetic acid at temperatures from about 0° C. to about 200° C., for example at temperatures from about 20° C. to about 120° C. The reaction can be carried out in neat conditions or in a suitable inert solvent. The reaction time is generally from 30 min to 48 h, preferably from 30 min to 16 h, depending on the composition of the mixture and the chosen temperature range. Depending on the solvents and conditions applied the preferred regioisomer of formula VIII can be easily isolated by precipitation from the reaction mixture.

The conversion of a compound of formula IX to a compound of formula Xa, in which G⁴ is a halide, for example a bromide or a chloride, is generally carried out by reaction with a phosphorhalide like phosphorous trichloride or phosphorous tribromide or a phosphorous oxyhalide like phosphorous oxychloride or phosphorous oxybromide. The reaction can be carried out in neat conditions or in a suitable inert solvent, for example a hydrocarbon, such as benzene, toluene or xylene, or a chlorinated hydrocarbon, such as chlorobenzene, or a mixture of solvents, at temperatures from about 20° C. to about 200° C., for example at temperatures from about 80° C. to about 120° C., favorably with addition of a base, for example a tertiary amine, such as triethylamine, ethyldiisopropylamine, N-methylmorpholine or 1,8-diazabicyclo[5.4.0]unde-7-ene. The reaction time is generally from 30 min to 48 h, preferably from 30 min to 4 h, depending on the composition of the mixture and the chosen temperature range. The conversion of a compound of formula IX to a compound of formula Xa, in which G⁴ is an alkylsulfonate, e.g. trifluoromethylsulfonate or methylsulfonate, is generally carried out by reaction with an alkanesulfonyl halide, such as methanesulfonyl chloride, or an alkane sulfonic anhydride, such as trifluoromethane sulfonic anhydride. The reaction can be carried out in neat conditions or in a suitable inert solvent, for example a hydrocarbon, such as benzene, toluene or xylene, or a chlorinated hydrocarbon, such as chlorobenzene, or an ether, such as THF, dioxane or DME, or a mixture of solvents, at temperatures from about 0° C. to about 200° C., for example at temperatures from about 20° C. to about 120° C., favorably with addition of a base, for example a tertiary amine, such as triethylamine, ethyldiisopropylamine, N-methylmorpholine or 1,8-diaza-bicyclo[5.4.0]unde-7-ene. The reaction time is generally from 30 min to 48 h, preferably from 30 min to 4 h, depending on the composition of the mixture and the chosen temperature range.

The reaction of the compound of the formula Xa with compounds of the formula XI to a compound of formula IIa is a Suzuki-type reaction and is generally carried out in the presence of catalytic palladium compound, for example a palladium(II) salt such as palladium(II) acetate or palladium(II) chloride, which can be employed in the presence of a phosphine such as tricyclohexylphosphine or triphenylphosphine, or a palladium complex such as tetrakis(triphenylphosphine)palladium(0), palladium(0) bis(tri-tert-butylphosphin) or bis(triphenylphosphine)palladium(II) chloride, and favourably in the presence of a base, for example an alkaline metal carbonate or phosphate such as sodium carbonate or tripotassium phosphate, in an inert solvent, for example a hydrocarbon, such as benzene, toluene or xylene, or an ether, such as THF, dioxane or DME, or water, or a mixture of solvents, at temperatures from about 20° C. to about 200° C., for example at temperatures from about 80° C. to about 120° C. The reaction time is generally from 30 min to 48 h, preferably from 30 min to 16 h, depending on the composition of the mixture and the chosen temperature range.

A compound of the formula IIa can already be a compound of formula II, if G¹ and G² are identical in the compounds of formula IIa and II and if G³ in the compound of formula IIa is H. If a compound of formula IIa is not already a compound of formula II, it can be transformed into a compound of formula II in one step or in several steps depending of the meaning of the groups G¹, G² and G³ as it was described above.

Alternatively, the compounds of the formula II can be obtained by reacting a ketone of formula XII with an oxalic acid derivative of formula XIII in a Claisen-type condensation to a compound of formula XIV, which is then reacted with an amino pyrazole compound of formula V to give a compound of formula IIa, which can be a compound of formula II already or which can be converted into a compound of formula II,

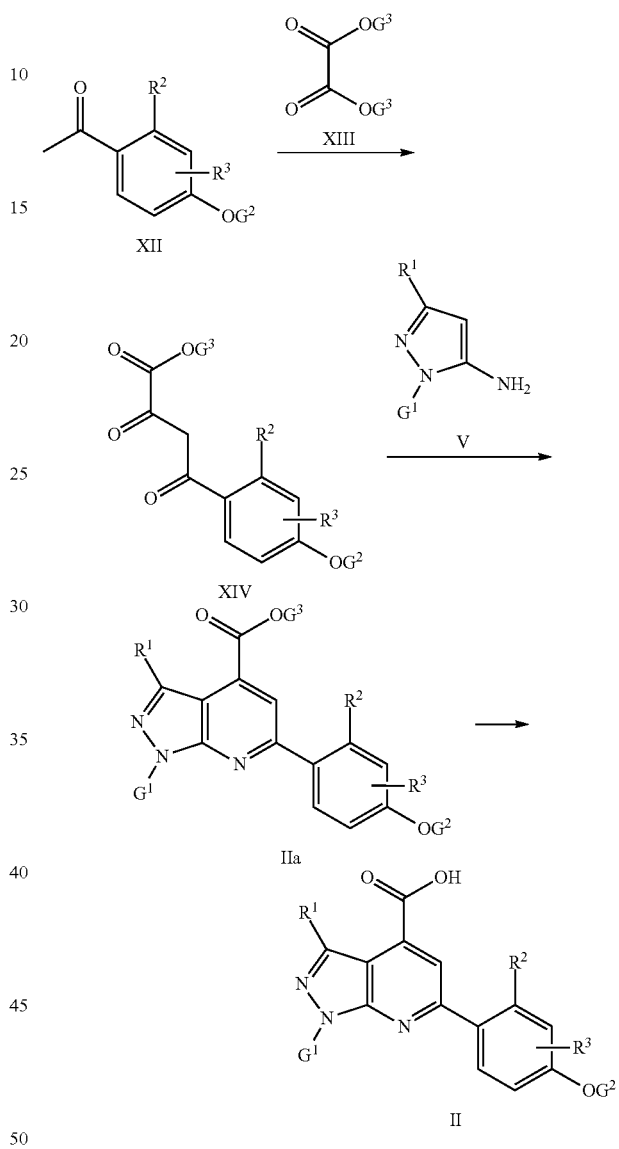

wherein the groups R¹, R² and R³ in the compounds of the formulae II, IIa, V, XII and XIV are defined as in the compounds of the formula I. The group G¹ in the compounds of formulae II, IIa and V is defined as a hydrogen or a protecting group for a pyrazole nitrogen, such as, for example, a 2-tetrahydropyranyl-group, a benzyl group, a 4-methoxybenzyl or a 2,5-dimethoxybenzyl group. The group G² in the compounds of formulae II, IIa, XII and XIV is defined as a hydrogen or a protecting group for a phenolic hydroxyl group, such as, for example, a 2-tetrahydropyranyl-group, a methoxymethyl group, a benzyl group, a 4-methoxybenzyl or a 2,5-dimethoxybenzyl group. The group G³ in the compounds of formulae IIa, XIII and XIV is hydrogen or a protecting group for a carboxylic acid, such as, for example, methyl, ethyl, propyl, tert-butyl or benzyl, preferably methyl or ethyl.

The Claisen-type condensation of a ketone of formula XII with an oxalic acid derivative of formula XIII is generally carried out in the presence of a base, for example an inorganic base such as an alkaline metal hydride, like sodium hydride, or an alkoxide or amide such as sodium methoxide, sodium ethoxide, potassium methoxide, potassium tert-butoxide, sodium amide or lithium diisopropylamide, and in an inert solvent, for example a hydrocarbon or chlorinated hydrocarbon such as benzene, toluene, xylene and chlorobenzene, an ether such as THF, dioxane, dibutyl ether, diisopropyl ether or DME, an alcohol such as methanol, ethanol, isopropanol or tert-butanol, or a mixture of solvents at temperatures from about 0° C. to about 200° C., for example at temperatures from about 20° C. to about 120° C. The reaction time is generally from 30 min to 48 h, preferably from 30 min to 8 h, depending on the composition of the mixture and the chosen temperature range. The compounds of formula XIV can be obtained in form of a tautomer and/or salt, e.g. as sodium 1-methoxycarbonyl-3-oxo-3-aryl-propen-1-olate for compounds of formula XIV, in which $G^3$ is methyl.

The reaction of a compound of formula XIV with an amino pyrazole compound of formula V to give a compound of the formula IIa is generally carried out in the presence of an acid, for example acetic acid or hydrochloric acid or trifluoro acetic acid. The reaction can be carried out neat or in suitable solvents at temperatures from about 0° C. to about 200° C., for example at temperatures from about 20° C. to about 150° C., preferably from about 80° C. to 120° C. The reaction time is generally from 30 min to 48 h, preferably from 30 min to 16 h, depending on the composition of the mixture and the chosen temperature range. Depending on the solvents and conditions applied the preferred regioisomer of formula IIa can be easily isolated by precipitation from the reaction mixture.

A compound of the formula IIa can already be a compound of formula II, if $G^1$ and $G^2$ are identical in the compounds of formula IIa and II and if $G^3$ in the compound of formula IIa is H. If a compound of formula IIa is not already a compound of formula II, it can be transformed into a compound of formula II in one step or in several steps depending of the meaning of the groups $G^1$, $G^2$ and $G^3$ as it was described above.

In another process for the preparation of compounds of the formula I, a compound of the formula II is converted into a compound of formula XV, the latter compound is then converted to a compound of formula XVII, and this compound is reacted with a compound of the formula III to give a compound of the formula Ia, which can be a compound of formula I already or which can be converted into a compound of formula I, or, alternatively, a compound of formula II is converted to a compound of formula XVI, either directly or via a compound of formula XV, and this compound of formula XVI is subsequently reacted with a compound of the formula III to give a compound of the formula Ia, which can be a compound of formula I already or which can be converted into a compound of formula I,

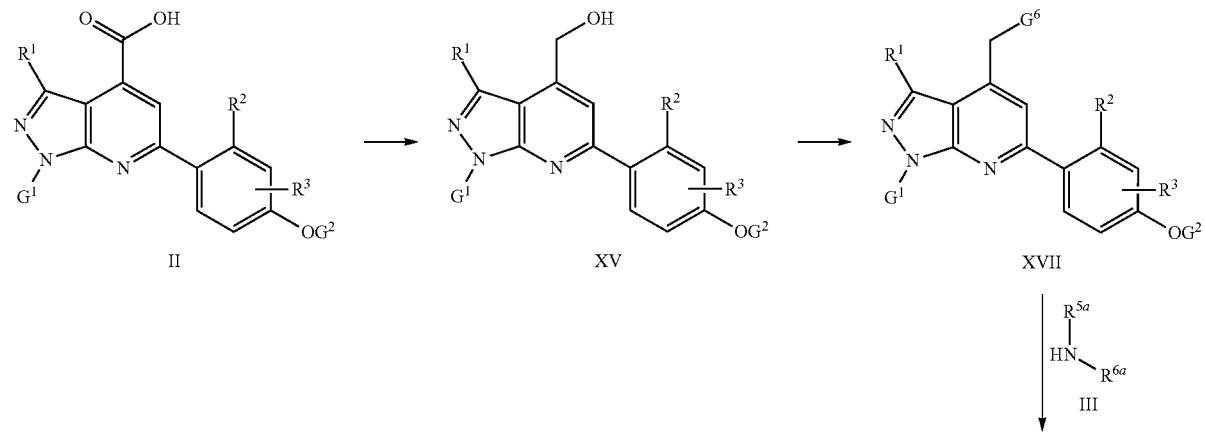

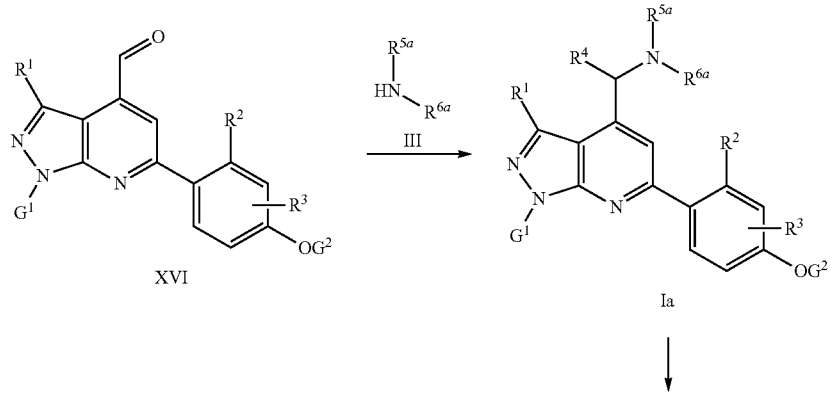

-continued

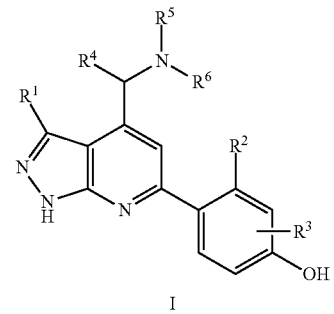

I wherein the groups $R^1$, $R^2$, $R^3$, $R^5$ and $R^6$ in the compounds of the formulae Ia, II, XV, XVI and XVII are defined as in the compounds of the formula I, wherein $R^4$ in the compounds of formulae I and Ia is hydrogen, and wherein the groups $R^{5a}$ and $R^{6a}$ in the compounds of formulae Ia and III, independently of each other, are either defined as the groups $R^5$ and $R^6$ in formula I, or they are precursors of the groups $R^5$ and $R^6$ in formula I, they can for example contain functional groups in protected form or functional groups which can be converted to obtain the final groups $R^5$ and $R^6$. The group $G^1$ in the compounds of formulae Ia, II, XV, XVI and XVII is defined as a hydrogen or a protecting group for a pyrazole nitrogen, such as, for example, a 2-tetrahydropyranyl-group, a benzyl group, a 4-methoxybenzyl or a 2,5-dimethoxybenzyl group. The group $G^2$ in the compounds of formulae Ia, II, XV, XVI and XVII is defined as a hydrogen or a protecting group for a phenolic hydroxyl group, such as, for example, a 2-tetrahydropyranyl-group, a methoxymethyl group, a benzyl group, a 4-methoxybenzyl or a 2,5-dimethoxybenzyl group. The group $G^6$ in the compounds of formula XVII is a leaving group, that can be replaced in a nucleophilic substitution reaction, such as a halide, e.g. a bromide or a chloride or as a sulfonate, e.g. a trifluoromethanesulfonate or a methanesulfonate.

The reduction of an acid of formula II to a compound of formula XV is generally performed in the presence of reducing agents, such as $BH_3$-THF, $BH_3$-DMS, lithium borohydride or sodium borohydride, DIBAL or $LiAlH_4$ or combinations thereof, preferably $BH_3$-DMS or $LiAlH_4$, more preferably $LiAlH_4$, and optionally in the presence of an additional activating agent, such as boron(III)fluoride-diethyl ether complex, and it can be performed either directly or by prior activation of the acid of formula II by treatment with an activating agent, such as thionyl chloride, CDI, benzotriazole or an alkyl chloroformate, e.g. methyl chloroformate or isobutyl chloroformate, in an appropriate inert solvent, for example a hydrocarbon or a chlorinated hydrocarbon such as benzene, toluene, chlorobenzene, dichloromethane, dichloroethane, chloroform, or an ether such as tetrahydrofurane, 1,4-dioxane, dibutylether, diisopropylether, methyl-tert-butylether, dimethoxyethane, or a in mixture of solvents, preferably in an ether, more preferably in tetrahydrofurane or 1,4-dioxane. The reaction temperature in this case is generally from −30° C. to 150° C., preferably from −20° C. to 100°, more preferably from 0° C. to 80° C. The reaction time is generally from 15 min to 6 days, preferably from 15 min to 16 h, depending on the composition of the mixture and the chosen temperature range.

The conversion of a compound of formula XV to a compound of formula XVII, in which $G^4$ is a halide, for example a bromide or a chloride, is generally carried out by reaction with thionyl chloride or a phosphorous oxyhalide like phosphorous oxychloride or phosphorous oxybromide. The reaction can be carried out in neat conditions or in a suitable inert solvent, for example a hydrocarbon, such as benzene, toluene or xylene, or a chlorinated hydrocarbon, such as chlorobenzene, or a mixture of solvents, at temperatures from about 20° C. to about 200° C., for example at temperatures from about 80° C. to about 120° C., favorably with addition of a base, for example a tertiary amine, such as triethylamine, ethyldiisopropylamine, N-methylmorpholine or 1,8-diazabicyclo[5.4.0]unde-7-ene, the reaction time is generally from 30 min to 48 h, preferably from 30 min to 4 h, depending on the composition of the mixture and the chosen temperature range, or, alternatively, the conversion of a compound of formula XV to a compound of formula XVII, in which $G^4$ is a halide, for example a bromide or a chloride, is carried out by reaction with triphenylphoshine and tetrachlorocarbon or N-chlorosuccinimide or N-bromo-succinimide in a suitable inert solvent, for example an ether such as tetrahydrofurane, 1,4-dioxane, dibutylether, diisopropylether, methyl-tert-butylether, dimethoxyethane, or in acetonitrile or a in mixture of solvents, preferably in an ether, more preferably in tetrahydrofurane or 1,4-dioxane, at temperatures from about −20° C. to about 180° C., for example at temperatures from about 0° C. to about 120° C., the reaction time is generally from 30 min to 48 h, preferably from 30 min to 4 h, depending on the composition of the mixture and the chosen temperature range. The conversion of a compound of formula XVI to a compound of formula XVII, in which $G^4$ is an alkylsulfonate, e.g. trifluoromethylsulfonate or methylsulfonate, is generally carried out by reaction with an alkanesulfonyl halide, such as methanesulfonyl chloride, or an alkane sulfonic anhydride, such as trifluoromethane sulfonic anhydride. The reaction can be carried out in neat conditions or in a suitable inert solvent, for example a hydrocarbon, such as benzene, toluene or xylene, or a chlorinated hydrocarbon, such as chlorobenzene, or an ether, such as THF, dioxane or DME, or a mixture of solvents, at temperatures from about 0° C. to about 200° C., for example at temperatures from about 20° C. to about 120° C., favorably with addition of a base, for example a tertiary amine, such as triethylamine, ethyldiisopropylamine, N-methylmorpholine or 1,8-diazabicyclo[5.4.0]unde-7-ene. The reaction time is generally from 30 min to 48 h, preferably from 30 min to 4 h, depending on the composition of the mixture and the chosen temperature range.

The reaction of compounds of formula XVII with compounds of formula III to form compounds of formula Ia, wherein $R^4$ is hydrogen, is generally carried out under neat conditions or in an appropriate inert solvent, for example a hydrocarbon or a chlorinated hydrocarbon such as benzene, toluene, chlorobenzene, dichloromethane, dichloroethane, chloroform, or an ether such as tetrahydrofurane, 1,4-dioxane, dibutylether, diisopropylether, methyl-tert-butylether, dimethoxyethane, or an ester such as ethyl acetate or ethyl butanoate or an amide such as N,N-dimethylformamide or N,N-dimethylacetamide or N-methyl-pyridone or a in mixture of solvents, it is carried out optionally in the presence of an additional base, such as TEA, DIPEA or N-methylmorpholin. The reaction temperature in this case is generally from 0° C. to 250° C., preferably from 20° C. to 250°, more preferably from 80° C. to 200° C. The reaction time is generally from 15 min to 6 days, preferably from 15 min to 16 h, depending on the composition of the mixture and the chosen temperature range.

Alternatively, an acid of formula II is reacted to a compound of formula XVI by a sequence of conversion of the acid of formula II to an acid chloride by means known to a person skilled in the art and then reacting it with a suitable reducing agent, such as lithium(tri-tertbutoxy)aluminiumhydride, in an appropriate inert solvent, for example an ether such as tetrahydrofurane, 1,4-dioxane, dibutylether, diisopropylether, methyl-tert-butylether, dimethoxyethane, or a in mixture of solvents, preferably in tetrahydrofurane or 1,4-dioxane. The reaction temperature in this case is generally from −80° C. to 100° C., preferably from −80° C. to 25°, more preferably from −20° C. to 0° C. The reaction time is generally from 15 min to 6 days, preferably from 15 min to 16 h, depending on the composition of the mixture and the chosen temperature range. A compound of formula XVI can also be obtained by reacting a compound of formula XV with a mild oxidizing agent, such as Dess-Martin periodinane, pyridinium chlorochromate, pyridinium dichromate, mangandioxide or DMSO/acetic anhydride, in an appropriate inert solvent, for example a hydrocarbon or a chlorinated hydrocarbon such as benzene, toluene, chlorobenzene, dichloromethane, dichloroethane, chloroform, or an ether such as tetrahydrofurane, 1,4-dioxane, dibutylether, diisopropylether, methyl-tert-butylether, dimethoxyethane, or a in mixture of solvents, preferably in an ether, more preferably in tetrahydrofurane or 1,4-dioxane. The reaction temperature in this case is generally from −30° C. to 150° C., preferably from −20° C. to 100°, more preferably from 0° C. to 80° C. The reaction time is generally from 15 min to 6 days, preferably from 15 min to 16 h, depending on the composition of the mixture and the chosen temperature range.

The reaction of compounds of formula XVI with compounds of formula III to form compounds of formula Ia, wherein $R^4$ is hydrogen, is a reductive amination, which is generally carried out in the presence of a reducing agent, such as sodium borhohydrate, lithium borohydride, or modified borohydride reagents, such as sodium triacetoxy borohydride or sodium cyanoborohydrate, or in the presence of a hydrogenation catalyst such as palladium in a hydrogen atmosphere or under hydrogen transfer conditions using, for example, formic acid as the source of reducing equivalents, and which is optionally carried out in the presence of an acid, such as acetic acid, or a base, such as a trialkylamine, e.g. triethylamine or di-isopropylethyl amine, or N-methylmorpholin or which is optionally carried out in the presence of molecular sieve, and which is carried out in an appropriate inert solvent, for example a hydrocarbon or a chlorinated hydrocarbon such as benzene, toluene, chlorobenzene, dichloromethane, dichloroethane, chloroform, or an ether such as tetrahydrofurane, 1,4-dioxane, dibutylether, diisopropylether, methyltert-butylether, dimethoxyethane, or an ester such as ethyl acetate or ethyl butanoate or an amide such as N,N-dimethylformamide or N,N-dimethylacetamide or N-methyl-pyridone or a in mixture of solvents. The reaction temperature in this case is generally from −40° C. to 200° C., preferably from −20° C. to 80°, more preferably from 0° C. to 20° C. The reaction time is generally from 15 min to 6 days, preferably from 15 min to 16 h, depending on the composition of the mixture and the chosen temperature range.

A compound of the formula Ia can already be a compound of formula I, if $G^1$ and $G^2$ are both H and if $R^{5a}$ is $R^5$ and $R^{6a}$ is $R^6$. If a compound of formula Ia is not already a compound of formula I, it can be transformed into a compound of formula I in one step or in several steps depending of the meaning of the groups $G^1$, $G^2$, $R^{5a}$ and $R^{6a}$, as it was described above.

In another process for the preparation of compounds of the formula I, a compound of the formula Xa is converted into a compound of formula X, if $G^3$ is not hydrogen; subsequently, a compound of formula X is converted to a compound of formula XVIII, and then the latter compound is reacted to form a compound of formula XX, followed by a reaction of the latter compound with a compound of the formula III to give a compound of the formula XXI, and a subsequent reaction of a compound of formula XXI with a compound of formula XI to a compound of formula Ia, which can be a compound of formula I already or which can be converted into a compound of formula I, or, alternatively, a compound of formula X is converted to a compound of formula IXX, either directly or via a compound of formula XVIII, and this compound of formula IXX is subsequently reacted with a compound of the formula III to give a compound of the formula XXI, and a subsequent reaction of a compound of formula XXI with a compound of formula XI to a compound of formula Ia, which can be a compound of formula I already or which can be converted into a compound of formula I,

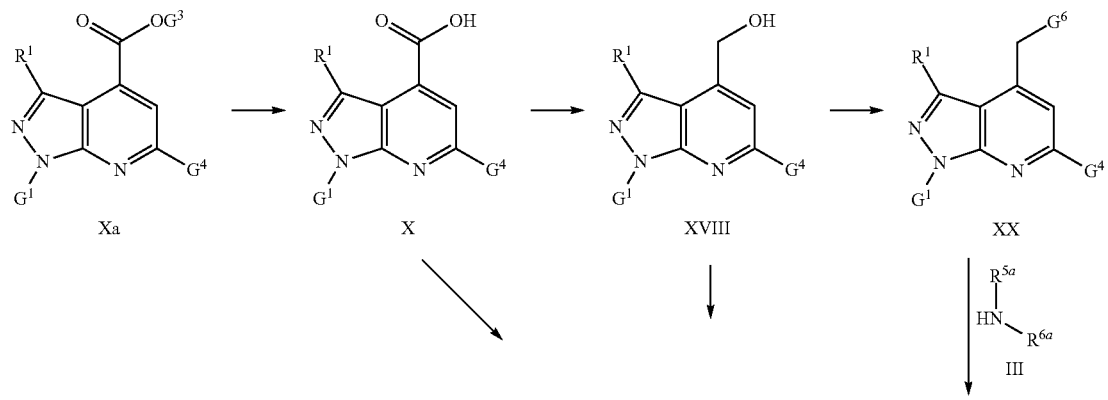

-continued

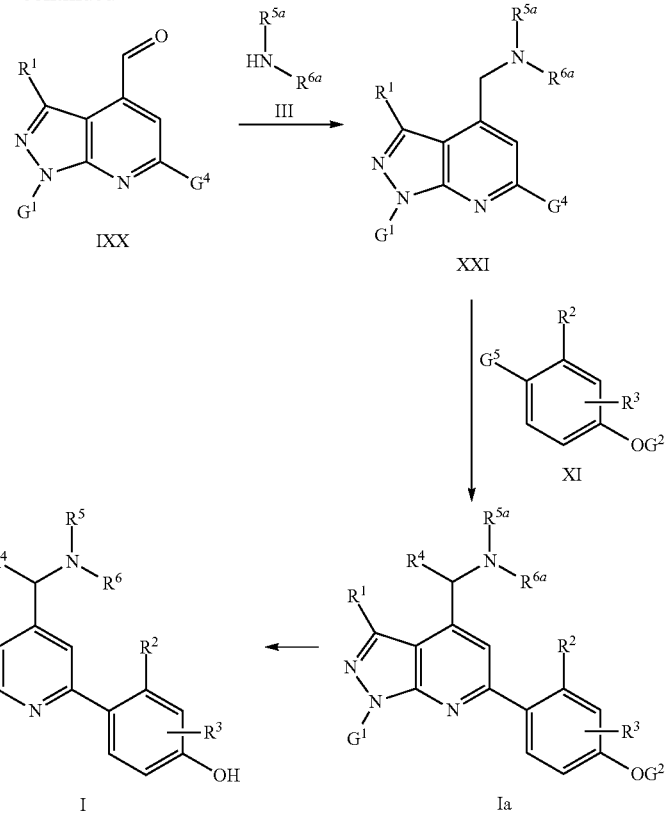

wherein the groups $R^1$, $R^2$, $R^3$, $R^5$ and $R^6$ in the compounds of the formulae Ia, Xa, X, XI, XVIII, IXX, XX and XXI are defined as in the compounds of the formula I, wherein $R^4$ in the compounds of formulae I and Ia is hydrogen, and wherein the groups $R^{5a}$ and $R^{6a}$ in the compounds of formulae Ia and III, independently of each other, are either defined as the groups $R^5$ and $R^6$ in formula I, or they are precursors of the groups $R^5$ and $R^6$ in formula I, they can for example contain functional groups in protected form or functional groups which can be converted to obtain the final groups $R^5$ and $R^6$. The group $G^1$ in the compounds of formulae Ia, Xa, X, XVIII, IXX, XX and XXI is defined as a hydrogen or a protecting group for a pyrazole nitrogen, such as, for example, a 2-tetrahydropyranyl-group, a benzyl group, a 4-methoxybenzyl or a 2,5-dimethoxybenzyl group. The group $G^2$ in the compounds of formulae Ia and XI is defined as a hydrogen or a protecting group for a phenolic hydroxyl group, such as, for example, a 2-tetrahydropyranyl-group, a methoxymethyl group, a benzyl group, a 4-methoxybenzyl or a 2,5-dimethoxybenzyl group. The group $G^3$ in the compounds of formulae Xa is hydrogen or a protecting group for a carboxylic acid, such as, for example methyl, ethyl, propyl, tert-butyl or benzyl, preferably methyl or ethyl. The group $G^4$ in the compounds of formula Xa, X, XVIII, IXX, XX and XXI is a leaving group, that can be replaced in a Suzuki-type reaction, such as a halide, e.g. a bromide or a chloride or as a sulfonate, e.g. a trifluoromethanesulfonate or methanesulfonate. The group $G^5$ in the compounds of formula XI is a boronic acid or a boronic ester or cyclic boronic ester. The group $G^6$ in the compounds of formula XVII is a leaving group, that can be replaced in a nucleophilic substitution reaction, such as a halide, e.g. a bromide or a chloride or as a sulfonate, e.g. a trifluoromethanesulfonate or a methanesulfonate.

A compound of formula Xa can already be a compound of formula X, if $G^3$ is hydrogen, and if $G^1$ and $G^4$ are identical in compounds of formula Xa and X. If $G^3$ is not hydrogen, the ester of formula Xa can be converted into an acid of formula X by means known to the persons skilled in the art, e.g. if $G^3$ is methyl, ethyl or propyl, the transformation can, for example, be achieved by a basic hydrolysis in the presence of sodium hydroxide or lithium hydroxide, if $G^3$ is a tert-butyl, the transformation can, for example, be achieved by an acidic cleavage in the presence of sulfuric acid, hydrochloric acid of trifluoro acetic acid, or if $G^3$ is a benzyl group, the transformation can, for example, be achieved by a hydrogenolytic cleavage in the presence of a hydrogenation catalyst, such as palladium, under hydrogen atmosphere. Care has to be taken to choose conditions compatible with other functional groups and protecting groups present in the compounds of formula Xa and X, as it is known to the presons skilled in the art.

The reduction of an acid of formula X to a compound of formula XVII is generally performed in the presence of reducing agents, such as $BH_3$-THF, $BH_3$-DMS, lithium borohydride or sodium borohydride, DIBAL or $LiAlH_4$ or combinations thereof, preferably $BH_3$-DMS or $LiAlH_4$, more preferably $LiAlH_4$, and optionally in the presence of an additional activating agent, such as boron(III)fluoride-diethyl ether complex, and it can be performed either directly or by prior activation of the acid of formula X by treatment with an activating agent, such as thionyl chloride, CDI, benzotriazole or an alkyl chloroformate, e.g. methyl chloroformate or isobutyl chloroformate, in an appropriate inert solvent, for example a hydrocarbon or a chlorinated hydrocarbon such as benzene, toluene, chlorobenzene, dichloromethane, dichloroethane, chloroform, or an ether such as tetrahydrofurane, 1,4-dioxane, dibutylether, diisopropylether, methyl-tert-butylether, dimethoxyethane, or a in mixture of solvents, preferably in an ether, more preferably in tetrahydrofurane or 1,4-dioxane. The reaction temperature in this case is generally from −30° C. to 150° C., preferably from −20° C. to 100°, more preferably from 0° C. to 80° C. The reaction time is generally from 15 min to 6 days, preferably from 15 min to 16 h, depending on the composition of the mixture and the chosen temperature range.

The conversion of a compound of formula XVIII to a compound of formula XX, in which $G^4$ is a halide, for example a bromide or a chloride, is generally carried out by reaction with thionyl chloride or a phosphorous oxyhalide like phosphorous oxychloride or phosphorous oxybromide. The reaction can be carried out in neat conditions or in a suitable inert solvent, for example a hydrocarbon, such as benzene, toluene or xylene, or a chlorinated hydrocarbon, such as chlorobenzene, or a mixture of solvents, at temperatures from about 20° C. to about 200° C., for example at temperatures from about 80° C. to about 120° C., favorably with addition of a base, for example a tertiary amine, such as triethylamine, ethyldiisopropylamine, N-methylmorpholine or 1,8-diazabicyclo[5.4.0]unde-7-ene, the reaction time is generally from 30 min to 48 h, preferably from 30 min to 4 h, depending on the composition of the mixture and the chosen temperature range, or, alternatively, the conversion of a compound of formula XVIII to a compound of formula XX, in which $G^4$ is a halide, for example a bromide or a chloride, is carried out by reaction with triphenylphoshine and tetrachlorocarbon or N-chloro-succinimide or N-bromo-succinimide in a suitable inert solvent, for example an ether such as tetrahydrofurane, 1,4-dioxane, dibutylether, diisopropylether, methyl-tert-butylether, dimethoxyethane, or in acetonitrile or a in mixture of solvents, preferably in an ether, more preferably in tetrahydrofurane or 1,4-dioxane, at temperatures from about −20° C. to about 180° C., for example at temperatures from about 0° C. to about 120° C., the reaction time is generally from 30 min to 48 h, preferably from 30 min to 4 h, depending on the composition of the mixture and the chosen temperature range. The conversion of a compound of formula XVIII to a compound of formula XX, in which $G^4$ is an alkylsulfonate, e.g. trifluoromethylsulfonate or methylsulfonate, is generally carried out by reaction with an alkanesulfonyl halide, such as methanesulfonyl chloride, or an alkane sulfonic anhydride, such as trifluoromethane sulfonic anhydride. The reaction can be carried out in neat conditions or in a suitable inert solvent, for example a hydrocarbon, such as benzene, toluene or xylene, or a chlorinated hydrocarbon, such as chlorobenzene, or an ether, such as THF, dioxane or DME, or a mixture of solvents, at temperatures from about 0° C. to about 200° C., for example at temperatures from about 20° C. to about 120° C., favorably with addition of a base, for example a tertiary amine, such as triethylamine, ethyldiisopropylamine, N-methylmorpholine or 1,8-diazabicyclo [5.4.0]unde-7-ene. The reaction time is generally from 30 min to 48 h, preferably from 30 min to 4 h, depending on the composition of the mixture and the chosen temperature range.

The reaction of compounds of formula XX with compounds of formula III to form compounds of formula XXI, wherein $R^4$ is hydrogen, is generally carried out under neat conditions or in an appropriate inert solvent, for example a hydrocarbon or a chlorinated hydrocarbon such as benzene, toluene, chlorobenzene, dichloromethane, dichloroethane, chloroform, or an ether such as tetrahydrofurane, 1,4-dioxane, dibutylether, diisopropylether, methyl-tert-butylether, dimethoxyethane, or an ester such as ethyl acetate or ethyl butanoate or an amide such as N,N-dimethylformamide or N,N-dimethylacetamide or N-methyl-pyridone or a in mixture of solvents, it is carried out optionally in the presence of an additional base, such as TEA, DIPEA or N-methylmorpholin. The reaction temperature in this case is generally from 0° C. to 250° C., preferably from 20° C. to 250°, more preferably from 80° C. to 200° C. The reaction time is generally from 15 min to 6 days, preferably from 15 min to 16 h, depending on the composition of the mixture and the chosen temperature range.

The reaction of the compound of the formula XXI with compounds of the formula XI to a compound of formula Ia, in which $R^4$ is hydrogen, is a Suzuki-type reaction and is generally carried out in the presence of catalytic palladium compound, for example a palladium(II) salt such as palladium(II) acetate or palladium(II) chloride, which can be employed in the presence of a phosphine such as tricyclohexylphosphine or triphenylphosphine, or a palladium complex such as tetrakis(triphenylphosphine)-palladium(0), palladium(0) bis (tri-tert-butylphosphin) or bis(triphenylphosphine)-palladium(II) chloride, and favourably in the presence of a base, for example an alkaline metal carbonate or phosphate such as sodium carbonate or tripotassium phosphate, in an inert solvent, for example a hydrocarbon, such as benzene, toluene or xylene, or an ether, such as THF, dioxane or DME, or water, or a mixture of solvents, at temperatures from about 20° C. to about 200° C., for example at temperatures from about 80° C. to about 120° C. The reaction time is generally from 30 min to 48 h, preferably from 30 min to 16 h, depending on the composition of the mixture and the chosen temperature range.

Alternatively, an acid of formula X is reacted to a compound of formula IXX by a sequence of conversion of the acid of formula X to an acid chloride by means known to a person skilled in the art and then reacting it with a suitable reducing agent, such as lithium(tri-tertbutoxy)aluminiumhydride, in an appropriate inert solvent, for example an ether such as tetrahydrofurane, 1,4-dioxane, dibutylether, diisopropylether, methyl-tert-butylether, dimethoxyethane, or a in mixture of solvents, preferably in tetrahydrofurane or 1,4-dioxane. The reaction temperature in this case is generally from −80° C. to 100° C., preferably from −80° C. to 25°, more preferably from −20° C. to 0° C. The reaction time is generally from 15 min to 6 days, preferably from 15 min to 16 h, depending on the composition of the mixture and the chosen temperature range. A compound of formula IXX can also be obtained by reacting a compound of formula XVIII with a mild oxidizing agent, such as Dess-Martin periodinane, pyridinium chlorochromate, pyridinium dichromate, mangandioxide or DMSO/acetic anhydride, in an appropriate inert solvent, for example a hydrocarbon or a chlorinated hydrocarbon such as benzene, toluene, chlorobenzene, dichloromethane, dichloroethane, chloroform, or an ether such as tetrahydrofurane, 1,4-dioxane, dibutylether, diisopropylether, methyl-tert-butylether, dimethoxyethane, or a in mixture of solvents, preferably in an ether, more preferably in tetrahydrofurane or 1,4-dioxane. The reaction temperature in this case is generally from −30° C. to 150° C., preferably from −20° C. to 100°, more preferably from 0° C. to 80° C. The reaction time is generally from 15 min to 6 days, preferably from 15 min to 16 h, depending on the composition of the mixture and the chosen temperature range.

The reaction of compounds of formula IXX with compounds of formula III to form compounds of formula Ia, wherein $R^4$ is hydrogen, is a reductive amination, which is generally carried out in the presence of a reducing agent, such as sodium borhohydrate, lithium borohydride, or modified borohydride reagents, such as sodium triacetoxy borohydride or sodium cyanoborohydrate, or in the presence of a hydrogenation catalyst such as palladium in a hydrogen atmosphere or under hydrogen transfer conditions using, for example, formic acid as the source of reducing equivalents, and which is optionally carried out in the presence of an acid, such as acetic acid, or a base, such as a trialkylamine, e.g. triethylamine or di-isopropylethyl amine, or N-methylmorpholin or which is optionally carried out in the presence of molecular sieve, and which is carried out in an appropriate inert solvent, for example a hydrocarbon or a chlorinated hydrocarbon such as benzene, toluene, chlorobenzene, dichloromethane, dichloroethane, chloroform, or an ether such as tetrahydrofurane, 1,4-dioxane, dibutylether, diisopropylether, methyl-tert-butylether, dimethoxyethane, or an ester such as ethyl acetate or ethyl butanoate or an amide such as N,N-dimethylformamide or N,N-dimethylacetamide or N-methyl-pyridone or a in mixture of solvents. The reaction temperature in this case is generally from −40° C. to 200° C., preferably from −20° C. to 80°, more preferably from 0° C. to 20° C. The reaction time is generally from 15 min to 6 days, preferably from 15 min to 16 h, depending on the composition of the mixture and the chosen temperature range. Care has to be taken to choose conditions compatible with other functional groups and protecting groups present in the compounds of formula X, XVIII and IXX, as it is known to the presons skilled in the art.

A compound of the formula Ia can already be a compound of formula I, if $G^1$ and $G^2$ are both H and if $R^{5a}$ is $R^5$ and $R^{6a}$ is $R^6$. If a compound of formula Ia is not already a compound of formula I, it can be transformed into a compound of formula I in one step or in several steps depending of the meaning of the groups $G^1$, $G^2$, $R^{5a}$ and $R^{6a}$, as it was described above.

In another process for the preparation of compounds of the formula I, wherein $R^4$ is not hydrogen, a compound of the formula II is converted into a compound of formula XXII, followed by the conversion of the latter compound into a compound of formula XXIV, and a subsequent reaction of a compound of formula XXIV with a compound of formula III to give a compound of the formula Ia, which can be a compound of formula I already or which can be converted into a compound of formula I,

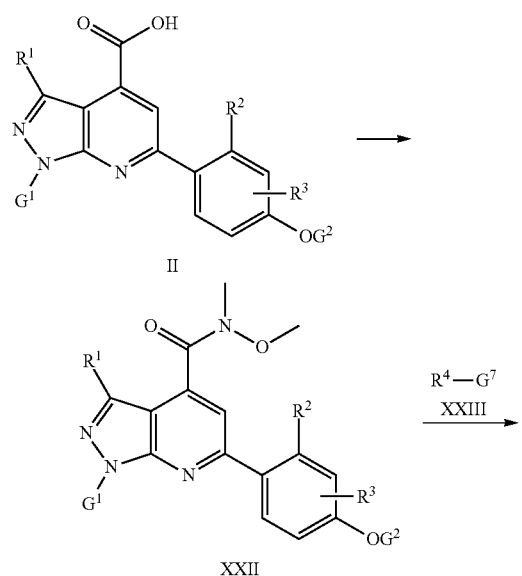

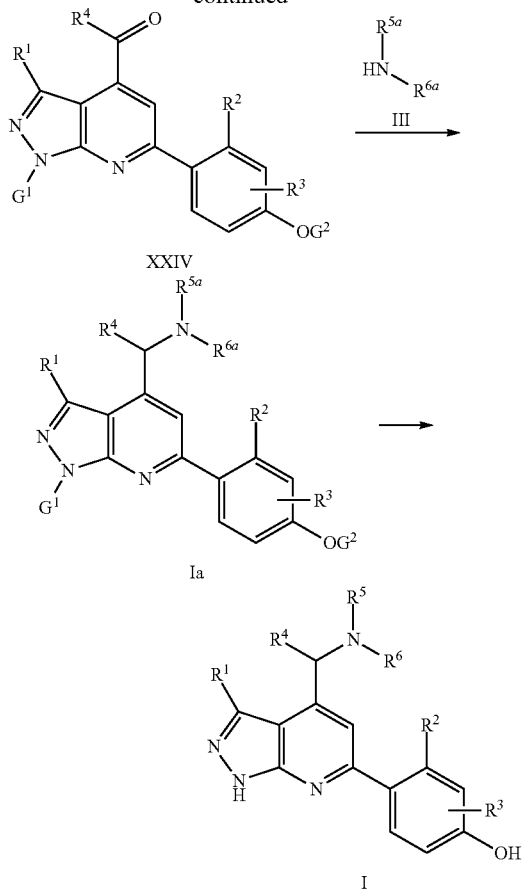

wherein the groups $R^1$, $R^2$, $R^3$, $R^5$ and $R^6$ in the compounds of the formulae Ia, II, XXII and XXIV are defined as in the compounds of the formula I and wherein the group $R^4$ in the compounds of formula I, Ia, XXIII and XXIV Ia is not defined as hydrogen. The groups $R^{5a}$ and $R^{6a}$ in the compounds of formulae Ia and III are, independently of each other, either defined as the groups $R^5$ and $R^6$ in formula I, or they are precursors of the groups $R^5$ and $R^6$ in formula I, they can for example contain functional groups in protected form or functional groups which can be converted to obtain the final groups $R^5$ and $R^6$. The group $G^1$ in the compounds of formulae Ia, II, XXII and XXIV is defined as a hydrogen or a protecting group for a pyrazole nitrogen, such as, for example, a 2-tetrahydropyranyl-group, a benzyl group, a 4-methoxybenzyl or a 2,5-dimethoxybenzyl group. The group $G^2$ in the compounds of formulae Ia, II, XXII and XXIV is defined as a hydrogen or a protecting group for a phenolic hydroxyl group, such as, for example, a 2-tetrahydropyranyl-group, a methoxymethyl group, a benzyl group, a 4-methoxy-benzyl or a 2,5-dimethoxybenzyl group. The group $G^7$ in the compounds of formula XXIII is lithium or magnesium-halide, e.g. magnesium chloride or magnesium bromide.

The reaction of the compound of the formulae II to form a compound of formula XXII employs N,O-dimethylhydroxylamine and is generally performed in the presence of activating agents, such as CDI, DCC, EDC, HOAt, HOBt, HATU, TOTU, TBTU BEP or combinations thereof, and optionally an additional base, such as TEA, DIPEA or N-methylmorpholin in an appropriate inert solvent, for example a hydrocarbon or a chlorinated hydrocarbon such as benzene, toluene, chlorobenzene, dichloromethane, dichloroethane, chloroform, or an ether such as tetrahydrofurane, 1,4-dioxane, dibutylether, diisopropylether, methyl-tert-butylether, dimethoxyethane, or an ester such as ethyl acetate or ethyl butanoate or an amide such as N,N-dimethylformamide or N,N-dimethylacetamide or N-methyl-pyridone or a in mixture of solvents. The reaction temperature in this case is generally from −30° C. to 200° C., preferably from −20° C. to 80°, more preferably from 0° C. to 20° C. The reaction time is generally from 15 min to 6 days, preferably from 15 min to 16 h, depending on the composition of the mixture and the chosen temperature range. The acids of formula II can be subjected to the reaction in form of their salts, for example their sodium salts. They can also be transformed into an activated derivative prior to the coupling with N,O-dimethylhydroxylamine, for example into an acid chloride or an acid anhydride by standard transformations. N,O-dimethylhydroxylamine can be subjected to the reaction in form of a salt, for example as hydrochloride or triflate salt, in which case usually an additional equivalent of the base is added to the reaction.

The reaction of a compound of the formulae XXII with an organometallic reagent of formula XXIII, which is for example a methyl-magnesiumchloride or -bromide reagent, for a case in which $R^4$ is methyl, is generally carried out in an appropriate inert solvent, for example an ether such as tetrahydrofurane, 1,4-dioxane, dibutylether, diisopropylether, methyl-tert-butylether, dimethoxyethane or a in mixture of solvents. The reaction temperature in this case is generally from −80° C. to 150° C., preferably from −20° C. to 80°, more preferably from 0° C. to 20° C. The reaction time is generally from 15 min to 6 days, preferably from 15 min to 16 h, depending on the composition of the mixture and the chosen temperature range.

The reaction of compounds of formula XXIV with compounds of formula III to form compounds of formula Ia, wherein $R^4$ is not hydrogen, is a reductive amination, which is generally carried out in the presence of a reducing agent, such as sodium borhohydrate, lithium borohydride, or modified borohydride reagents, such as sodium triacetoxy borohydride or sodium cyanoborohydrate, or in the presence of a hydrogenation catalyst such as palladium in a hydrogen atmosphere or under hydrogen transfer conditions using, for example, formic acid as the source of reducing equivalents, and which is optionally carried out in the presence of an acid, such as acetic acid, or a base, such as a trialkylamine, e.g. triethylamine or di-isopropylethyl amine, or N-methylmorpholin or which is optionally carried out in the presence of molecular sieve, and which is carried out in an appropriate inert solvent, for example a hydrocarbon or a chlorinated hydrocarbon such as benzene, toluene, chlorobenzene, dichloromethane, dichloroethane, chloroform, or an ether such as tetrahydrofurane, 1,4-dioxane, dibutylether, diisopropylether, methyl-tert-butylether, dimethoxyethane, or an ester such as ethyl acetate or ethyl butanoate or an amide such as N,N-dimethylformamide or N,N-dimethylacetamide or N-methyl-pyridone or a in mixture of solvents. The reaction temperature in this case is generally from −40° C. to 200° C., preferably from −20° C. to 80°, more preferably from 0° C. to 20° C. The reaction time is generally from 15 min to 6 days, preferably from 15 min to 16 h, depending on the composition of the mixture and the chosen temperature range.

A compound of the formula Ia can already be a compound of formula I, if $G^1$ and $G^2$ are both H and if $R^{5a}$ is $R^5$ and $R^{6a}$ is $R^6$. If a compound of formula Ia is not already a compound of formula I, it can be transformed into a compound of formula I in one step or in several steps depending of the meaning of the groups $G^1$, $G^2$, $R^{5a}$ and $R^{6a}$, as it was described above.

All reactions used in the above-described syntheses of the compounds of the formula I are per se well known to the skilled person and can be carried out under standard conditions according to, or analogously to, procedures described in the literature, for example in Houben-Weyl, Methoden der Organischen Chemie (Methods of Organic Chemistry), Thieme-Verlag, Stuttgart, or Organic Reactions, John Wiley & Sons, New York. If desired, the obtained compounds of the formula I, as well as any intermediate compounds, can be purified by customary purification procedures, for example by re-crystallization or chromatography. As already mentioned, all starting compounds and intermediates employed into the above-described syntheses which contain an acidic or basic group, can also be employed in the form of salts, and all intermediates and final target compounds can also be obtained in the form of salts. As likewise mentioned above, depending on the circumstances of the specific case, in order to avoid an unwanted course of a reaction or side reactions during the synthesis of a compound it can generally be necessary or advantageous to temporarily block functional groups by introducing protective groups and deprotect them at a later stage of the synthesis, or to introduce functional groups in the form of precursor groups which later are converted into the desired functional groups. As examples of protecting groups amino-protecting groups may be mentioned which can be acyl groups or alkyloxycarbonyl groups, for example a tert-butyloxycarbonyl group (=Boc) which can be removed by treatment with trifluoroacetic acid (=TFA), a benzyloxycarbonyl group which can be removed by catalytic hydrogenation, or a fluoren-9-ylmethoxycarbonyl group which can be removed by treatment with piperidine, and protecting groups of carboxylic acid groups which can be protected as ester groups, such as tert-butyl esters which can be deprotected by treatment with trifluoroacetic acid, or benzyl esters which can be deprotected by catalytic hydrogenation. As an example of a precursor group the nitro group may be mentioned, which can be converted into an amino group by reduction, for example by catalytic hydrogenation. Such synthesis strategies, and protective groups and precursor groups which are suitable in a specific case, are known to the skilled person.

Another subject of the present invention are the novel starting compounds and intermediates occurring in the synthesis of the compounds of the formula I, including the compounds of the formulae Ia, II, IIa, III, IV, V, VI, VII, VIII, IX, X, Xa, XI, XII, XIII, XIV, XV, XVI, XVII, XVIII, IXX, XX, XXI, XXII, XXIII and XIV, wherein $R^1$, $R^2$, $R^3$, $R^4$, $R^5$, $R^6$, $R^{5a}$ and $R^{6a}$, $G^1$, $G^2$, $G^3$, $G^4$, $G^5$, $G^6$ and $G^7$ are defined as above, in any of their stereoisomeric forms or a mixture of stereoisomeric forms in any ratio, and their salts, and solvates of any of them, and their use as intermediates. The invention also includes all tautomeric forms of the said intermediates and starting compounds. All explanations given above and embodiments specified above with respect to the compounds of the formula I apply correspondingly to the said intermediates and starting compounds. Another subject of the invention are in particular the novel specific starting compounds and intermediates disclosed herein. Independently thereof whether they are disclosed as a free compound and/or as a specific salt, they are a subject of the invention both in the form of the free compounds and in the form of their salts, and if a specific salt is disclosed, additionally in the form of this specific salt, and in the form of solvates of any of them.

The following examples illustrate the invention.

When example compounds containing a basic group were purified by preparative high pressure liquid chromatography (HPLC) on reversed phase (RP) column material and, as customary, the eluent was a gradient mixture of water and acetonitrile containing trifluoroacetic acid (TFA), they were in part obtained in the form of their acid addition salt with trifluoroacetic acid, depending on the details of the workup such as evaporation or lyophilization conditions. In the names of the example compounds and their structural formulae any such contained trifluoroacetic acid is not specified. When example compounds containing a basic group were obtained after an acidic deprotection step, they were in part obtained in the form of their acid addition salt with hydrochloric acid, depending on the details of the workup such as washing steps with bases or evaporation or lyophilization conditions. In the names of the example compounds and their structural formulae any such contained hydrochloric acid may or may not be specified.

The prepared compounds were in general characterized by spectroscopic data and chromatographic data, in particular mass spectra (MS) and HPLC retention times ($R_t$; in min) which were obtained by combined analytical HPLC/MS characterization (LC/MS), and/or nuclear magnetic resonance (NMR) spectra. In the NMR characterization, the chemical shift δ (in ppm), the number of hydrogen atoms and the multiplicity (s=singlet, d=doublet, dd=double doublet, t=triplet, dt=double triplet, q=quartet, m=multiplet; b=broad) of the peaks is given. In the MS characterization, in general the mass number (m/z) of the peak of the molecular ion M, e.g. $M^+$, or of a related ion such as the ion M+1, e.g. $[M+1]^+$, i.e. the protonated molecular ion $[M+H]^+$, which was formed depending on the ionization method used, is given. Generally, the ionization method was electrospray ionization (ESI). The LC/MS conditions used were as follows.

Method LC1:
Column: BEH C18 2.1×50 mm; 1.7 μm; flow: 0.9 ml; solvent A: water+0.1% formic acid; solvent B: acetonitrile+0.08% formic acid; gradient from 95% A+5% B to 5% A+95% B in 1.1 min; then 5% A+95% B for 0.6 min; MS ionisation method: $ESI^+$.

Method LC2:
Column: Waters Xbridge C18 4.6 mm×50 mm, 2.5 μM; flow: 1.3 ml/min; solvent A: water+0.05% TFA; solvent B: methanol+0.05% TFA; gradient from 98% A+2% B for 1 min, then from 98% A+2% B to 5% A+95% B in 4 min, then 5% A+95% B for 1.25 min; MS ionisation method: $ESI^+$.

Method LC3:
Column: Waters Xbridge C18 4.6 mm×50 mm, 2.5 μM; flow: 1.3 ml/min; solvent A: water+0.1% formic acid; solvent B: acetonitrile+0.1% formic acid; gradient from 97% A+3% B to 40% A+60% B in 3.5 min, then to 2% A+98% B in 0.5 min; then 2% A+98% B for 1.0 min; MS ionisation method: $ESI^+$.

Method LC4:
Column: Phenomenex, 10×2 mm, 1.7 μm; flow: 1.1 ml/min; solvent A: water+0.05% trifluoroacetic acid; solvent B: acetonitrile; gradient: from 93% A+7% B to 5% A+95% B in 1.2 min, then 5% A+95% B for 0.2 min; MS-Ionisation method: $ESI^+$.

Method LC5:
Column: BEH C18 2.1×50 mm; 1.7 μm, flow: 0.9 ml, solvent A water+0.05% formic acid; solvent B: acetonitrile+0.035% formic acid; gradient from 95% A+5% B to 5% A+95% B in 1.1 min; then 5% A+95% B for 0.6 min; MS ionisation method: $ESI^+$.

Method LC6:
Column: YMC-Pack Jsphere H80 33×2.1 mm, 4 μm; flow: 1.3 ml/min; solvent A: water+0.05% trifluoroacetic acid; solvent B: acetonitrile+0.05% trifluoroacetic acid; gradient from 95% A+5% B to 5% A+95% B in 2.5 min, then to 95% A+5% B in 0.7 min; MS-Ionisationmethod: $ESI^+$.

Method LC7:
Column: YMC-Pack Jsphere H80 33×2.1 mm, 4 μm; flow: 1.3 ml/min; solvent A: water+0.05% trifluoroacetic acid; solvent B: acetonitrile+0.05% trifluoroacetic acid; gradient from 95% A+5% B to 5% A+95% B in 2.5 min, MS-Ionisationmethod: $ESI^+$ Method LC8:
Column Waters Xbridge C18 4.6 mm×50 mm, 2.5 μM; flow: 1.3 ml/min; solvent A: water+0.1% formic acid; solvent B: acetonitrile+0.1% formic acid; gradient from 97% A+3% B to 40% A+60% B in 3.5 min, then to 2% A+98% B in 0.5 min; then 2% A+98% B for 1.0 min; then to 97% A+3% B in 0.2 min, then 97% A+3% B for 1.3 min; MS ionisation method: $ESI^+$.

Method LC9:
Instrument: Waters UPLC, column: BEH C18, 2.1×50 mm; 1.7 μm, flow: 0.9 ml, solvent A water+0.05% formic acid; solvent B: acetonitrlie+0.035% formic acid; gradient from 98% A+2% B to 5% A+95% B in 2 min, then 5% A+95% B for 0.6 min; MS-Ionisationmethod: $ESI^+$.

Method LC10:
Column: Phenomenex, 4 μm, 10×2 mm, 1.7 μm; flow: 1.1 ml/min; solvent A: Water+0.05% Trifluoroacetic acid; solvent B: acetonitrile; gradient: from 80% A+20% B to 5% A+95% B in 0.8 min, then 5% A+95% B for 0.6 min; MS-Ionisationmethod: $ESI^+$ List of Abbreviations
BEP 2-bromo-1-ethyl-pyridinium tetrafluoroborate
BOC tert.butoxy carbonyl
CDI N,N'-carbonyldiimidazole
DCC 1,3-dicyclohexylcarbodiimide
DCM dichloromethane
DEA diethylamine
DMF N,N-dimethylformamide
EDC 1-(3-dimethylaminopropyl)-3-ethylcarbodiimide hydrochloride
EtOAc ethyl acetate
EtOH ethanol
Exp. No. Example number
h hour/s
HOAt 1-hydroxy-aza-benzotriazole
HOBt 1-hydroxy-benzotirazole
HATU O-(7-azabenzotriazol-1-yl)-N,N,N',N'-tetramethyluronium hexafluorophosphate
HPLC high pressure liquid chromatography
LC liquid chromatography
MeOH methanol
min minutes
MS mass spectroscopy
precond. preconditioned
iPrOH iso-Propanol
$R_t$ retention time
r.t. room temperature
sep. separation
TBTU [(benzotriazol-1-yloxy)-dimethylamino-methylene]-dimethyl-ammonium tetrafluoroborate
TEA triethylamine
TFA trifluoroacetic acid
THF tetrahydrofurane
TOTU O-(cyano(ethoxycarbonyl)methyleneamino)-N,N,N',N'-tetramethyluronium tetrafluoroborate

EXAMPLE 1

3-Fluoro-4-[3-methyl-4-(2-phenyl-piperazin-1-ylmethyl)-1H-pyrazolo[3,4-b]pyridin-6-yl]-phenol

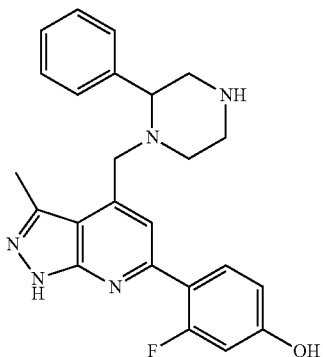 [SMILES: Cc1n[nH]c2nc(-c3ccc(O)cc3F)cc(CN3CCNCC3c3ccccc3)c12]

(a) 6-Hydroxy-3-methyl-1H-pyrazolo[3,4-b]pyridine-4-carboxylic acid ethyl ester

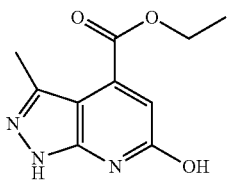 [SMILES: CCOC(=O)c1cc(O)nc2[nH]nc(C)c12]

A mixture of 3-amino-5-methylpyrazole (50.0 g), diethyl oxalate sodium salt (127.3 g) and acetic acid (113 mL) in 1N hydrochloric acid (625 mL) was stirred at 80° C. for 14 h, then refluxed for 3 h, cooled to r.t., and the precipitate formed was filtered by suction filtration and dried in vacuum at 60° C. The crude product was stirred in 500 mL ethyl acetate at r.t. and the solid was filtered off and dried in air. 6-Hydroxy-3-methyl-1H-pyrazolo[3,4-b]pyridine-4-carboxylic acid ethyl ester (40.2 g, 35%) was obtained as pale yellow solid.

1H-NMR (500 MHz, d6-DMSO): 1.33 (t, 3H), 2.45 (s, 3H), 4.34 (q, 2H), 6.44 (s, 1H), 11.90 (br s, 1H), 13.05 (br s, 1H).
LC/MS (Method LC1): Rt=0.91 min; m/z=222.1 [M+H]$^+$.

(b) 6-Bromo-3-methyl-1-(tetrahydro-pyran-2-yl)-1H-pyrazolo[3,4-b]pyridine-4-carboxylic acid ethyl ester

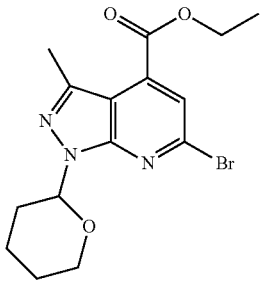 [SMILES: CCOC(=O)c1cc(Br)nc2c1c(C)nn2C1CCCCO1]

A mixture of 6-hydroxy-3-methyl-1H-pyrazolo[3,4-b]pyridine-4-carboxylic acid ethyl ester (13.7 g) and phosphorous oxybromide (19.5 g) in toluene (300 mL) was stirred at 110° C. for 5 h, cooled to r.t., and added dropwise into an ice cold solution of potassium acetate (18.2 g) in water (300 mL). The mixture was extracted twice with ethyl acetate, the combined organic phases were washed with brine, dried over magnesium sulfate and concentrated in a membrane pump vacuum. 6-Bromo-3-methyl-1H-pyrazolo[3,4-b]pyridine-4-carboxylic acid ethyl ester (4.6 g, 26% yield) was obtained. This material was dissolved in THF (60 mL), and 3,4-dihydro-2H-pyran (1.6 mL) and p-toluenesulfonic acid monohydrate (0.91 g) was added. The solution was stirred at r.t. for 48 h, then 3,4-dihydro-2H-pyran (1.6 mL) was added and the solution stirred again for 48 h. The mixture was poured into water and extracted with ethyl acetate, the organic layer was dried over magnesium sulfate and concentrated in a membrane pump vacuum. The residue was purified by flash chromatography (silica, heptane/ethyl acetate gradient). 6-Bromo-3-methyl-1-(tetrahydro-pyran-2-yl)-1H-pyrazolo[3,4-b]pyridine-4-carboxylic acid ethyl ester (2.2 g, 38%) was obtained.

1H-NMR (500 MHz, d6-DMSO): 1.38 (t, 3H), 1.52-1.63 (m, 2H), 1.73-1.85 (m, 1H), 1.87-1.94 (m, 1H), 1.97-2.06 (m, 1H), 2.37-2.46 (m, 1H), 2.60 (s, 3H), 3.65-3.73 (m, 1H), 3.90-3.96 (m, 1H), 4.43 (q, 2H), 5.92 (dd, 1H), 7.73 (s, 1H).
LC/MS (Method LC1): Rt=1.41 min; m/z=286.1 [M+H—C5H9O]$^+$.

(c) 6-(4-Benzyloxy-2-fluoro-phenyl)-3-methyl-1-(tetrahydro-pyran-2-yl)-1H-pyrazolo[3,4-b]pyridine-4-carboxylic acid

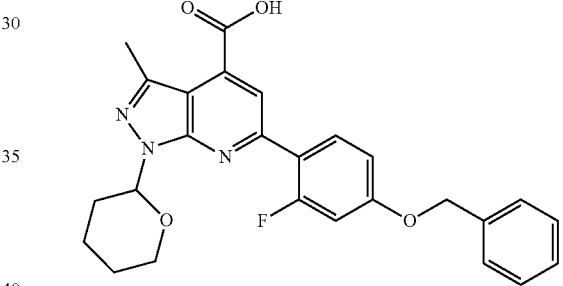

To mixture of 6-bromo-3-methyl-1-(tetrahydro-pyran-2-yl)-1H-pyrazolo[3,4-b]pyridine-4-carboxylic acid ethyl ester (21.0 g), 4-benzyloxy-2-fluorophenylboronic acid (16.8 g) and potassium carbonate (8.7 g) in DME/water (v/v=2/1, 300 mL) at r.t. under Ar-atmosphere palladium(0) bis(tri-tert-butylphosphine) (0.99 g) was added and the mixture was stirred at 85° C. for 90 min. To the mixture water was added and it was extracted with ethyl acetate. The organic phase was washed several times with water, finally with brine. Methanol was added and the precipitate formed was filtered off, dried in air to give 6-(4-Benzyloxy-2-fluoro-phenyl)-3-methyl-1-(tetrahydro-pyran-2-yl)-1H-pyrazolo[3,4-b]pyridine-4-carboxylic acid ethyl ester (23.0 g, 82%). This material was dissolved in isopropanol (100 mL), and 1N sodium hydroxide solution (140 mL) was added. The solution was stirred overnight, filtered, then the filtrate was adjusted to pH 2-3 and the precipitate formed was dried in air giving 6-(4-benzyloxy-2-fluoro-phenyl)-3-methyl-1-(tetrahydro-pyran-2-yl)-1H-pyrazolo[3,4-b]pyridine-4-carboxylic acid (18.0 g, 83%).

1H-NMR (500 MHz, d6-DMSO): 1.54-1.66 (m, 2H), 1.76-1.88 (m, 1H), 1.89-1.94 (m, 1H), 2.03-2.10 (m, 1H), 2.47-2.56 (m, 1H), 2.61 (s, 3H), 3.70-3.77 (m, 1H), 3.91-3.96 (m, 1H), 5.30 (2, 2H), 6.13 (dd, 1H), 7.35-7.47 (m, 3H), 7.49-7.52 (m, 2H), 8.03-8.09 (m, 2H), 8.12-8.16 (m, 1H), 14.0 (br s, 1H).
LC/MS (Method LC1): Rt=1.38 min; m/z=462.2 [M+H]$^+$.

(d) 4-[6-(4-Benzyloxy-2-fluoro-phenyl)-3-methyl-1-(tetrahydro-pyran-2-yl)-1H-pyrazolo[3,4-b]pyridine-4-carbonyl]-3-phenyl-piperazine-1-carboxylic acid tert-butyl ester

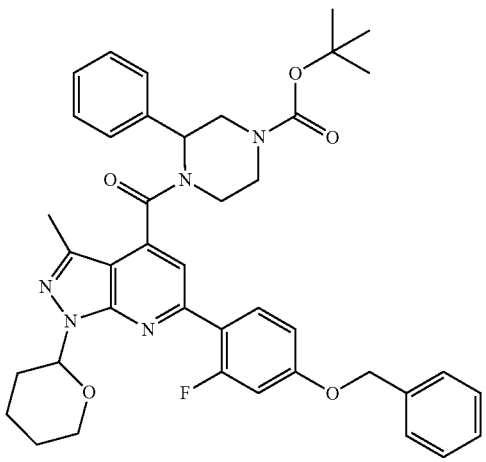 [SMILES: Cc1nn(C2CCCCO2)c2nc(-c3ccc(OCc4ccccc4)cc3F)cc(C(=O)N3CCN(C(=O)OC(C)(C)C)CC3c3ccccc3)c12]

To a suspension of 571 mg of 6-(4-benzyloxy-2-fluoro-phenyl)-3-methyl-1-(tetrahydro-pyran-2-yl)-1H-pyrazolo[3,4-b]pyridine-4-carboxylic acid in 14 ml of DCM were added 0.64 ml of Hünig's base, 408 mg of BEP and 390 mg of 3-phenyl-piperazine-1-carboxylic acid tert-butyl ester. The reaction was stirred overnight at r.t. For workup it was diluted with water and DCM and the layers were separated. The organic layer was washed with water twice, dried over Na$_2$SO$_4$, filtered and concentrated in vacuo. The residue was purified by flash chromatography (silica, heptane/EtOAc gradient) to obtain 900 mg (100%) of the title compound.

LC/MS (Method LC4): Rt=1.32 min; m/z=706.35 [M+H]$^+$.

(e) 4-[6-(4-Benzyloxy-2-fluoro-phenyl)-3-methyl-1-(tetrahydro-pyran-2-yl)-1H-pyrazolo[3,4-b]pyridin-4-ylmethyl]-3-phenyl-piperazine-1-carboxylic acid tert-butyl ester

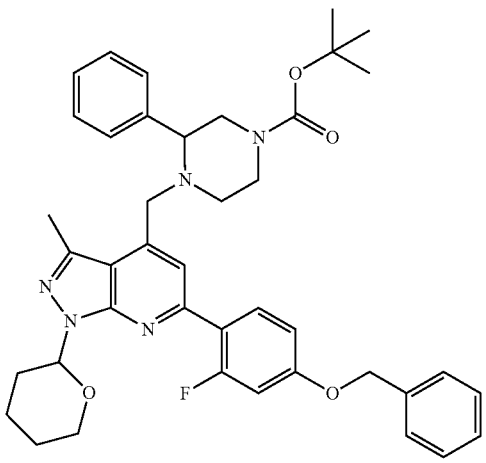 [SMILES: Cc1nn(C2CCCCO2)c2nc(-c3ccc(OCc4ccccc4)cc3F)cc(CN3CCN(C(=O)OC(C)(C)C)CC3c3ccccc3)c12]

To a solution of 529 mg of 4-[6-(4-benzyloxy-2-fluoro-phenyl)-3-methyl-1-(tetrahydro-pyran-2-yl)-1H-pyrazolo[3,4-b]pyridine-4-carbonyl]-3-phenyl-piperazine-1-carboxylic acid tert-butyl ester in 15 ml of dry THF 6 ml of borane-dimethylsulfide complex (1 M in DCM) was added slowly at r.t., and the reaction was heated to reflux for 30 min. The reaction was quenched by the addition of 3.75 ml of methanol, and the solvents were evaporated. The residue was purified by preparative HPLC (C18 column, acetonitrile/water gradient) yielding 266 mg (51%) of the title compound.

LC/MS (Method LC4): Rt=1.39 min; m/z=692.35 [M+H]$^+$.

(f) 4-[6-(2-Fluoro-4-hydroxy-phenyl)-3-methyl-1-(tetrahydro-pyran-2-yl)-1H-pyrazolo[3,4-b]pyridin-4-ylmethyl]-3-phenyl-piperazine-1-carboxylic acid tert-butyl ester

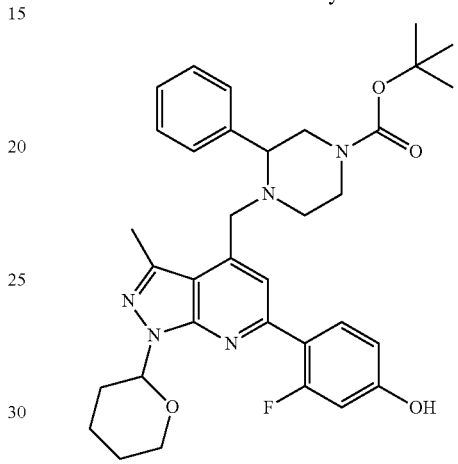

264 mg 4-[6-(4-bBenzyloxy-2-fluoro-phenyl)-3-methyl-1-(tetrahydro-pyran-2-yl)-1H-pyrazolo[3,4-b]pyridin-4-yl-methyl]-3-phenyl-piperazine-1-carboxylic acid tert-butyl ester was dissolved in 3 ml ethanol and 5 ml of THF and purged with argon. 20 mg Palladium (10% on charcoal) was added and the mixture was hydrogenated at 5 bar and r.t. for 24 h. 20 mg Palladium (10% on charcoal) was added and the reaction was hydrogenated at 5 bar and r.t. for 16 h. The catalyst was filtered off and the solvents were evaporated. The residue was purified by preparative HPLC (C18 column, acetonitrile/water gradient) yielding 178 mg (78%) of the title compound.

LC/MS (Method LC4): Rt=1.14 min; m/z=602.30 [M+H]$^+$.

(g) 3-Fluoro-4-[3-methyl-4-(2-phenyl-piperazin-1-ylmethyl)-1H-pyrazolo[3,4-b]pyridin-6-yl]-phenol

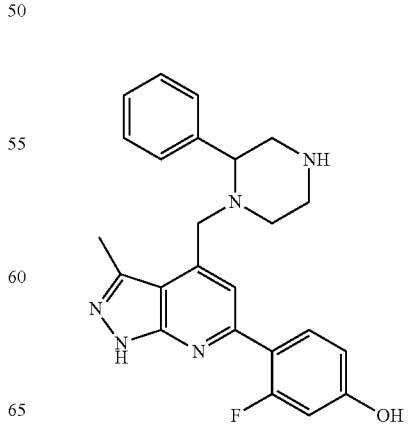

178 mg 4-[6-(2-fluoro-4-hydroxy-phenyl)-3-methyl-1-(tetrahydro-pyran-2-yl)-1H-pyrazolo[3,4-b]pyridin-4-ylmethyl]-3-phenyl-piperazine-1-carboxylic acid tert-butyl ester were dissolved in 3 ml dry 1,4-dioxane and 2 ml HCl (4N in 1,4-dioxane) was added. After stirring the reaction at r.t. for 30 min the volatiles were removed in vacuo and the resulting residue was purified by preparative HPLC (C18 column, acetonitrile/water gradient). 63 mg (51%) of the title compound were obtained.

LC/MS (Method LC1): Rt=0.95 min; m/z=418.14 [M+H]⁺.

The following examples have ben prepared following a similar procedure as described for Example 1 (steps (d) to (g)), starting from 6-(4-Benzyloxy-2-fluoro-phenyl)-3-methyl-1-(tetrahydro-pyran-2-yl)-1H-pyrazolo[3,4-b]pyridine-4-carboxylic acid and the respective amine precursors:

| Exp. No | Name | Structure | LC/MS method | m/z [M + H]⁺ | R$_t$ [min] |
|---|---|---|---|---|---|
| 2 | 3-Fluoro-4-{4-[2-(4-isopropyl-phenyl)-piperazin-1-ylmethyl]-3-methyl-1H-pyrazolo[3,4-b]pyridin-6-yl}-phenol | 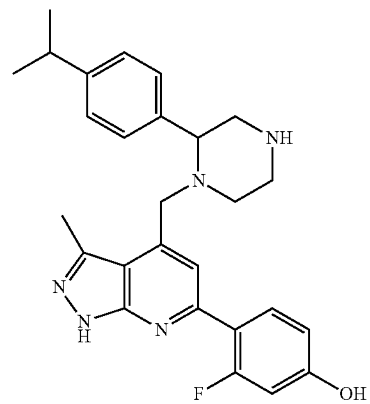 [SMILES: Cc1n[nH]c2nc(-c3ccc(O)cc3F)cc(CN3CCNCC3c3ccc(C(C)C)cc3)c12] | LC5 | 460.18 | 1.06 |
| 3 | 3-Fluoro-4-{3-methyl-4-[2-(4-trifluoromethyl-phenyl)piperazin-1-ylmethyl]-1H-pyrazolo[3,4-b]pyridin-6-yl}phenol | 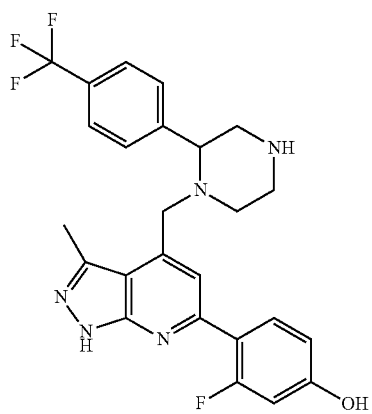 [SMILES: Cc1n[nH]c2nc(-c3ccc(O)cc3F)cc(CN3CCNCC3c3ccc(C(F)(F)F)cc3)c12] | LC5 | 486.31 | 0.90 |
| 4 | 3-Fluoro-4-{4-[2-(4-fluoro-phenyl)-piperazin-1-ylmethyl]-3-methyl-1H-pyrazolo[3,4-b]pyridin-6-yl}-phenol | 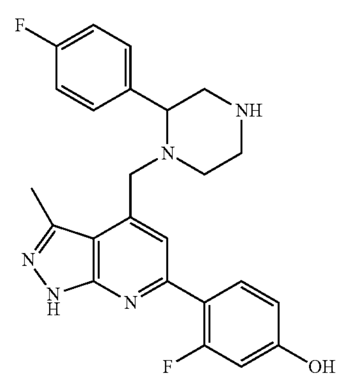 [SMILES: Cc1n[nH]c2nc(-c3ccc(O)cc3F)cc(CN3CCNCC3c3ccc(F)cc3)c12] | LC5 | 436.29 | 0.85 |

-continued

| Exp. No | Name | Structure | LC/MS method | m/z [M + H]+ | R_t [min] |
|---|---|---|---|---|---|
| 5 | 3-Fluoro-4-[3-methyl-4-(2-trifluoromethyl-piperazin-1-ylmethyl)-1H-pyrazolo[3,4-b]pyridin-6-yl]-phenol | 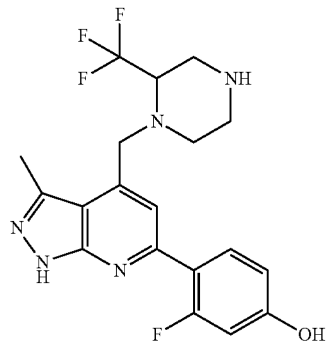 [SMILES: Cc1n[nH]c2nc(-c3ccc(O)cc3F)cc(CN3CCNCC3C(F)(F)F)c12] | LC1 | 410.2 | 0.76 |
| 6 | 3-Fluoro-4-{4-[2-(3-fluoro-phenyl)-piperazin-1-ylmethyl]-3-methyl-1H-pyrazolo[3,4-b]pyridin-6-yl}-phenol | 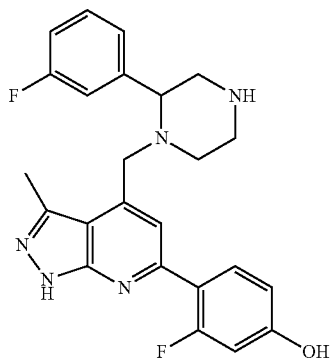 [SMILES: Cc1n[nH]c2nc(-c3ccc(O)cc3F)cc(CN3CCNCC3c3cccc(F)c3)c12] | LC5 | 436.08 | 0.95 |
| 7 | 4-[4-(6,9-Diaza-spiro[4.5]dec-6-ylmethyl)-3-methyl-1H-pyrazolo[3,4-b]pyridin-6-yl]-3-fluoro-phenol | 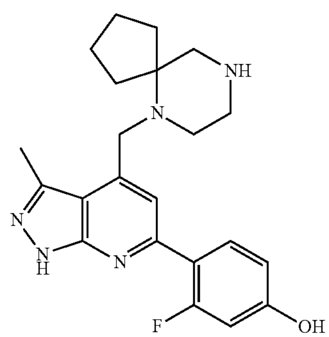 [SMILES: Cc1n[nH]c2nc(-c3ccc(O)cc3F)cc(CN3CCNCC34CCCC4)c12] | LC5 | 396.12 | 0.92 |
| 8 | 3-Fluoro-4-{3-methyl-4-[2-(3-trifluoromethyl-phenyl)-piperazin-1-ylmethyl]-1H-pyrazolo[3,4-b]pyridin-6-yl}-phenol | 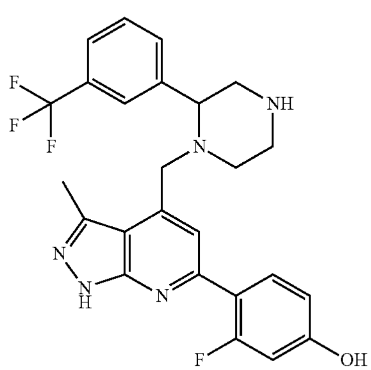 [SMILES: Cc1n[nH]c2nc(-c3ccc(O)cc3F)cc(CN3CCNCC3c3cccc(C(F)(F)F)c3)c12] | LC5 | 486.07 | 0.99 |

-continued

| Exp. No | Name | Structure | LC/MS method | m/z [M + H]+ | R$_t$ [min] |
|---|---|---|---|---|---|
| 9 | 4-{4-[2-(3,5-Difluoro-phenyl)-piperazin-1-ylmethyl]-3-methyl-1H-pyrazolo[3,4-b]pyridin-6-yl}-3-fluoro-phenol | 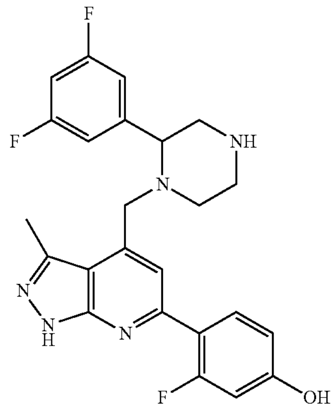 [SMILES: Cc1n[nH]c2nc(-c3ccc(O)cc3F)cc(CN3CCNCC3c3cc(F)cc(F)c3)c12] | LC5 | 454.07 | 0.96 |
| 10 | 3-Fluoro-4-{4-[2-(2-fluoro-phenyl)-piperazin-1-ylmethyl]-3-methyl-1H-pyrazolo[3,4-b]pyridin-6-yl}-phenol | 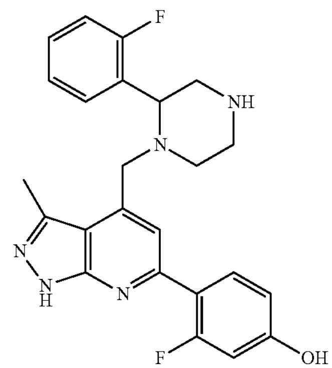 [SMILES: Cc1n[nH]c2nc(-c3ccc(O)cc3F)cc(CN3CCNCC3c3ccccc3F)c12] | LC5 | 436.07 | 0.95 |
| 11 | 3-Fluoro-4-[3-methyl-4-(2,2,5-trimethyl-piperazin-1-ylmethyl)-1H-pyrazolo[3,4-b]pyridin-6-yl]-phenol | 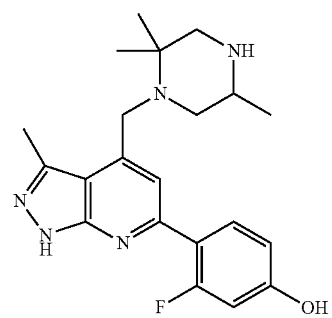 [SMILES: Cc1n[nH]c2nc(-c3ccc(O)cc3F)cc(CN3CC(C)NCC3(C)C)c12] | LC3 | 384.25 | 2.46 |
| 12 | 3-Fluoro-4-[3-methyl-4-(2-methyl-2-phenyl-piperazin-1-ylmethyl)-1H-pyrazolo[3,4-b]pyridin-6-yl]-phenol | 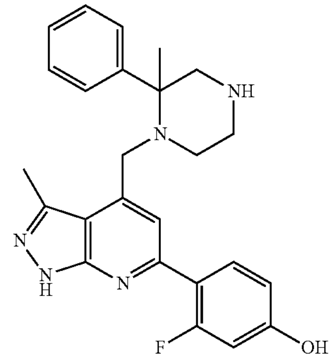 [SMILES: Cc1n[nH]c2nc(-c3ccc(O)cc3F)cc(CN3CCNCC3(C)c3ccccc3)c12] | LC5 | 432.26 | 0.96 |

-continued

| Exp. No | Name | Structure | LC/MS method | m/z [M + H]+ | R$_t$ [min] |
|---|---|---|---|---|---|
| 13 | 3-Fluoro-4-(3-methyl-4-piperazin-1-ylmethyl-1H-pyrazolo[3,4-b]pyridin-6-yl)-phenol | 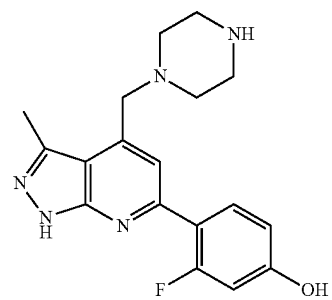 [SMILES: Cc1n[nH]c2nc(-c3ccc(O)cc3F)cc(CN3CCNCC3)c12] | LC5 | 342.21 | 0.81 |
| 14 | 4-[4-(4,7-Diaza-spiro[2.5]oct-4-ylmethyl)-3-methyl-1H-pyrazolo[3,4-b]pyridin-6-yl]-3-fluoro-phenol | 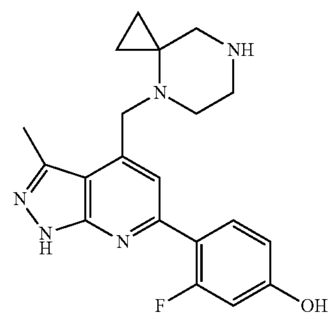 [SMILES: Cc1n[nH]c2nc(-c3ccc(O)cc3F)cc(CN3CCNCC34CC4)c12] | LC3 | 368.22 | 2.32 |
| 15 | 4-[4-(8,8-Dimethyl-6,9-diaza-spiro[4.5]dec-6-ylmethyl)-3-methyl-1H-pyrazolo[3,4-b]pyridin-6-yl]-3-fluoro-phenol | 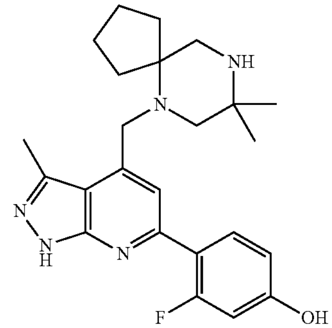 [SMILES: Cc1n[nH]c2nc(-c3ccc(O)cc3F)cc(CN3CC(C)(C)NCC34CCCC4)c12] | LC9 | 424.36 | 1.41 |
| 16 | 3-Fluoro-4-[3-methyl-4-(8-methyl-6,9-diaza-spiro[4.5]dec-6-ylmethyl)-1H-pyrazolo[3,4-b]pyridin-6-yl]-phenol | 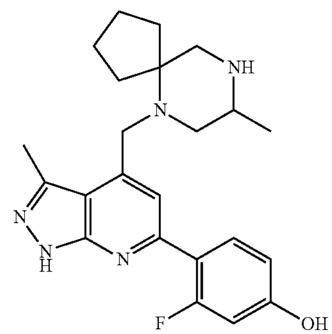 [SMILES: Cc1n[nH]c2nc(-c3ccc(O)cc3F)cc(CN3CC(C)NCC34CCCC4)c12] | LC9 | 410.34 | 1.20 |

| Exp. No | Name | Structure | LC/MS method | m/z [M + H]+ | R_t [min] |
|---|---|---|---|---|---|
| 17 | 4-[4-(5,8-Diaza-spiro[3.5]non-5-ylmethyl)-3-methyl-1H-pyrazolo[3,4-b]pyridin-6-yl]-3-fluoro-phenol | 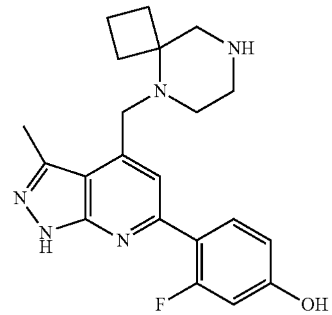 [SMILES: Cc1n[nH]c2nc(-c3ccc(O)cc3F)cc(CN3CCNCC34CCC4)c12] | LC9 | 382.30 | 1.13 |
| 18 | 4-[4-(2,2-Diethyl-piperazin-1-ylmethyl)-3-methyl-1H-pyrazolo[3,4-b]pyridin-6-yl]-3-fluoro-phenol | 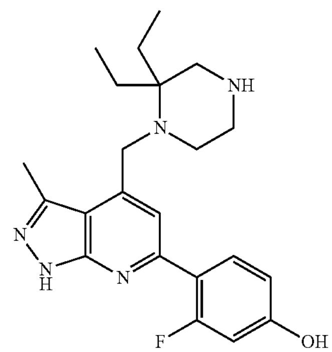 [SMILES: CCC1(CC)CNCCN1Cc1cc(-c2ccc(O)cc2F)nc2[nH]nc(C)c12] | LC9 | 398.33 | 1.39 |
| 19 | 3-Fluoro-4-[3-methyl-4-(5-methyl-2-trifluoromethyl-piperazin-1-ylmethyl)-1H-pyrazolo[3,4-b]pyridin-6-yl]-phenol | 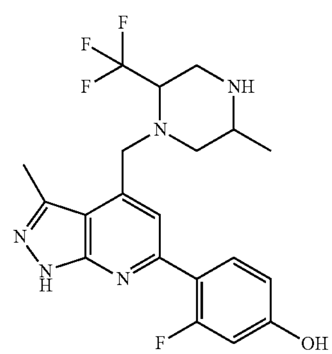 [SMILES: Cc1n[nH]c2nc(-c3ccc(O)cc3F)cc(CN3CC(C)NCC3C(F)(F)F)c12] | LC9 | 424.24 | 1.32 |
| 20 | 3-Fluoro-4-[4-(5-isopropyl-2,2-dimethyl-piperazin-1-ylmethyl)-3-methyl-1H-pyrazolo[3,4-b]pyridin-6-yl]-phenol | 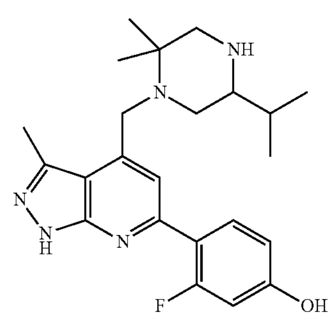 [SMILES: Cc1n[nH]c2nc(-c3ccc(O)cc3F)cc(CN3CC(C(C)C)NCC3(C)C)c12] | LC9 | 410.38 | 1.33 |

-continued

| Exp. No | Name | Structure | LC/MS method | m/z [M + H]+ | R$_t$ [min] |
|---|---|---|---|---|---|
| 21 | 4-[4-(5-Ethyl-2,2,5-trimethyl-piperazin-1-ylmethyl)-3-methyl-1H-pyrazolo[3,4-b]pyridin-6-yl]-3-fluoro-phenol | 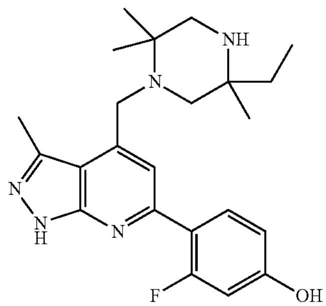 [SMILES: CCC1(C)CN(Cc2cc(-c3ccc(O)cc3F)nc3[nH]nc(C)c23)C(C)(C)CN1] | LC9 | 412.31 | 1.35 |
| 22 | 4-[4-(5,5-Diethyl-2,2-dimethyl-piperazin-1-ylmethyl)-3-methyl-1H-pyrazolo[3,4-b]pyridin-6-yl]-3-fluoro-phenol | 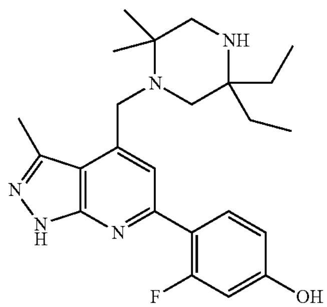 [SMILES: CCC1(CC)CN(Cc2cc(-c3ccc(O)cc3F)nc3[nH]nc(C)c23)C(C)(C)CN1] | LC9 | 426.33 | 1.22 |
| 23 | 4-[4-(5-Cyclopropyl-2,2,5-trimethyl-piperazin-1-ylmethyl)-3-methyl-1H-pyrazolo[3,4-b]pyridin-6-yl]-3-fluoro-phenol | 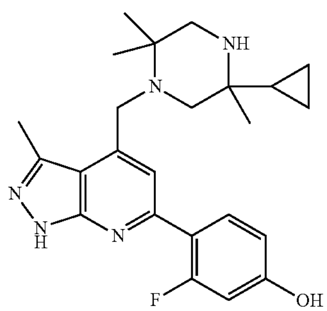 [SMILES: Cc1n[nH]c2nc(-c3ccc(O)cc3F)cc(CN3CC(C)(C4CC4)NCC3(C)C)c12] | LC9 | 424.28 | 1.20 |
| 24 | 4-[4-(3-Amino-3-methyl-piperidin-1-ylmethyl)-3-methyl-1H-pyrazolo[3,4-b]pyridin-6-yl]-3-fluoro-phenol | 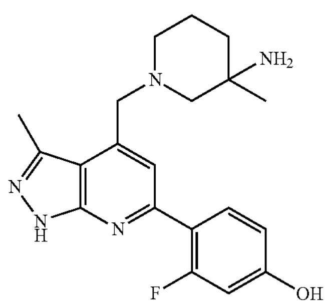 [SMILES: Cc1n[nH]c2nc(-c3ccc(O)cc3F)cc(CN3CCCC(C)(N)C3)c12] | LC9 | 370.18 | 1.17 |
| 25 | 3-Fluoro-4-[3-methyl-4-(3-methyl-[1,4]diazepan-1-ylmethyl)-1H-pyrazolo[3,4-b]pyridin-6-yl]-phenol | 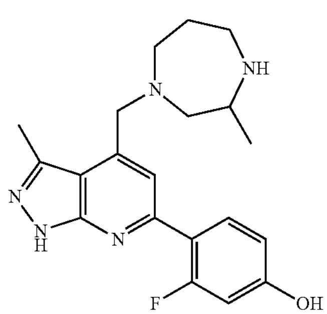 [SMILES: Cc1n[nH]c2nc(-c3ccc(O)cc3F)cc(CN3CCCNC(C)C3)c12] | LC9 | 370.30 | 1.07 |

EXAMPLE 26

4-[4-(2,2-Dimethyl-piperazin-1-ylmethyl)-3-methyl-1H-pyrazolo[3,4-b]pyridin-6-yl]-3-fluoro-phenol

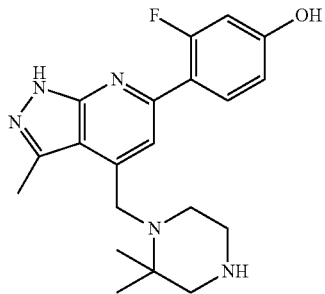 [SMILES: Cc1n[nH]c2nc(-c3ccc(O)cc3F)cc(CN3CCNCC3(C)C)c12]

(a) (4-Benzyl-2,2-dimethyl-piperazin-1-yl)-[6-(4-benzyloxy-2-fluoro-phenyl)-3-methyl-1-(tetrahydro-pyran-2-yl)-1H-pyrazolo[3,4-b]pyridin-4-yl]-methanone

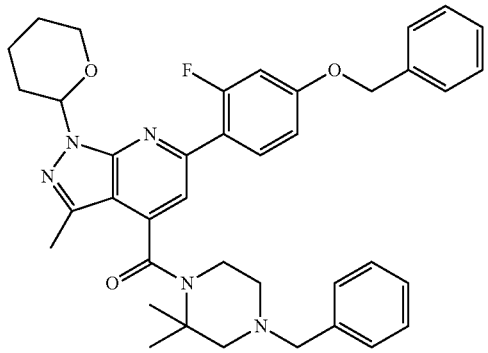 [SMILES: Cc1nn(C2CCCCO2)c2nc(-c3ccc(OCc4ccccc4)cc3F)cc(C(=O)N3CCN(Cc4ccccc4)CC3(C)C)c12]

In analogy to Example 1 step (d) 300 mg 6-(4-benzyloxy-2-fluoro-phenyl)-3-methyl-1-(tetrahydro-pyran-2-yl)-1H-pyrazolo[3,4-b]pyridine-4-carboxylic acid was reacted with 160 mg 1-benzyl-3,3-dimethyl-piperazine to obtain 410 mg (94%) of the title compound.

LC/MS (Method LC4): Rt=1.00 min; m/z=648.20 [M+H]⁺.

(b) 4-(4-Benzyl-2,2-dimethyl-piperazin-1-ylmethyl)-6-(4-benzyloxy-2-fluoro-phenyl)-3-methyl-1-(tetrahydro-pyran-2-yl)-1H-pyrazolo[3,4-b]pyridine

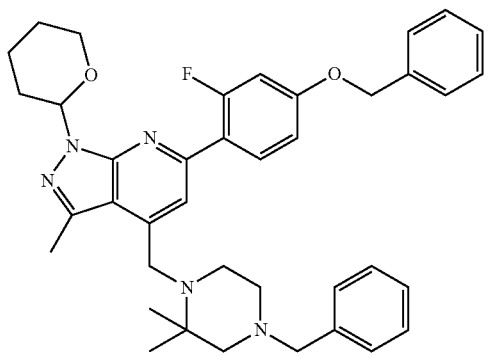 [SMILES: Cc1nn(C2CCCCO2)c2nc(-c3ccc(OCc4ccccc4)cc3F)cc(CN3CCN(Cc4ccccc4)CC3(C)C)c12]

410 mg of (4-benzyl-2,2-dimethyl-piperazin-1-yl)-[6-(4-benzyloxy-2-fluoro-phenyl)-3-methyl-1-(tetrahydro-pyran-2-yl)-1H-pyrazolo[3,4-b]pyridin-4-yl]-methanone were dissolved in 8 ml of THF. Under Argon-atmosphere, 0.53 ml of lithium aluminium hydride (2.4M in THF) was added and the reaction was heated to reflux for 2 h. The reaction was then cooled to 0° C., and quenched by the addition of 3 ml EtOAc and 3 ml water. The mixture was filtered over celite by suction and washed with EtOAc. The solvents were removed in vacuo and 200 mg (50%) of the title compound were obtained and used without further purification.

LC/MS (Method LC4): Rt=1.06 min; m/z=634.20 [M+H]⁺.

(c) 4-[4-(2,2-Dimethyl-piperazin-1-ylmethyl)-3-methyl-1-(tetrahydro-pyran-2-yl)-1H-pyrazolo[3,4-b]pyridin-6-yl]-3-fluoro-phenol

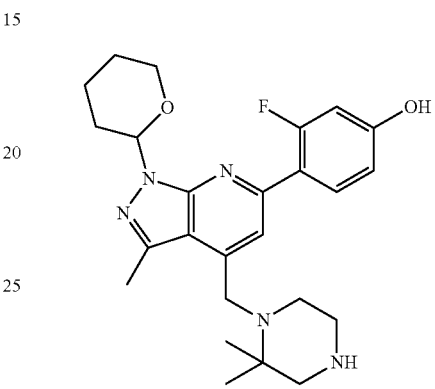

200 mg 4-(4-benzyl-2,2-dimethyl-piperazin-1-ylmethyl)-6-(4-benzyloxy-2-fluoro-phenyl)-3-methyl-1-(tetrahydro-pyran-2-yl)-1H-pyrazolo[3,4-b]pyridine was dissolved in 6 ml methanol and purged with argon. 18 mg Palladium (10% on charcoal) was added and the mixture was hydrogenated at 3 bar and r.t. for 16 h. The catalyst was filtered off and the solvents were evaporated. 130 mg (45%) of the title compound were obtained.

LC/MS (Method LC4): Rt=0.74 min; m/z=454.20 [M+H]⁺.

(d) 4-[4-(2,2-Dimethyl-piperazin-1-ylmethyl)-3-methyl-1H-pyrazolo[3,4-b]pyridin-6-yl]-3-fluoro-phenol

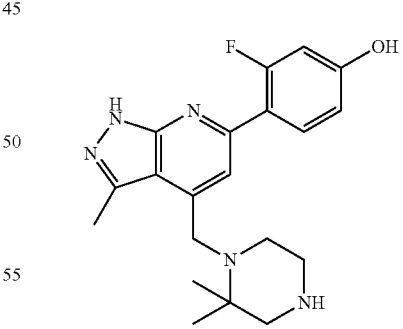

130 mg 4-[4-(2,2-dimethyl-piperazin-1-ylmethyl)-3-methyl-1-(tetrahydro-pyran-2-yl)-1H-pyrazolo[3,4-b]pyridin-6-yl]-3-fluoro-phenol were dissolved in 5 ml dry tetrahydrofurane and 1 ml HCl (4N in 1,4-dioxane) was added. After stirring the reaction at r.t. for 60 min the volatiles were removed in vacuo and the resulting residue was purified by flash chromatography (silica, heptane/ethyl acetate/methanol gradient). 60 mg (23%) of the title compound were obtained.

LC/MS (Method LC1): Rt=0.88 min; m/z=370.21 [M+H]⁺.

EXAMPLE 27

4-[4-((2S,5R)-2,5-Dimethyl-piperazin-1-ylmethyl)-3-methyl-1H-pyrazolo[3,4-b]pyridin-6-yl]-3-fluoro-phenol

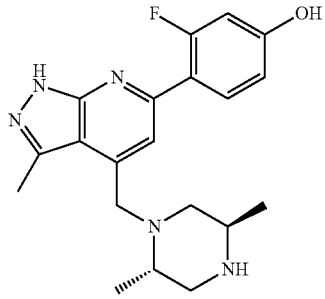 [SMILES: Cc1n[nH]c2nc(-c3ccc(O)cc3F)cc(CN3C[C@@H](C)NC[C@@H]3C)c12]

The title compound was obtained in analogy to Example 26 starting from 6-(4-benzyloxy-2-fluoro-phenyl)-3-methyl-1-(tetrahydro-pyran-2-yl)-1H-pyrazolo[3,4-b]pyridine-4-carboxylic acid and (2R,5S)-1-benzyl-2,5-dimethyl-piperazine.
LC/MS (Method LC1): Rt=0.87 min; m/z=370.20 [M+H]$^+$.

EXAMPLE 28

3-Fluoro-4-[3-methyl-4-(2,2,5,5-tetramethyl-piperazin-1-ylmethyl)-1H-pyrazolo[3,4-b]pyridin-6-yl]-phenol

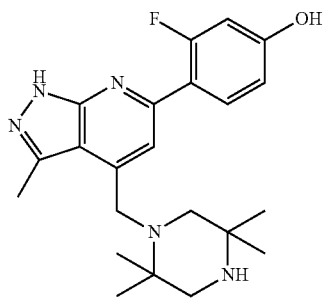 [SMILES: Cc1n[nH]c2nc(-c3ccc(O)cc3F)cc(CN3CC(C)(C)NCC3(C)C)c12]

The title compound was obtained in analogy to Example 26 starting from 6-(4-benzyloxy-2-fluoro-phenyl)-3-methyl-1-(tetrahydro-pyran-2-yl)-1H-pyrazolo[3,4-b]pyridine-4-carboxylic acid and 1-benzyl-2,2,5,5-tetramethyl-piperazine.
LC/MS (Method LC1): Rt=0.91 min; m/z=398.24 [M+H]$^+$.

EXAMPLE 29

3-Fluoro-4-[3-methyl-4-(trans-2-methyl-5-phenyl-piperazin-1-ylmethyl)-1H-pyrazolo[3,4-b]pyridin-6-yl]-phenol

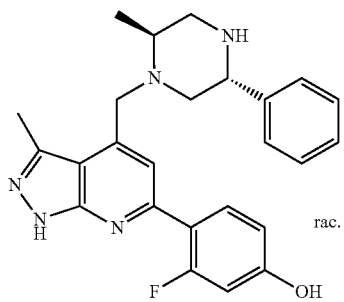 [SMILES: Cc1n[nH]c2nc(-c3ccc(O)cc3F)cc(CN3C[C@@H](c4ccccc4)NC[C@@H]3C)c12]

(a) (trans-4-Benzyl-2-methyl-5-phenyl-piperazin-1-yl)-[6-(4-benzyloxy-2-fluoro-phenyl)-3-methyl-1-(tetrahydro-pyran-2-yl)-1H-pyrazolo[3,4-b]pyridin-4-yl]-methanone

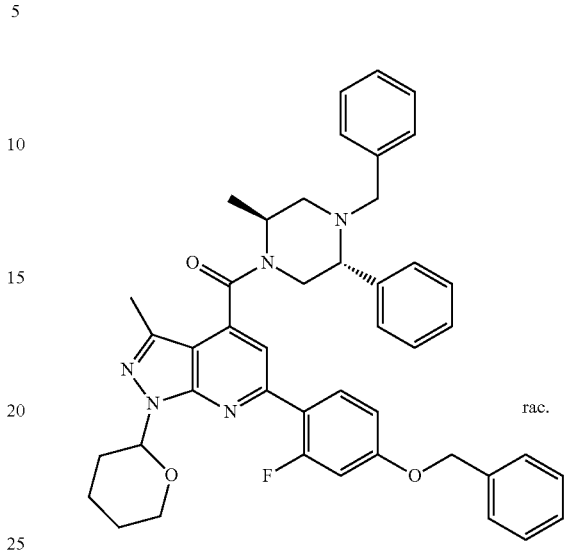

In analogy to Example 1 step (d) 500 mg 6-(4-benzyloxy-2-fluoro-phenyl)-3-methyl-1-(tetrahydro-pyran-2-yl)-1H-pyrazolo[3,4-b]pyridine-4-carboxylic acid was reacted with 376 mg trans-1-benzyl-5-methyl-2-phenyl-piperazine to obtain 549 mg (75%) of the title compound.
LC/MS (Method LC4): Rt=1.22 min; m/z=710.35 [M+H]$^+$.

(b) 4-(trans-4-Benzyl-2-methyl-5-phenyl-piperazin-1-ylmethyl)-6-(4-benzyloxy-2-fluoro-phenyl)-3-methyl-1-(tetrahydro-pyran-2-yl)-1H-pyrazolo[3,4-b]pyridine

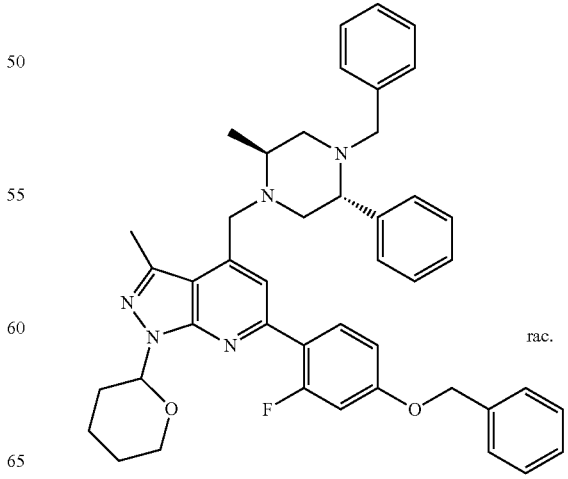

In analogy to Example 1 step (e) 545 mg of (trans-4-benzyl-2-methyl-5-phenyl-piperazin-1-yl)-[6-(4-benzyloxy-2-fluoro-phenyl)-3-methyl-1-(tetrahydro-pyran-2-yl)-1H-pyrazolo[3,4-b]pyridin-4-yl]-methanone were reacted with borane-dimethylsulfide complex and 431 mg (81%) of the title compound were obtained.

LC/MS (Method LC4): Rt=1.01 min; m/z=696.35 [M+H]$^+$.

(c) 3-Fluoro-4-[3-methyl-4-(trans-2-methyl-5-phenyl-piperazin-1-ylmethyl)-1-(tetrahydro-pyran-2-yl)-1H-pyrazolo[3,4-b]pyridin-6-yl]-phenol

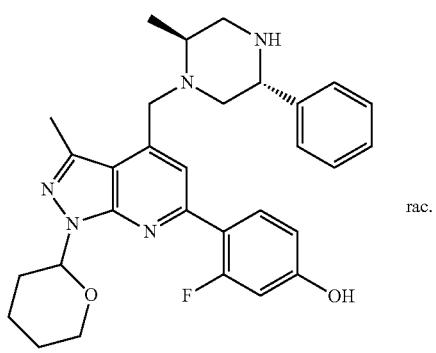 [SMILES: Cc1nn(C2CCCCO2)c2nc(-c3ccc(O)cc3F)cc(CN3C[C@@H](c4ccccc4)NC[C@@H]3C)c12]

In analogy to Example 26 step (c) 430 mg of 4-(trans-4-benzyl-2-methyl-5-phenyl-piperazin-1-ylmethyl)-6-(4-benzyloxy-2-fluoro-phenyl)-3-methyl-1-(tetrahydro-pyran-2-yl)-1H-pyrazolo[3,4-b]pyridine were hydrogenated to obtain 100 mg (31%) of the title compound.

LC/MS (Method LC4): Rt=0.76 min; m/z=516.05 [M+H]$^+$.

(d) 3-Fluoro-4-[3-methyl-4-(trans-2-methyl-5-phenyl-piperazin-1-ylmethyl)-1H-pyrazolo[3,4-b]pyridin-6-yl]-phenol

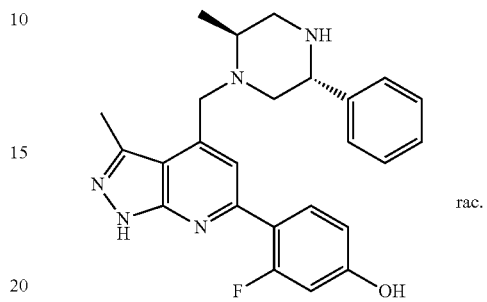

In analogy to Example 26 step (d) 98 mg of 3-fluoro-4-[3-methyl-4-(trans-2-methyl-5-phenyl-piperazin-1-ylmethyl)-1-(tetrahydro-pyran-2-yl)-1H-pyrazolo[3,4-b]pyridin-6-yl]-phenol were deprotected to obtain 60 mg (73%) of the title compound.

LC/MS (Method LC5): Rt=0.94 min; m/z=432.14 [M+H]$^+$.

The following examples have ben prepared following a similar procedure as described for Example 29, starting from 6-(4-benzyloxy-2-fluoro-phenyl)-3-methyl-1-(tetrahydro-pyran-2-yl)-1H-pyrazolo[3,4-b]pyridine-4-carboxylic acid and the respective amine precursors:

| Exp. No. | Name | Structure | LC/MS method | m/z [M + H]$^+$ | R$_t$ [min] |
|---|---|---|---|---|---|
| 30 | 4-[4-((2S,5R)-5-Ethyl-2-methyl-piperazin-1-ylmethyl)-3-methyl-1H-pyrazolo[3,4-b]pyridin-6-yl]-3-fluoro-phenol | 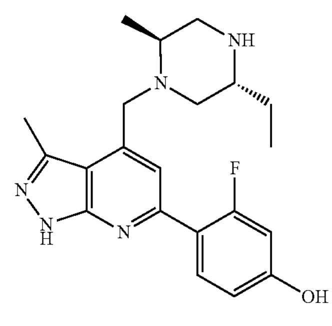 [SMILES: CC[C@@H]1CN(Cc2cc(-c3ccc(O)cc3F)nc3[nH]nc(C)c23)[C@@H](C)CN1] | LC5 | 384.23 | 0.72 |
| 31 | 4-[4-(2-Ethyl-2,5,5-trimethyl-piperazin-1-ylmethyl)-3-methyl-1H-pyrazolo[3,4-b]pyridin-6-yl]-3-fluoro-phenol | 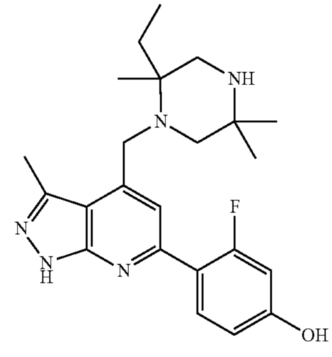 [SMILES: CCC1(C)CNC(C)(C)CN1Cc1cc(-c2ccc(O)cc2F)nc2[nH]nc(C)c12] | LC9 | 410.42 | 1.38 |

-continued

| Exp. No. | Name | Structure | LC/MS method | m/z [M + H]+ | R_t [min] |
|---|---|---|---|---|---|
| 32 | 4-[4-(2,2-Diethyl-5,5-dimethyl-piperazin-1-ylmethyl)-3-methyl-1H-pyrazolo[3,4-b]pyridin-6-yl]-3-fluoro-phenol | 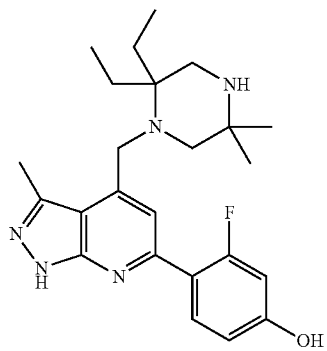 [SMILES: CCC1(CC)CNC(C)(C)CN1Cc1cc(-c2ccc(O)cc2F)nc2[nH]nc(C)c12] | LC9 | 426.49 | 1.24 |
| 33 | 4-[3-Methyl-4-(8-methyl-6,9-diaza-spiro[4.5]dec-9-ylmethyl)-1H-pyrazolo[3,4-b]pyridin-6-yl]-phenol | 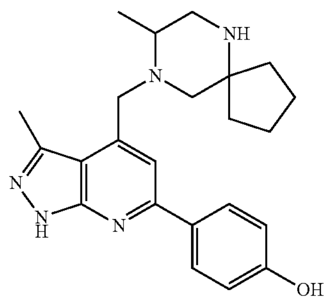 [SMILES: Cc1n[nH]c2nc(-c3ccc(O)cc3)cc(CN3CC4(CCCC4)NCC3C)c12] | LC9 | 392.32 | 1.30 |
| 34 | 4-[4-(2-Cyclopropyl-2,5,5-trimethyl-piperazin-1-ylmethyl)-3-methyl-1H-pyrazolo[3,4-b]pyridin-6-yl]-3-fluoro-phenol | 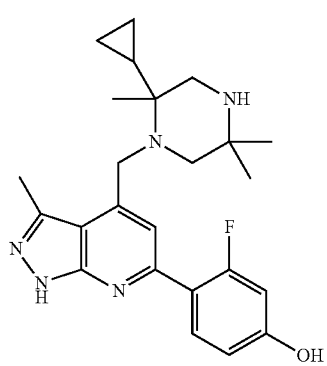 [SMILES: Cc1n[nH]c2nc(-c3ccc(O)cc3F)cc(CN3CC(C)(C)NCC3(C)C3CC3)c12] | LC9 | 424.32 | 1.40 |
| 35 | 3-Fluoro-4-[3-methyl-4-(8-methyl-6,9-diaza-spiro[4.5]dec-9-ylmethyl)-1H-pyrazolo[3,4-b]pyridin-6-yl]-phenol | 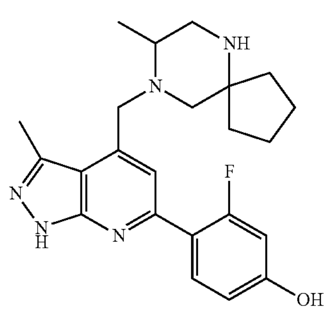 [SMILES: Cc1n[nH]c2nc(-c3ccc(O)cc3F)cc(CN3CC4(CCCC4)NCC3C)c12] | LC9 | 410.41 | 1.13 |

-continued

| Exp. No. | Name | Structure | LC/MS method | m/z [M + H]⁺ | R_t [min] |
|---|---|---|---|---|---|
| 36 | 4-[4-(8,8-Dimethyl-6,9-diaza-spiro[4.5]dec-9-ylmethyl)-3-methyl-1H-pyrazolo[3,4-b]pyridin-6-yl]-3-fluoro-phenol | 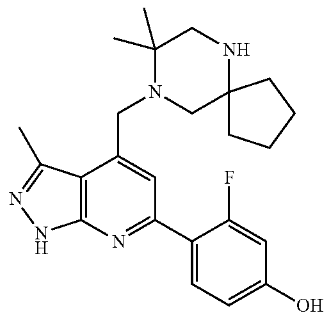 [SMILES: Cc1n[nH]c2nc(-c3ccc(O)cc3F)cc(CN3CC4(CCCC4)NCC3(C)C)c12] | LC9 | 424.37 | 1.36 |
| 37 | 3-Fluoro-4-[4-(2-isopropyl-5,5-dimethyl-piperazin-1-ylmethyl)-3-methyl-1H pyrazolo[3,4-b]pyridin-6-yl]-phenol | 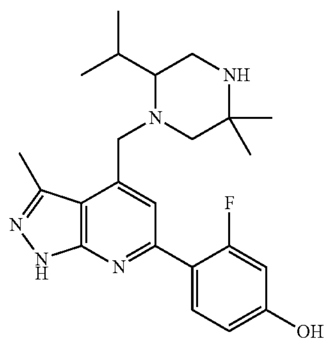 [SMILES: Cc1n[nH]c2nc(-c3ccc(O)cc3F)cc(CN3CC(C)(C)NCC3C(C)C)c12] | LC9 | 412.35 | 1.42 |
| 38 | 3-Fluoro-4-[3-methyl-4-(2,5,5-trimethyl-piperazin-1-ylmethyl)-1H-pyrazolo[3,4-b]pyridin-6-yl]-phenol | 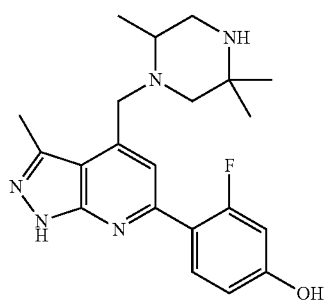 [SMILES: Cc1n[nH]c2nc(-c3ccc(O)cc3F)cc(CN3CC(C)(C)NCC3C)c12] | LC9 | 382.42 | 1.30 |
| 39 | 4-[4-(2-Ethyl-5,5-dimethyl-piperazin-1-ylmethyl)-3-methyl-1H-pyrazolo[3,4-b]pyridin-6-yl]-3-fluoro-phenol | 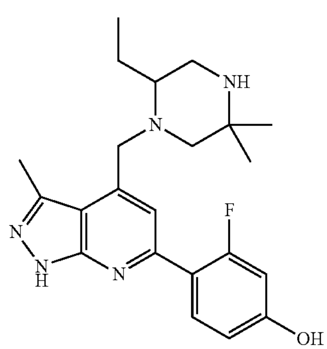 [SMILES: CCC1CNC(C)(C)CN1Cc1cc(-c2ccc(O)cc2F)nc2[nH]nc(C)c12] | LC9 | 398.23 | 1.19 |

EXAMPLE 40

4-[4-(4,7-Diaza-spiro[2.5]oct-4-ylmethyl)-3-methyl-1H-pyrazolo[3,4-b]pyridin-6-yl]-phenol

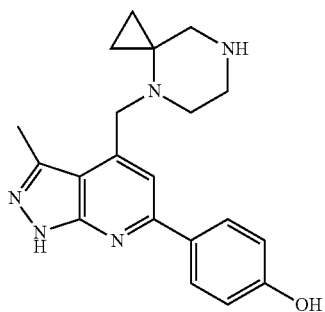 [SMILES: Cc1n[nH]c2nc(-c3ccc(O)cc3)cc(CN3CCNCC34CC4)c12]

(a) 3-Methyl-1-(tetrahydro-pyran-2-yl)-6-[4-(tetrahydro-pyran-2-yloxy)-phenyl]-1H-pyrazolo[3,4-b]pyridine-4-carboxylic acid

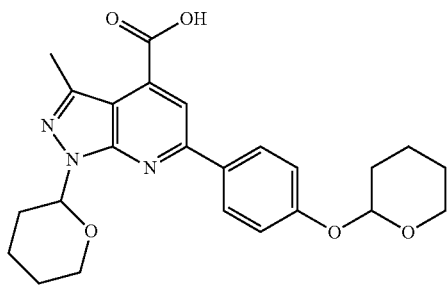 [SMILES: Cc1nn(C2CCCCO2)c2nc(-c3ccc(OC4CCCCO4)cc3)cc(C(=O)O)c12]

To a mixture of 6-bromo-3-methyl-1-(tetrahydro-pyran-2-yl)-1H-pyrazolo[3,4-b]pyridine-4-carboxylic acid ethyl ester (6.00 g), 4-(tetrahydro-2H-pyran-2-yloxy)-phenylboronic acid (4.34 g) and potassium carbonate (2.93 g) in DME/water (v/v=2/1, 200 mL) was added at r.t. under Ar-atmosphere palladium(0) bis(tri-tert-butylphosphine) (0.42 g) and the mixture was stirred at 85° C. for 90 min. To the mixture water was added and it was extracted with ethyl acetate. The organic phase was washed with water, dried over magnesium sulfate, and concentrated in vacuo. The resulting residue was purified by flash chromatography (silica, heptane/ethyl acetate) to give 3-methyl-1-(tetrahydro-pyran-2-yl)-6-[4-(tetrahydro-pyran-2-yloxy)-phenyl]-1H-pyrazolo[3,4-b]pyridine-4-carboxylic acid ethyl ester (7.00 g, 92%). This material was dissolved in isopropanol (30 mL), and 1N sodium hydroxide solution (15 mL) was added. The solution was stirred overnight, then the mixture was contentrated in vacuo to about a third of its volume. The precipitated solid was isolated by filtration and dried in air giving the sodium salt of 3-methyl-1-(tetrahydro-pyran-2-yl)-6-[4-(tetrahydro-pyran-2-yloxy)-phenyl]-1H-pyrazolo[3,4-b]pyridine-4-carboxylic acid (6.2 g, 87%).

LC/MS (Method LC4): Rt=1.08 min; m/z=438.1 [M+H]$^+$.

(b) 4-{3-Methyl-1-(tetrahydro-pyran-2-yl)-6-[4-(tetrahydro-pyran-2-yloxy)-phenyl]-1H-pyrazolo[3,4-b]pyridine-4-carbonyl}-4,7-diaza-spiro[2.5]octane-7-carboxylic acid tert-butyl ester

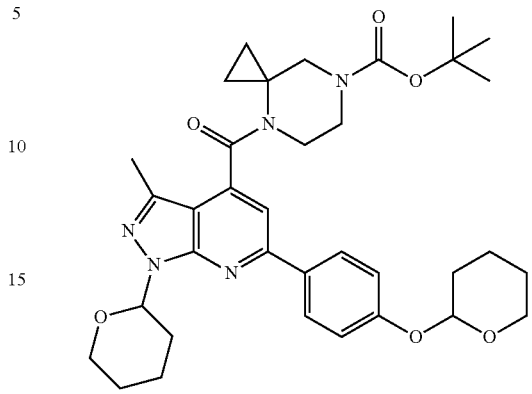

To a suspension of 300 mg of 3-methyl-1-(tetrahydro-pyran-2-yl)-6-[4-(tetrahydro-pyran-2-yloxy)-phenyl]-1H-pyrazolo[3,4-b]pyridine-4-carboxylic acid sodium salt in 7.5 ml of DCM were added 0.12 ml of Hünig's base, 376 mg of BEP and 146 mg of 4,7-diaza-spiro[2.5]octane-7-carboxylic acid tert-butyl ester. The reaction was stirred overnight at r.t. For workup it was diluted with water and DCM and the layers were separated. The organic layer was washed with water twice, dried over Na$_2$SO$_4$, filtered and concentrated in vacuo. The residue was purified by flash chromatography (silica, heptane/EtOAc gradient) to obtain 280 mg (66%) of the title compound.

LC/MS (Method LC4): Rt=1.24 min; m/z=632.20 [M+H]$^+$.

(c) 4-[6-(4-Hydroxy-phenyl)-3-methyl-1-(tetrahydro-pyran-2-yl)-1H-pyrazolo[3,4-b]pyridin-4-ylmethyl]-4,7-diaza-spiro[2.5]octane-7-carboxylic acid tert-butyl ester

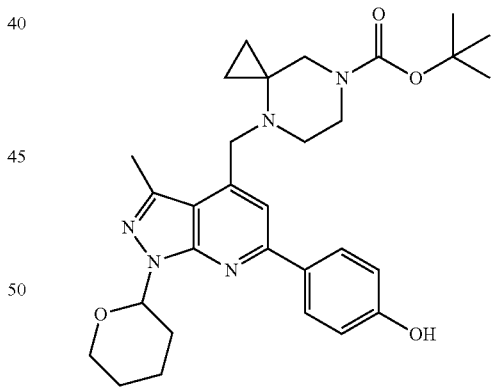

To a solution of 272 mg of) 4-{3-methyl-1-(tetrahydro-pyran-2-yl)-6-[4-(tetrahydro-pyran-2-yloxy)-phenyl]-1H-pyrazolo[3,4-b]pyridine-4-carbonyl}-4,7-diaza-spiro[2.5]-octane-7-carboxylic acid tert-butyl ester in 4 ml of dry THF 3.5 ml of borane-dimethyl-sulfide complex (1 M in DCM) was added slowly at r.t., and the reaction was heated to reflux for 60 min. The reaction was quenched by the addition of 2.2 ml of methanol, and the solvents were evaporated. The residue was purified by flash chromatography (silica, heptane/EtOAc gradient) to obtain 170 mg (74%) of the title compound.

LC/MS (Method LC4): Rt=1.03 min; m/z=534.20 [M+H]$^+$.

(d) 4-[4-(4,7-Diaza-spiro[2.5]oct-4-ylmethyl)-3-methyl-1H-pyrazolo[3,4-b]pyridin-6-yl]-phenol

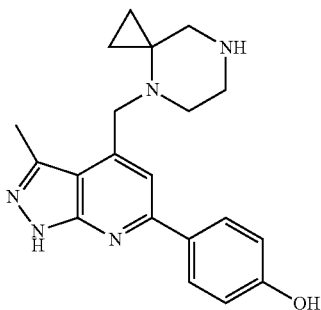 [SMILES: Cc1n[nH]c2nc(-c3ccc(O)cc3)cc(CN3CCNCC34CC4)c12]

160 mg 4-[6-(4-hydroxy-phenyl)-3-methyl-1-(tetrahydro-pyran-2-yl)-1H-pyrazolo[3,4-b]pyridin-4-ylmethyl]-4,7-diaza-spiro[2.5]octane-7-carboxylic acid tert-butyl ester were dissolved in 6 ml HCl (4N in 1,4-dioxane). After stirring the reaction at r.t. for 15 min the precipitated residue was isolated by filtration and washed with 1,4-dioxane and THF. It was taken up in water and freeze dried in vacuo. 115 mg (100%) of the title compound were obtained.

LC/MS (Method LC5): Rt=0.83 min; m/z=350.25 [M+H]$^+$.

The following examples have ben prepared following a similar procedure as described for Example 40, starting from 3-methyl-1-(tetrahydro-pyran-2-yl)-6-[4-(tetrahydro-pyran-2-yloxy)-phenyl]-1H-pyrazolo[3,4-b]pyridine-4-carboxylic acid and the respective amine precursors:

| Exp. No. | Name | Structure | LC/MS method | m/z [M + H]+ | Rt [min] |
|---|---|---|---|---|---|
| 41 | 4-[3-Methyl-4-(2-phenyl-piperazin-1-ylmethyl)-1H-pyrazolo[3,4-b]pyridin-6-yl]-phenol | 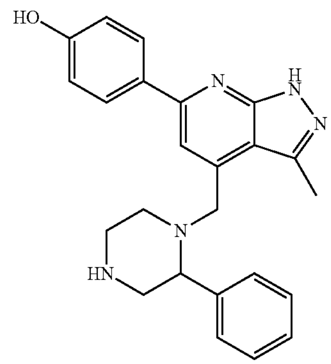 [SMILES: Cc1n[nH]c2nc(-c3ccc(O)cc3)cc(CN3CCNCC3c3ccccc3)c12] | LC1 | 400.3 | 0.83 |
| 42 | 4-{4-[2-(4-Fluoro-phenyl)-piperazin-1-ylmethyl]-3-methyl-1H-pyrazolo[3,4-b]pyridin-6-yl}-phenol | 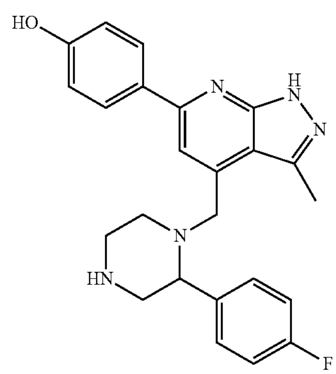 [SMILES: Cc1n[nH]c2nc(-c3ccc(O)cc3)cc(CN3CCNCC3c3ccc(F)cc3)c12] | LC1 | 418.2 | 0.82 |
| 43 | 4-[3-Methyl-4-(trans-5-methyl-2-phenyl-piperazin-1-ylmethyl)-1H-pyrazolo[3,4-b]pyridin-6-yl]-phenol | 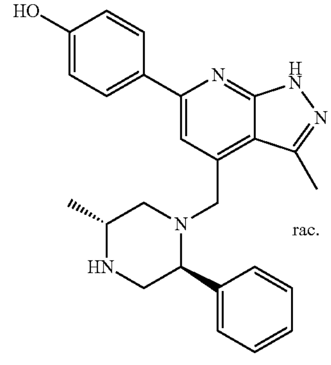 [SMILES: Cc1n[nH]c2nc(-c3ccc(O)cc3)cc(CN3C[C@@H](C)NC[C@@H]3c3ccccc3)c12] | LC5 | 414.15 | 0.93 |

-continued

| Exp. No. | Name | Structure | LC/MS method | m/z [M + H]+ | Rt [min] |
|---|---|---|---|---|---|
| 44 | 4-{3-Methyl-4-[2-(4-trifluoromethyl-phenyl)-piperazin-1-ylmethyl]-1H-pyrazolo[3,4-b]pyridin-6-yl}-phenol | 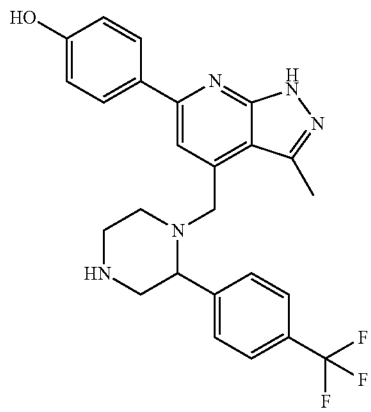 [SMILES: Cc1n[nH]c2nc(-c3ccc(O)cc3)cc(CN3CCNCC3c3ccc(C(F)(F)F)cc3)c12] | LC5 | 468.1 | 1.00 |
| 45 | 4-{4-[2-(4-Isopropyl-phenyl)-piperazin-1-ylmethyl]-3-methyl-1H-pyrazolo[3,4-b]pyridin-6-yl}-phenol | 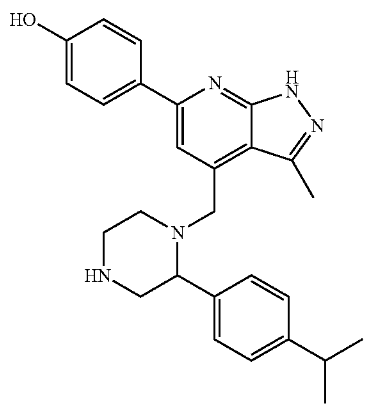 [SMILES: Cc1n[nH]c2nc(-c3ccc(O)cc3)cc(CN3CCNCC3c3ccc(C(C)C)cc3)c12] | LC5 | 442.2 | 1.02 |
| 46 | 4-{4-[(3-Ethyl-piperidin-3-ylamino)-methyl]-3-methyl-1H-pyrazolo[3,4-b]pyridin-6-yl}-phenol | 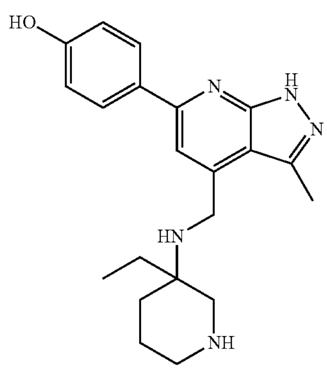 [SMILES: CCC1(NCc2cc(-c3ccc(O)cc3)nc3[nH]nc(C)c23)CCCNC1] | LC3 | 366.28 | 2.31 |
| 47 | 4-[4-(6,9-Diaza-spiro[4.5]dec-6-ylmethyl)-3-methyl-1H-pyrazolo[3,4-b]pyridin-6-yl]-phenol | 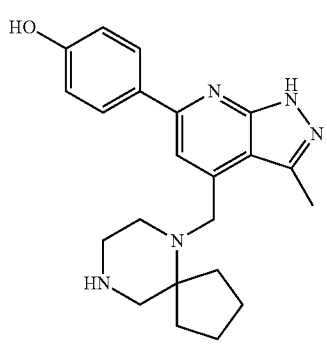 [SMILES: Cc1n[nH]c2nc(-c3ccc(O)cc3)cc(CN3CCNCC34CCCC4)c12] | LC9 | 378.31 | 1.33 |

| Exp. No. | Name | Structure | LC/MS method | m/z [M + H]+ | Rt [min] |
|---|---|---|---|---|---|
| 48 | 4-[3-Methyl-4-(2,2,5-trimethyl-piperazin-1-ylmethyl)-1H-pyrazolo-[3,4-b]pyridin-6-yl]-phenol | 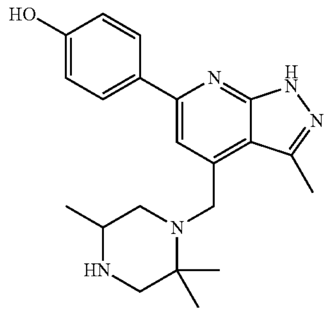 [SMILES: Cc1n[nH]c2nc(-c3ccc(O)cc3)cc(CN3CC(C)NCC3(C)C)c12] | LC9 | 366.29 | 1.06 |

EXAMPLE 49

4-[3-Methyl-4-(2,2,5,5-tetramethyl-piperazin-1-ylmethyl)-1H-pyrazolo[3,4-b]pyridin-6-yl]-phenol

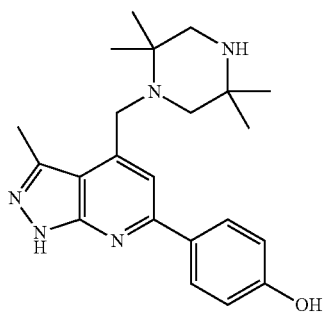 [SMILES: Cc1n[nH]c2nc(-c3ccc(O)cc3)cc(CN3CC(C)(C)NCC3(C)C)c12]

(a) (4-Benzyl-2,2,5,5-tetramethyl-piperazin-1-yl)-{3-methyl-1-(tetrahydro-pyran-2-yl)-6-[4-(tetrahydro-pyran-2-yloxy)-phenyl]-1H-pyrazolo[3,4-b]pyridin-4-yl}-methanone

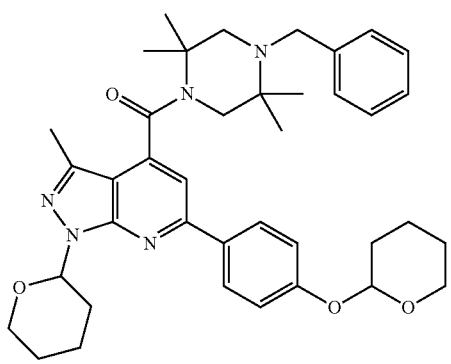 [SMILES: Cc1nn(C2CCCCO2)c2nc(-c3ccc(OC4CCCCO4)cc3)cc(C(=O)N3CC(C)(C)N(Cc4ccccc4)CC3(C)C)c12]

In a similar manner as in Exampe 40 step (b) 400 mg of 3-methyl-1-(tetrahydro-pyran-2-yl)-6-[4-(tetrahydro-pyran-2-yloxy)-phenyl]-1H-pyrazolo[3,4-b]pyridine-4-carboxylic acid was reacted with 212 mg 1-benzyl-2,2,5,5-tetramethyl-piperazine to obtain 450 mg (76%) of the title compound.

LC/MS (Method LC4): Rt=1.04 min; m/z=652.30 [M+H]+.

(b) 4-[4-(4-Benzyl-2,2,5,5-tetramethyl-piperazin-1-ylmethyl)-3-methyl-1-(tetrahydro-pyran-2-yl)-1H-pyrazolo[3,4-b]pyridin-6-yl]-phenol

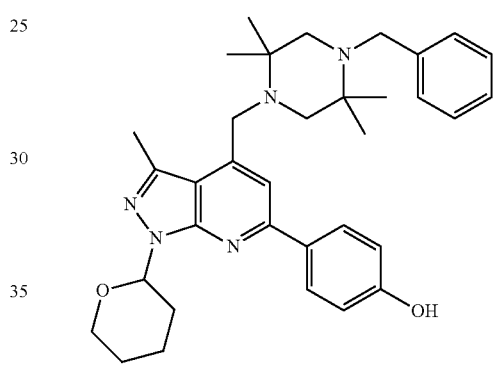

In a similar manner as in Example 40 step (c) 450 mg of (4-benzyl-2,2,5,5-tetramethyl-piperazin-1-yl)-{3-methyl-1-(tetrahydro-pyran-2-yl)-6-[4-(tetrahydro-pyran-2-yloxy)-phenyl]-1H-pyrazolo[3,4-b]pyridin-4-yl}-methanone were reacted with borane-dimethyl-sulfide complex to obtain 250 mg (49%) of the title compound.

LC/MS (Method LC4): Rt=0.82 min; m/z=554.20 [M+H]+.

(c) 4-[3-Methyl-1-(tetrahydro-pyran-2-yl)-4-(2,2,5,5-tetramethyl-piperazin-1-ylmethyl)-1H-pyrazolo[3,4-b]pyridin-6-yl]-phenol

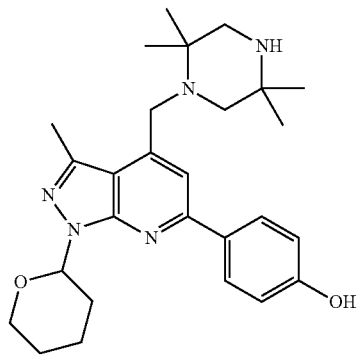 [SMILES: Cc1nn(C2CCCCO2)c2nc(-c3ccc(O)cc3)cc(CN3CC(C)(C)NCC3(C)C)c12]

250 mg 4-[4-(4-benzyl-2,2,5,5-tetramethyl-piperazin-1-ylmethyl)-3-methyl-1-(tetra-hydro-pyran-2-yl)-1H-pyrazolo[3,4-b]pyridin-6-yl]-phenol was dissolved in 20 ml methanol and purged with argon. 25 mg Palladium (10% on charcoal) were added and the mixture was hydrogenated at r.t. for 30 min. The catalyst was filtered off and the solvents were evaporated. 150 mg (72%) of the title compound were obtained.

LC/MS (Method LC4): Rt=0.73 min; m/z=464.20 [M+H]$^+$.

(d) 4-[3-Methyl-4-(2,2,5,5-tetramethyl-piperazin-1-ylmethyl)-1H-pyrazolo[3,4-b]pyridin-6-yl]-phenol

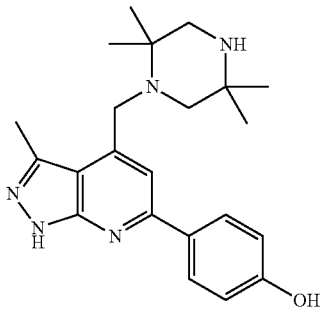 [SMILES: Cc1n[nH]c2nc(-c3ccc(O)cc3)cc(CN3CC(C)(C)NCC3(C)C)c12]

150 mg 4-[3-methyl-1-(tetrahydro-pyran-2-yl)-4-(2,2,5,5-tetramethyl-piperazin-1-ylmethyl)-1H-pyrazolo[3,4-b]pyridin-6-yl]-phenol were dissolved in 10 ml of tetrahydrofurane and 0.65 ml HCl (4N in 1,4-dioxane) were added. After stirring the reaction at r.t. for 30 min the precipitated residue was isolated by filtration and washed with THF.

It was taken up in water and freeze dried in vacuo. 180 mg (96%) of the title compound were obtained.

LC/MS (Method LC5): Rt=0.88 min; m/z=380.16 [M+H]$^+$.

EXAMPLE 50

4-[4-(2-Ethyl-2,5,5-trimethyl-piperazin-1-ylmethyl)-3-methyl-1H-pyrazolo[3,4-b]pyridin-6-yl]-phenol

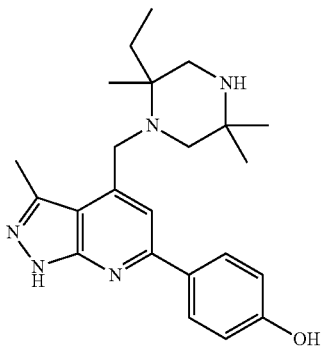

4-[4-(2-ethyl-2,5,5-trimethyl-piperazin-1-ylmethyl)-3-methyl-1H-pyrazolo[3,4-b]pyridin-6-yl]-phenol was synthesized in analogy to Example 49 (4-[3-Methyl-4-(2,2,5,5-tetramethyl-piperazin-1-ylmethyl)-1H-pyrazolo[3,4-b]pyridin-6-yl]-phenol) starting from 3-methyl-1-(tetrahydro-pyran-2-yl)-6-[4-(tetrahydro-pyran-2-yloxy)-phenyl]-1H-pyrazolo[3,4-b]pyridine-4-carboxylic acid and 1-benzyl-5-ethyl-2,2,5-trimethyl-piperazine.

LC/MS (Method LC9): Rt=1.35 min; m/z=394.32 [M+H]$^+$.

EXAMPLE 51

4-[4-(2,2-Diethyl-5,5-dimethyl-piperazin-1-ylmethyl)-3-methyl-1H-pyrazolo[3,4-b]pyridin-6-yl]-phenol

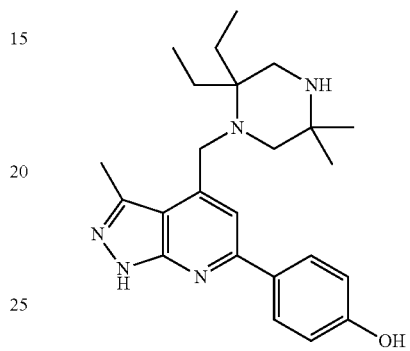

4-[4-(2,2-diethyl-5,5-dimethyl-piperazin-1-ylmethyl)-3-methyl-1H-pyrazolo[3,4-b]pyridin-6-yl]-phenol was synthesized in analogy to Example 49 (4-[3-Methyl-4-(2,2,5,5-tetramethyl-piperazin-1-ylmethyl)-1H-pyrazolo[3,4-b]pyridin-6-yl]-phenol) starting from 3-methyl-1-(tetrahydro-pyran-2-yl)-6-[4-(tetrahydro-pyran-2-yloxy)-phenyl]-1H-pyrazolo[3,4-b]pyridine-4-carboxylic acid and 1-benzyl-5,5-diethyl-2,2-dimethyl-piperazine.

LC/MS (Method LC9): Rt=1.38 min; m/z=406.41 [M+H]$^+$.

EXAMPLE 52

4-[3-Methyl-4-(2,5,5-trimethyl-piperazin-1-ylmethyl)-1H-pyrazolo[3,4-b]pyridin-6-yl]-phenol

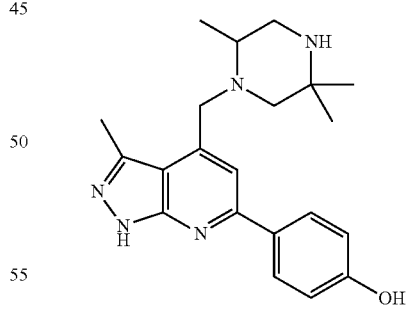

4-[3-Methyl-4-(2,5,5-trimethyl-piperazin-1-ylmethyl)-1H-pyrazolo[3,4-b]pyridin-6-yl]-phenol was synthesized in analogy to Example 49 (4-[3-Methyl-4-(2,2,5,5-tetramethyl-piperazin-1-ylmethyl)-1H-pyrazolo[3,4-b]pyridin-6-yl]-phenol) starting from 3-methyl-1-(tetrahydro-pyran-2-yl)-6-[4-(tetrahydro-pyran-2-yloxy)-phenyl]-1H-pyrazolo[3,4-b]pyridine-4-carboxylic acid and 1-benzyl-2,2,5-trimethyl-piperazine.

LC/MS (Method LC9): Rt=1.08 min; m/z=366.28 [M+H]$^+$.

EXAMPLE 53

4-[4-(2-Ethyl-5,5-dimethyl-piperazin-1-ylmethyl)-3-methyl-1H-pyrazolo[3,4-b]pyridin-6-yl]-phenol

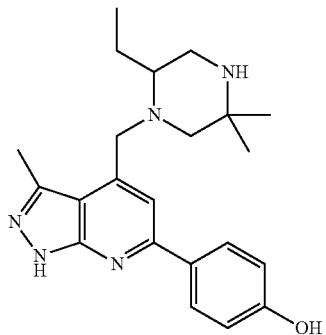 [SMILES: CCC1CNC(C)(C)CN1Cc1cc(-c2ccc(O)cc2)nc2[nH]nc(C)c12]

(a) 6-(4-Benzyloxy-phenyl)-3-methyl-1-(tetrahydro-pyran-2-yl)-1H-pyrazolo[3,4-b]pyridine-4-carboxylic acid

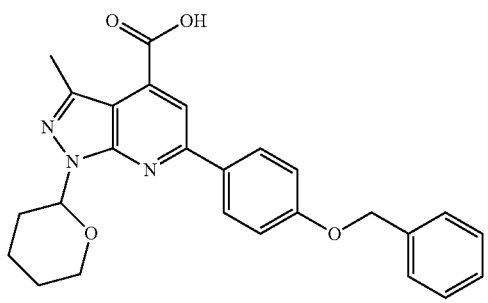 [SMILES: Cc1nn(C2CCCCO2)c2nc(-c3ccc(OCc4ccccc4)cc3)cc(C(=O)O)c12]

In analogy to Example 1 step (c) the title compound was synthesized starting from 6-bromo-3-methyl-1-(tetrahydro-pyran-2-yl)-1H-pyrazolo[3,4-b]pyridine-4-carboxylic acid ethyl ester and 4-benzyloxy-phenylboronic acid.

LC/MS (Method LC4): Rt=1.13 min; m/z=444.10 [M+H]$^+$.

(b) (4-Benzyl-2-ethyl-5,5-dimethyl-piperazin-1-yl)-[6-(4-benzyloxy-phenyl)-3-methyl-1-(tetrahydro-pyran-2-yl)-1H-pyrazolo[3,4-b]pyridin-4-yl]-methanone

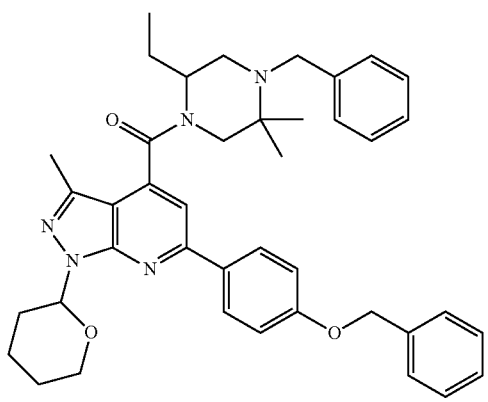 [SMILES: CCC1CN(Cc2ccccc2)C(C)(C)CN1C(=O)c1cc(-c2ccc(OCc3ccccc3)cc2)nc2c1c(C)nn2C1CCCCO1]

In analogy to Example 29 step (a) the title compound was synthezised using 6-(4-benzyloxy-phenyl)-3-methyl-1-(tetrahydro-pyran-2-yl)-1H-pyrazolo[3,4-b]pyridine-4-carboxylic acid and 1-Benzyl-5-ethyl-2,2-dimethyl-piperazine.

LC/MS (Method LC4): Rt=1.04 min; m/z=658.30 [M+H]$^+$.

(c) 4-(4-Benzyl-2-ethyl-5,5-dimethyl-piperazin-1-ylmethyl)-6-(4-benzyloxy-phenyl)-3-methyl-1-(tetrahydro-pyran-2-yl)-1H-pyrazolo[3,4-b]pyridine

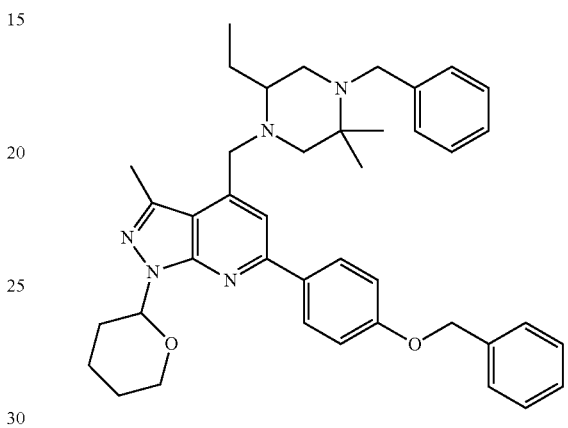

In analogy to Example 29 step (b) the title compound was synthezised using (4-benzyl-2-ethyl-5,5-dimethyl-piperazin-1-yl)-[6-(4-benzyloxy-phenyl)-3-methyl-1-(tetrahydro-pyran-2-yl)-1H-pyrazolo[3,4-b]pyridin-4-yl]-methanone.

LC/MS (Method LC4): Rt=1.05 min; m/z=644.30 [M+H]$^+$.

(d) 4-[4-(2-Ethyl-5,5-dimethyl-piperazin-1-ylmethyl)-3-methyl-1-(tetrahydro-pyran-2-yl)-1H-pyrazolo[3,4-b]pyridin-6-yl]-phenol

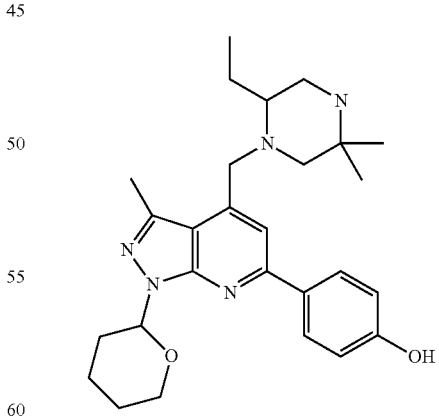

In analogy to Example 29 step (c) the title compound was synthezised using 4-(4-benzyl-2-ethyl-5,5-dimethyl-piperazin-1-ylmethyl)-6-(4-benzyloxy-phenyl)-3-methyl-1-(tetrahydro-pyran-2-yl)-1H-pyrazolo[3,4-b]pyridine.

LC/MS (Method LC4): Rt=0.77 min; m/z=464.20 [M+H]$^+$

(e) 4-[4-(2-Ethyl-5,5-dimethyl-piperazin-1-ylmethyl)-3-methyl-1H-pyrazolo[3,4-b]pyridin-6-yl]-phenol

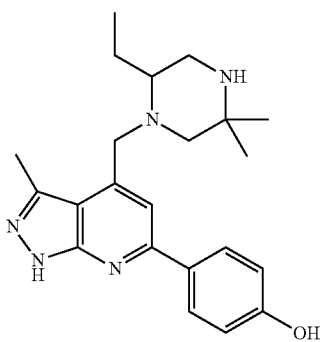

In analogy to Example 29 step (d) the title compound was synthezised using 4-[4-(2-ethyl-5,5-dimethyl-piperazin-1-ylmethyl)-3-methyl-1-(tetrahydro-pyran-2-yl)-1H-pyrazolo[3,4-b]pyridin-6-yl]-phenol.

LC/MS (Method LC9): Rt=1.15 min; m/z=380.25 [M+H]$^+$.

EXAMPLE 54

4-[4-((2S,5R)-2,5-Dimethyl-piperazin-1-ylmethyl)-3-methyl-1H-pyrazolo[3,4-b]pyridin-6-yl]-phenol

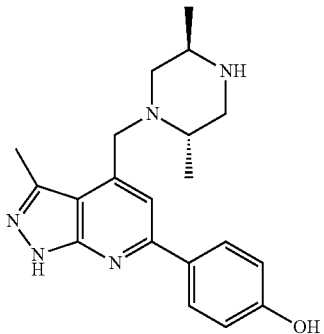 [SMILES: Cc1n[nH]c2nc(-c3ccc(O)cc3)cc(CN3C[C@@H](C)NC[C@@H]3C)c12]

(a) 6-(4-Hydroxy-phenyl)-3-methyl-1H-pyrazolo[3,4-b]pyridine-4-carboxylic acid methyl ester

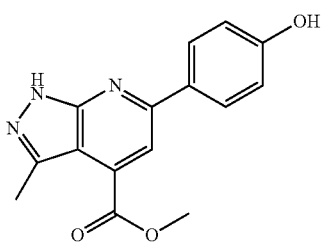 [SMILES: COC(=O)c1cc(-c2ccc(O)cc2)nc2[nH]nc(C)c12]

A mixture of 3-amino-5-methylpyrazole (50.0 g), pyruvic acid methyl ester (58.4 g) and 4-hydroxybenzaldehyde (62.9 mL) in acetic acid/methanol (v/v=1/1, 300 mL) was stirred at 75° C. for 15 h, cooled to r.t., and the precipitate formed was isolated by suction filtration and dried in vacuum at 60° C. 6-(4-Hydroxy-phenyl)-3-methyl-1H-pyrazolo[3,4-b]pyridine-4-carboxylic acid methyl ester (15 g, 10% yield) were obtained as pale yellow solid.

$^1$H-NMR (500 MHz, d$_6$-DMSO): 2.59 (s, 3H), 4.02 (s, 3H), 6.93 (d, 2H), 7.96 (s 2H), 8.04 (d, 2H), 11.9 (s, 1H), 13.4 (s, 1H).

LC/MS (Method LC3): Rt=3.55 min; m/z=284.14 [M+H]$^+$.

(b) 6-(4-Hydroxy-phenyl)-3-methyl-1-(tetrahydro-pyran-2-yl)-1H-pyrazolo[3,4-b]pyridine-4-carboxylic acid methyl ester

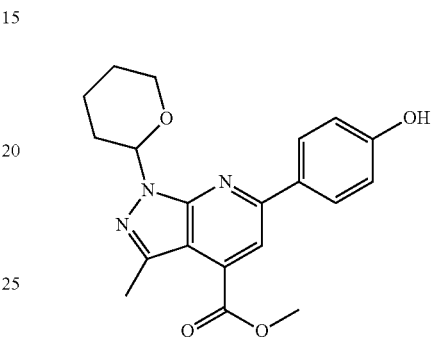

A mixture of 6-(4-hydroxy-phenyl)-3-methyl-1H-pyrazolo[3,4-b]pyridine-4-carboxylic acid methyl ester (15.0 g), 3,4-dihydro-2H-pyran (24 mL) and p-toluenesulfonic acid monohydrate (3.0 g) in THF (400 mL) was stirred at r.t. until the reaction was complete. Water was added and the mixture was extracted with ethyl acetate, the combined organic phases were washed with water and brine, dried over magnesium sulfate and concentrated. The residue was chromatographed over a short path column (silica, heptane/ethyl acetate gradient). The product containing fractions were combined, concentrated, and the residue was triturated with ether to give 6-(4-hydroxy-phenyl)-3-methyl-1-(tetrahydro-pyran-2-yl)-1H-pyrazolo[3,4-b]pyridine-4-carboxylic acid methyl ester (11 g, 57% yield).

$^1$H-NMR (500 MHz, d$_6$-DMSO): 1.54-1.68 (m, 2H), 1.78-1.90 (m, 1H), 1.91-1.98 (m, 1H), 2.04-2.12 (m, 1H), 2.45-2.60 (m, 1H), 2.60 (s, 3H), 3.68-3.75 (m, 1H), 3.93-4.02 (m, 1H), 4.02 (s, 3H), 6.10 (dd, 1H), 6.93 (d, 2H), 8.02 (s 2H), 8.12 (d, 2H), 10 (s, 1H).

LC/MS (Method LC1): Rt=1.27 min; m/z=368.2 [M+H]$^+$.

(c) 6-(4-Hydroxy-phenyl)-3-methyl-1-(tetrahydro-pyran-2-yl)-1H-pyrazolo[3,4-b]pyridine-4-carboxylic acid

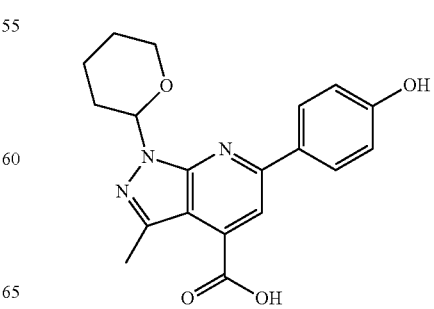

A mixture of 6-(4-hydroxy-phenyl)-3-methyl-1H-pyrazolo[3,4-b]pyridine-4-carboxylic acid methyl ester (10.9 g) and sodium hydroxide solution (1N, 80 mL) in isopropanol (80 mL) was stirred at r.t. for 90 min. The pH was adjusted to 3 with 1N HCl and the mixture was poured onto water. The precipitate formed was filtered off and dried in air to give 6-(4-Hydroxy-phenyl)-3-methyl-1-(tetrahydro-pyran-2-yl)-1H-pyrazolo[3,4-b]pyridine-4-carboxylic acid (10.2 g, 97% yield).

$^1$H-NMR (500 MHz, d$_6$-DMSO): 1.54-1.65 (m, 2H), 1.74-1.86 (m, 1H), 1.87-1.95 (m, 1H), 2.02-2.10 (m, 1H), 2.46-2.57 (m, 1H), 2.60 (s, 3H), 3.68-3.75 (m, 1H), 3.91-4.00 (m, 1H), 6.09 (dd, 1H), 6.93 (d, 2H), 8.00 (s 2H), 8.12 (d, 2H), 9.90 (s, 1H), 13.9 (br s, 1H).

LC/MS (Method LC1): R$_t$=1.15 min; m/z=354.2 [M+H]$^+$.

(d) ((2S,5R)-4-Benzyl-2,5-dimethyl-piperazin-1-yl)-[6-(4-hydroxy-phenyl)-3-methyl-1-(tetrahydro-pyran-2-yl)-1H-pyrazolo[3,4-b]pyridin-4-yl-methanone

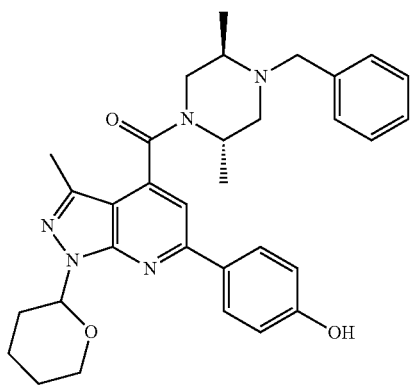 [SMILES: Cc1nn(C2CCCCO2)c2nc(-c3ccc(O)cc3)cc(C(=O)N3C[C@@H](C)N(Cc4ccccc4)C[C@@H]3C)c12]

To a suspension of 3.80 g of 6-(4-hydroxy-phenyl)-3-methyl-1-(tetrahydro-pyran-2-yl)-1H-pyrazolo[3,4-b]pyridine-4-carboxylic acid in 100 ml of DCM were added 5.5 ml of Hünig's base, 6.48 g of BEP and 2.41 g of (2R,5S)-dimethyl-1-benzylpiperazine. The reaction was stirred overnight at r.t. Then 3 ml of sodium methanolate (30% in methanol) were added, and the reation was stirred for 30 min. The pH was then brought to 5 by the addition of 2 M aqueous hydrochloric acid. The mixture was then diluted with EtOAc and the layers were separated. The organic layer was washed with saturated aqueous sodium bicarbonate solution, saturated aqueous ammonium chloride solution and water, dried over Na$_2$SO$_4$, filtered and concentrated in vacuo. The residue was purified by flash chromatography (silica, heptane/EtOAc gradient) to obtain 2.10 g (36%) of the title compound.

LC/MS (Method LC5): Rt=1.02 min; m/z=540.38 [M+H]$^+$.

(e) 4-[4-((2S,5R)-4-Benzyl-2,5-dimethyl-piperazin-1-ylmethyl)-3-methyl-1-(tetrahydro-pyran-2-yl)-1H-pyrazolo[3,4-b]pyridin-6-yl]-phenol

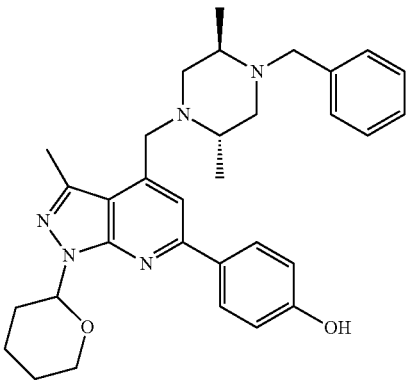 [SMILES: Cc1nn(C2CCCCO2)c2nc(-c3ccc(O)cc3)cc(CN3C[C@@H](C)N(Cc4ccccc4)C[C@@H]3C)c12]

600 mg of ((2S,5R)-4-benzyl-2,5-dimethyl-piperazin-1-yl)-[6-(4-hydroxy-phenyl)-3-methyl-1-(tetrahydro-pyran-2-yl)-1H-pyrazolo[3,4-b]pyridin-4-yl]-methanone were dissolved in 10 ml of THF. Under Argon-atmosphere, 1.1 ml of lithium aluminium hydride (2.4M in THF) was added and the reaction was heated to reflux for 2 h. The reaction was then cooled to 0° C., and quenched by the addition of 5 ml EtOAc and 5 ml water. The mixture was filtered over celite by suction and washed with EtOAc. The solvents were removed in vacuo and 500 mg (86%) of the title compound were obtained and used without further purification.

LC/MS (Method LC4): Rt=0.81 min; m/z=526.30 [M+H]$^+$.

(f) 4-[4-((2S,5R)-2,5-Dimethyl-piperazin-1-ylmethyl)-3-methyl-1H-pyrazolo[3,4-b]pyridin-6-yl]-phenol

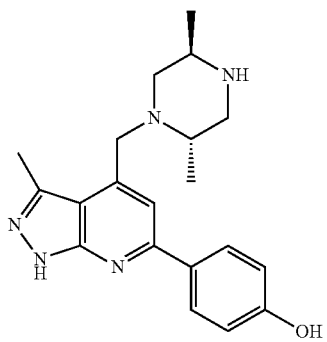 [SMILES: Cc1n[nH]c2nc(-c3ccc(O)cc3)cc(CN3C[C@@H](C)NC[C@@H]3C)c12]

585 mg 4-[4-((2S,5R)-4-benzyl-2,5-dimethyl-piperazin-1-ylmethyl)-3-methyl-1-(tetra-hydro-pyran-2-yl)-1H-pyrazolo[3,4-b]pyridin-6-yl]-phenol were dissolved in 10 ml methanol and 5 ml of THF and purged with argon. 50 mg Palladium (10% on charcoal) were added and the mixture was hydrogenated at r.t. for 15 h. The catalyst was filtered off and the solvents were evaporated. The residue was taken up in ethyl acetate and 1N aqueous hydrochloric acid. The phases were separated and the aqueous phase was washed with dichloromethane. To the aqueous phase was then added 1 ml concentrated aqueous hydrochloric acid and the reaction was left standing overnight. After freeze-drying 390 mg (90%) of the title compound were obtained.

LC/MS (Method LC5): Rt=0.73 min; m/z=352.27 [M+H]+.

EXAMPLE 55

4-[4-(3,3-Dimethyl-piperazin-1-ylmethyl)-3-methyl-1H-pyrazolo[3,4-b]pyridin-6-yl]-3-fluoro-phenol

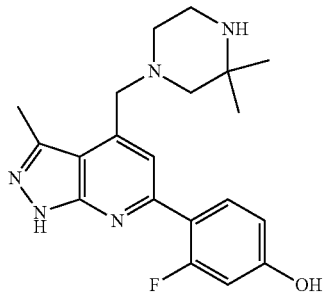 [SMILES: Cc1n[nH]c2nc(-c3ccc(O)cc3F)cc(CN3CCNC(C)(C)C3)c12]

(a) [6-(4-Benzyloxy-2-fluoro-phenyl)-3-methyl-1-(tetrahydro-pyran-2-yl)-1H-pyrazolo[3,4-b]pyridin-4-yl]-methanol

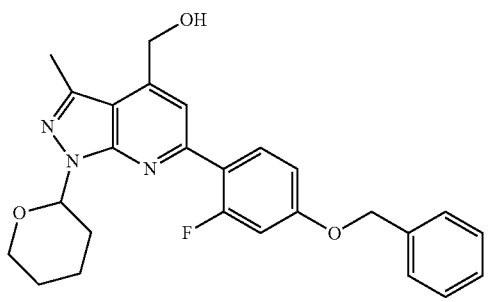 [SMILES: Cc1nn(C2CCCCO2)c2nc(-c3ccc(OCc4ccccc4)cc3F)cc(CO)c12]

At 0° C. to a solution of 3.00 g of 6-(4-benzyloxy-2-fluoro-phenyl)-3-methyl-1-(tetra-hydro-pyran-2-yl)-1H-pyrazolo[3,4-b]pyridine-4-carboxylic acid in 50 ml of dry tetrahydrofurane were added 1.2 ml of Hünig's base, followed by slow addition of 0.7 ml of ethyl chlorformate. After 30 min at 0° C. the resulting suspension was filtered. Under argon atmosphere to the filtrate were added 290 mg of sodium borohydride and 15 ml of water. After 2 h at 0° C. sat. aqueous ammonium chloride solution was added. The layers were separated and the aqueous layer was extracted with methyl tert-butyl ether. The combined organic layers were dried over sodium sulphate, filtered and concentrated in vacuo. 1.60 g (55%) of the title compound were obtained.

LC/MS (Method LC4): Rt=1.11 min; m/z=448.10 [M+H]+.

(b) 6-(4-Benzyloxy-2-fluoro-phenyl)-3-methyl-1-(tetrahydro-pyran-2-yl)-1H-pyrazolo[3,4-b]pyridine-4-carbaldehyde

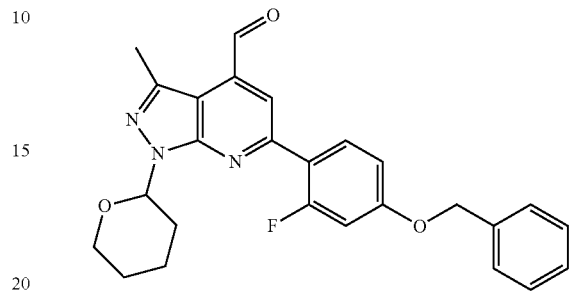

1.10 g of [6-(4-benzyloxy-2-fluoro-phenyl)-3-methyl-1-(tetrahydro-pyran-2-yl)-1H-pyrazolo[3,4-b]pyridin-4-yl]-methanol were dissolved in 5 ml of dichloromethane. At 0° C. 0.52 g Dess-Martin-Periodinane were added. After 16 h at r.t. the reaction was diluted with dichloromethane, and washed subsequently with 1 N aqueous hydrochloric acid and sat. aqueous sodium hydrogencarbonate solution. The organic layer was then dried over sodium sulphate, filtered and concentrated in vacuo to yield 1.10 g (100%) of the crude title compound, which was used without further purification in the next step.

LC/MS (Method LC4): Rt=1.27 min; m/z=446.10 [M+H]+.

(c) 4-[6-(4-Benzyloxy-2-fluoro-phenyl)-3-methyl-1-(tetrahydro-pyran-2-yl)-1H-pyrazolo[3,4-b]pyridin-4-ylmethyl]-2,2-dimethyl-piperazine-1-carboxylic acid tert-butyl ester

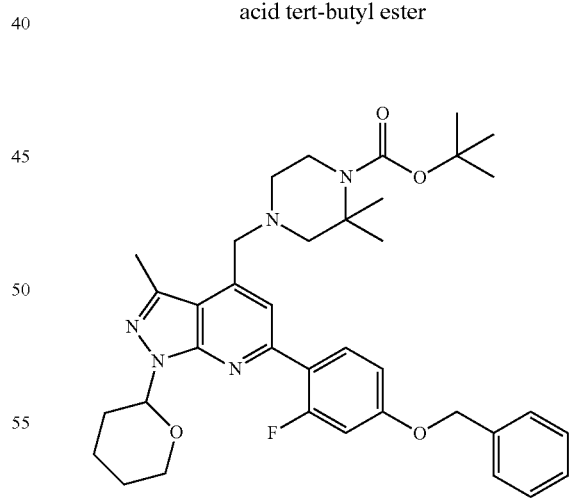

To a solution of 106 mg 2,2-dimethyl-piperazine-1-carboxylic acid tert-butyl ester in 5 ml of dichloromethane was added 200 mg of freshly prepared 6-(4-benzyloxy-2-fluoro-phenyl)-3-methyl-1-(tetrahydro-pyran-2-yl)-1H-pyrazolo[3,4-b]pyridine-4-carbaldehyde. 143 mg of sodium triacetoxyborohydride and 15 mg of acetic acid were added and the reaction was stirred at r.t. for 16 h. The reaction was then diluted with dichloromethane and shaken with sat. aqueous ammonium chloride solution. The layers were separated and the organic layer was dried over sodium sulphate, filtered and concentrated in vacuo. 318 mg (100%) of the crude title compound were obtained which were used in the next step without further purification.

LC/MS (Method LC4): Rt=1.26 min; m/z=644.30 [M+H]⁺.

(d) 4-[6-(2-Fluoro-4-hydroxy-phenyl)-3-methyl-1-(tetrahydro-pyran-2-yl)-1H-pyrazolo[3,4-b]pyridin-4-ylmethyl]-2,2-dimethyl-piperazine-1-carboxylic acid tert-butyl ester

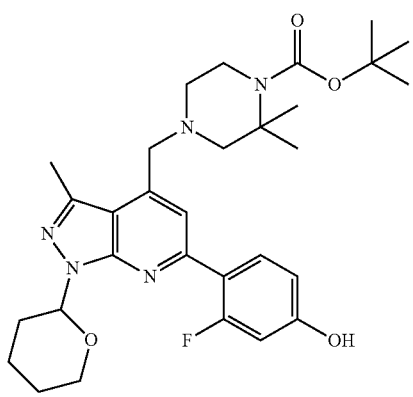 [SMILES: Cc1nn(C2CCCCO2)c2nc(-c3ccc(O)cc3F)cc(CN3CCN(C(=O)OC(C)(C)C)C(C)(C)C3)c12]

318 mg 4-[6-(2-Fluoro-4-hydroxy-phenyl)-3-methyl-1-(tetrahydro-pyran-2-yl)-1H-pyrazolo[3,4-b]pyridin-4-ylmethyl]-2,2-dimethyl-piperazine-1-carboxylic acid tert-butyl ester were dissolved in 5 ml methanol and purged with argon. 50 mg Palladium (10% on charcoal) were added and the mixture was hydrogenated at 3 bar and r.t. for 48 h. The catalyst was filtered off and the solvents were evaporated. 310 mg of the crude title compound were obtained, which were used in the next step without further purification.

LC/MS (Method LC4): Rt=0.99 min; m/z=554.20 [M+H]⁺.

(e) 4-[4-(3,3-Dimethyl-piperazin-1-ylmethyl)-3-methyl-1H-pyrazolo[3,4-b]pyridin-6-yl]-3-fluoro-phenol

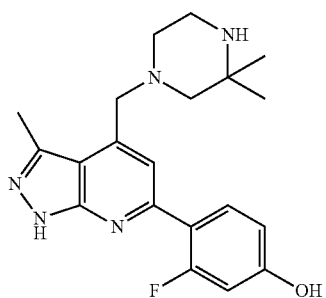 [SMILES: Cc1n[nH]c2nc(-c3ccc(O)cc3F)cc(CN3CCNC(C)(C)C3)c12]

274 mg of 4-[6-(2-Fluoro-4-hydroxy-phenyl)-3-methyl-1-(tetrahydro-pyran-2-yl)-1H-pyrazolo[3,4-b]pyridin-4-ylmethyl]-2,2-dimethyl-piperazine-1-carboxylic acid tert-butyl ester were dissolved in 5 ml of dichloromethane, and 1 m of hydrochloric acid (4N in 1,4-dioxane) was added. After stirring at r.t. for 16 h the volatiles were removed in vacuo and the resulting residue was purified by HPLC to obtain 12 mg (7%) of the title compound.

LC/MS (Method LC3): Rt=2.33 min; m/z=370.28 [M+H]⁺.

EXAMPLE 56

3-Fluoro-4-[3-methyl-4-(2,2,5,5-tetramethyl-morpholin-4-ylmethyl)-1H-pyrazolo[3,4-b]pyridin-6-yl]-phenol

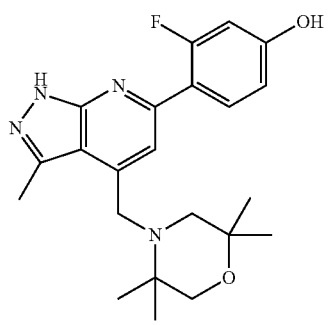 [SMILES: Cc1n[nH]c2nc(-c3ccc(O)cc3F)cc(CN3CC(C)(C)OCC3(C)C)c12]

The title compound was prepared in analogy to Example 1 steps (d) to (g) starting from 6-(4-benzyloxy-2-fluoro-phenyl)-3-methyl-1-(tetrahydro-pyran-2-yl)-1H-pyrazolo[3,4-b]pyridine-4-carboxylic acid and 2,2,5,5-tetramethyl-morpholine, however, in the last step only the THP-protecting group on the pyrazole ring was removed.

LC/MS (Method LC9): Rt=1.77 min; m/z=399.31 [M+H]⁺.

EXAMPLE 57

4-[4-(5-Ethyl-2,2,5-trimethyl-piperazin-1-ylmethyl)-3-methyl-1H-pyrazolo[3,4-b]pyridin-6-yl]-phenol

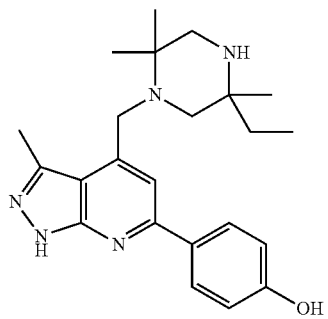 [SMILES: CCC1(C)CN(Cc2cc(-c3ccc(O)cc3)nc3[nH]nc(C)c23)C(C)(C)CN1]

(a) [6-Bromo-3-methyl-1-(tetrahydro-pyran-2-yl)-1H-pyrazolo[3,4-b]pyridin-4-yl]-methanol

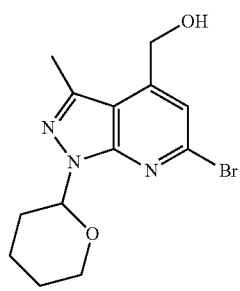 [SMILES: Cc1nn(C2CCCCO2)c2nc(Br)cc(CO)c12]

A solution of 139 mg 6-bromo-3-methyl-1-(tetrahydro-pyran-2-yl)-1H-pyrazolo[3,4-b]-pyridine-4-carboxylic acid ethyl ester in 8 ml of dry THF was cooled to −20° C. and 18 mg of lithium borohydride was added. After 10 min at −20° C., the reaction was slowly brought to rt. After 1.5 h at rt water and ethyl acetate were added to the reaction. The phases were separated and the organic phase was dried over sodium sulphate, filtrated and concentrated in vacuo to obtain 130 mg (98%) of the title compound as a crude product, which was used without purification in the subsequent step.

LC/MS (Method LC4): Rt=0.80 min; m/z=328.00 [M+H]+.

(b) Methanesulfonic acid 6-bromo-3-methyl-1-(tetrahydro-pyran-2-yl)-1H-pyrazolo[3,4-b]pyridin-4-ylmethyl ester

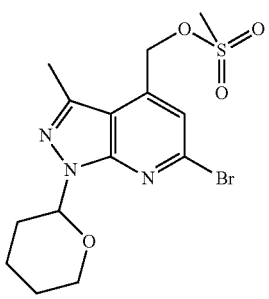 [SMILES: Cc1nn(C2CCCCO2)c2nc(Br)cc(COS(C)(=O)=O)c12]

To a solutuion of 130 mg [6-bromo-3-methyl-1-(tetrahydro-pyran-2-yl)-1H-pyrazolo[3,4-b]pyridin-4-yl]-methanol in 5 ml of dry DCM at 0° C. 77 μl of TEA were added, after 10 min followed by the addition of 60 mg of methanesulfonyl chloride. After 20 min at 0° C. the reaction was brought to rt and extracted with sat. aqueous ammonium chloride solution. The organic layer was separated, dried over sodium sulphate and freeze-dried to obtain 138 mg (85%) of the title compound as a crude product, which was used without purification in the subsequent step.

LC/MS (Method LC4): Rt=0.95 min; m/z=406.00 [M+H]+.

(c) 4-[6-Bromo-3-methyl-1-(tetrahydro-pyran-2-yl)-1H-pyrazolo[3,4-b]pyridin-4-ylmethyl]-2-ethyl-2,5,5-trimethyl-piperazine-1-carboxylic acid tert-butyl ester

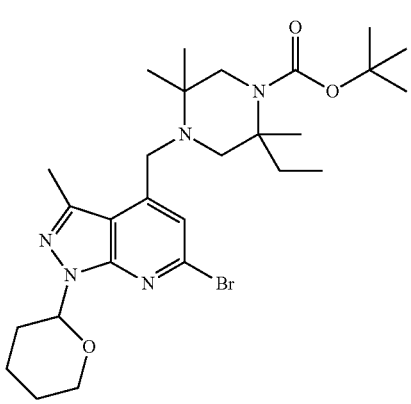 [SMILES: CCC1(C)CN(Cc2cc(Br)nc3c2c(C)nn3C2CCCCO2)C(C)(C)CN1C(=O)OC(C)(C)C]

A mixture of 130 mg of methanesulfonic acid 6-bromo-3-methyl-1-(tetrahydro-pyran-2-yl)-1H-pyrazolo[3,4-b]pyridin-4-ylmethyl ester, 99 mg of 2-ethyl-2,5,5-trimethyl-piperazine-1-carboxylic acid tert-butyl ester, 0.11 ml of DIPEA and 5 mg of potassium iodide in 2 ml of dry THF was heated to 160° C. for 50 min in a microwave reactor. For workup the mixture was taken up in water and ethyl acetate, the phases were separated, and the aqueous phase was extracted with ethyl acetate. The combined organic phases were dried over sodium sulphate, filtrated and concentrated in vacuo and the resulting residue was purified by flash chromatography (silica, heptane/ethyl acetate). 75 mg (41%) of the title compound were obtained.

LC/MS (Method LC10): Rt=1.02 min; m/z=566.20 [M+H]+.

(d) 2-Ethyl-4-[6-(4-hydroxy-phenyl)-3-methyl-1-(tetrahydro-pyran-2-yl)-1H-pyrazolo[3,4-b]pyridin-4-ylmethyl]-2,5,5-trimethyl-piperazine-1-carboxylic acid tert-butyl ester

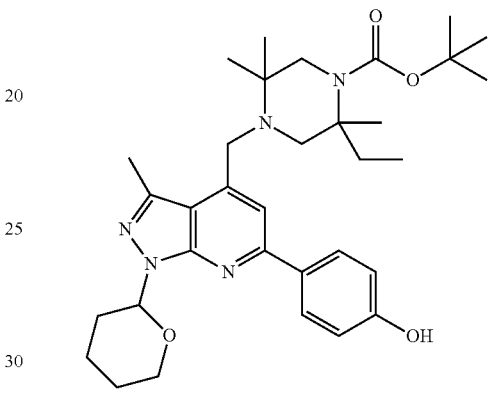

To a degassed mixture of 70 mg 4-[6-bromo-3-methyl-1-(tetrahydro-pyran-2-yl)-1H-pyrazolo[3,4-b]pyridin-4-ylmethyl]-2-ethyl-2,5,5-trimethyl-piperazine-1-carboxylic acid tert-butyl ester, 21 mg 4-hydroxyphenylboronic acid and 19 mg potassium carbonate in DME/water (v/v=2/1, 0.7 mL) at r.t. and under Ar-atmosphere 2 mg palladium(0) bis(tri-tert-butylphosphine) was added and the mixture was stirred at 85° C. for 75 min in a microwave reactor. To the mixture water and ethyl acetate were added, the phases were separated and the aqueous phase was extracted with ethyl acetate. The combined organic phases were concentrated in vacuo and the resulting residue was purified by flash chromatography (silica, heptane/ethyl acetate). 19 mg (27%) of the title compound were obtained.

LC/MS (Method LC4): Rt=1.09 min; m/z=578.30 [M+H]+.

(e) 4-[4-(5-Ethyl-2,2,5-trimethyl-piperazin-1-ylmethyl)-3-methyl-1H-pyrazolo[3,4-b]pyridin-6-yl]-phenol

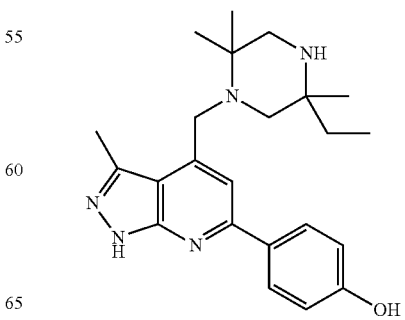

19 mg of 2-ethyl-4-[6-(4-hydroxy-phenyl)-3-methyl-1-(tetrahydro-pyran-2-yl)-1H-pyrazolo[3,4-b]pyridin-4-ylmethyl]-2,5,5-trimethyl-piperazine-1-carboxylic acid tert-butyl ester were dissolved in 0.4 ml of THF and treated with 1.5 ml of hydrochloric acid (4M in dry dioxane). After stirring at rt overnight and at 40° C. for 2 h the volatiles were removed in vacuo. The residue was triturated with dioxane and the resulting solid was isolated by suction. 8 mg (57%) of the title compound were obtained.

LC/MS (Method LC9): Rt=1.15 min; m/z=394.27 [M+H]+.

EXAMPLE 58

4-[4-(5,5-Diethyl-2,2-dimethyl-piperazin-1-ylmethyl)-3-methyl-1H-pyrazolo[3,4-b]pyridin-6-yl]-2-fluoro-phenol

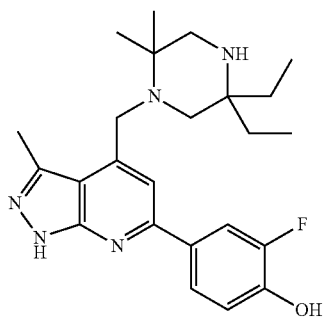 [SMILES: CCC1(CC)CN(Cc2cc(-c3ccc(O)c(F)c3)nc3[nH]nc(C)c23)C(C)(C)CN1]

(a) 4-[6-Bromo-3-methyl-1-(tetrahydro-pyran-2-yl)-1H-pyrazolo[3,4-b]pyridin-4-ylmethyl]-2,2-diethyl-5,5-dimethyl-piperazine-1-carboxylic acid tert-butyl ester

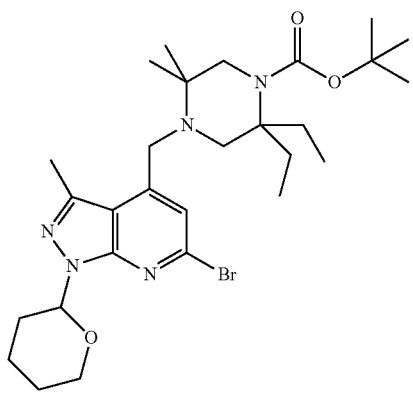 [SMILES: CCC1(CC)CN(Cc2cc(Br)nc3c2c(C)nn3C2CCCCO2)C(C)(C)CN1C(=O)OC(C)(C)C]

A mixture of 500 mg of methanesulfonic acid 6-bromo-3-methyl-1-(tetrahydro-pyran-2-yl)-1H-pyrazolo[3,4-b]pyridin-4-ylmethyl ester, 400 mg of 2,2-diethyl-5,5-dimethyl-piperazine-1-carboxylic acid tert-butyl ester and 0.43 ml of DIPEA in 8 ml of dry THF was heated to 160° C. for 30 min in a microwave reactor. For workup the mixture was taken up in water and ethyl acetate, the phases were separated, and the aqueous phase was extracted with ethyl acetate. The combined organic phases were dried over sodium sulphate, filtrated and concentrated in vacuo and the resulting residue was purified by flash chromatography (silica, heptane/ethyl acetate). 369 mg (50%) of the title compound were obtained.

LC/MS (Method LC10): Rt=1.03 min; m/z=580.20 [M+H]+.

(b) 2,2-Diethyl-4-[6-(3-fluoro-4-hydroxy-phenyl)-3-methyl-1-(tetrahydro-pyran-2-yl)-1H-pyrazolo[3,4-b]pyridin-4-ylmethyl]-5,5-dimethyl-piperazine-1-carboxylic acid tert-butyl ester

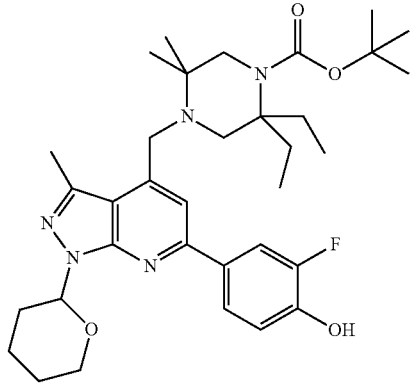 [SMILES: CCC1(CC)CN(Cc2cc(-c3ccc(O)c(F)c3)nc3c2c(C)nn3C2CCCCO2)C(C)(C)CN1C(=O)OC(C)(C)C]

To a solution of 150 mg 4-[6-Bromo-3-methyl-1-(tetrahydro-pyran-2-yl)-1H-pyrazolo[3,4-b]pyridin-4-ylmethyl]-2,2-diethyl-5,5-dimethyl-piperazine-1-carboxylic acid tert-butyl ester and 48 mg 3-fluoro-4-hydroxy-phenylboronic acid in 8 ml of DEM and 0.45 ml of water were added 40 mg of potassium carbonate. To the degassed reaction mixture 4 mg of bis(tri-tert-butyl-phosphin)palladium(0) were added. The reaction was heated to 120° C. in a microwave reactor for 2 h. The mixture was diluted with ethyl acetate and washed with water. The aqueous phase was extracted with ethyl acetate twice. The combined organic layers were dried and concentrated in vacuo. The resulting residue was purified by HPLC. 53 mg (34%) of the title compound were obtained.

LC/MS (Method LC4): Rt=0.88 min; m/z=610.30 [M+H]+.

(c) 4-[4-(5,5-Diethyl-2,2-dimethyl-piperazin-1-ylmethyl)-3-methyl-1H-pyrazolo[3,4-b]pyridin-6-yl]-2-fluoro-phenol

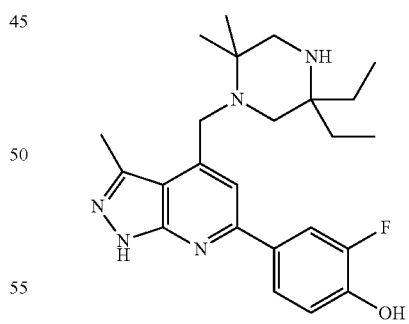

50 mg of 2,2-Diethyl-4-[6-(3-fluoro-4-hydroxy-phenyl)-3-methyl-1-(tetrahydro-pyran-2-yl)-1H-pyrazolo[3,4-b]pyridin-4-ylmethyl]-5,5-dimethyl-piperazine-1-carboxylic acid tert-butyl ester in 2 ml abs. THF were reacted with 0.5 ml of hydrochloric acid (4 M in dry dioxane). After standing at rt for 16 h and stirring at 40° C. for 5 h the volatiles were removed in vacuo, and the resulting residue was purified by HPLC. 9 mg (26%) of the title compound were obtained.

LC/MS (Method LC9): Rt=1.21 min; m/z=426.32 [M+H]+.

EXAMPLE 59

3-Chloro-4-[4-(5,5-diethyl-2,2-dimethyl-piperazin-1-ylmethyl)-3-methyl-1H-pyrazolo[3,4-b]pyridin-6-yl]-phenol

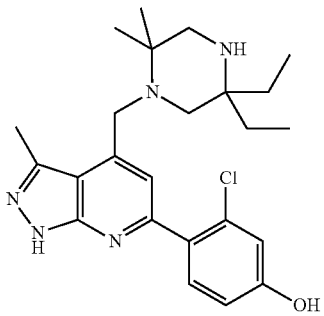 [SMILES: CCC1(CC)CN(Cc2cc(-c3ccc(O)cc3Cl)nc3[nH]nc(C)c23)C(C)(C)CN1]

The title compound was synthesized in a similar manner as Example 58 (4-[4-(5,5-Diethyl-2,2-dimethyl-piperazin-1-ylmethyl)-3-methyl-1H-pyrazolo[3,4-b]pyridin-6-yl]-2-fluoro-phenol) employing 3-chloro-4-(5,5-dimethyl-1,3,2-dioxaborinan-2-yl)phenol in step (b).

LC/MS (Method LC9): Rt=1.21 min; m/z=442.29 [M+H]$^+$.

EXAMPLE 60

4-{4-[(3,3-Dimethyl-piperidin-4-ylamino)-methyl]-3-methyl-1H-pyrazolo[3,4-b]pyridin-6-yl}-phenol

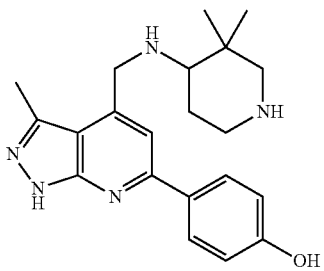 [SMILES: Cc1n[nH]c2nc(-c3ccc(O)cc3)cc(CNC3CCNCC3(C)C)c12]

(a) [6-(4-Methoxymethoxy-phenyl)-3-methyl-1-(tetrahydro-pyran-2-yl)-1H-pyrazolo[3,4-b]pyridin-4-yl]-methanol

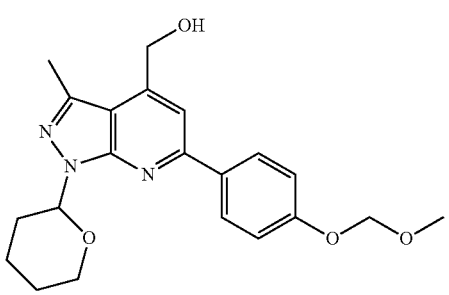 [SMILES: COCOc1ccc(-c2cc(CO)c3c(C)nn(C4CCCCO4)c3n2)cc1]

To a degassed mixture of 141 mg [6-Bromo-3-methyl-1-(tetrahydro-pyran-2-yl)-1H-pyrazolo[3,4-b]pyridin-4-yl]-methanol, 95 mg 4-(methoxymethoxy)phenylboronic acid and 65 mg potassium carbonate in DME/water (v/v=2/1, 2.3 mL) at r.t. and under Ar-atmosphere 6 mg palladium(0) bis(tri-tert-butylphosphine) was added and the mixture was stirred at 85° C. for 40 min in a microwave reactor. Then 6 mg palladium(0) bis(tri-tert-butylphosphine) and 95 mg 4-(methoxymethoxy)phenylboronic acid were added and the mixture was stirred at 100° C. for 20 min. To the mixture water and ethyl acetate were added, the phases were separated and the aqueous phase was extracted with ethyl acetate. The combined organic phases were concentrated in vacuo and the residue was triturated with ethyl acetate. The resulting solid was isolated by filtration. 171 mg (100%) of the title compound were obtained.

LC/MS (Method LC4): Rt=0.93 min; m/z=384.10 [M+H]$^+$.

(b) Methanesulfonic acid 6-(4-methoxymethoxy-phenyl)-3-methyl-1-(tetrahydro-pyran-2-yl)-1H-pyrazolo[3,4-b]pyridin-4-ylmethyl ester

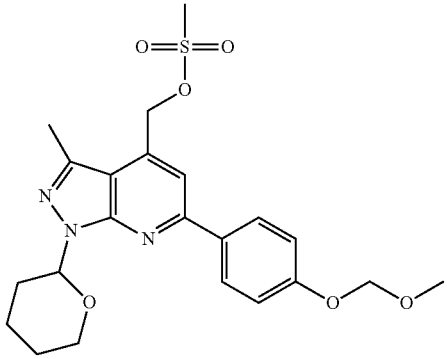 [SMILES: COCOc1ccc(-c2cc(COS(C)(=O)=O)c3c(C)nn(C4CCCCO4)c3n2)cc1]

A solution of 120 mg [6-(4-methoxymethoxy-phenyl)-3-methyl-1-(tetrahydro-pyran-2-yl)-1H-pyrazolo[3,4-b]pyridin-4-yl]-methanol and 44 mg of triethylamine in 4 ml of dry dichloromethane was cooled to 0° C. and 47 mg of methanesulfonyl chloride were added. The reaction was brought to room temperature, dichloromethane and water were added and the phasese were separated. The aqueous phase was extracted with dichloromethane. The combined organic phases were dried over sodium sulphate, filtrated and concentrated. 170 mg (quant.) of the crude product were obtained as a yellow solid, which was used without further purification.

LC/MS (Method LC4): Rt=1.03 min; m/z=462.10 [M+H]$^+$.

(c) 4-{[6-(4-Methoxymethoxy-phenyl)-3-methyl-1-(tetrahydro-pyran-2-yl)-1H-pyrazolo[3,4-b]pyridin-4-ylmethyl]-amino}-3,3-dimethyl-piperidine-1-carboxylic acid tert-butyl ester

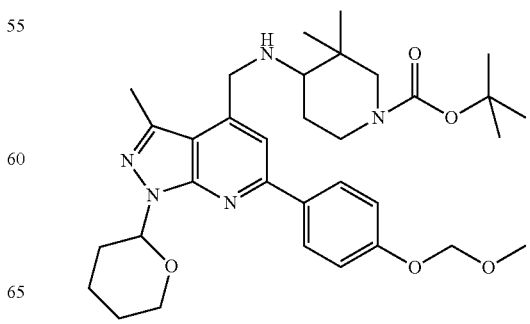

To a solution of 170 mg of methanesulfonic acid 6-(4-methoxymethoxy-phenyl)-3-methyl-1-(tetrahydro-pyran-2-yl)-1H-pyrazolo[3,4-b]pyridin-4-ylmethyl ester, and 101 mg 4-amino-3,3,-dimthylpiperidin-1-carboxylic acid tert-butyl-lester in 3 ml of dry THF were added 0.13 ml of DIPEA. The reaction was heated to 140° C. for 30 min in a microwave reactor. The reaction was diluted with ethyl acetate and water and the aqueous phase was extracted with ethyl acetate. The combined organic phases were dried over sodium sulphaste, filtrated and concentrated. The resulting oil was purified by chromatography (silica, heptanes/ethyl acetate). 40 mg (19%) of the title compound were obtained.

LC/MS (Method LC4): Rt=0.89 min; m/z=594.3 [M+H]$^+$.

(d) 4-{4-[(3,3-Dimethyl-piperidin-4-ylamino)-methyl]-3-methyl-1H-pyrazolo[3,4-b]pyridin-6-yl}-phenol

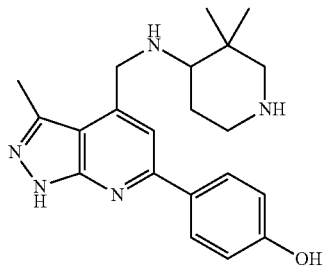 [SMILES: Cc1n[nH]c2nc(-c3ccc(O)cc3)cc(CNC3CCNCC3(C)C)c12]

60 mg of 4-{[6-(4-methoxymethoxy-phenyl)-3-methyl-1-(tetrahydro-pyran-2-yl)-1H-pyrazolo[3,4-b]pyridin-4-ylmethyl]-amino}-3,3-dimethyl-piperidine-1-carboxylic acid tert-butyl ester were dissolved in 1.2 ml of 1,4-dioxane and treated with 1.5 ml of hydrochloric acid (4 M in dry dioxane). After standing at rt for 48 h the volatiles were removed in vacuo, The residue was triturated with dioxane and the resulting solid was isolated by suction. 30 mg (74%) of the title compound were obtained.

LC/MS (Method LC9): Rt=0.77 min; m/z=366.30 [M+H]$^+$.

EXAMPLE 61

4-[3-Methyl-4-(2,2,5-trimethyl-4-pyridin-3-ylmethyl-piperazin-1-ylmethyl)-1H-pyrazolo[3,4-b]pyridin-6-yl]-phenol

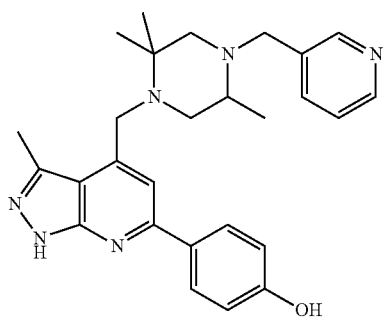 [SMILES: Cc1n[nH]c2nc(-c3ccc(O)cc3)cc(CN3CC(C)N(Cc4cccnc4)CC3(C)C)c12]

(a) 6-(4-Methoxymethoxy-phenyl)-3-methyl-1-(tetrahydro-pyran-2-yl)-4-(2,2,5-trimethyl-4-pyridin-3-ylmethyl-piperazin-1-ylmethyl)-1H-pyrazolo[3,4-b]pyridine

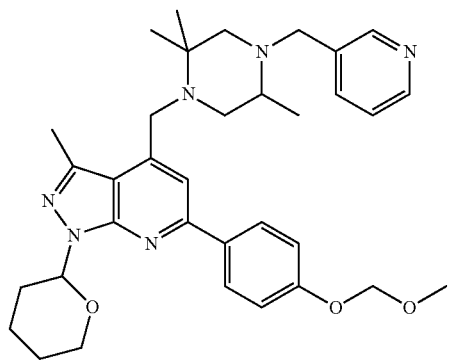 [SMILES: COCOc1ccc(-c2cc(CN3CC(C)N(Cc4cccnc4)CC3(C)C)c3c(C)nn(C4CCCCO4)c3n2)cc1]

To a solution of 150 mg of methanesulfonic acid 6-(4-methoxymethoxy-phenyl)-3-methyl-1-(tetrahydro-pyran-2-yl)-1H-pyrazolo[3,4-b]pyridin-4-ylmethyl ester, and 85 mg 2,5,5-trimethyl-1-(pyridin-3-ylmethyl)piperazine in 4 ml of dry THF were added 0.28 ml of DIPEA. The reaction was heated to 140° C. for 60 min in a microwave reactor. The reaction was diluted with ethyl acetate and water and the aqueous phase was extracted with ethyl acetate. The combined organic phases were dried over sodium sulphaste, filtrated and concentrated. The resulting oil was purified by chromatography (silica, heptanes/ethyl acetate). 69 mg of the title compound were obtained.

LC/MS (Method LC4): Rt=0.77 min; m/z=585.30 [M+H]$^+$.

(b) 4-[3-Methyl-4-(2,2,5-trimethyl-4-pyridin-3-ylmethyl-piperazin-1-ylmethyl)-1H-pyrazolo[3,4-b]pyridin-6-yl]-phenol

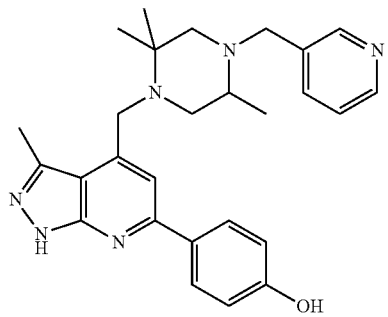 [SMILES: Cc1n[nH]c2nc(-c3ccc(O)cc3)cc(CN3CC(C)N(Cc4cccnc4)CC3(C)C)c12]

65 mg of 6-(4-Methoxymethoxy-phenyl)-3-methyl-1-(tetrahydro-pyran-2-yl)-4-(2,2,5-trimethyl-4-pyridin-3-ylmethyl-piperazin-1-ylmethyl)-1H-pyrazolo[3,4-b]pyridine were dissolved in 1.5 ml of 1,4-dioxane and treated with 1.5 ml of hydrochloric acid (4 M in dry dioxane). After standing at rt for 10 min the volatiles were removed in vacuo. The residue purified by HPLC and 65 mg of the title compound were obtained.

LC/MS (Method LC9): Rt=1.23 min; m/z=457.34 [M+H]$^+$.

The following examples have ben prepared following a similar procedure as described for Example 61 (4-[3-Methyl-4-(2,2,5-trimethyl-4-pyridin-3-ylmethyl-piperazin-1-ylmethyl)-1H-pyrazolo[3,4-b]pyridin-6-yl]-phenol) employing the respective aldehydes:

| Exp. No. | Name | Structure | LC/MS method | m/z [M + H]+ | Rt [min] |
|---|---|---|---|---|---|
| 62 | 4-{3-Methyl-4-[2,2,5-trimethyl-4-(tetrahydro-furan-2-ylmethyl)-piperazin-1-ylmethyl]-1H-pyrazolo[3,4-b]pyridin-6-yl}-phenol | 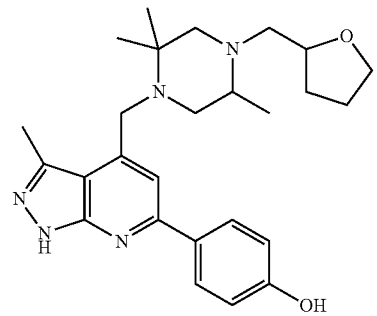 [SMILES: Cc1n[nH]c2nc(-c3ccc(O)cc3)cc(CN3CC(C)N(CC4CCCO4)CC3(C)C)c12] | LC9 | 450.34 | 1.40 |
| 63 | 4-{4-[4-(2-Methoxy-ethyl)-2,2,5-trimethyl-piperazin-1-ylmethyl]-3-methyl-1H-pyrazolo[3,4-b]pyridin-6-yl}-phenol | 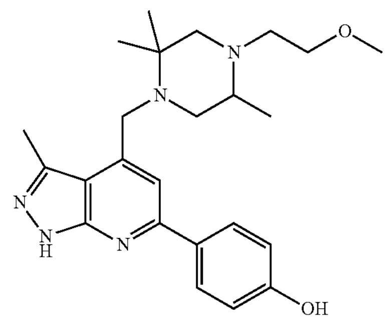 [SMILES: COCCN1CC(C)(C)N(Cc2cc(-c3ccc(O)cc3)nc3[nH]nc(C)c23)CC1C] | LC9 | 424.32 | 1.33 |
| 64 | 4-{4-[4-(3-Methoxy-propyl)-2,2,5-trimethyl-piperazin-1-ylmethyl]-3-methyl-1H-pyrazolo[3,4-b]pyridin-6-yl}-phenol | 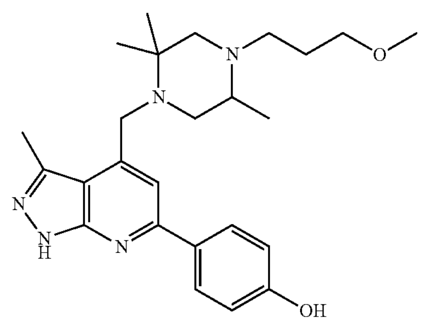 [SMILES: COCCCN1CC(C)(C)N(Cc2cc(-c3ccc(O)cc3)nc3[nH]nc(C)c23)CC1C] | LC9 | 438.41 | 1.18 |

EXAMPLE 65

3-Fluoro-4-{3-methyl-4-[2,2,5,5-tetramethyl-4-(3,3,3-trifluoro-propyl)-piperazin-1-ylmethyl]-1H-pyrazolo[3,4-b]pyridin-6-yl}-phenol

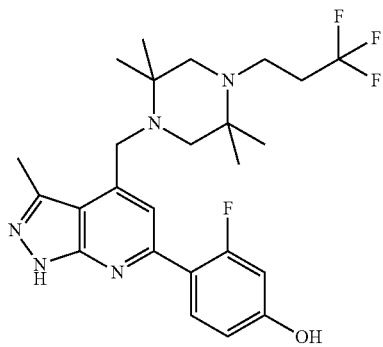 [SMILES: Cc1n[nH]c2nc(-c3ccc(O)cc3F)cc(CN3CC(C)(C)N(CCC(F)(F)F)CC3(C)C)c12]

To a solution of 300 mg of 3-fluoro-4-[3-methyl-4-(2,2,5,5-tetramethyl-piperazin-1-ylmethyl)-1H-pyrazolo[3,4-b]pyridin-6-yl]-phenol, 387 mg 3,3,3-trifluoropropanal and 134 mg DIPEA in 6 ml dichloromethane and 6 ml THF was added 732 mg of sodium triacetoxyborohydride. The reaction was stirred at rt overnight. The solvents were removed in vacuo, and the residue was taken up in ethyl acetate and water. The pH was brought to neutral, and the phases were separated. The aqueous phase was extracted with ethyl acetate twice. The combined organic phases were dried over sodium sulphate, filtrated and concentrated in vacuo. The residue was purified by HPLC and 214 mg (63%) of the title compound were obtained.

LC/MS (Method LC4): Rt=0.70 min; m/z=494.2 [M+H]+.

The following examples have ben prepared following a similar procedure as described for Example 65 (3-Fluoro-4-{3-methyl-4-[2,2,5,5-tetramethyl-4-(3,3,3-trifluoro-propyl)-piperazin-1-ylmethyl]-1H-pyrazolo[3,4-b]pyridin-6-yl}-phenol), employing the respective aldehydes:

| Exp. No. | Name | Structure | LC/MS method | m/z [M + H]+ | Rt [min] |
|---|---|---|---|---|---|
| 66 | 3-Fluoro-4-[3-methyl-4-(2,2,4,5,5-penta-methyl-piperazin-1-ylmethyl)-1H-pyrazolo[3,4-b]-pyridin-6-yl]-phenol | 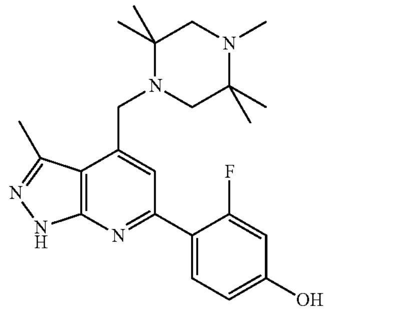 [SMILES: Cc1n[nH]c2nc(-c3ccc(O)cc3F)cc(CN3CC(C)(C)N(C)CC3(C)C)c12] | LC9 | 410.22 | 1.16 |
| 67 | 3-Fluoro-4-{4-[4-(3-methoxy-propyl)-2,2,5,5-tetramethyl-piperazin-1-ylmethyl]-3-methyl-1H-pyrazolo[3,4-b]pyridin-6-yl}-phenol | 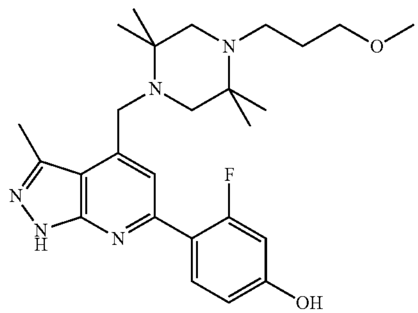 [SMILES: COCCCN1CC(C)(C)N(Cc2cc(-c3ccc(O)cc3F)nc3[nH]nc(C)c23)CC1(C)C] | LC9 | 470.34 | 1.44 |
| 68 | 3-Fluoro-4-(3-methyl-4-{2,2,5,5-tetramethyl-4-[2-(tetrahydro-pyran-4-yl)-ethyl]-piperazin-1-ylmethyl}-1H-pyrazolo[3,4-b]pyridin-6-yl)-phenol | 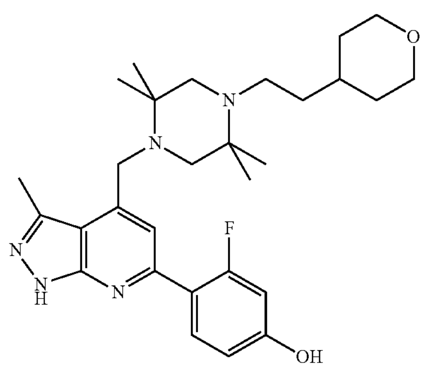 [SMILES: Cc1n[nH]c2nc(-c3ccc(O)cc3F)cc(CN3CC(C)(C)N(CCC4CCOCC4)CC3(C)C)c12] | LC9 | 510.36 | 1.43 |
| 69 | 4-{4-[4-((S)-2,2-Dimethyl-[1,3]dioxolan-4-ylmethyl)-2,2,5,5-tetramethyl-piperazin-1-ylmethyl]-3-methyl-1H-pyrazolo[3,4-b]pyridin-6-yl}-3-fluoro-phenol | 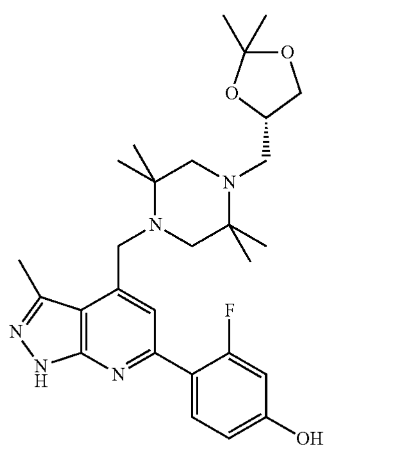 [SMILES: Cc1n[nH]c2nc(-c3ccc(O)cc3F)cc(CN3CC(C)(C)N(C[C@H]4COC(C)(C)O4)CC3(C)C)c12] | LC9 | 512.33 | 1.49 |

| Exp. No. | Name | Structure | LC/MS method | m/z [M + H]+ | Rt [min] |
|---|---|---|---|---|---|
| 70 | 3-Fluoro-4-{3-methyl-4-[2,2,5,5-tetramethyl-4-(tetrahydro-pyran-4-ylmethyl)-piperazin-1-ylmethyl]-1H-pyrazolo[3,4-b]pyridin-6-yl}-phenol | 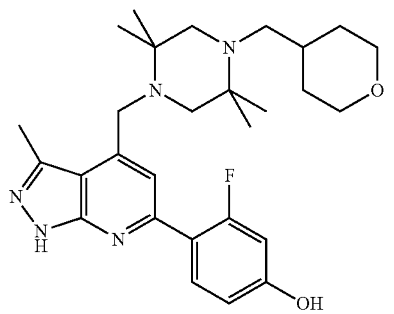 [SMILES: Cc1n[nH]c2nc(-c3ccc(O)cc3F)cc(CN3CC(C)(C)N(CC4CCOCC4)CC3(C)C)c12] | LC9 | 496.36 | 1.40 |

EXAMPLE 71

3-Fluoro-4-[3-methyl-4-(6,8,8-trimethyl-6,9-diaza-spiro[4.5]dec-9-ylmethyl)-1H-pyrazolo[3,4-b]pyridin-6-yl]-phenol

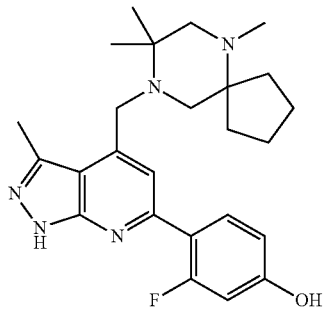 [SMILES: Cc1n[nH]c2nc(-c3ccc(O)cc3F)cc(CN3CC4(CCCC4)N(C)CC3(C)C)c12]

The title compound was prepared in analogy to Example 65 (3-Fluoro-4-{3-methyl-4-[2,2,5,5-tetramethyl-4-(3,3,3-trifluoro-propyl)-piperazin-1-ylmethyl]-1H-pyrazolo[3,4-b]pyridin-6-yl}-phenol) using 4-[4-(8,8-Dimethyl-6,9-diaza-spiro[4.5]dec-9-ylmethyl)-3-methyl-1H-pyrazolo[3,4-b]pyridin-6-yl]-3-fluoro-phenol and aqueous formaldehyde.

LC/MS (Method LC9): Rt=1.37 min; m/z=438.36 [M+H]⁺.

EXAMPLE 72

3-Fluoro-4-{4-[4-(2-hydroxy-ethyl)-2,2,5,5-tetramethyl-piperazin-1-ylmethyl]-3-methyl-1H-pyrazolo[3,4-b]pyridin-6-yl}-phenol

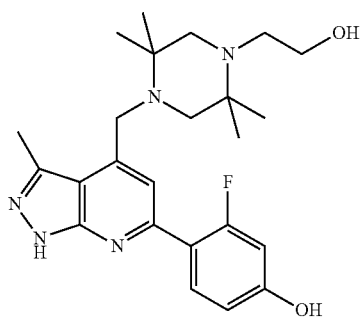 [SMILES: Cc1n[nH]c2nc(-c3ccc(O)cc3F)cc(CN3CC(C)(C)N(CCO)CC3(C)C)c12]

(a) 4-{4-[4-(2-Benzyloxy-ethyl)-2,2,5,5-tetramethyl-piperazin-1-ylmethyl]-3-methyl-1H-pyrazolo[3,4-b]pyridin-6-yl}-3-fluoro-phenol

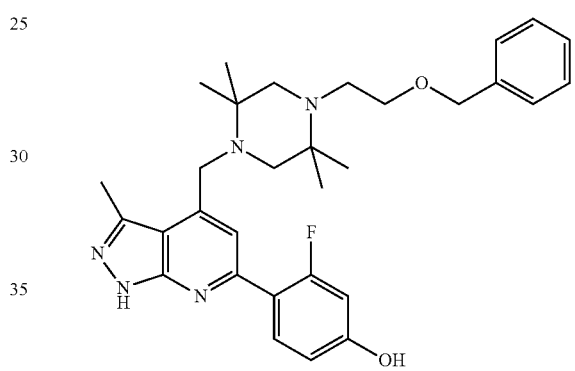

The title compound was preparerd in analogy to the synthesis of Example 65 (3-Fluoro-4-{3-methyl-4-[2,2,5,5-tetramethyl-4-(3,3,3-trifluoro-propyl)-piperazin-1-ylmethyl]-1H-pyrazolo[3,4-b]pyridin-6-yl}-phenol) using 3-fluoro-4-[3-methyl-4-(2,2,5,5-tetramethyl-piperazin-1-ylmethyl)-1H-pyrazolo[3,4-b]pyridin-6-yl]-phenol and benzyloxyacetaldehyde.

LC/MS (Method LC4): Rt=0.80 min; m/z=532.20 [M+H]⁺.

(b) 3-Fluoro-4-{4-[4-(2-hydroxy-ethyl)-2,2,5,5-tetramethyl-piperazin-1-ylmethyl]-3-methyl-1H-pyrazolo[3,4-b]pyridin-6-yl}-phenol

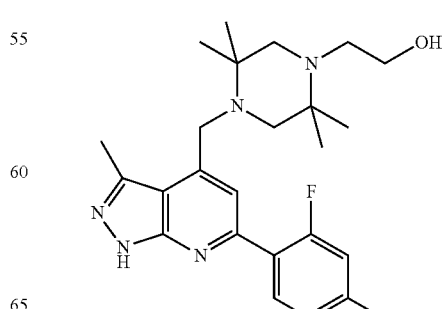

63 mg of 4-{4-[4-(2-Benzyloxy-ethyl)-2,2,5,5-tetramethyl-piperazin-1-ylmethyl]-3-methyl-1H-pyrazolo[3,4-b]pyridin-6-yl}-3-fluoro-phenol were dissolved in 5 ml of methanol. 2 mg of Pd/C (10%) were added and the mixture was hydrogenated for 5 h at 5 bar. Then 1 ml of hydrorchloric acid (1M in dioxane) was added and the mixture was again hydrogenated at 5 bar for 24 h. The reaction was filtrated and concentrated in vacuo. After purification by HPLC 1 mg of the title compound was obtained.

LC/MS (Method LC4): Rt=0.61 min; m/z=442.20 [M+H]+.

EXAMPLE 73

(S)-3-{4-[6-(2-Fluoro-4-hydroxy-phenyl)-3-methyl-1H-pyrazolo[3,4-b]pyridin-4-ylmethyl]-2,2,5,5-tetramethyl-piperazin-1-yl}-propane-1,2-diol

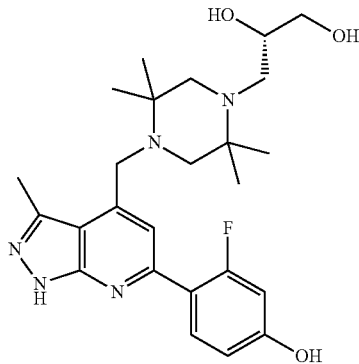 [SMILES: Cc1n[nH]c2nc(-c3ccc(O)cc3F)cc(CN3CC(C)(C)N(C[C@H](O)CO)CC3(C)C)c12]

208 mg 4-{4-[4-((S)-2,2-Dimethyl-[1,3]dioxolan-4-ylmethyl)-2,2,5,5-tetramethyl-piperazin-1-ylmethyl]-3-methyl-1H-pyrazolo[3,4-b]pyridin-6-yl}-3-fluoro-phenol were dissolved in 2 ml of dioxane and 0.3 ml of water. 2 ml of hydrorchloric acid (4M in dioxane) were added. After 1.5 h at rt the volatiles were removed in vacuo and the residue was purified by HPLC. 60 mg of the title compound ewre obtained.

LC/MS (Method LC9): Rt=1.30 min; m/z=470.41 [M+H]+.

EXAMPLE 74

{4-[6-(2-Fluoro-4-hydroxy-phenyl)-3-methyl-1H-pyrazolo[3,4-b]pyridin-4-ylmethyl]-2,2,5,5-tetramethyl-piperazin-1-yl}acetic acid methyl ester

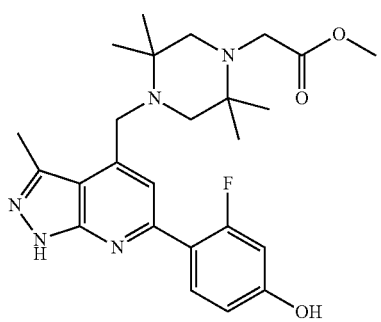 [SMILES: COC(=O)CN1CC(C)(C)N(Cc2cc(-c3ccc(O)cc3F)nc3[nH]nc(C)c23)CC1(C)C]

To a solution of 30 mg of 3-fluoro-4-[3-methyl-4-(2,2,5,5-tetramethyl-piperazin-1-ylmethyl)-1H-pyrazolo[3,4-b]pyridin-6-yl]-phenol in 1 ml of dry THF were added 13 mg of DIPEA and 11 mg of methyl bromoacetate. The reaction was stirred at r.t. for 2 h and then heated in a microwave reactor for 3 h at 120° C. Then ethyl acetate and water were added and the pH was adjusted to 7-8. The phases were separated and the aqueous phase was extracted with ethyl acetate twice. The combined organic phases were dried over Na2SO4, filtered and concentrated in vacuo. After purification by preparative HPLC (C18 column, acetonitrile/water gradient) 12 mg (37%) of the title compound were obtained.

LC/MS (Method LC9): Rt=1.28 min; m/z=470.25 [M+H]+.

EXAMPLE 75

1-{4-[6-(2-Fluoro-4-hydroxy-phenyl)-3-methyl-1H-pyrazolo[3,4-b]pyridin-4-ylmethyl]-2,2,5,5-tetramethyl-piperazin-1-yl}-2-methoxy-ethanone

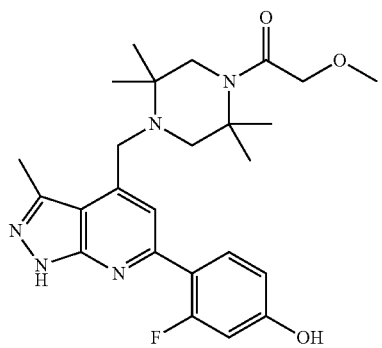 [SMILES: COCC(=O)N1CC(C)(C)N(Cc2cc(-c3ccc(O)cc3F)nc3[nH]nc(C)c23)CC1(C)C]

To a solution of 30 mg of 3-fluoro-4-[3-methyl-4-(2,2,5,5-tetramethyl-piperazin-1-ylmethyl)-1H-pyrazolo[3,4-b]pyridin-6-yl]-phenol in 1 ml of dry THF were added 13 mg of DIPEA and 7 mg of methoxyacetyl chloride. The reaction was stirred overnight and additional 4 mg of methoxyacetyl chloride were added. To the reaction 1 M aqueous sodium hydroxide solution was added and the reaction was stirred for 20 min. The pH was then adjusted to 7-8, ethyl acetate was added and the phases were separated. The aqueous phase was extracted with ethyl acetate twice. The combined organic phases were dried over Na2SO4, filtered and concentrated in vacuo. After purification by preparative HPLC (C18 column, acetonitrile/water gradient) 15 mg (46%) of the title compound were obtained.

LC/MS (Method LC9): Rt=1.59 min; m/z=470.28 [M+H]+.

The following examples have ben prepared following a similar procedure as described for Example 75 (1-{4-[6-(2-Fluoro-4-hydroxy-phenyl)-3-methyl-1H-pyrazolo[3,4-b]pyridin-4-ylmethyl]-2,2,5,5-tetramethyl-piperazin-1-yl}-2-methoxy-ethanone, employing the respective acid chlorides or anhydrides:

| Exp. No. | Name | Structure | LC/MS method | m/z [M + H]+ | Rt [min] |
|---|---|---|---|---|---|
| 76 | 1-{4-[6-(2-Fluoro-4-hydroxy-phenyl)-3-methyl-1H-pyrazolo[3,4-b]pyridin-4-ylmethyl]-2,2,5,5-tetramethyl-piperazin-1-yl}-3-methoxy-propan-1-one | 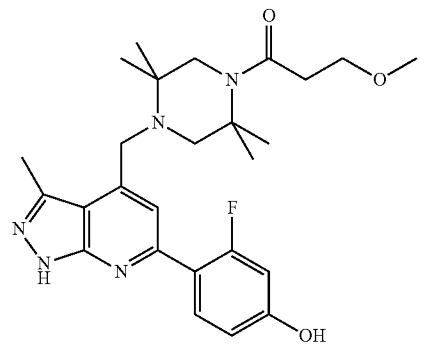 [SMILES: COCCC(=O)N1CC(C)(C)N(Cc2cc(-c3ccc(O)cc3F)nc3[nH]nc(C)c23)CC1(C)C] | LC9 | 484.34 | 1.76 |
| 77 | {4-[6-(2-Fluoro-4-hydroxy-phenyl)-3-methyl-1H-pyrazolo[3,4-b]pyridin-4-ylmethyl]-2,2,5,5-tetramethyl-piperazin-1-yl}-(tetrahydro-furan-3-yl)-methanone | 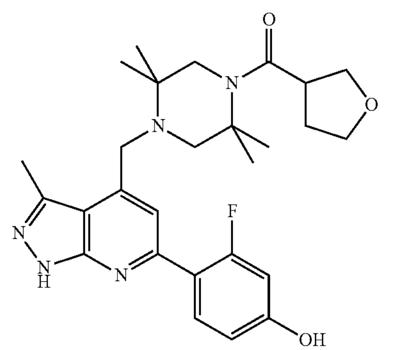 [SMILES: Cc1n[nH]c2nc(-c3ccc(O)cc3F)cc(CN3CC(C)(C)N(C(=O)C4CCOC4)CC3(C)C)c12] | LC9 | 496.32 | 1.74 |
| 78 | 1-{4-[6-(2-Fluoro-4-hydroxy-phenyl)-3-methyl-1H-pyrazolo[3,4-b]pyridin-4-ylmethyl]-2,2,5,5-tetramethyl-piperazin-1-yl}-ethanone | 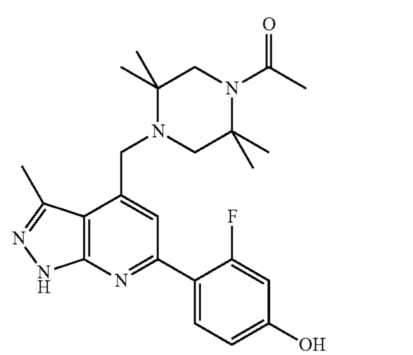 [SMILES: CC(=O)N1CC(C)(C)N(Cc2cc(-c3ccc(O)cc3F)nc3[nH]nc(C)c23)CC1(C)C] | LC9 | 440.30 | 1.73 |

EXAMPLE 79

1-{4-[6-(2-Fluoro-4-hydroxy-phenyl)-3-methyl-1H-pyrazolo[3,4-b]pyridin-4-ylmethyl]-2-methyl-[1,4]diazepan-1-yl}-2-methoxy-ethanone

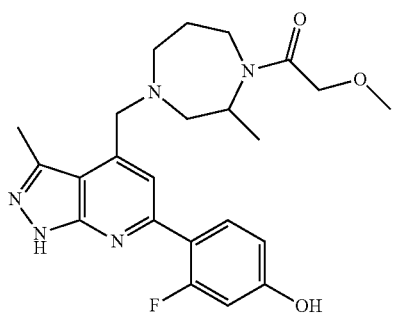 [SMILES: COCC(=O)N1CCCN(Cc2cc(-c3ccc(O)cc3F)nc3[nH]nc(C)c23)CC1C]

The title compound has been prepared following a similar procedure as described for Example 75 (1-{4-[6-(2-Fluoro-4-hydroxy-phenyl)-3-methyl-1H-pyrazolo[3,4-b]pyridin-4-ylmethyl]-2,2,5,5-tetramethyl-piperazin-1-yl}-2-methoxy-ethanone, employing 3-fluoro-4-(3-methyl-4-((3-methyl-1,4-diazepan-1-yl)methyl)-1H-pyrazolo[3,4-b]pyridin-6-yl)phenol and methoxyacetyl chloride.

LC/MS (Method LC9): Rt=1.39 min; m/z=440.36 [M+H]$^+$.

EXAMPLE 80

1-{4-[6-(2-Fluoro-4-hydroxy-phenyl)-3-methyl-1H-pyrazolo[3,4-b]pyridin-4-ylmethyl]-2,2,5,5-tetramethyl-piperazin-1-yl}-2-hydroxy-ethanone

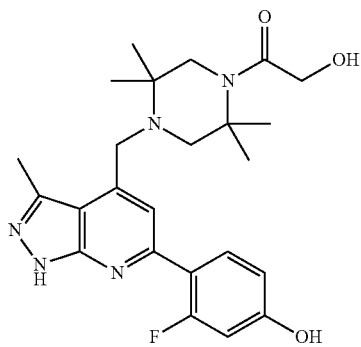 [SMILES: Cc1n[nH]c2nc(-c3ccc(O)cc3F)cc(CN3CC(C)(C)N(C(=O)CO)CC3(C)C)c12]

The title compound was prepared in analogy to Example 75 (1-{4-[6-(2-Fluoro-4-hydroxy-phenyl)-3-methyl-1H-pyrazolo[3,4-b]pyridin-4-ylmethyl]-2,2,5,5-tetramethyl-piperazin-1-yl}-2-methoxy-ethanone) using 3-fluoro-4-[3-methyl-4-(2,2,5,5-tetramethyl-piperazin-1-ylmethyl)-1H-pyrazolo[3,4-b]pyridin-6-yl]-phenol and acetoxyacetyl chloride.

LC/MS (Method LC9): Rt=1.52 min; m/z=456.28 [M+H]$^+$.

EXAMPLE 81

N-{1-[6-(2-Fluoro-4-hydroxy-phenyl)-3-methyl-1H-pyrazolo[3,4-b]pyridin-4-ylmethyl]-3-methyl-piperidin-3-yl}-2-methoxy-acetamide

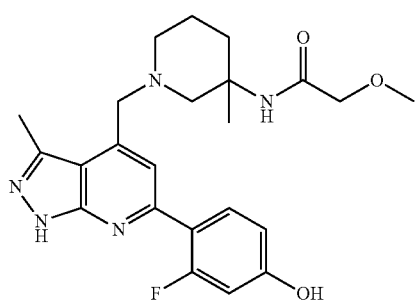 [SMILES: COCC(=O)NC1(C)CCCN(Cc2cc(-c3ccc(O)cc3F)nc3[nH]nc(C)c23)C1]

The title compound was prepared in analogy to Example 75 (1-{4-[6-(2-Fluoro-4-hydroxy-phenyl)-3-methyl-1H-pyrazolo[3,4-b]pyridin-4-ylmethyl]-2,2,5,5-tetramethyl-piperazin-1-yl}-2-methoxy-ethanone) using 4-[4-(3-Amino-3-methyl-piperidin-1-ylmethyl)-3-methyl-1H-pyrazolo[3,4-b]pyridin-6-yl]-3-fluoro-phenol and methoxyacetyl chloride.

LC/MS (Method LC9): Rt=1.37 min; m/z=442.27 [M+H]$^+$.

EXAMPLE 82

1-{9-[6-(4-Hydroxy-phenyl)-3-methyl-1H-pyrazolo[3,4-b]pyridin-4-ylmethyl]-8-methyl-6,9-diaza-spiro[4.5]dec-6-yl}-2-methoxy-ethanone

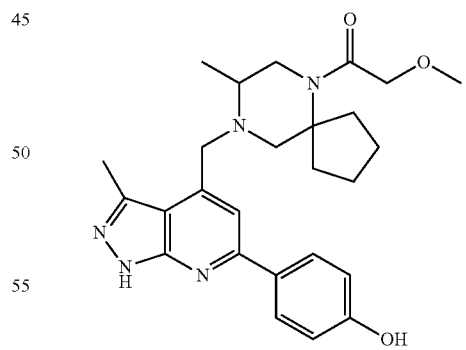

The title compound was prepared in analogy to Example 75 (1-{4-[6-(2-Fluoro-4-hydroxy-phenyl)-3-methyl-1H-pyrazolo[3,4-b]pyridin-4-ylmethyl]-2,2,5,5-tetramethyl-piperazin-1-yl}-2-methoxy-ethanone) using 4-[3-Methyl-4-(8-methyl-6,9-diaza-spiro[4.5]dec-9-ylmethyl)-1H-pyrazolo[3,4-b]pyridin-6-yl]-phenol and methoxyacetyl chloride.

LC/MS (Method LC9): Rt=1.53 min; m/z=464.36 [M+H]$^+$.

EXAMPLE 83

4-{3-Methyl-4-[2,2,5,5-tetramethyl-4-(3,3,3-trifluoro-propyl)-piperazin-1-ylmethyl]-1H-pyrazolo[3,4-b]pyridin-6-yl}-phenol

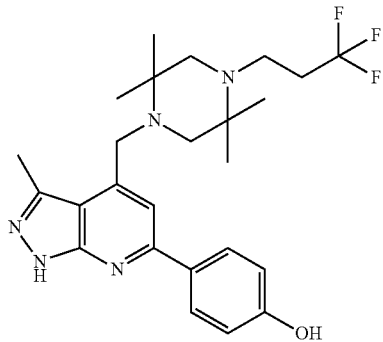 [SMILES: Cc1n[nH]c2nc(-c3ccc(O)cc3)cc(CN3CC(C)(C)N(CCC(F)(F)F)CC3(C)C)c12]

(a) 6-(4-Methoxymethoxy-phenyl)-3-methyl-1-(tetrahydro-pyran-2-yl)-1H-pyrazolo[3,4-b]pyridine-4-carboxylic acid ethyl ester

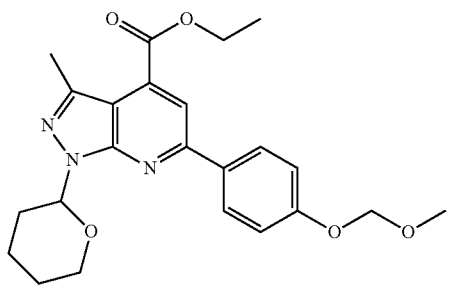 [SMILES: CCOC(=O)c1cc(-c2ccc(OCOC)cc2)nc2c1c(C)nn2C1CCCCO1]

To a degassed mixture of 1.68 g 6-bromo-3-methyl-1-(tetrahydro-pyran-2-yl)-1H-pyrazolo[3,4-b]pyridine-4-carboxylic acid ethyl ester, 1.00 g 4-(methoxymethoxy)-phenylboronic acid and 0.70 g potassium carbonate in DME/water (v/v=2/1, 24 mL) at r.t. and under Ar-atmosphere 70 mg palladium(0) bis(tri-tert-butylphosphine) was added and the mixture was stirred at 85° C. for 1 h. To the mixture water and ethyl acetate were added, the phases were separated and the aqueous phase was extracted with ethyl acetate. The combined organic phases were dried over Na$_2$SO$_4$, filtered and concentrated in vacuo. 2.08 g (100%) of the title compound were obtained.

LC/MS (Method LC4): Rt=0.88 min; m/z=426.10 [M+H]$^+$.

(b) 6-(4-Methoxymethoxy-phenyl)-3-methyl-1-(tetrahydro-pyran-2-yl)-1H-pyrazolo[3,4-b]pyridine-4-carboxylic acid

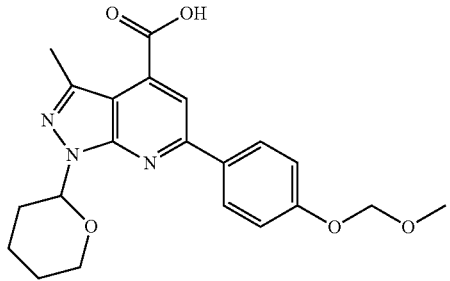 [SMILES: COCOc1ccc(-c2cc(C(=O)O)c3c(C)nn(C4CCCCO4)c3n2)cc1]

To 2.09 g 6-(4-methoxymethoxy-phenyl)-3-methyl-1-(tetrahydro-pyran-2-yl)-1H-pyrazolo[3,4-b]pyridine-4-carboxylic acid ethyl ester in 140 ml ethanol was added 100 ml of 1M aqueous sodium hydroxide solution. After 3 h at r.t. the volatiles were removed in vacuo. The residue was taken up in water and the pH was adjusted to 4-5. The aqueous phase was extracted with ethyl acetate three times. The combined organic phases were dried over Na$_2$SO$_4$, filtered and concentrated in vacuo. The residue was purified by flash chromatography (silica, dichloromethane/MeOH gradient with addition of aqueous ammonia) to obtain 1.74 g (90%) of the title compound.

LC/MS (Method LC4): Rt=0.98 min; m/z=398.1 [M+H]$^+$.

(c) (4-Benzyl-2,2,5,5-tetramethyl-piperazin-1-yl)-[6-(4-methoxymethoxy-phenyl)-3-methyl-1-(tetrahydro-pyran-2-yl)-1H-pyrazolo[3,4-b]pyridin-4-yl]-methanone

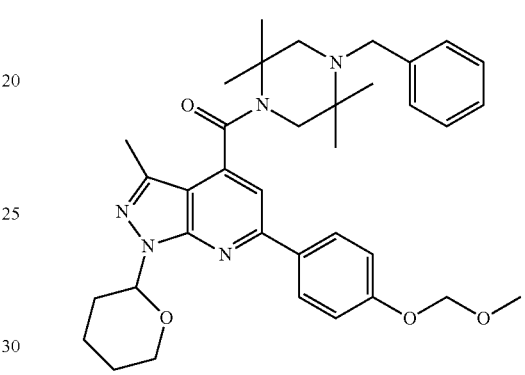

To a suspension of 1.24 g of 6-(4-methoxymethoxy-phenyl)-3-methyl-1-(tetrahydro-pyran-2-yl)-1H-pyrazolo[3,4-b]pyridine-4-carboxylic acid in 15 ml of DCM were added 2.1 ml of Hünig's base, 1.03 g of BEP and 0.87 g of 1-Benzyl-2,2,5,5-tetramethyl-piperazine. The reaction was stirred at r.t. for 3 h. For workup it was diluted with water and DCM and the layers were separated. The organic layer was washed with water twice, dried over Na$_2$SO$_4$, filtered and concentrated in vacuo. The residue was purified by flash chromatography (silica, heptane/EtOAc gradient) to obtain 1.54 g (81%) of the title compound.

LC/MS (Method LC4): Rt=0.94 min; m/z=612.3 [M+H]$^+$.

(d) 4-(4-Benzyl-2,2,5,5-tetramethyl-piperazin-1-ylmethyl)-6-(4-methoxymethoxy-phenyl)-3-methyl-1-(tetrahydro-pyran-2-yl)-1H-pyrazolo[3,4-b]pyridine

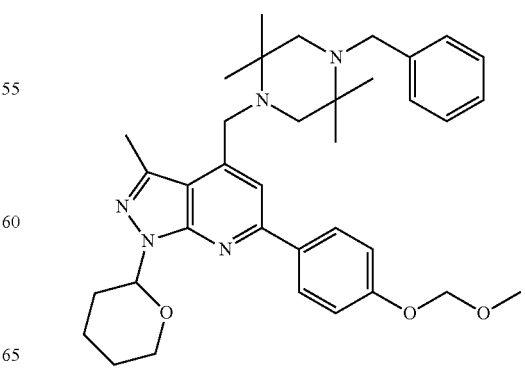

To a solution of 1.54 g of (4-benzyl-2,2,5,5-tetramethyl-piperazin-1-yl)-[6-(4-methoxy-methoxy-phenyl)-3-methyl-1-(tetrahydro-pyran-2-yl)-1H-pyrazolo[3,4-b]pyridin-4-yl]-methanone in 9 ml of dry THF 20 ml of borane-dimethylsulfide complex (1 M in DCM) was added slowly at r.t., and the reaction was heated to reflux for 12 h. The reaction was quenched by the addition of 13 ml of methanol, and the solvents were evaporated. The residue was purified by flash chromatography (silica, heptanes/ethyl acetate) yielding 1.44 g (96%) of the title compound.

LC/MS (Method LC4): Rt=0.96 min; m/z=598.3 [M+H]$^+$.

(e) 6-(4-Methoxymethoxy-phenyl)-3-methyl-1-(tetrahydro-pyran-2-yl)-4-(2,2,5,5-tetramethyl-piperazin-1-ylmethyl)-1H-pyrazolo[3,4-b]pyridine

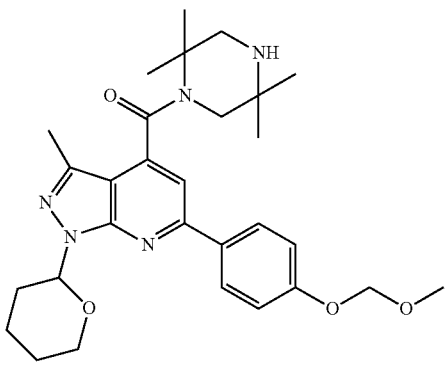 [SMILES: COCOc1ccc(-c2cc(C(=O)N3CC(C)(C)NCC3(C)C)c3c(C)nn(C4CCCCO4)c3n2)cc1]

1.44 g of 4-(4-benzyl-2,2,5,5-tetramethyl-piperazin-1-ylmethyl)-6-(4-methoxymethoxy-phenyl)-3-methyl-1-(tetrahydro-pyran-2-yl)-1H-pyrazolo[3,4-b]pyridine were dissolved in 16 ml dichloromethane and purged with argon. 1.44 g Palladium (10% on charcoal) were added and the mixture was hydrogenated at r.t. for 5 h. The catalyst was filtered off using celite and the solvents were evaporated. 1.13 g (93%) of the crude title compound were obtained, which were used in the next step without further purification.

LC/MS (Method LC4): Rt=0.88 min; m/z=508.20 [M+H]$^+$.

(f) 6-(4-Methoxymethoxy-phenyl)-3-methyl-1-(tetrahydro-pyran-2-yl)-4-[2,2,5,5-tetramethyl-4-(3,3,3-trifluoro-propyl)-piperazin-1-ylmethyl]-1H-pyrazolo[3,4-b]pyridine

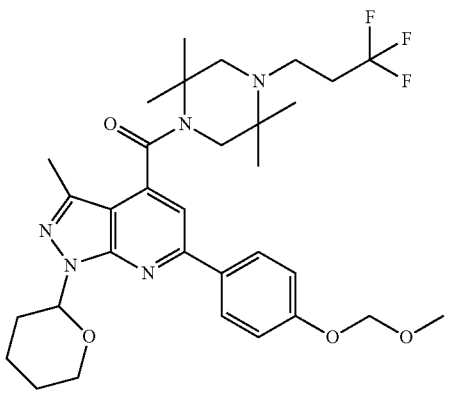 [SMILES: COCOc1ccc(-c2cc(C(=O)N3CC(C)(C)N(CCC(F)(F)F)CC3(C)C)c3c(C)nn(C4CCCCO4)c3n2)cc1]

To a solution of 150 mg of 6-(4-methoxymethoxy-phenyl)-3-methyl-1-(tetrahydro-pyran-2-yl)-4-(2,2,5,5-tetramethyl-piperazin-1-ylmethyl)-1H-pyrazolo[3,4-b]pyridine, 33 mg 3,3,3-trifluoropropanal and 5 mg of acetic acid in 2 ml dichloromethane was added 94 mg of sodium triacetoxyborohydride. After 1 h at rt 33 mg 3,3,3-trifluoropropanal and 94 mg of sodium triacetoxyborohydride were added and the reaction was stirred overnight. Then another 33 mg 3,3,3-trifluoropropanal and 94 mg of sodium triacetoxyborohydride were added and the reaction was stirred overnight. The reaction was diluted with ethyl acetate and water. The pH was adjusted to 8, and the phases were separated. The aqueous phase was extracted with ethyl acetate twice. The combined organic phases were dried over sodium sulphate, filtrated and concentrated in vacuo. 167 mg (94%) of the title compound were obtained.

LC/MS (Method LC4): Rt=0.92 min; m/z=604.2 [M+H]$^+$.

(g) 4-{3-Methyl-4-[2,2,5,5-tetramethyl-4-(3,3,3-trifluoro-propyl)-piperazin-1-ylmethyl]-1H-pyrazolo[3,4-b]pyridin-6-yl}-phenol

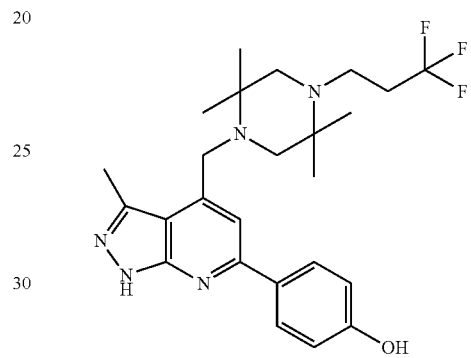

167 mg of 6-(4-methoxymethoxy-phenyl)-3-methyl-1-(tetrahydro-pyran-2-yl)-4-[2,2,5,5-tetramethyl-4-(3,3,3-trifluoro-propyl)-piperazin-1-ylmethyl]-1H-pyrazolo[3,4-b]pyridine were dissolved in 2 ml of 1,4-dioxane and treated with 1.5 ml of hydrochloric acid (4M in dry dioxane). After standing at rt for 16 h the volatiles were removed in vacuo. The residue was purified by preparative HPLC (C18 column, acetonitrile/water gradient) and 62 mg (47%) of the title compound were obtained.

LC/MS (Method LC9): Rt=1.37 min; m/z=476.30 [M+H]$^+$.

EXAMPLE 84

4-[3-Methyl-4-(2,2,4,5,5-pentamethyl-piperazin-1-ylmethyl)-1H-pyrazolo[3,4-b]pyridin-6-yl]-phenol

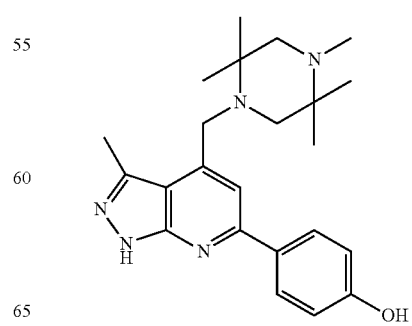

The title compound was synthesized in analogy to Example 83 (4-{3-Methyl-4-[2,2,5,5-tetramethyl-4-(3,3,3-trifluoro-propyl)-piperazin-1-ylmethyl]-1H-pyrazolo[3,4-b]pyridin-6-yl}-phenol), steps (f) and (g) using aqueous formaldehyde.

LC/MS (Method LC9): Rt=1.12 min; m/z=394.35 [M+H]⁺.

EXAMPLE 85

4-{3-Methyl-4-[2,2,5,5-tetramethyl-4-(2-methylamino-ethyl)-piperazin-1-ylmethyl]-1H-pyrazolo[3,4-b]pyridin-6-yl}-phenol

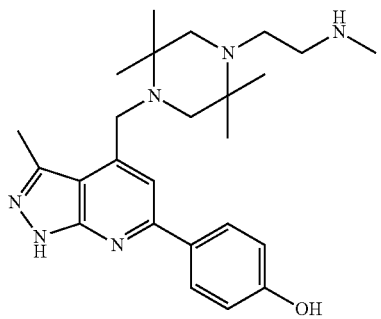 [SMILES: CNCCN1CC(C)(C)N(Cc2cc(-c3ccc(O)cc3)nc3[nH]nc(C)c23)CC1(C)C]

(a) (2-{4-[6-(4-Methoxymethoxy-phenyl)-3-methyl-1-(tetrahydro-pyran-2-yl)-1H-pyrazolo[3,4-b]pyridin-4-ylmethyl]-2,2,5,5-tetramethyl-piperazin-1-yl}-ethyl)-methyl-carbamic acid tert-butyl ester

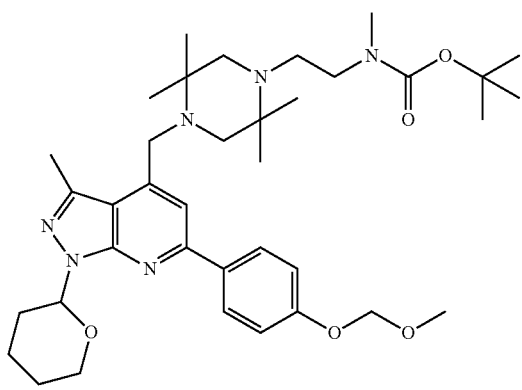 [SMILES: COCOc1ccc(-c2cc(CN3CC(C)(C)N(CCN(C)C(=O)OC(C)(C)C)CC3(C)C)c3c(C)nn(C4CCCCO4)c3n2)cc1]

To a solution of 290 mg of 6-(4-methoxymethoxy-phenyl)-3-methyl-1-(tetrahydro-pyran-2-yl)-4-(2,2,5,5-tetramethyl-piperazin-1-ylmethyl)-1H-pyrazolo[3,4-b]pyridine and 1040 mg N-Boc-(methylamino)acetaldehyde in 5 ml dichloromethane was added 250 mg of sodium triacetoxyborohydride. After 1 h at rt the reaction was diluted with ethyl acetate and water. The phases were separated. The aqueous phase was extracted with ethyl acetate twice. The combined organic phases were dried over sodium sulphate, filtrated and concentrated in vacuo. 1535 mg of a crude product of the title compound were obtained, which was used without purification in the next step.

LC/MS (Method LC4): Rt=1.00 min; m/z=665.30 [M+H]⁺.

(b) 4-{3-Methyl-4-[2,2,5,5-tetramethyl-4-(2-methylamino-ethyl)-piperazin-1-ylmethyl]-1H-pyrazolo[3,4-b]pyridin-6-yl}-phenol

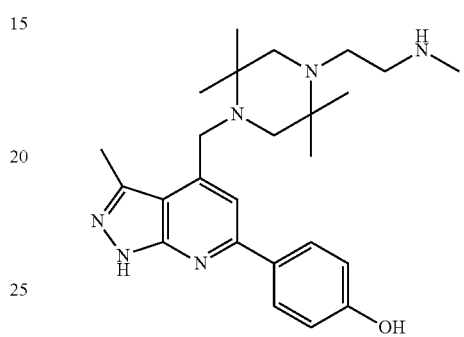

1320 mg of the crude (2-{4-[6-(4-Methoxymethoxy-phenyl)-3-methyl-1-(tetrahydro-pyran-2-yl)-1H-pyrazolo[3,4-b]pyridin-4-ylmethyl]-2,2,5,5-tetramethyl-piperazin-1-yl}-ethyl)-methyl-carbamic acid tert-butyl ester were dissolved in 6 ml of 1,4-dioxane and treated with 4 ml of hydrochloric acid (4M in dry dioxane). After standing at rt for 1.5 h the volatiles were removed in vacuo. The residue was purified by preparative HPLC (C18 column, acetonitrile/water gradient) and 45 mg (5%) of the title compound were obtained.

LC/MS (Method LC4): Rt=0.52 min; m/z=437.20 [M+H]⁺.

EXAMPLE 86

{4-[6-(4-Hydroxy-phenyl)-3-methyl-1H-pyrazolo[3,4-b]pyridin-4-ylmethyl]-2,2,5,5-tetramethyl-piperazin-1-yl}-acetic acid methyl ester

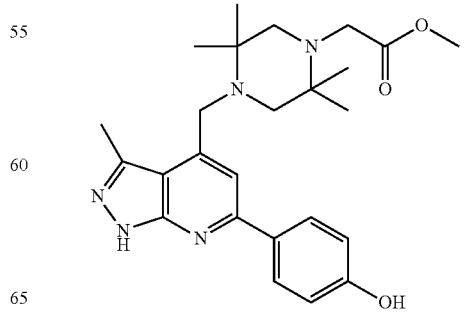

217

(a) {4-[6-(4-Methoxymethoxy-phenyl)-3-methyl-1-(tetrahydro-pyran-2-yl)-1H-pyrazolo[3,4-b]pyridin-4-ylmethyl]-2,2,5,5-tetramethyl-piperazin-1-yl}-acetic acid methyl ester

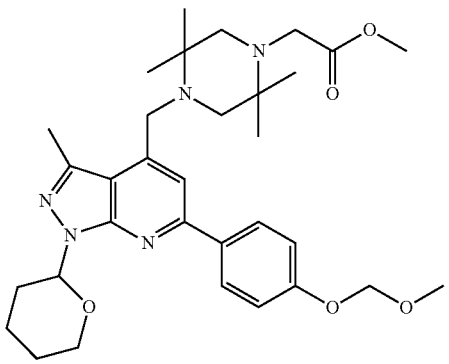 [SMILES: COCOc1ccc(-c2cc(CN3CC(C)(C)N(CC(=O)OC)CC3(C)C)c3c(C)nn(C4CCCCO4)c3n2)cc1]

The title compound was prepared in analogy to Example 74 ({4-[6-(2-Fluoro-4-hydroxy-phenyl)-3-methyl-1H-pyrazolo[3,4-b]pyridin-4-ylmethyl]-2,2,5,5-tetramethyl-piperazin-1-yl}-acetic acid methyl ester employing 6-(4-Methoxymethoxy-phenyl)-3-methyl-1-(tetrahydro-pyran-2-yl)-4-(2,2,5,5-tetramethyl-piperazin-1-ylmethyl)-1H-pyrazolo[3,4-b]pyridine and methyl bromoacetate and was used without further purification.

(b) {4-[6-(4-Hydroxy-phenyl)-3-methyl-1H-pyrazolo[3,4-b]pyridin-4-ylmethyl]-2,2,5,5-tetramethyl-piperazin-1-yl}acetic acid methyl ester

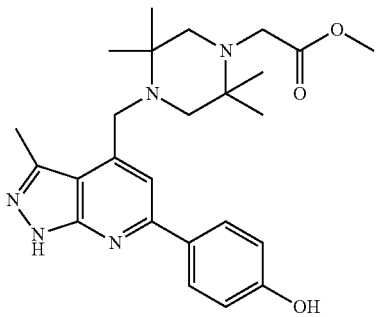 [SMILES: COC(=O)CN1CC(C)(C)N(Cc2cc(-c3ccc(O)cc3)nc3[nH]nc(C)c23)CC1(C)C]

78 mg of {4-[6-(4-Methoxymethoxy-phenyl)-3-methyl-1-(tetrahydro-pyran-2-yl)-1H-pyrazolo[3,4-b]pyridin-4-ylmethyl]-2,2,5,5-tetramethyl-piperazin-1-yl}-acetic acid methyl ester were reacted with hydrochloric acid (4M in dioxane) and the volatiles were removed after 5 h. After purification by preparative HPLC 14 mg (21%) of the title compound were obtained.

LC/MS (Method LC9): Rt=1.42 min; m/z=450.46 [M+H]+.

218

EXAMPLE 87

({4-[6-(4-Hydroxy-phenyl)-3-methyl-1H-pyrazolo[3,4-b]pyridin-4-yl methyl]-2,2,5,5-tetramethyl-piperazine-1-carbonyl}-amino)-acetic acid methyl ester

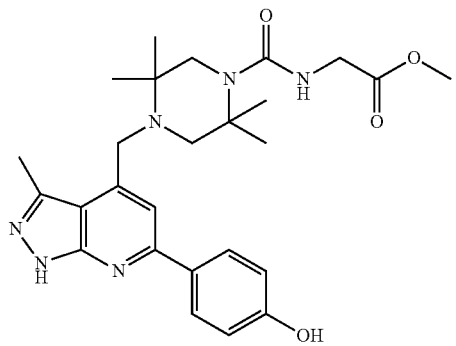 [SMILES: COC(=O)CNC(=O)N1CC(C)(C)N(Cc2cc(-c3ccc(O)cc3)nc3[nH]nc(C)c23)CC1(C)C]

(a) ({4-[6-(4-Methoxymethoxy-phenyl)-3-methyl-1-(tetrahydro-pyran-2-yl)-1H-pyrazolo[3,4-b]pyridin-4-ylmethyl]-2,2,5,5-tetramethyl-piperazine-1-carbonyl}-amino)-acetic acid ethyl ester

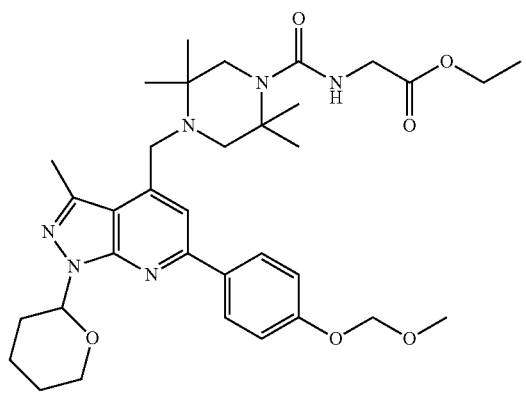 [SMILES: CCOC(=O)CNC(=O)N1CC(C)(C)N(Cc2cc(-c3ccc(OCOC)cc3)nc3c2c(C)nn3C2CCCCO2)CC1(C)C]

To a solution of 200 mg 6-(4-Methoxymethoxy-phenyl)-3-methyl-1-(tetrahydro-pyran-2-yl)-4-(2,2,5,5-tetramethyl-piperazin-1-ylmethyl)-1H-pyrazolo[3,4-b]pyridine in 3 ml abs. THF were added 51 mg ethyl isocyanatoacetate and 51 mg Hünig's base. After 16 h at rt water was added, and the pH was adjusted to neutral. The mixture was extracted with ethyl acetate twice and the combined organic layers were dried and concentrated in vacuo. 70 mg of the title compound were obtained, which were subjected to the subsequent reaction without further purification.

LC/MS (Method LC4): Rt=0.98 min; m/z=637.30 [M+H]+.

(b) ({4-[6-(4-Hydroxy-phenyl)-3-methyl-1H-pyrazolo[3,4-b]pyridin-4-ylmethyl]-2,2,5,5-tetramethyl-piperazine-1-carbonyl}aminoyacetic acid methyl ester

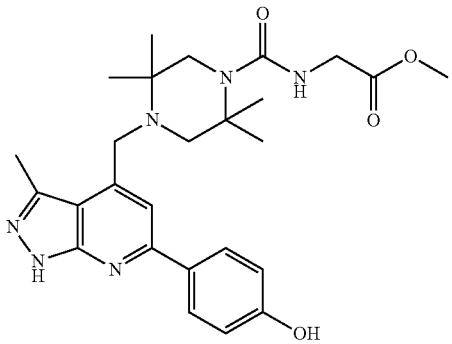 [SMILES: COC(=O)CNC(=O)N1CC(C)(C)N(Cc2cc(-c3ccc(O)cc3)nc3[nH]nc(C)c23)CC1(C)C]

70 mg of ({4-[6-(4-Methoxymethoxy-phenyl)-3-methyl-1-(tetrahydro-pyran-2-yl)-1H-pyrazolo[3,4-b]pyridin-4-ylmethyl]-2,2,5,5-tetramethyl-piperazine-1-carbonyl}-amino)-acetic acid ethyl ester were reacted with 1.5 ml hydrochloric acid (4M in dioxane) and 1 ml of methanol was added. After 16 h at rt the volatiles were removed in vacuo. After purification by preparative HPLC 10 mg (17%) of the title compound were obtained.

LC/MS (Method LC9): Rt=1.59 min; m/z=495.34 [M+H]⁺.

EXAMPLE 88

4-[6-(4-Hydroxy-phenyl)-3-methyl-1H-pyrazolo[3,4-b]pyridin-4-ylmethyl]-2,2,5,5-tetramethyl-piperazine-1-carboxylic acid ethylamide

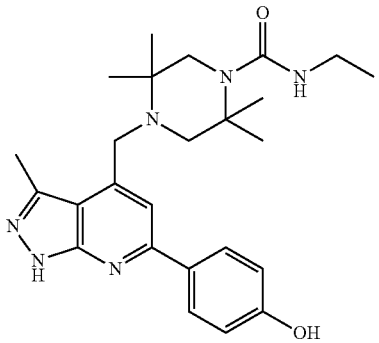

(a) 4-[6-(4-Methoxymethoxy-phenyl)-3-methyl-1-(tetrahydro-pyran-2-yl)-1H-pyrazolo[3,4-b]pyridin-4-ylmethyl]-2,2,5,5-tetramethyl-piperazine-1-carboxylic acid ethylamide

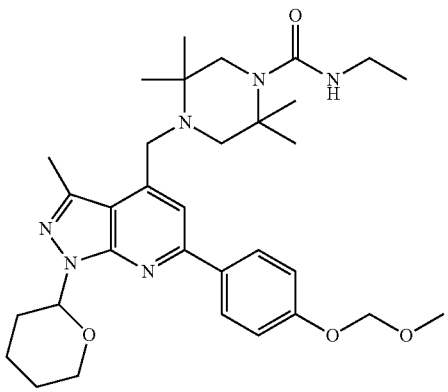 [SMILES: CCNC(=O)N1CC(C)(C)N(Cc2cc(-c3ccc(OCOC)cc3)nc3c2c(C)nn3C2CCCCO2)CC1(C)C]

To a solution of 290 mg 6-(4-Methoxymethoxy-phenyl)-3-methyl-1-(tetrahydro-pyran-2-yl)-4-(2,2,5,5-tetramethyl-piperazin-1-ylmethyl)-1H-pyrazolo[3,4-b]pyridine in 3 ml abs. THF were added 41 mg ethyl isocyanate and 75 mg Hünig's base. After 16 h at rt water was added, and the pH was adjusted to neutral. The mixture was extracted with ethyl acetate twice and the combined organic layers were dried and concentrated in vacuo. 325 mg of the title compound were obtained, which were subjected to the subsequent reaction without further purification.

LC/MS (Method LC4): Rt=0.96 min; m/z=579.30 [M+H]⁺.

(b) 4-[6-(4-Hydroxy-phenyl)-3-methyl-1H-pyrazolo[3,4-b]pyridin-4-ylmethyl]-2,2,5,5-tetramethyl-piperazine-1-carboxylic acid ethylamide

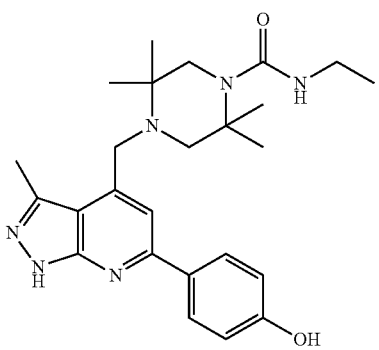

325 mg of 4-[6-(4-Methoxymethoxy-phenyl)-3-methyl-1-(tetrahydro-pyran-2-yl)-1H-pyrazolo[3,4-b]pyridin-4-ylmethyl]-2,2,5,5-tetramethyl-piperazine-1-carboxylic acid ethylamide in 2 ml of dioxane were reacted with 2 ml hydrochloric acid (4M in dioxane). After 4 h at rt the volatiles were removed in vacuo. After purification by preparative HPLC 142 mg (56%) of the title compound were obtained.

LC/MS (Method LC9): Rt=1.64 min; m/z=451.33 [M+H]⁺.

EXAMPLE 89

4-[6-(2-Fluoro-4-hydroxy-phenyl)-3-methyl-1H-pyrazolo[3,4-b]pyridin-4-ylmethyl]-2-methyl-[1,4]diazepane-1-carboxylic acid ethylamide

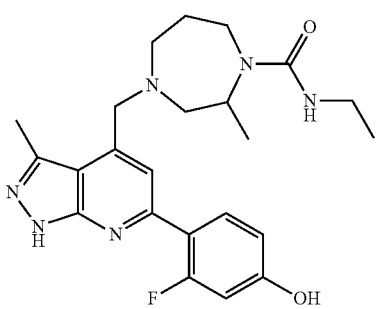 [SMILES: CCNC(=O)N1CCCN(Cc2cc(-c3ccc(O)cc3F)nc3[nH]nc(C)c23)CC1C]

To a solution of 75 mg 3-Fluoro-4-[3-methyl-4-(3-methyl-[1,4]diazepan-1-ylmethyl)-1H-pyrazolo[3,4-b]pyridin-6-yl]-phenol in 1.5 ml abs. THF were added 15 mg ethyl isocyanate and 26 mg Hünig's base. After 16 h at rt water was added, and the pH was adjusted to neutral. The mixture was extracted with ethyl acetate twice and the combined organic layers were dried and concentrated in vacuo. After purification by HPLC 29 mg (32%) of the title compound were obtained.

LC/MS (Method LC4): Rt=1.31 min; m/z=441.27 [M+H]$^+$.

EXAMPLE 90

1-{4-[6-(4-Hydroxy-phenyl)-3-methyl-1H-pyrazolo[3,4-b]pyridin-4-ylmethyl]-2,2,5,5-tetramethyl-piperazin-1-yl}-2-methoxy-ethanone

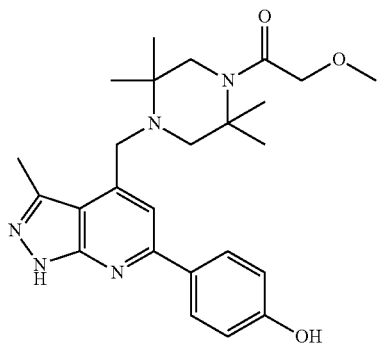 [SMILES: COCC(=O)N1CC(C)(C)N(Cc2cc(-c3ccc(O)cc3)nc3[nH]nc(C)c23)CC1(C)C]

(a) 2-Methoxy-1-{4-[6-(4-methoxymethoxy-phenyl)-3-methyl-1-(tetrahydro-pyran-2-yl)-1H-pyrazolo[3,4-b]pyridin-4-ylmethyl]-2,2,5,5-tetramethyl-piperazin-1-yl}-ethanone

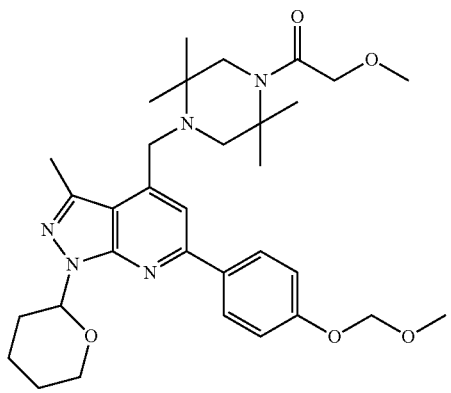 [SMILES: COCOc1ccc(-c2cc(CN3CC(C)(C)N(C(=O)COC)CC3(C)C)c3c(C)nn(C4CCCCO4)c3n2)cc1]

To 16 mg sodium hydride (60% in mineral oil) in 2 ml of abs. THF were added 80 mg of 6-(4-methoxymethoxy-phenyl)-3-methyl-1-(tetrahydro-pyran-2-yl)-4-(2,2,5,5-tetramethyl-piperazin-1-ylmethyl)-1H-pyrazolo[3,4-b]pyridine and after 10 min 17 mg of 2-methoxyacetyl chloride were added. After 16 h at rt the reaction was quenched by the addition of water, the layers were separated and the aqueous layer was extracted with ethyl acetate twice. The combined organic layers were dried and concetrated in vacuo. 93 mg of the title compound were obtained.

LC/MS (Method LC4): Rt=1.00 min; m/z=580.40 [M+H]$^+$.

(b) 1-{4-[6-(4-Hydroxy-phenyl)-3-methyl-1H-pyrazolo[3,4-b]pyridin-4-ylmethyl]-2,2,5,5-tetramethyl-piperazin-1-yl}-2-methoxy-ethanone

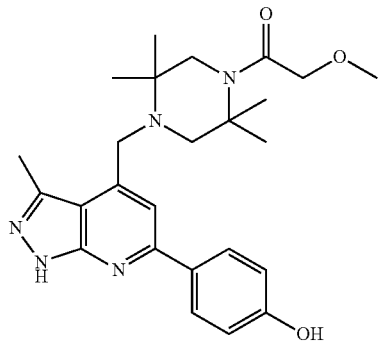 [SMILES: COCC(=O)N1CC(C)(C)N(Cc2cc(-c3ccc(O)cc3)nc3[nH]nc(C)c23)CC1(C)C]

93 mg of 2-Methoxy-1-{4-[6-(4-methoxymethoxy-phenyl)-3-methyl-1-(tetrahydro-pyran-2-yl)-1H-pyrazolo[3,4-b]pyridin-4-ylmethyl]-2,2,5,5-tetramethyl-piperazin-1-yl}-ethanone were dissolved in 2.5 ml of dioxane and reacted with 2 ml hydrochloric acid (4M in dioxane). The volatiles were removed after 16 h. After purification by preparative HPLC 25 mg of the title compound were obtained.

LC/MS (Method LC9): Rt=1.68 min; m/z=450.41 [M+H]$^+$.

EXAMPLE 91

4-{3-Methyl-4-[(R)-3-(2,2,2-trifluoro-ethyl)-piperazin-1-ylmethyl]-1H-pyrazolo[3,4-b]pyridin-6-yl}-phenol

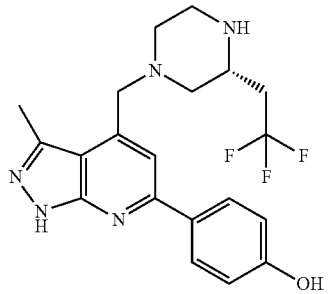 [SMILES: Cc1n[nH]c2nc(-c3ccc(O)cc3)cc(CN3CCN[C@H](CC(F)(F)F)C3)c12]

(a) [(R)-4-Benzyl-3-(2,2,2-trifluoro-ethyl)-piperazin-1-yl]6-(4-methoxymethoxy-phenyl)-3-methyl-1-(tetrahydro-pyran-2-yl)-1H-Pyrazolo[3,4-b]pyridin-4-yl]-methanone

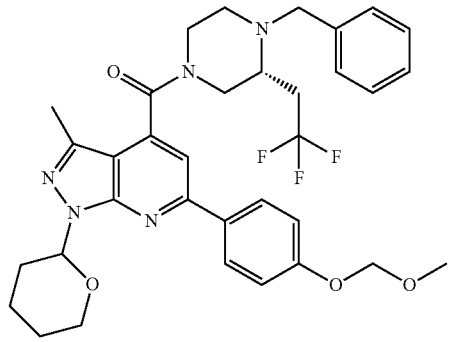 [SMILES: COCOc1ccc(-c2cc(C(=O)N3CCN(Cc4ccccc4)[C@H](CC(F)(F)F)C3)c3c(C)nn(C4CCCCO4)c3n2)cc1]

To a suspension of 440 mg of 6-(4-methoxymethoxy-phenyl)-3-methyl-1-(tetrahydro-pyran-2-yl)-1H-pyrazolo[3,4-b]pyridine-4-carboxylic acid in 8 ml of DCM were added 0.9 ml of Hünig's base, 371 mg of BEP and 391 mg of (R)-1-benzyl-2-(2,2,2-trifluoroethyl)piperazine hydrochloride. The reaction was stirred at r.t. for 2 h. For workup it was diluted with water and DCM and the layers were separated. The organic layer was washed with water twice, dried over Na₂SO₄, filtered and concentrated in vacuo. The residue was purified by flash chromatography (silica, heptane/EtOAc gradient) to obtain 350 mg (50%) of the title compound.

LC/MS (Method LC4): Rt=1.11 min; m/z=638.2 [M+H]⁺.

(b) 4-[(R)-4-Benzyl-3-(2,2,2-trifluoro-ethyl)-piperazin-1-ylmethyl]-6-(4-methoxymethoxy-phenyl)-3-methyl-1-(tetrahydro-pyran-2-yl)-1H-pyrazolo[3,4-b]pyridine

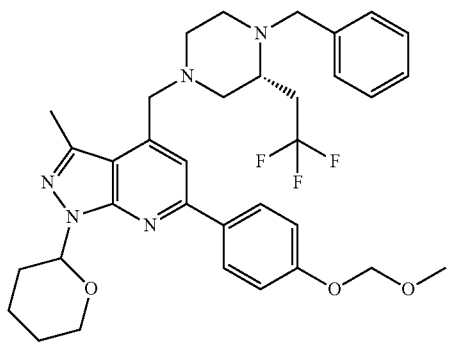 [SMILES: COCOc1ccc(-c2cc(CN3CCN(Cc4ccccc4)[C@H](CC(F)(F)F)C3)c3c(C)nn(C4CCCCO4)c3n2)cc1]

To a solution of 350 mg of [(R)-4-Benzyl-3-(2,2,2-trifluoro-ethyl)-piperazin-1-yl]-[6-(4-methoxymethoxy-phenyl)-3-methyl-1-(tetrahydro-pyran-2-yl)-1H-pyrazolo[3,4-b]pyridin-4-yl]-methanone in 6 ml of dry THF 4.4 ml of borane-dimethylsulfide complex (1 M in DCM) was added slowly at r.t., and the reaction was heated to reflux for 6 h. The reaction was quenched by the addition of methanol, and the solvents were evaporated. The residue was purified by flash chromatography (silica, heptanes/ethyl acetate) yielding 217 mg (63%) of the title compound.

LC/MS (Method LC4): Rt=0.97 min; m/z=624.20 [M+H]⁺.

(c) 6-(4-Methoxymethoxy-phenyl)-3-methyl-1-(tetrahydro-pyran-2-yl)-4-[(R)-3-(2,2,2-trifluoro-ethyl)-piperazin-1-ylmethyl]-1H-pyrazolo[3,4-b]pyridine

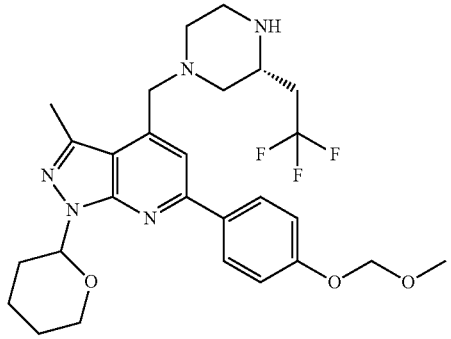 [SMILES: COCOc1ccc(-c2cc(CN3CCN[C@H](CC(F)(F)F)C3)c3c(C)nn(C4CCCCO4)c3n2)cc1]

217 mg of 4-[(R)-4-Benzyl-3-(2,2,2-trifluoro-ethyl)-piperazin-1-ylmethyl]-6-(4-methoxymethoxy-phenyl)-3-methyl-1-(tetrahydro-pyran-2-yl)-1H-pyrazolo[3,4-b]pyridine were dissolved in 2.5 ml dichloromethane and 2.5 ml methanol and purged with argon. 22 mg Palladium (10% on charcoal) were added and the mixture was hydrogenated at 5 bar and at r.t. for 1.5 h. The catalyst was filtered off using celite and the solvents were evaporated. 188 mg (100%) of the crude title compound were obtained, which were used in the next step without further purification.

LC/MS (Method LC4): Rt=0.87 min; m/z=534.20 [M+H]⁺.

(d) 4-{3-Methyl-4-[(R)-3-(2,2,2-trifluoro-ethyl)-piperazin-1-ylmethyl]-1H-pyrazolo[3,4-b]pyridin-6-yl}-phenol

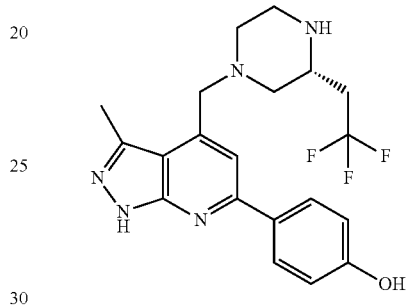

188 mg of 6-(4-Methoxymethoxy-phenyl)-3-methyl-1-(tetrahydro-pyran-2-yl)-4-[(R)-3-(2,2,2-trifluoro-ethyl)-piperazin-1-ylmethyl]-1H-pyrazolo[3,4-b]pyridine were dissolved in 2 ml of 1,4-dioxane and treated with 2 ml of hydrochloric acid (4M in dry dioxane). After standing at rt for 1.5 h the volatiles were removed in vacuo. The residue was purified by preparative HPLC (C18 column, acetonitrile/water gradient) and 73 mg (50%) of the title compound were obtained.

LC/MS (Method LC4): Rt=0.59 min; m/z=406.10 [M+H]⁺.

EXAMPLE 92

4-{3-Methyl-4-[(R)-2-(2,2,2-trifluoro-ethyl)-piperazin-1-ylmethyl]-1H-pyrazolo[3,4-b]pyridin-6-yl}-phenol

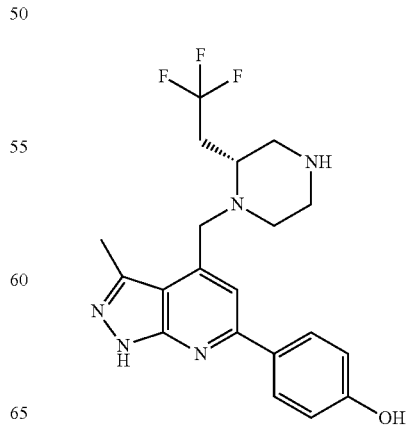

225

(a) (R)-4-[6-(4-Methoxymethoxy-phenyl)-3-methyl-1-(tetrahydro-pyran-2-yl)-1H-pyrazolo[3,4-b]pyridine-4-carbonyl]-3-(2,2,2-trifluoro-ethyl)-piperazine-1-carboxylic acid tert-butyl ester

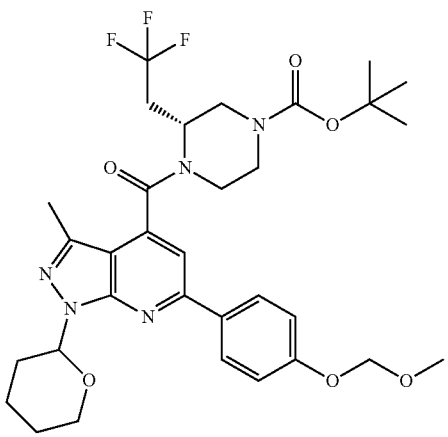 [SMILES: COCOc1ccc(-c2cc(C(=O)N3CCN(C(=O)OC(C)(C)C)C[C@H]3CC(F)(F)F)c3c(C)nn(C4CCCCO4)c3n2)cc1]

To a suspension of 0.80 g of 6-(4-methoxymethoxy-phenyl)-3-methyl-1-(tetrahydro-pyran-2-yl)-1H-pyrazolo[3,4-b]pyridine-4-carboxylic acid in 12 ml of DCM were added 1 ml of Hünig's base, 0.48 g of BEP and 0.50 g of (R)-3-(2,2,2-trifluoroethyl)-piperazine-1-carboxylic acid tert-butyl ester. The reaction was stirred at r.t. for 2 d. For workup it was diluted with water and DCM and the layers were separated. The organic layer was washed with water twice, dried over $Na_2SO_4$, filtered and concentrated in vacuo. The residue was purified by flash chromatography (silica, heptane/EtOAc gradient) to obtain 0.58 g (60%) of the title compound.

LC/MS (Method LC4): Rt=1.21 min; m/z=648.2 $[M+H]^+$.

(b) (R)-4-[6-(4-Methoxymethoxy-phenyl)-3-methyl-1-(tetrahydro-pyran-2-yl)-1H-pyrazolo[3,4-b]pyridin-4-ylmethyl]-3-(2,2,2-trifluoro-ethyl)-piperazine-1-carboxylic acid tert-butyl ester

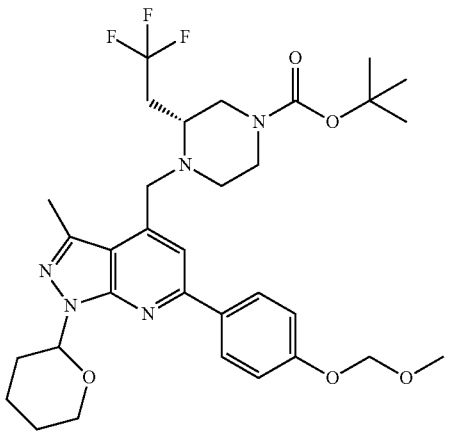 [SMILES: COCOc1ccc(-c2cc(CN3CCN(C(=O)OC(C)(C)C)C[C@H]3CC(F)(F)F)c3c(C)nn(C4CCCCO4)c3n2)cc1]

226

To a solution of 557 mg of (R)-4-[6-(4-Methoxymethoxy-phenyl)-3-methyl-1-(tetrahydro-pyran-2-yl)-1H-pyrazolo[3,4-b]pyridine-4-carbonyl]-3-(2,2,2-trifluoro-ethyl)-piperazine-1-carboxylic acid tert-butyl ester in 8 ml of dry THF 6.9 ml of borane-dimethylsulfide complex (1 M in DCM) was added slowly at r.t., and the reaction was heated to reflux for 3.5 h. The reaction was quenched by the addition of methanol, and the solvents were evaporated. The residue was purified by flash chromatography (silica, heptanes/ethyl acetate) yielding 460 mg (84%) of the title compound.

LC/MS (Method LC4): Rt=1.32 min; m/z=634.20 $[M+H]^+$.

(c) 4-{3-Methyl-4-[(R)-2-(2,2,2-trifluoro-ethyl)-piperazin-1-ylmethyl]-1H-pyrazolo[3,4-b]pyridin-6-yl}-phenol 460 mg of (R)-4-[6-(4-Methoxymethoxy-phenyl)-3-methyl-1-(tetrahydro-pyran-2-yl)-1H-pyrazolo[3,4-b]pyridin-4-ylmethyl]-3-(2,2,2-trifluoro-ethyl)-piperazine-1-carboxylic acid tert-butyl ester were dissolved in 3 ml of dioxane and reacted with 3 ml hydrochloric acid (4M in dioxane). The volatiles were removed after 0.5 h. After purification by preparative HPLC 160 mg (54%) of the title compound were obtained.

LC/MS (Method LC9): Rt=130 min; m/z=406.24 $[M+H]^+$.

The following examples have ben prepared following a similar procedure as described for Example 92 (4-{3-Methyl-4-[(R)-2-(2,2,2-trifluoro-ethyl)-piperazin-1-ylmethyl]-1H-pyrazolo[3,4-b]pyridin-6-yl}-phenol, employing the respective BOC-protected diamines:

| Exp. No. | Name | Structure | LC/MS method | m/z [M + H]+ | Rt [min] |
|---|---|---|---|---|---|
| 93 | 4-[3-Methyl-4-(3-methylamino-pyrrolidin-1-ylmethyl)-1H-pyrazolo[3,4-b]pyridin-6-yl]-phenol | 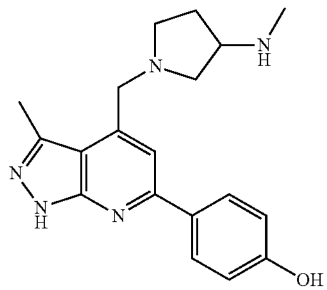 [SMILES: CNC1CCN(Cc2cc(-c3ccc(O)cc3)nc3[nH]nc(C)c23)C1] | LC9 | 338.1 | 0.41 |
| 94 | 4-{3-Methyl-4-[(methyl-pyrrolidin-3-yl-amino)-methyl]-1H-pyrazolo[3,4-b]pyridin-6-yl}-phenol | 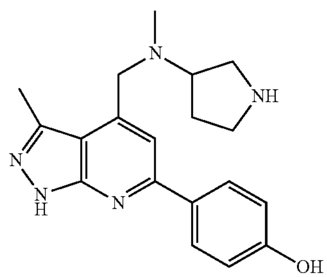 [SMILES: Cc1n[nH]c2nc(-c3ccc(O)cc3)cc(CN(C)C3CCNC3)c12] | LC9 | 338.2 | 0.42 |

EXAMPLE 95

4-(3-Cyclopropyl-4-piperazin-1-ylmethyl-1H-pyrazolo[3,4-b]pyridin-6-yl)-phenol (a) 3-Cyclopropyl-6-(4-hydroxy-phenyl)-1H-pyrazolo[3,4-b]pyridine-4-carboxylic acid methyl ester

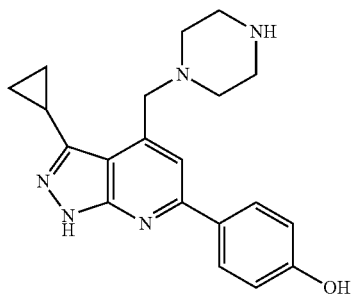 [SMILES: Oc1ccc(-c2cc(CN3CCNCC3)c3c(C4CC4)n[nH]c3n2)cc1]

A mixture of 3-amino-5-cyclopropylpyrazole (8.95 g), pyruvic acid methyl ester (8.24 g) and 4-hydroxybenzaldehyde (8.87 g) in acetic acid/methanol (v/v=1/1, 120 mL) was stirred at 75° C. for 14 h. The methanol was removed in vacuo, and the remaining mixture was poured unto water, and extracted with ethyl acetate three times. The combined organic phases were washed with brine, dried over magnesium sulfate, filtrated and concentrated in vacuo. The residue was dissolved in 50 ml of acetic acid/methanol (v/v=1/1), heated to reflux for 1 h and cooled to r.t. The precipitated product was isolated by filtration and dried in vacuo at 60° C. 3.80 g (17%) of the title compound were obtained.

$^1$H-NMR (500 MHz, d$_6$-DMSO): 0.90 (m, 4H), 2.45 (m, 1H), 4.05 (s, 3H), 6.95 (d, 2H), 7.90 (s, 1H), 8.05 (d, 2H), 10.0 (s, 1H), 13.5 (s, 1H).

LC/MS (Method LC4): Rt=0.79 min; m/z=310.05 [M+H]$^+$.

(b) 3-Cyclopropyl-6-(4-hydroxy-phenyl)-1-(tetrahydro-pyran-2-yl)-1H-pyrazolo[3,4-b]pyridine-4-carboxylic acid methyl ester

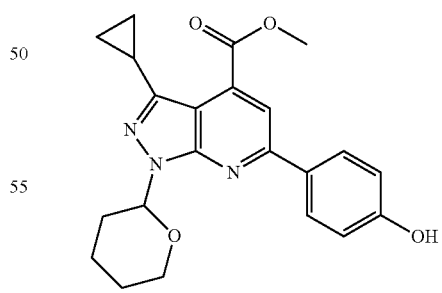

A mixture of 3-cyclopropyl-6-(4-hydroxy-phenyl)-1H-pyrazolo[3,4-b]pyridine-4-carboxylic acid methyl ester (12.9 g), 3,4-dihydro-2H-pyran (5.26 g) and p-toluenesulfonic acid monohydrate (2.38 g) in THF (300 mL) was stirred at r.t. until the reaction was complete. Water was added and the mixture was extracted with ethyl acetate, the combined organic phases were washed with water and brine, dried over magnesium sulfate and concentrated. The residue was chromatographed over a short path column (heptane/ethyl acetate gradient). 11.4 g (70%) of the title compound were obtained.

LC/MS (Method LC4): Rt=1.01 min; m/z=394.15 [M+H]+.

(c) 3-Cyclopropyl-6-(4-hydroxy-phenyl)-1-(tetrahydro-pyran-2-yl)-1H-pyrazolo[3,4-b]pyridine-4-carboxylic acid

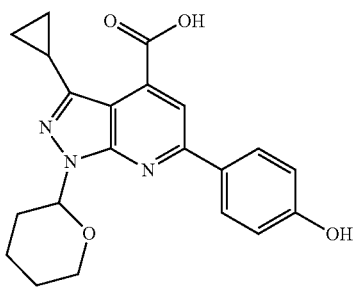 [SMILES: O=C(O)c1cc(-c2ccc(O)cc2)nc2c1c(C1CC1)nn2C1CCCCO1]

A mixture of 3-cyclopropyl-6-(4-hydroxy-phenyl)-1-(tetrahydro-pyran-2-yl)-1H-pyrazolo[3,4-b]pyridine-4-carboxylic acid methyl ester (11.3 g) and sodium hydroxide solution (1N, 100 mL) in isopropanol (100 mL) was stirred at r.t. for 5 h. The mixture was poured onto ice-water and the pH was adjusted to 5 with acetic acid. The mixture was extracted with dichloromethane three times and the combined organic layers were dried over magnesium sulphate, filtrated and concentrated in vacuo. 10.35 g (95%) of the title compound were obtained.

$^1$H-NMR (500 MHz, d$_6$-DMSO): 0.90 (m, 4H), 1.60 (m, 2H), 1.75 (m, 1H), 1.85 (m, 1H), 2.05 (m, 1H), 2.45 (m, 1H), 2.65 (m, 1H), 3.70 (m, 1H), 3.95 (m, 1H), 6.05 (dd, 1H), 6.90 (d, 2H), 7.95 (s, 1H), 8.10 (d, 2H), 9.90 (s, 1H), 13.9 (br s, 1H).

LC/MS (Method LC4): R$_t$=0.87 min; m/z=380.15 [M+H]+.

(d) 4-[3-Cyclopropyl-6-(4-hydroxy-phenyl)-1-(tetrahydro-pyran-2-yl)-1H-pyrazolo[3,4-b]pyridine-4-carbonyl]-piperazine-1-carboxylic acid tert-butyl ester

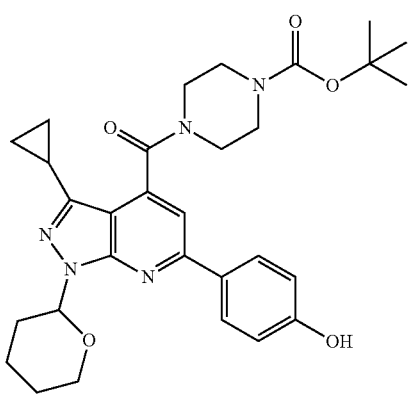 [SMILES: CC(C)(C)OC(=O)N1CCN(C(=O)c2cc(-c3ccc(O)cc3)nc3c2c(C2CC2)nn3C2CCCCO2)CC1]

To a suspension of 0.80 g of 3-cyclopropyl-6-(4-hydroxy-phenyl)-1-(tetrahydro-pyran-2-yl)-1H-pyrazolo[3,4-b]pyridine-4-carboxylic acid in 13 ml of DCM were added 1.4 ml of Hünig's base, 0.98 g of BEP and 0.47 g of tert-butyl-1-piperazine carboxylate. The reaction was stirred at r.t. for 4 h. For workup it was diluted with water and DCM and the layers were separated. The organic layer was washed with water twice, dried over Na$_2$SO$_4$, filtered and concentrated in vacuo. The residue was purified by flash chromatography (silica, heptane/EtOAc gradient) to obtain 0.79 g (68%) of the title compound.

LC/MS (Method LC4): Rt=1.04 min; m/z=548.6 [M+H]+.

(e) 4-[3-Cyclopropyl-6-(4-hydroxy-phenyl)-1-(tetrahydro-pyran-2-yl)-1H-pyrazolo[3,4-b]pyridin-4-ylmethyl]-piperazine-1-carboxylic acid tert-butyl ester

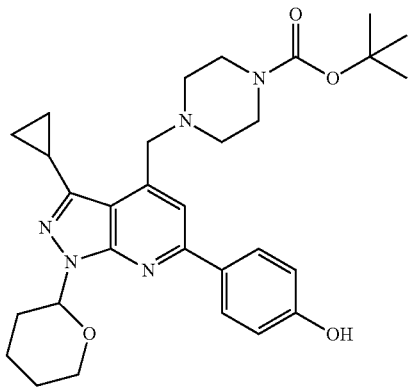 [SMILES: CC(C)(C)OC(=O)N1CCN(Cc2cc(-c3ccc(O)cc3)nc3c2c(C2CC2)nn3C2CCCCO2)CC1]

To a solution of 790 mg of 4-[3-cyclopropyl-6-(4-hydroxy-phenyl)-1-(tetrahydro-pyran-2-yl)-1H-pyrazolo[3,4-b]pyridine-4-carbonyl]-piperazine-1-carboxylic acid tert-butyl ester in 6 ml of dry THF 11.5 ml of borane-dimethylsulfide complex (1 M in DCM) was added slowly at r.t., and the reaction was heated to reflux for 0.5 h. The reaction was quenched by the addition of 7 ml of methanol, and the solvents were evaporated. The residue was purified by flash chromatography (silica, heptanes/ethyl acetate) yielding 635 mg (82%) of the title compound.

LC/MS (Method LC4): Rt=0.89 min; m/z=534.2 [M+H]+.

(f) 4-(3-Cyclopropyl-4-piperazin-1-ylmethyl-1H-pyrazolo[3,4-b]pyridin-6-yl)-phenol

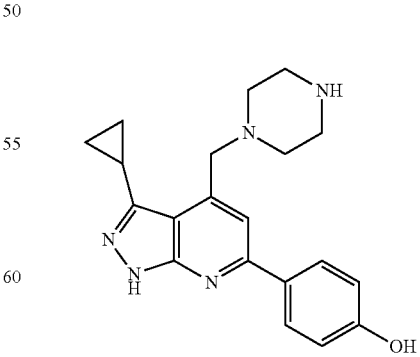

600 mg of 4-[3-cyclopropyl-6-(4-hydroxy-phenyl)-1-(tetrahydro-pyran-2-yl)-1H-pyrazolo[3,4-b]pyridin-4-ylmethyl]-piperazine-1-carboxylic acid tert-butyl ester were dissolved in 6 ml of 1,4-dioxane and 2 ml of dichloromethane and treated with 4.8 ml of hydrochloric acid (4M in dry dioxane). After standing at rt for 16 h the volatiles were removed in vacuo. The residue was purified by preparative HPLC (C18 column, acetonitrile/water gradient) and 315 mg (73%) of the title compound were obtained as hydrochloride.

$^1$H-NMR (500 MHz, d$_6$-DMSO): 0.95 (m, 4H), 2.40 (m, 1H), 2.65 (s, br, 4H), 3.10 (s, br, 4H), 4.00 (s, 2H), 6.90 (d, 2H), 7.55 (s, 1H), 7.95 (d, 2H), 8.70 (s, br, 2H), 9.80 (s, 1H), 13.0 (s, 1H).

LC/MS (Method LC9): Rt=1.06 min; m/z=350.25 [M+H]$^+$.

EXAMPLE 96

4-(3-Ethyl-4-piperazin-1-ylmethyl-1H-pyrazolo[3,4-b]pyridin-6-yl)-phenol

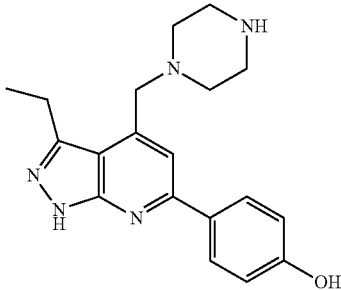 [SMILES: CCc1n[nH]c2nc(-c3ccc(O)cc3)cc(CN3CCNCC3)c12]

In analogy to the synthesis of Example 95 (4-(3-Cyclopropyl-4-piperazin-1-ylmethyl-1H-pyrazolo[3,4-b]pyridin-6-yl)-phenol) the title compound could be synthesized employing 3-ethyl-1H-pyrazol-5-amine instead of 3-cyclopropyl-1H-pyrazol-5-amine.

$^1$H-NMR (500 MHz, d$_6$-DMSO): 1.30 (t, 3H), 2.65 (s, br, 4H), 3.05 (t, 2H), 3.10 (s, br, 4H), 3.90 (s, br, 2H), 6.85 (d, 2H), 7.55 (s, 1H), 8.00 (d, 2H), 8.75 (s, br, 2H), 9.90 (s, 1H), 13.1 (s, 1H).

LC/MS (Method LC9): Rt=1.19 min; m/z=338.32 [M+H]$^+$.

EXAMPLE 97

3-Fluoro-4-[3-methyl-4-(1-piperazin-1-yl-ethyl)-1H-pyrazolo[3,4-b]pyridin-6-yl]-phenol

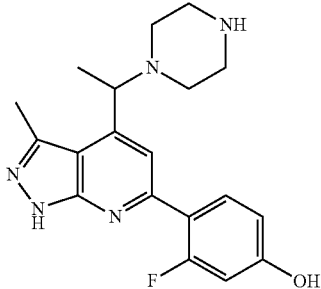 [SMILES: Cc1n[nH]c2nc(-c3ccc(O)cc3F)cc(C(C)N3CCNCC3)c12]

(a) 6-(4-Benzyloxy-2-fluoro-phenyl)-3-methyl-1-(tetrahydro-pyran-2-yl)-1H-pyrazolo[3,4-b]pyridine-4-carboxylic acid methoxy-methyl-amide

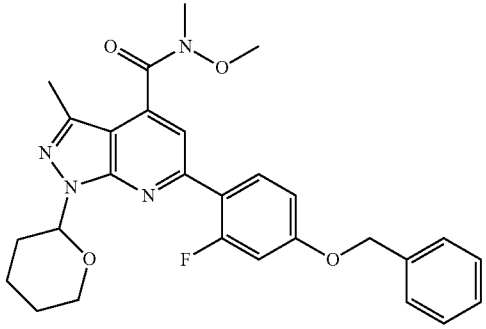 [SMILES: CON(C)C(=O)c1cc(-c2ccc(OCc3ccccc3)cc2F)nc2c1c(C)nn2C1CCCCO1]

6-(4-Benzyloxy-2-fluoro-phenyl)-3-methyl-1-(tetrahydro-pyran-2-yl)-1H-pyrazolo[3,4-b]pyridine-4-carboxylic acid (3.00 g) was dissolved in dichloromethane (50 mL), DIPEA (3.34 mL), N,O-dimethylhydroxylamine hydrochloride (0.63 g) and finally BEP (3.92 g) were added. The mixture was stirred at r.t. overnight, then extracted with sat. sodium carbonate solution, washed with 1N HCl and finally again with sodium carbonate solution. The solvent was evaporated and the residue was crystallized from methanol and filtered off giving 6-(4-benzyloxy-2-fluoro-phenyl)-3-methyl-1-(tetrahydro-pyran-2-yl)-1H-pyrazolo[3,4-b]pyridine-4-carboxylic acid methoxy-methyl-amide (2.28 g, 70%) as a solid.

1H-NMR (500 MHz, d6-DMSO): 1.54-1.66 (m, 2H), 1.76-1.88 (m, 1H), 1.89-1.95 (m, 1H), 2.02-2.10 (m, 1H), 2.47-2.56 (m, 1H), 2.38 (s, 3H), 3.32 (s, 3H), 3.38/3.47 (2s, 3H), 3.70-3.77 (m, 1H), 3.93-3.99 (m, 1H), 5.30 (2, 2H), 6.10 (dd, 1H), 7.33-7.46 (m, 3H), 7.49-7.52 (m, 2H), 7.90 (s, 1H), 8.03-8.09 (m, 1H), 8.12-8.18 (m, 1H).

LC/MS (Method LC1): Rt=1.38 min; m/z=505.3 [M+H]$^+$.

(b) 1-[6-(4-Benzyloxy-2-fluoro-phenyl)-3-methyl-1-(tetrahydro-pyran-2-yl)-1H-pyrazolo[3,4-b]pyridin-4-yl]-methanone

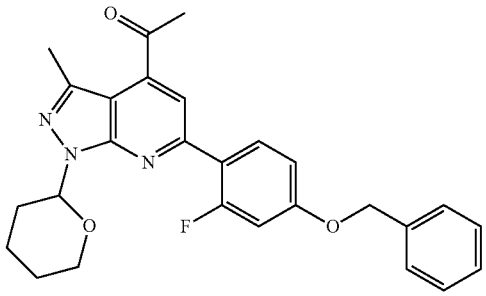 [SMILES: CC(=O)c1cc(-c2ccc(OCc3ccccc3)cc2F)nc2c1c(C)nn2C1CCCCO1]

6-(4-Benzyloxy-2-fluoro-phenyl)-3-methyl-1-(tetrahydro-pyran-2-yl)-1H-pyrazolo[3,4-b]pyridine-4-carboxylic acid methoxy-methyl-amide (1.0 g) was dissolved in THF (25 mL). At 0° C. methylmagnesium bromide solution (1 M, 3.9 mL) was added slowly, the mixture was warmed to r.t. while stirring overnight. Saturated ammonium chloride solution was added, the mixture was extracted with dichloromethane, the organic phases were dried over magnesium sulfate and concentrated in a membrane pump vacuum. The residue was purified by fish chromatography (silica, heptane/ethyl acetate gradient) giving 1-[6-(4-benzyloxy-2-fluoro-phenyl)-3-methyl-1-(tetrahydro-pyran-2-yl)-1H-pyrazolo[3,4-b]pyridin-4-yl]-methanone (1.0 g, quantitative yield with impurities).

1H-NMR (500 MHz, d6-DMSO): 1.54-1.66 (m, 2H), 1.74-1.86 (m, 1H), 1.87-1.92 (m, 1H), 2.02-2.09 (m, 1H), 2.47-2.56 (m, 1H), 2.45 (s, 3H), 2.72 (s, 3H), 3.70-3.77 (m, 1H), 3.93-3.99 (m, 1H), 5.30 (2, 2H), 6.11 (dd, 1H), 7.33-7.46 (m, 3H), 7.50-7.53 (m, 2H), 8.11-8.15 (m, 1H), 8.16 (s, 1H), 8.20-8.24 (m, 1H).

LC/MS (Method LC1): Rt=1.43 min; m/z=460.2 [M+H]+.

(c) 3-Fluoro-4-[3-methyl-4-(1-piperazin-1-yl-ethyl)-1H-pyrazolo[3,4-b]pyridin-6-yl]-phenol

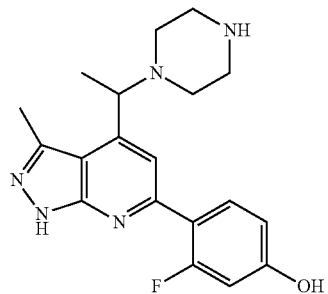 [SMILES: Cc1n[nH]c2nc(-c3ccc(O)cc3F)cc(C(C)N3CCNCC3)c12]

A mixture of 1-[6-(4-benzyloxy-2-fluoro-phenyl)-3-methyl-1-(tetrahydro-pyran-2-yl)-1H-pyrazolo[3,4-b]pyridin-4-yl]-ethanone (390 mg), acetic acid (25 µL), piperazine-1-carboxylic acid tert-butyl ester (158 mg) and sodium triacetoxy borohydride (270 mg) in dichloromethane (7.5 mL) was stirred at 40° C. overnight. Then additional triacetoxy borohydride (90 mg) was added. The reaction mixture was concentrated in a membrane pump vacuum, and the residue was purified by flash chromatography (silica, heptane/ethyl acetate gradient) giving 4-{1-[6-(4-Benzyloxy-2-fluoro-phenyl)-3-methyl-1-(tetrahydro-pyran-2-yl)-1H-pyrazolo[3,4-b]pyridin-4-yl]-ethyl}-piperazine-1-carboxylic acid tert-butyl ester (90 mg). This material was dissolved in methanol (5 mL), purged with argon, then with hydrogen and palladium (10% on charcoal, 8 mg) was added. The reaction mixture was stirred at 40° C. until the reaction was complete (according to HPLC/MS). The catalyst was filtered off and the filtrate was concentrated in a membrane pump vacuum. The residue was taken up in THF (2 mL), and conc. hydrochloric acid (1 mL) was added. The solution was stirred at r.t., then the solvents were evaporated and the residue was purified by preparative HPLC (C18 column, acetonitrile/water gradient) giving 3-fluoro-4-[3-methyl-4-(1-piperazin-1-yl-ethyl)-1H-pyrazolo[3,4-b]pyridin-6-yl]-phenol (30 mg, 9%).

LC/MS (Method LC1): Rt=0.86 min; m/z=356.2 [M+H]+.

EXAMPLE 98

4-{4-[1-((3S,5R)-3,5-Dimethyl-piperazin-1-yl)-ethyl]-3-methyl-1H-pyrazolo[3,4-b]pyridin-6-yl}-3-fluoro-phenol

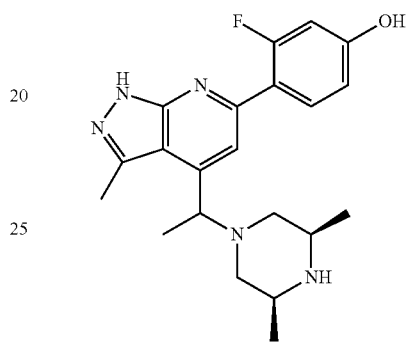

The title compound was prepared in analogy to Example 97 starting from 1-[6-(4-benzyloxy-2-fluoro-phenyl)-3-methyl-1-(tetrahydro-pyran-2-yl)-1H-pyrazolo[3,4-b]pyridin-4-yl]-ethanone and (2S,6R)-tert-butyl 2,6-dimethylpiperazine-1-carboxylate.

LC/MS (Method LC1): Rt=0.90 min; m/z=384.16 [M+H]+.

The following stereoisomers (enantiomers or diastereomers) were obtained after separation of the racemates or diastereomeric mixtures by preparative HPLC using a Waters Alliance 2695 system and chiral columns and solvent mixtures as given in the following tables.

| Exp. No. | Structure and chemical name of racemic mixture | Conditions of chiral sep. | No. of stereoisomer | Rt [min] (chiral sep.) | LCMS method (non-chiral) | m/z [M + H]+ | Rt [min] (non-chiral) |
|---|---|---|---|---|---|---|---|
| 99<br>100 | 3-Fluoro-4-[3-methyl-4-(trans-2-methyl-5-phenyl-piperazin-1-ylmethyl)-1H-pyrazolo[3,4-b]pyridin-6-yl]-phenol<br>trans rac. | LC_5, 0.75 ml/min, AD-H-83 + 67; 4.6 × 250 mm, EtOH:MeOH 1:1 + 0.1% DEA | 1<br>2 | 10.0<br>10.7 | LC5<br>LC5 | 432.14<br>432.15 | 0.91<br>0.91 |

| Exp. No. | Structure and chemical name of racemic mixture | Conditions of chiral sep. | No. of enantiomer | Rt [min] (chiral sep.) | LCMS method (non-chiral) | m/z [M + H]+ | Rt [min] (non-chiral) |
|---|---|---|---|---|---|---|---|
| 101 | 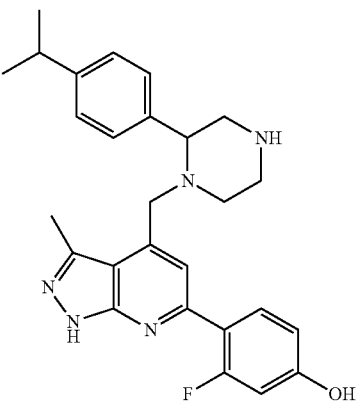 3-Fluoro-4-{4-[2-4-(isopropyl-phenyl)-piperazin-1-yl-methyl]-3-methyl-1H-pyrazolo[3,4-b]pyridin-6-yl}-phenol | LC_5, 1.0 ml/min, AD-H-83; 4.6 × 250 mm, heptane: EtOH 10:1 + 0.1% DEA | 1 | 16.2 | LC5 | 460.29 | 0.93 |
| 102 | | | 2 | 22.0 | LC5 | 460.32 | 0.93 |

| Exp. No. | Structure and chemical name of racemic mixture | Conditions of chiral sep. | No. of enantiomer | Rt [min] (chiral sep.) | LCMS method (non-chiral) | m/z [M + H]+ | Rt [min] (non-chiral) |
|---|---|---|---|---|---|---|---|
| 103 | 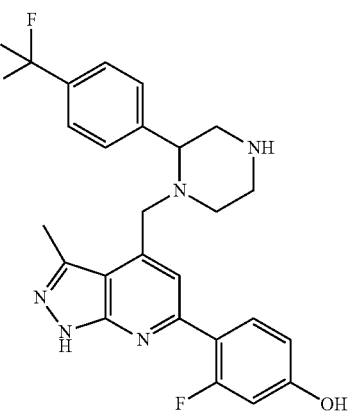 3-Fluoro-4-{3-methyl-4-[2-(4-trifluoromethyl-phenyl)-piperazin-1-yl-methyl]-1H-pyrazolo[3,4-b]pyridin-6-yl}-phenol | LC_5, 1.0 ml/min, AD-H-83; 4.6 × 250 mm, heptane: EtOH 10:1 + 0.1% DEA | 1 | 7.5 | LC5 | 486.21 | 0.89 |
| 104 | | | 2 | 9.9 | LC5 | 486.23 | 0.89 |

| Exp. No. | Structure and chemical name of racemic mixture | Conditions of chiral sep. | No. of enantiomer | Rt [min] (chiral sep.) | LCMS method (non-chiral) | m/z [M + H]+ | Rt [min] (non-chiral) |
|---|---|---|---|---|---|---|---|
| 105 | 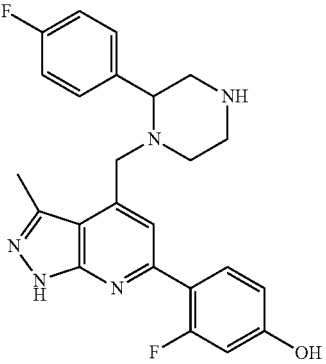<br>3-Fluoro-4-{4-[2-(4-fluoro-phenyl)-piperazin-1-yl-methyl]-3-methyl-1H-pyrazolo[3,4-b]pyridin-6-yl}-phenol | LC_5, 1.0 ml/min, AS-H-75; 4.6 × 250 mm, heptane:EtOH:MeOH 10:1:1 + 0.1% DEA | 1 | 7.8 | LC5 | 436.1 | 0.96 |
| 106 | | | 2 | 9.3 | LC5 | 436.1 | 0.96 |

| Exp. No. | Structure and chemical name of racemic mixture | Conditions of chiral sep. | No. of enantiomer | Rt [min] (chiral sep.) | LCMS method (non-chiral) | m/z [M + H]+ | Rt [min] (non-chiral) |
|---|---|---|---|---|---|---|---|
| 107 | 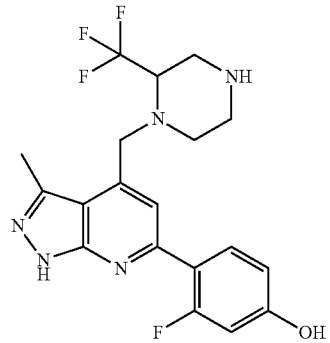<br>3-Fluoro-4-[3-methyl-4-(2-trifluoro-methyl-piperazin-1-ylmethyl)-1H-pyrazolo[3,4-b]pyridin-6-yl]-phenol | LC_5, 1.0 ml/min, AS-H-75; 4.6 × 250 mm, heptane:EtOH:MeOH 5:1:1 + 0.1% DEA | 1 | 4.2 | LC5 | 410.07 | 0.89 |
| 108 | | | 2 | 6.3 | LC5 | 410.07 | 0.89 |

| Exp. No. | Structure and chemical name of racemic mixture | Conditions of chiral sep. | No. of enantiomer | Rt [min] (chiral sep.) | LCMS method (non-chiral) | m/z [M + H]+ | Rt [min] (non-chiral) |
|---|---|---|---|---|---|---|---|
| 109 110 | 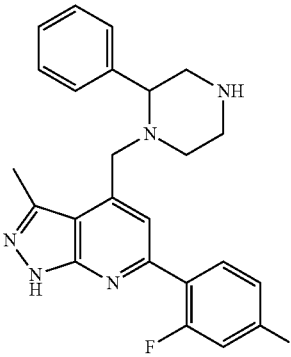<br>3-Fluoro-4-[3-methyl-4-(-2-phenyl-piperazin-1-yl-methyl)-1H-pyrazolo[3,4-b]pyridin-6-yl]-phenol | LC_10, 1.0 ml/min, Chiralpak AS-H/53; 4.6 × 250 mm, heptane:iPrOH:MeOH 10:1:1 + 0.1% DEA | 1<br>2 | 11.0<br>13.4 | LC5<br>LC5 | 418.11<br>418.11 | 0.94<br>0.94 |

| Exp. No. | Structure and chemical name of racemic mixture | Conditions of chiral sep. | No. of enantiomer | Rt [min] (chiral sep.) | LCMS method (non-chiral) | m/z [M + H]+ | Rt [min] (non-chiral) |
|---|---|---|---|---|---|---|---|
| 111 112 | 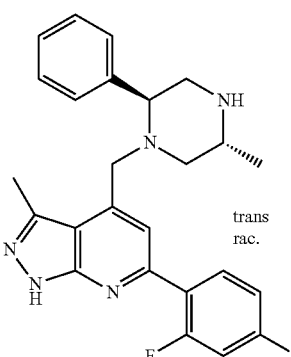<br>4-[3-Methyl-4-(trans-5-methyl-2-phenyl-piperazin-1-ylmethyl)-1H-pyrazolo[3,4-b]pyridin-6-yl]-phenol | LC_1, 1.0 ml/min, Chiralpak IC/155; 4.6 × 250 mm, heptane:EtOH 6:1 + 0.1% DEA | 1<br>2 | 12.0<br>13.3 | LC5<br>LC5 | 414.3<br>414.3 | 0.93<br>0.93 |

| Exp. No. | Structure and chemical name of racemic mixture | Conditions of chiral sep. | No. of enantiomer | Rt [min] (chiral sep.) | LCMS method (non-chiral) | m/z [M + H]+ | Rt [min] (non-chiral) |
|---|---|---|---|---|---|---|---|
| 113 114 | 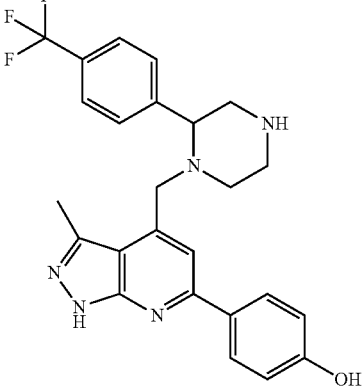 4-{3-Methyl-4-[2-(4-trifluoromethyl-phenyl)-piperazin-1-yl-methyl]-1H-pyrazolo[3,4-b]pyridin-6-yl}-phenol | LC_1, 1.0 ml/min, Chiralpak IC/155; 4.6 × 250 mm, heptane:iPrOH 5:1 + 0.1% DEA | 1 2 | 13.2 16.2 | LC3 LC5 | 468.25 468.25 | 2.99 0.99 |

| Exp. No. | Structure and chemical name of racemic mixture | Conditions of chiral sep. | No. of enantiomer | Rt [min] (chiral sep.) | LCMS method (non-chiral) | m/z [M + H]+ | Rt [min] (non-chiral) |
|---|---|---|---|---|---|---|---|
| 115 116 | 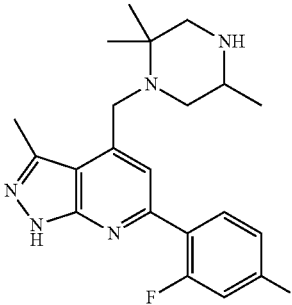 3-Fluoro-4-[3-methyl-4-(-2,5,5-trimethyl-piperazin-1-ylmethyl)-1H-pyrazolo[3,4-b]pyridin-6-yl]-phenol | LC_1, 1.0 ml/min, Chiralcel OJ/H 58; 4.6 × 250 mm, heptane:EtOH:MeOH 1:1:1 precond. with DEA | 1 2 | 4.2 7.2 | LC5 LC5 | 384.26 384.26 | 0.88 0.88 |

| Exp. No. | Structure and chemical name of racemic mixture | Conditions of chiral sep. | No. of enantiomer | Rt [min] (chiral sep.) | LCMS method (non-chiral) | m/z [M + H]+ | Rt [min] (non-chiral) |
|---|---|---|---|---|---|---|---|
| 117 118 | 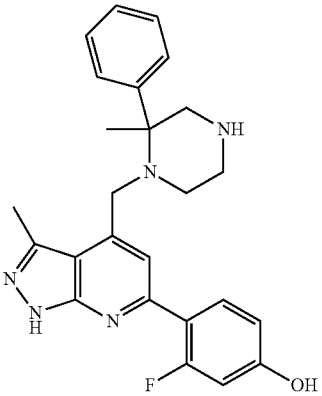<br>3-Fluoro-4-[3-methyl-4-(2-methyl-2-phenyl-piperazin-1-ylmethyl)-1H-pyrazolo[3,4-b]pyridin-6-yl]-phenol | LC_1, 1.0 ml/min, Chiralcel OJ/H 58; 4.6 × 250 mm, heptane:EtOH:MeOH 2:1:1 + 0.1% DEA | 1<br>2 | 6.2<br>10.9 | LC1<br>LC5 | 432.30<br>432.33 | 0.96<br>0.84 |

| Exp. No. | Structure and chemical name of racemic mixture | Conditions of chiral sep. | No. of enantiomer | Rt [min] (chiral sep.) | LCMS method (non-chiral) | m/z [M + H]+ | Rt [min] (non-chiral) |
|---|---|---|---|---|---|---|---|
| 119 120 | 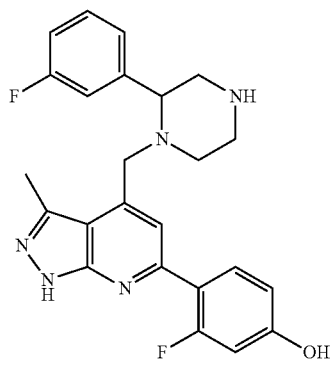<br>3-Fluoro-4-{4-[2-(3-fluoro-phenyl)-piperazin-1-ylmethyl]-3-methyl-1H-pyrazolo[3,4-b]pyridin-6-yl}-phenol | LC_3, 1.0 ml/min, Chiralcel OJ/H 59; 4.6 × 250 mm, heptane:EtOH:MeOH 10:1::2 + 0.1% DEA | 1<br>2 | 21.4<br>31.4 | LC9<br>LC9 | 436.28<br>436.28 | 1.42<br>1.42 |

| Exp. No. | Structure and chemical name of racemic mixture | Conditions of chiral sep. | No. of enantiomer | Rt [min] (chiral sep.) | LCMS method (non-chiral) | m/z [M + H]+ | Rt [min] (non-chiral) |
|---|---|---|---|---|---|---|---|
| 121 122 | 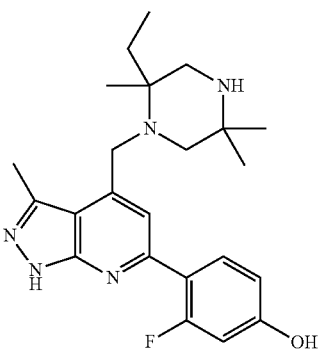<br>4-[4-(2-Ethyl-2,5,5-trimethyl-piperazin-1-ylmethyl)-3-methyl-1H-pyrazolo[3,4-b]pyridin-6-yl]-3-fluoro-phenol | LC_3, 1.0 ml/min, Chiralcel OJ/H 59; 4.6 × 250 mm, heptane: EtOH:MeOH 10:1::2 + 0.1% DEA | 1<br>2 | 6.0<br>13.0 | LC9<br>LC9 | 412.30<br>412.31 | 1.37<br>1.36 |

| Exp. No. | Structure and chemical name of racemic mixture | Conditions of chiral sep. | No. of enantiomer | Rt [min] (chiral sep.) | LCMS method (non-chiral) | m/z [M + H]+ | Rt [min] (non-chiral) |
|---|---|---|---|---|---|---|---|
| 123 124 | 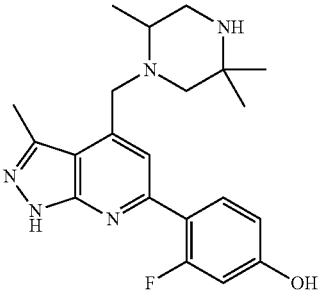<br>3-Fluoro-4-[3-methyl-4-(2,5,5-trimethyl-piperazin-1-ylmethyl)-1H-pyrazolo[3,4-b]pyridin-6-yl]-phenol | LC_4, 1.0 ml/min, Chiralcel OD-H; 4.6 × 250 mm, heptane: EtOH 5:1 + 0.1% DEA | 1<br>2 | 6.4<br>8.9 | LC9<br>LC9 | 482.27<br>482.15 | 1.13<br>1.13 |

| Exp. No. | Structure and chemical name of racemic mixture | Conditions of chiral sep. | No. of enantiomer | Rt [min] (chiral sep.) | LCMS method (non-chiral) | m/z [M + H]+ | Rt [min] (non-chiral) |
|---|---|---|---|---|---|---|---|
| 125 126 | 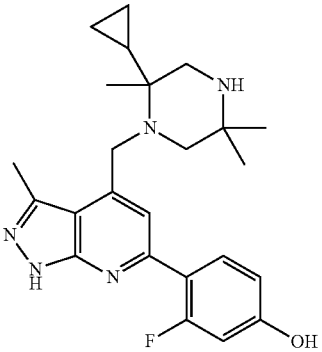<br>4-[4-(2-Cyclopropyl-2,5,5-trimethyl-piperazin-1-ylmethyl)-3-methyl-1H-pyrazolo[3,4-b]pyridin-6-yl]-3-fluoro-phenol | LC_4, 1.0 ml/min, Chiralpak AS-H; 4.6 × 250 heptane:EtOH:MeOH 10:1:1 + 0.1% DEA | 1<br>2 | 4.7<br>6.2 | LC9<br>LC9 | 424.30<br>424.30 | 1.25<br>1.26 |

| Exp. No. | Structure and chemical name of racemic mixture | Conditions of chiral sep. | No. of enantiomer | Rt [min] (chiral sep.) | LCMS method (non-chiral) | m/z [M + H]+ | Rt [min] (non-chiral) |
|---|---|---|---|---|---|---|---|
| 127 128 | 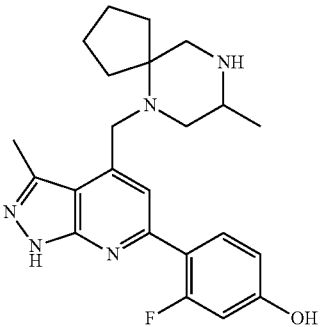<br>3-Fluoro-4-[3-methyl-4-(8-methyl-6,9-diaza-spiro[4.5]dec-6-ylmethyl)-1H-pyrazolo[3,4-b]pyridin-6-yl]-phenol | LC_4, 1.0 ml/min, Chiralcel AS-H; 4.6 × 250 mm, heptane:EtOH 5:1 + 0.1% DEA | 1<br>2 | 5.6<br>8.5 | LC9<br>LC9 | 410.25<br>410.28 | 1.24<br>1.24 |

| Exp. No. | Structure and chemical name of racemic mixture | Conditions of chiral sep. | No. of enantiomer | Rt [min] (chiral sep.) | LCMS method (non-chiral) | m/z [M + H]+ | Rt [min] (non-chiral) |
|---|---|---|---|---|---|---|---|
| 129 130 | 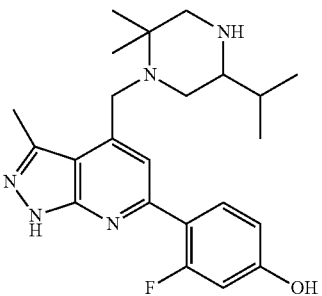<br>3-Fluoro-4-[4-(5-isopropyl-2,2-dimethyl-piperazin-1-ylmethyl)-3-methyl-1H-pyrazolo[3,4-b]pyridin-6-yl]-phenol | LC_4, 1.0 ml/min, Chiralcel AS-H; 4.6 × 250 mm, heptane:EtOH 5:1 + 0.1% DEA | 1<br>2 | 4.5<br>6.1 | LC9<br>LC9 | 410.30<br>410.26 | 1.19<br>1.19 |

| Exp. No. | Structure and chemical name of racemic mixture | Conditions of chiral sep. | No. of enantiomer | Rt [min] (chiral sep.) | LCMS method (non-chiral) | m/z [M + H]+ | Rt [min] (non-chiral) |
|---|---|---|---|---|---|---|---|
| 131 132 | 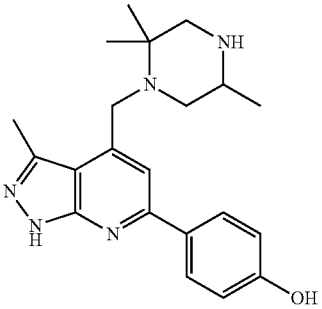<br>4-[3-Methyl-4-(2,5,5-trimethyl-piperazin-1-ylmethyl)-1H-pyrazolo[3,4-b]pyridin-6-yl]-phenol | LC_4, 1.0 ml/min, Chiralpak AS-H; 4.6 × 250 mm, heptane:EtOH:MeOH 20:1:1 + 0.1% DEA | 1<br>2 | 9-3<br>12.6 | LC4<br>LC4 | 366.0<br>366.0 | 0.55<br>0.55 |

| Exp. No. | Structure and chemical name of racemic mixture | Conditions of chiral sep. | No. of enantiomer | Rt [min] (chiral sep.) | LCMS method (non-chiral) | m/z [M + H]+ | Rt [min] (non-chiral) |
|---|---|---|---|---|---|---|---|
| 133 134 | 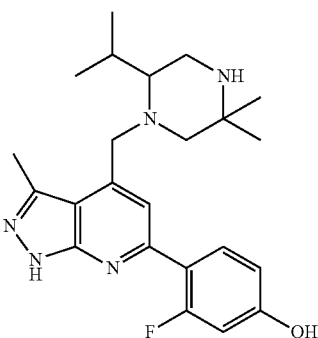 3-Fluoro-4-[4-(2-isopropyl-5,5-dimethyl-piperazin-1-ylmethyl)-3-methyl-1H-pyrazolo[3,4-b]pyridin-6-yl]-phenol | LC_4, 1.0 ml/min, Chiralpak AS-H; 4.6 × 250 mm, heptane:EtOH 15:1 + 0.1% DEA | 1 2 | 20.4 24.6 | LC9 LC9 | 412.26 412.26 | 1.26 1.26 |

| Exp. No. | Structure and chemical name of racemic mixture | Conditions of chiral sep. | No. of enantiomer | Rt [min] (chiral sep.) | LCMS method (non-chiral) | m/z [M + H]+ | Rt [min] (non-chiral) |
|---|---|---|---|---|---|---|---|
| 135 136 | 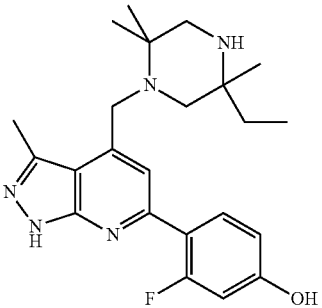 4-[4-(5-Ethyl-2,5,5-trimethyl-piperazin-1-ylmethyl)-3-methyl-1H-pyrazolo[3,4-b]pyridin-6-yl]-3-fluoro-phenol | LC_4, 1.0 ml/min, Chiralpak AS-H; 4.6 × 250 mm, heptane:EtOH:MeOH 20:1:1 + 0.1% DEA | 1 2 | 7.9 9.1 | LC9 LC9 | 412.27 412.26 | 1.19 1.18 |

| Exp. No. | Structure and chemical name of racemic mixture | Conditions of chiral sep. | No. of enantiomer | Rt [min] (chiral sep.) | LCMS method (non-chiral) | m/z [M + H]+ | Rt [min] (non-chiral) |
|---|---|---|---|---|---|---|---|
| 137<br>138 | 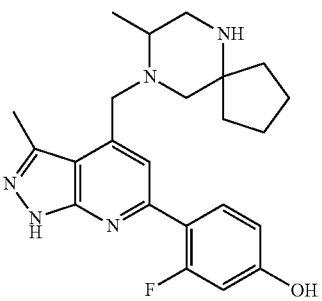<br>3-Fluoro-4-[3-methyl-4-(8-methyl-6,9-diaza-spiro-[4.5]dec-9-yl-methyl)-1H-pyrazolo[3,4-b]pyridin-6-yl]-phenol | LC_4, 1.0 ml/min, Chiralpak AS-H; 4.6 × 250 mm, heptane:EtOH:MeOH 30:1:1 + 0.1% DEA | 1<br>2 | 23.0<br>26.6 | LC9<br>LC9 | 410.14<br>410.18 | 1.17<br>1.17 |

| Exp. No. | Structure and chemical name of racemic mixture | Conditions of chiral sep. | No. of enantiomer | Rt [min] (chiral sep.) | LCMS method (non-chiral) | m/z [M + H]+ | Rt [min] (non-chiral) |
|---|---|---|---|---|---|---|---|
| 139<br>140 | 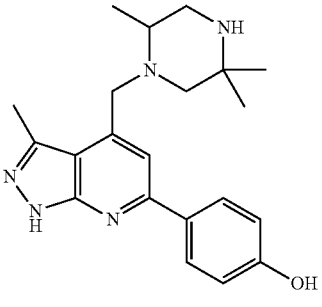<br>4-[3-Methyl-4-(2,5,5-trimethyl-piperazin-1-ylmethyl)-1H-pyrazolo[3,4-b]pyridin-6-yl]-phenol | LC_4, 1.0 ml/min, Chiralcel OD-H; 4.6 × 250 mm, heptane:EtOH 8:1 + 0.1% DEA | 1<br>2 | 13.4<br>23.4 | LC9<br>LC9 | 366.12<br>366.01 | 1.07<br>1.07 |

| Exp. No. | Structure and chemical name of racemic mixture | Conditions of chiral sep. | No. of enantiomer | Rt [min] (chiral sep.) | LCMS method (non-chiral) | m/z [M + H]+ | Rt [min] (non-chiral) |
|---|---|---|---|---|---|---|---|
| 141 142 | 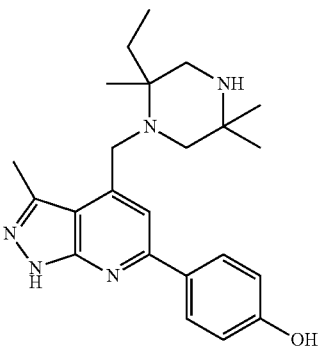 4-[4-(2-Ethyl-2,5,5-trimethyl-piperazin-1-ylmethyl)-3-methyl-1H-pyrazolo[3,4-b]pyridin-6-yl]-phenol | LC_4, 1.0 ml/min, Chiralpak AS-H; 4.6 × 250 mm, heptane:EtOH:MeOH 15:1:1 + 0.1% DEA | 1 2 | 8.3 11.2 | LC9 LC9 | 394.25 394.26 | 1.18 1.18 |

| Exp. No. | Structure and chemical name of racemic mixture | Conditions of chiral sep. | No. of enantiomer | Rt [min] (chiral sep.) | LCMS method (non-chiral) | m/z [M + H]+ | Rt [min] (non-chiral) |
|---|---|---|---|---|---|---|---|
| 143 144 | 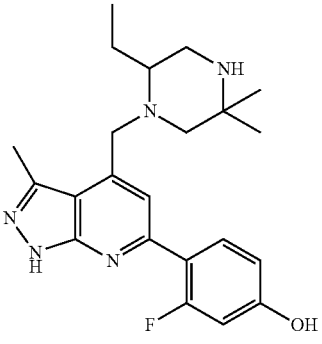 4-[4-(2-Ethyl-5,5-dimethyl-piperazin-1-ylmethyl)-3-methyl-1H-pyrazolo[3,4-b]pyridin-6-yl]-3-fluoro-phenol | LC_4, 1.0 ml/min, Chiralcel OD-H; 4.6 × 250 mm, heptane:EtOH 5:1 + 0.1% DEA | 1 2 | 6.6 8.6 | LC9 LC9 | 398.28 398.27 | 1.37 1.37 |

| Exp. No. | Structure and chemical name of racemic mixture | Conditions of chiral sep. | No. of enantiomer | Rt [min] (chiral sep.) | LCMS method (non-chiral) | m/z [M + H]+ | Rt [min] (non-chiral) |
|---|---|---|---|---|---|---|---|
| 145 | 4-[4-(2-Ethyl-5,5-dimethyl-piperazin-1-ylmethyl)-3-methyl-1H-pyrazolo[3,4-b]pyridin-6-yl]-phenol | LC_4, 1.0 ml/min, Chiralcel OD-H; 4.6 × 250 mm, heptane:EtOH 5:1 + 0.1% DEA | 1 | 8.3 | LC9 | 378.24 | 1.15 |
| 146 | | | 2 | 11.3 | LC9 | 378.22 | 1.15 |

| Exp. No. | Structure and chemical name of racemic mixture | Conditions of chiral sep. | No. of enantiomer | Rt [min] (chiral sep.) | LCMS method (non-chiral) | m/z [M + H]+ | Rt [min] (non-chiral) |
|---|---|---|---|---|---|---|---|
| 147 | 4-[4-(3-Amino-3-methyl-piperidin-1-ylmethyl)-3-methyl-1H-pyrazolo[3,4-b]pyridin-6-yl]-3-fluoro-phenol | 1.0 ml/min, Chiralpak AD-H; 4.6 × 250 mm, heptane:EtOH:MeOH 8:1:1 + 0.1% DEA | 1 | 10.8 | LC4 | 370.1 | 0.63 |
| 148 | | | 2 | 12.9 | LC4 | 370.1 | 0.63 |

| Exp. No. | Structure and chemical name of racemic mixture | Conditions of chiral sep. | No. of enantiomer | Rt [min] (chiral sep.) | LCMS method (non-chiral) | m/z [M + H]+ | Rt [min] (non-chiral) |
|---|---|---|---|---|---|---|---|
| 149 | 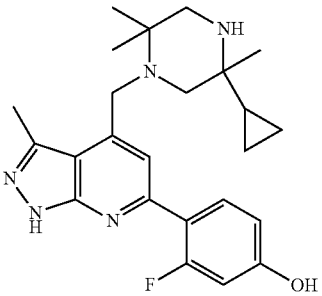<br>4-[4-(5-Cyclopropyl-2,5,5-trimethyl-piperazin-1-ylmethyl)-3-methyl-1H-pyrazolo[3,4-b]pyridin-6-yl]-3-fluoro-phenol | ClH 1.0 ml/min, Chiralcel (2x) OD- 4.6 × 250 mm, heptane: EtOH: MeOH 30:1:1 + 0.1% DEA | 1 | 35.3 | LC9 | 423.24 | 1.34 |
| 150 | | | 2 | 39.7 | LC9 | 423.24 | 1.35 |

| Exp. No. | Structure and chemical name of diastereomeric mixture | Conditions of chiral sep. | No. of diastereomer | Rt [min] (chiral sep.) | LCMS method (non-chiral) | m/z [M + H]+ | Rt [min] (non-chiral) |
|---|---|---|---|---|---|---|---|
| 151 | 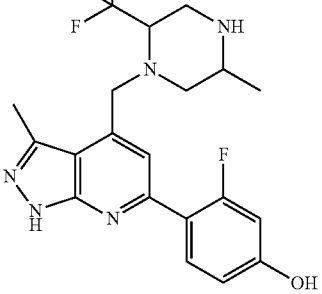<br>3-Fluoro-4-[3-methyl-4-(5-methyl-2-trifluoromethyl-piperazin-1-ylmethyl)-1H-pyrazolo[3,4-b]pyridin-6-yl]-phenol | LC_4, 1.0 ml/min, Chiralpak AD-H; 4.6 × 250 mm, heptane: EtOH 5:1 + 0.1% DEA | 1 | 7.1 | LC9 | 424.29 | 1.15 |
| 152 | | | 2 | 8.8 | LC9 | 424.17 | 1.11 |
| 153 | | | 3 | 9.7 | LC9 | 424.18 | 1.15 |
| 154 | | | 4 | 14.9 | LC9 | 424.24 | 1.11 |

Synthesis of Intermediates

1-Benzyl-3,3-dimethyl-piperazine

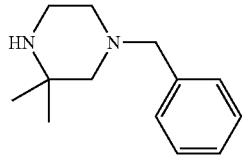

(a) 4-Benzyl-2,2-dimethyl-piperazine-1-carboxylic acid tert-butyl ester

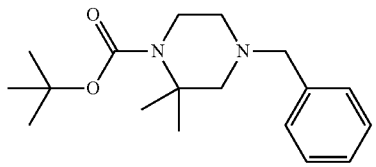 [SMILES: CC(C)(C)OC(=O)N1CCN(Cc2ccccc2)CC1(C)C]

To a solution of 2.20 g of 2,2-dimethyl-piperazine-1-carboxylic acid tert-butyl ester in 50 ml DCM was added 1.15 ml of benzaldehyde, followed by the addition of 2.61 g of sodium triacetoxyborohydride in small portions. The reaction was stirred at r.t. overnight. To the reaction was then added water. The layers were separated and the organic layer was washed with brine, dried over $Na_2SO_4$, filtered and concentrated in vacuo. 3.30 g (100%) of the title compound were obtained and used without further purification.

LC/MS (Method LC4): Rt=0.67 min; m/z=305.20 [M+H]$^+$.

(b) 1-Benzyl-3,3-dimethyl-piperazine

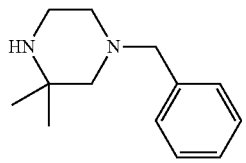

3.30 g of 4-benzyl-2,2-dimethyl-piperazine-1-carboxylic acid tert-butyl ester were dissolved in 50 ml methanol, and 25 ml of 1N aqueous hydrochloric acid were added. After stirring overnight 5 ml of concentrated aqueous hydrochloric acid were added. After 2 h the volatiles were removed in vacuo and 2.40 g (97%) of the title compound were obtained as hydrochloride salt, which could be use without further purification.

LC/MS (Method LC4): Rt=0.15 min; m/z=205.10 [M+H]$^+$.

trans-1-Benzyl-5-methyl-2-phenyl-piperazine

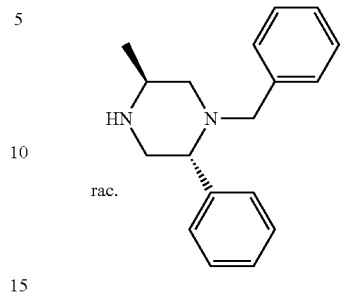

trans-1-Benzyl-5-methyl-2-phenyl-piperazine was prepared in analogy to the preparation of benzyl-2,5-dimethyl-piperazine (see above) starting form trans-2-methyl-5-phenyl-piperazine-1-carboxylic acid tert-butyl ester.

LC/MS (Method LC4): Rt=0.64 min; m/z=267.15 [M+H]$^+$.

1-Benzyl-2,2,5-trimethyl-piperazine

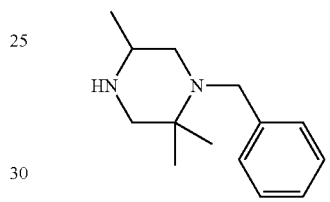

1-Benzyl-2,2,5-trimethyl-piperazine was prepared in analogy to the preparation of benzyl-2,5-dimethyl-piperazine (see above) starting form 2,5,5-trimethyl-piperazine-1-carboxylic acid tert-butyl ester.

LC/MS (Method LC4): Rt=0.15 min; m/z=219.20 [M+H]$^+$.

(2R,5S)-2-Ethyl-1-(4-methoxy-benzyl)-5-methyl-piperazine

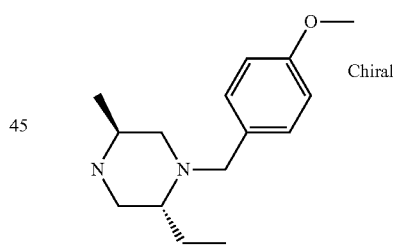

(a) (R)-2-(4-Methoxy-benzylamino)-butyric acid methyl ester

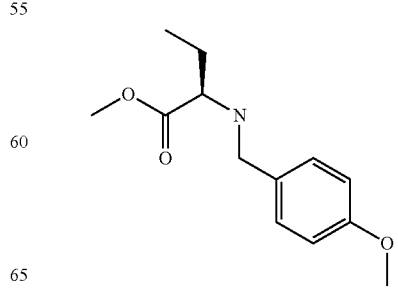

10.0 g of p-methoxybenzaldehyde and 12.98 g of methyl D-homoalaninate-hydrochloride were dissolved in 160 ml of DCM and at 0° C. 11.35 ml of TEA were added. After 10 min at 0° C. 23.36 g of sodium triacetoxyborohydride were added in small portions. The reaction was stirred at r.t. overnight. To the reaction was then added aqueous sodium carbonate solution (10%). The layers were separated and the organic layer was washed with water until neutral, dried over $Na_2SO_4$, filtered and concentrated in vacuo. 18.72 g of the title compound were obtained and used without further purification.

LC/MS (Method LC4): Rt=0.43 min; m/z=238.15 $[M+H]^+$.

(b) (R)-2-[((S)-2-tert-Butoxycarbonylamino-propionyl)-(4-methoxy-benzyl)-amino]-butyric acid methyl ester

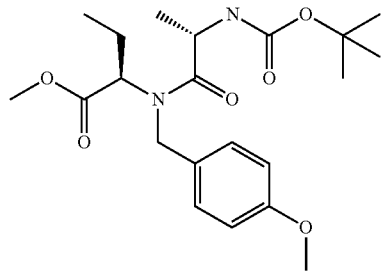 [SMILES: CC[C@H](C(=O)OC)N(Cc1ccc(OC)cc1)C(=O)[C@H](C)NC(=O)OC(C)(C)C]

To a solution of 3.99 g of Boc-L-alanine in 50 ml of DMF were added 12.02 g of HATU, 4.3 ml of Hünig's base and 5.00 g (R)-2-(4-Methoxy-benzylamino)-butyric acid methyl ester. The reation was stirred overnight, and 6.01 g of HATU and 2.1 ml of Hünig's base were added, and the reaction was stirred for 24 h at r.t. and then for 4 h at 50° C. The reaction was poured unto water, the layers were separated and the aqueous phase was extracted with EtOAc twice. The combined organic layers wer washed with 10% aqueous citric acid twice, dried over $Na_2SO_4$, fitrered and concentrated in vacuo. The residue was purified by flash chromatography (silica, heptane/EtOAc) to obtain 7.60 g (88%) of the title compound.

LC/MS (Method LC4): Rt=0.89 min; m/z=409.15 $[M+H]^+$.

(c) (3S,6R)-6-Ethyl-1-(4-methoxy-benzyl)-3-methyl-piperazine-2,5-dione

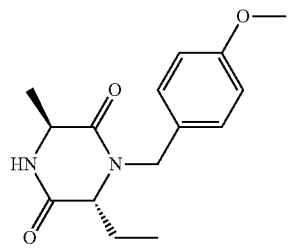 [SMILES: CC[C@@H]1C(=O)N[C@@H](C)C(=O)N1Cc1ccc(OC)cc1]

To a solution of 7.60 g of (R)-2-[((S)-2-tert-butoxycarbonylamino-propionyl)-(4-methoxy-benzyl)-amino]-butyric acid methyl ester in 116 ml DCM were added 116 ml of TFA at 0° C. during 1 h. After 2 h at 0° C. the reaction mixture was allowed to come to r.t. and stirred for another 1.5 h. The reaction mixture was then concentrated in vacuo, dissolved in EtOAc, and 120 ml of 1M aqueous $NaHCO_3$-solution were added. After stirring for 1 h, the layers were separated. The organic layer was washed with brine, dried over $Na_2SO_4$ and concentrated in vacuo to yield 5.34 g (100%) of the title compound, which was used without further purification.

LC/MS (Method LC4): Rt=0.59 min; m/z=277.15 $[M+H]^+$.

(d) (2R,5S)-2-Ethyl-1-(4-methoxy-benzyl)-5-methyl-piperazine

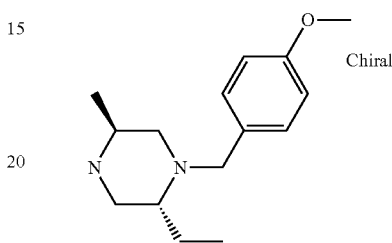

To a mixture of (3S,6R)-6-ethyl-1-(4-methoxy-benzyl)-3-methyl-piperazine-2,5-dione (5.34 g) in 130 ml of THF was added 160 ml of a 1 M solution of lithium aluminium hydride in THF. The mixture was stirred overnight and then heated to reflux for 4 h. At 0° C. 5 ml of water, followed by 16 ml of 1 M aqueous KOH-solution were added. The resulting suspension was stirred for 30 min at r.t. and filtered by suction over Celite. The filtrate was concentrated in vacuo and freeze-dried. 3.68 g (77%) of the title compound were obtained and used without further purification.

LC/MS (Method LC4): Rt=0.14 min; m/z=249.20 $[M+H]^+$.

8,8-Dimethyl-6,9-diaza-spiro[4.5]decane-9-carboxylic acid tert-butyl ester

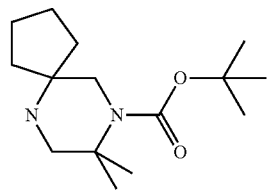 [SMILES: CC(C)(C)OC(=O)N1CC2(CCCC2)NCC1(C)C]

(a) 8,8-Dimethyl-6,9-diaza-spiro[4.5]decan-10-one

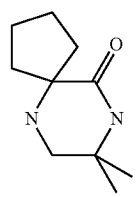

To a solution of 6.1 ml of 1,2-diamino-2-methylpropane in 17 ml water 5.7 ml of 1-hydroxycyclopentane-1-carbonitrile was slowly added. The reaction was kept at reflux for 48 h, and the cooled to r.t. The precipitated product was isolated by suction and washed with water. From the filtrate additional solid could be obtained. The combined solids were freeze-dried and 9.32 g (90%) of the title compound were obtained, which could be used in the next step without further purification.

LC/MS (Method LC4): Rt=0.06 min; m/z=183.10 [M+H]$^+$.

(b) 6-Benzyl-8,8-dimethyl-6,9-diaza-spiro[4.5]decan-10-one

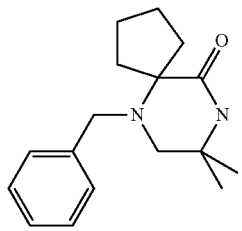 [SMILES: CC1(C)CN(Cc2ccccc2)C2(CCCC2)C(=O)N1]

To a solution of 6.72 g of 8,8-dimethyl-6,9-diaza-spiro[4.5]decan-10-one in 35 ml of DMF were added 4.8 ml of benzyl bromide and 6.9 ml of Hünig's base. The reaction was stirred at r.t overnight. The precipitated product was isolated by suction and washed with DMF and EtOAc. The filtrate was concentrated and the resulting residue was dissolved in EtOAc, washed with water, dried over Na$_2$SO$_4$, filtered and concentrated to yield a second fraction of the product. 9.62 g (96%) of the title compound were obtained.

LC/MS (Method LC4): Rt=0.62 min; m/z=273.20 [M+H]$^+$.

(c) 6-Benzyl-8,8-dimethyl-6,9-diaza-spiro[4.5]decane

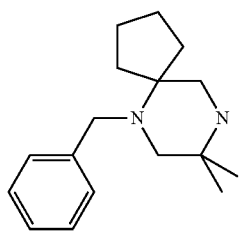 [SMILES: CC1(C)CN(Cc2ccccc2)C2(CCCC2)CN1]

Under Argon atmosphere to a solution of 10.78 g of 6-benzyl-8,8-dimethyl-6,9-diaza-spiro[4.5]decan-10-one in 160 ml of THF 33 ml of a 2.4 M solution of lithium aluminium hydride in THF were slowly added. The reaction was heated to 55° C., and 5 ml of chlorotrimethylsilane were added dropwise. The reaction was kept at 55-60° C. for 2.5 h and then cooled to 0° C. 16 ml of water were added dropwise, and THF was added. The mixture was filtered by suction over celite and the filtrate was concentrated in vacuo. The product was precipitated by treatment with methyl tert-butyl ether. 9.47 g (93%) of the title compound were obtained.

LC/MS (Method LC4): Rt=0.63 min; m/z=259.25 [M+H]$^+$.

(d) 6-Benzyl-8,8-dimethyl-6,9-diaza-spiro[4.5]decane-9-carboxylic acid tert-butyl ester

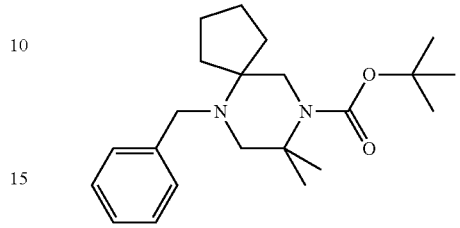

4.5 g of 6-benzyl-8,8-dimethyl-6,9-diaza-spiro[4.5]decane were dissolved in 40 ml of DCM and 4.18 g of di-tert-butyl dicarbonate were added. After stirring at r.t. for 1 h the reaction was concentrated in vacuo to yield 6.8 g (100%) of the title compound, which was used without further purification.

LC/MS (Method LC4): Rt=0.77 min; m/z=359.20 [M+H]$^+$.

(e) 8,8-Dimethyl-6,9-diaza-spiro[4.5]decane-9-carboxylic acid tert-butyl ester

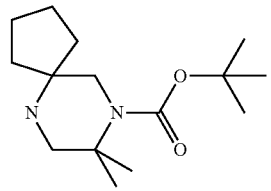 [SMILES: CC(C)(C)OC(=O)N1CC2(CCCC2)NCC1(C)C]

To 7.58 g of 6-benzyl-8,8-dimethyl-6,9-diaza-spiro[4.5]decane-9-carboxylic acid tert-butyl ester in 140 ml of methanol was added 1.13 g Palladium on charcoal (10%) and the mixture was hydrogenated at r.t. and ambient pressure for 16 h. The catalyst was removed by filtration over celite and the filtrate was concentrated in vacuo to yield 5.38 g (95%) of the title compound, which was used without further purification.

LC/MS (Method LC4): Rt=0.66 min; m/z=269.25 [M+H]$^+$.

1-Benzyl-2,2,5,5-tetramethyl-piperazine

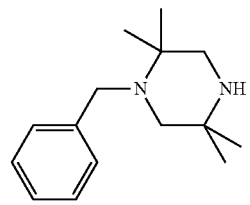 [SMILES: CC1(C)CN(Cc2ccccc2)C(C)(C)CN1]

1-Benzyl-2,2,5,5-tetramethyl-piperazine was synthesized in analogy to 6-benzyl-8,8-dimethyl-6,9-diaza-spiro[4.5]decane starting from 2-methyl-propane-1,2-diamine and acetone cyanohydrin.

LC/MS (Method LC5): Rt=0.99 min; m/z=233.20 [M+H]⁺.

1-Benzyl-5-ethyl-2,2,5-trimethyl-piperazine

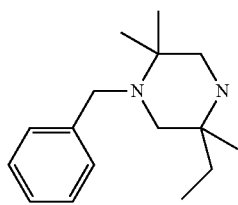 [SMILES: CCC1(C)CN(Cc2ccccc2)C(C)(C)CN1]

1-Benzyl-5-ethyl-2,2,5-trimethyl-piperazine was synthesized in analogy to 6-benzyl-8,8-dimethyl-6,9-diaza-spiro[4.5]decane starting from 2-methylbutane 1,2-diamine and acetone cyanohydrin.

LC/MS (Method LC4): Rt=0.59 min; m/z=247.20 [M+H]⁺.

2-Ethyl-2,5,5-trimethyl-piperazine-1-carboxylic acid tert-butyl ester

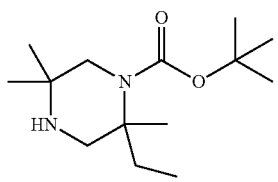 [SMILES: CCC1(C)CNC(C)(C)CN1C(=O)OC(C)(C)C]

2-Ethyl-2,5,5-trimethyl-piperazine-1-carboxylic acid tert-butyl ester was synthesized in analogy to 8,8-dimethyl-6,9-diaza-spiro[4.5]decane-9-carboxylic acid tert-butyl ester starting from 2-methylbutane 1,2-diamine and acetone cyanohydrin.

LC/MS (Method LC4): Rt=0.64 min; m/z=257.2 [M+H]⁺.

1-Benzyl-5,5-diethyl-2,2-dimethyl-piperazine

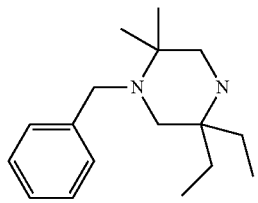 [SMILES: CCC1(CC)CN(Cc2ccccc2)C(C)(C)CN1]

1-Benzyl-5,5-diethyl-2,2-dimethyl-piperazine was synthesized in analogy to 6-benzyl-8,8-dimethyl-6,9-diaza-spiro[4.5]decane starting from 3-(aminomethyl)pentane-3-amine and acetone cyanohydrin.

LC/MS (Method LC4): Rt=0.65 min; m/z=261.20 [M+H]⁺.

2,2-Diethyl-5,5-dimethyl-piperazine-1-carboxylic acid tert-butyl ester

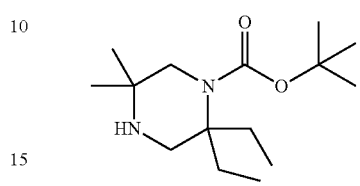

2,2-Diethyl-5,5-dimethyl-piperazine-1-carboxylic acid tert-butyl ester was synthesized in analogy to 8,8-dimethyl-6,9-diaza-spiro[4.5]decane-9-carboxylic acid tert-butyl ester starting from 2-ethyl-butane-1,2-diamine and acetone cyanohydrin.

LC/MS (Method LC4): Rt=0.69 min; m/z=271.2 [M+H]⁺.

6-Benzyl-8-methyl-6,9-diaza-spiro[4.5]decane

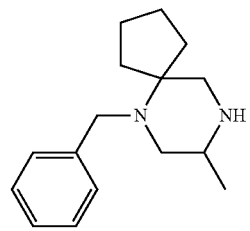 [SMILES: CC1CN(Cc2ccccc2)C2(CCCC2)CN1]

6-Benzyl-8-methyl-6,9-diaza-spiro[4.5]decane was synthesized in analogy to 6-benzyl-8,8-dimethyl-6,9-diaza-spiro[4.5]decane starting from 1,2-diamino-propane and 1-hydroxycyclopentane-1-carbonitrile.

LC/MS (Method LC4): Rt=0.22 min; m/z=245.20 [M+H]⁺.

8-Methyl-6,9-diaza-spiro[4.5]decane-9-carboxylic acid tert-butyl ester

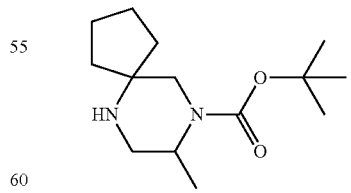

8-Methyl-6,9-diaza-spiro[4.5]decane-9-carboxylic acid tert-butyl ester was synthesized in analogy to 8,8-dimethyl-6,9-diaza-spiro[4.5]decane-9-carboxylic acid tert-butyl ester starting from 1,2-diamino-propane and 1-hydroxycyclopentane-1-carbonitrile.

LC/MS (Method LC4): Rt=0.56 min; m/z=255.20 [M+H]⁺.

1-Benzyl-5-cyclopropyl-2,2,5-trimethyl-piperazine

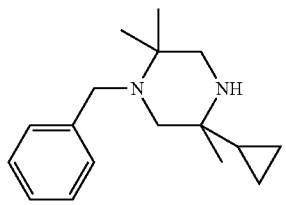 [SMILES: CC1(C2CC2)CN(Cc2ccccc2)C(C)(C)CN1]

1-Benzyl-5-cyclopropyl-2,2,5-trimethyl-piperazine was synthesized in analogy to 6-benzyl-8,8-dimethyl-6,9-diaza-spiro[4.5]decane starting from 2-cyclopropyl-propane-1,2-diamine and acetone cyanohydrin.

LC/MS (Method LC4): Rt=0.65 min; m/z=259.10 [M+H]⁺.

2-Cyclopropyl-2,5,5-trimethyl-piperazine-1-carboxylic acid tert-butyl ester

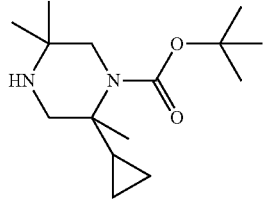 [SMILES: CC1(C)CN(C(=O)OC(C)(C)C)C(C)(C2CC2)CN1]

2-Cyclopropyl-2,5,5-trimethyl-piperazine-1-carboxylic acid tert-butyl ester was synthesized in analogy to 8,8-dimethyl-6,9-diaza-spiro[4.5]decane-9-carboxylic acid tert-butyl ester starting from 2-cyclopropyl-propane-1,2-diamine and acetone cyanohydrin.

LC/MS (Method LC4): Rt=0.68 min; m/z=269.20 [M+H]⁺.

1-Benzyl-5-isopropyl-2,2-dimethyl-piperazine

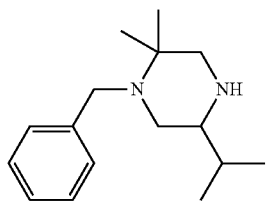 [SMILES: CC(C)C1CN(Cc2ccccc2)C(C)(C)CN1]

1-Benzyl-5-isopropyl-2,2-dimethyl-piperazine was synthesized in analogy to 6-benzyl-8,8-dimethyl-6,9-diaza-spiro[4.5]decane starting from 3-methyl-butane-1,2-diamine and acetone cyanohydrin.

LC/MS (Method LC4): Rt=0.29 min; m/z=247.2.10 [M+H]⁺.

2-Isopropyl-5,5-dimethyl-piperazine-1-carboxylic acid tert-butyl ester

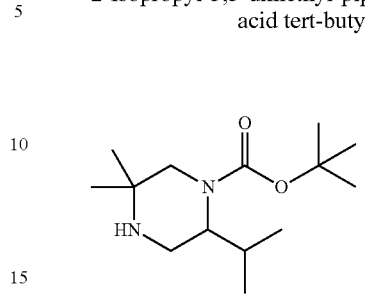

2-Isopropyl-5,5-dimethyl-piperazine-1-carboxylic acid tert-butyl ester was synthesized in analogy to 8,8-dimethyl-6,9-diaza-spiro[4.5]decane-9-carboxylic acid tert-butyl ester starting from 3-methyl-butane-1,2-diamine and acetone cyanohydrin.

LC/MS (Method LC4): Rt=0.63 min; m/z=257.2.10 [M+H]⁺.

1-Benzyl-5-ethyl-2,2-dimethyl-piperazine

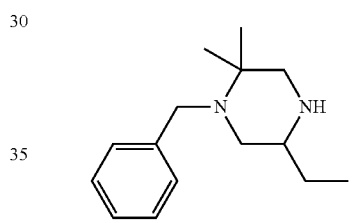

1-Benzyl-5-ethyl-2,2-dimethyl-piperazine was synthesized in analogy to 6-benzyl-8,8-dimethyl-6,9-diaza-spiro[4.5]decane starting from butane-1,2-diamine and acetone cyanohydrin.

LC/MS (Method LC4): Rt=0.21 min; m/z 233.20 [M+H]⁺.

2-Methyl-5-trifluoromethyl-piperazine-1-carboxylic acid tert-butyl ester

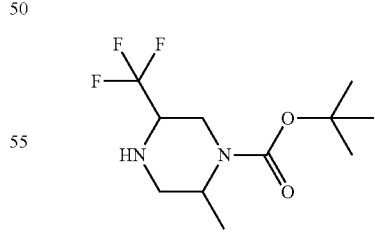

To a solution of 5.0 g 2-methyl-5-trifluoromethyl-piperazine in 50 ml dichloromethane was added 6.5 g di-tert-butyl dicarbonate and the reaction was stirred at r.t. for 1.5 h. Then the volatiles were removed in vacuo and 7.2 g (91%) of the title compound were obtained.

LC/MS (Method LC4): Rt=0.60 min; m/z=213.10 [M-FH-tBu]⁺.

Determination of PKC βII Inhibition

PKC βII inhibition was determined according to the following protocol:

Active human full-length recombinant PKC βII and the peptide substrate, Fluorescein-RFARKGSLRQKNV, were purchased from Invitrogen GmbH, Darmstadt, Germany. Adenosine-5'-triphosphate (ATP), bovine serum albumine (BSA), dimethylsulphoxide (DMSO), 4-(2-hydroxyethyl) piperazine-1-ethanesulfonic acid (Hepes), Triton X-100, 1,2-Dioleoyl-sn-glycerol (DAG), L-α-Phosphatidyl-L-serine (PS), calcium chloride ($CaCl_2$), and Pluronic F-68 were purchased from Sigma-Aldrich, Munich, Germany. Magnesium chloride, 1 M sodium hydroxide solution, 1M hydrochloric acid solution and EDTA were obtained from Merck Biosciences, Darmstadt, Germany.

Test compounds were diluted to three times the test concentration in buffer 1 (30 mM Hepes-NaOH, pH 7.4, 0.01% Pluronic F-68 and 3% (v/v) DMSO). The PKC 011 enzyme was diluted to a concentration of 30 ng/ml in buffer 2 (30 mM Hepes-NaOH, pH 7.4, 15 mM $MgCl_2$, 150 μM $CaCl_2$, 150 μg/ml PS, 60 μg/ml DAG, and 0.045% (w/v) Triton X-100). The peptide substrate and ATP were diluted to concentrations of 3 μM and 120 μM, respectively, in buffer 2. Two μl of the compound solution were mixed with 2 μl of the diluted enzyme in a 384-well small volume microtiter plate (Greiner, Bio-One, Frickenhausen, Germany), and the kinase reaction was initiated by addition of 2 μl of the solution containing peptide substrate and ATP. After 60 min incubation at 32° C., the reaction was stopped by addition of 20 μl of a solution containing 130 mM Hepes-NaOH, pH 7.4, 0.0195% (v/v) Brij-35, 6.5 mM EDTA, 0.13% chip coating reagent 3 (Caliper Lifescience Inc, Hopkinton, Mass.) and 6.5% (v/v) DMSO. Phosphorylation of the substrate peptide was then detected on a Caliper 3000 instrument essentially as described by Pommereau et al (J. Biomol. Screening 2004, 9(5), 409-416). Separation conditions were as follows: Pressure −0.8 psi, upstream voltage −3000 V, downstream voltage −800 V. Positive controls (buffer 1 instead of compound) and negative controls (buffer 1 instead of compound and buffer 2 instead of kinase solution) were run in parallel on each plate. Fractional turnover (R) was determined as the height of the peak of the phosphorylated peptide product divided by the sum of the unphosphorylated substrate and phosphorylated product peak heights. Percent-inhibition values for the test compounds were determined using the formula % Inhibition=$100*(1-(R_{compound}-R_{negative\ control})/(R_{positive\ control}-R_{negative\ control})$.

In the following table % inhibition values observed with example compounds at a final concentration of 1.14 μM (±0.15 μM) are listed:

| Exp. No. | % Inhibition |
| --- | --- |
| 1 | 95 |
| 2 | 65 |
| 3 | 68 |
| 4 | 94 |
| 5 | 109 |
| 6 | 91 |
| 7 | 103 |
| 8 | 92 |
| 9 | 81 |
| 10 | 102 |
| 11 | 104 |
| 12 | 94 |
| 13 | 81 |
| 14 | 98 |
| 15 | 96 |
| 16 | 99 |
| 17 | 98 |
| 18 | 98 |
| 19 | 99 |
| 20 | 98 |
| 21 | 93 |
| 22 | 89 |
| 23 | 99 |
| 24 | 94 |
| 25 | 102 |
| 26 | 92 |
| 27 | 83 |
| 28 | 97 |
| 29 | 90 |
| 30 | 97 |
| 31 | 101 |
| 32 | 101 |
| 33 | 93 |
| 34 | 73 |
| 35 | 78 |
| 36 | 94 |
| 37 | 94 |
| 38 | 99 |
| 39 | 100 |
| 40 | 97 |
| 41 | 93 |
| 42 | 94 |
| 43 | 58 |
| 44 | 38 |
| 45 | 54 |
| 46 | 90 |
| 47 | 101 |
| 48 | 99 |
| 49 | 95 |
| 50 | 96 |
| 51 | 98 |
| 52 | 91 |
| 53 | 99 |
| 54 | 98 |
| 55 | 86 |
| 56 | 85 |
| 57 | 93 |
| 58 | 91 |
| 59 | 96 |
| 60 | 92 |
| 61 | 84 |
| 62 | 99 |
| 63 | 97 |
| 64 | 94 |
| 65 | 88 |
| 66 | 100 |
| 67 | 103 |
| 68 | 101 |
| 69 | 92 |
| 70 | 96 |
| 71 | 98 |
| 72 | 100 |
| 73 | 97 |
| 74 | 95 |
| 75 | 96 |
| 76 | 95 |
| 77 | 98 |
| 78 | 97 |
| 79 | 65 |
| 80 | 93 |
| 81 | 97 |
| 82 | 85 |
| 83 | 69 |
| 84 | 98 |
| 85 | 101 |
| 86 | 86 |
| 87 | 92 |
| 88 | 89 |
| 89 | 76 |
| 90 | 99 |
| 91 | 81 |
| 92 | 99 |

-continued

| Exp. No. | % Inhibition |
|---|---|
| 93 | 81 |
| 94 | 92 |
| 95 | 53 |
| 96 | 74 |
| 97 | 96 |
| 98 | 87 |
| 99 | 92 |
| 100 | 86 |
| 101 | 52 |
| 102 | 85 |
| 103 | 53 |
| 104 | 83 |
| 105 | 100 |
| 106 | 104 |
| 107 | 101 |
| 108 | 102 |
| 109 | 91 |
| 110 | 42 |
| 111 | 88 |
| 112 | 85 |
| 113 | 81 |
| 114 | 57 |
| 115 | 94 |
| 116 | 95 |
| 117 | 99 |
| 118 | 84 |
| 119 | 86 |
| 120 | 102 |
| 121 | 100 |
| 122 | 100 |
| 123 | 88 |
| 124 | 83 |
| 125 | 87 |
| 126 | 91 |
| 127 | 87 |
| 128 | 71 |
| 129 | 97 |
| 130 | 98 |
| 131 | 103 |
| 132 | 97 |
| 133 | 103 |
| 134 | 102 |
| 135 | 106 |
| 136 | 104 |
| 137 | 98 |
| 138 | 98 |
| 139 | 95 |
| 140 | 98 |
| 141 | 98 |
| 142 | 100 |
| 143 | 101 |
| 144 | 98 |
| 145 | 95 |
| 146 | 99 |
| 147 | 100 |
| 148 | 99 |
| 149 | 98 |
| 150 | 100 |
| 151 | 90 |
| 152 | 93 |
| 153 | 97 |
| 154 | 92 |

What is claimed is:

1. A compound of formula I

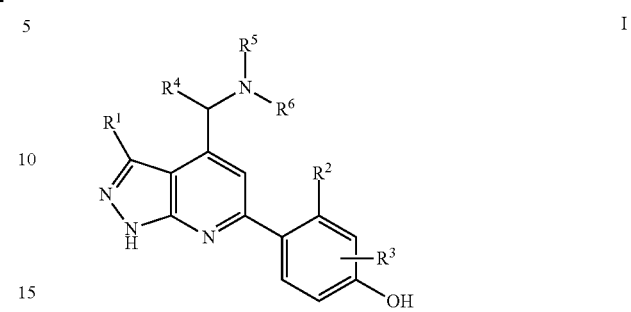

wherein
$R^1$ is $(C_1-C_4)$-alkyl, $CF_3$, cyclopropyl or cyclobutyl;
$R^2$ is H, halogen, methyl or $CF_3$;
$R^3$ is H, halogen, methyl or $CF_3$;
$R^4$ is H, $(C_1-C_4)$-alkyl or $CF_3$;
$R^5$ is H or $(C_1-C_4)$-alkyl;
$R^6$ is a 4- to 8-membered monocyclic heterocycle comprising a ring nitrogen, which is unsubstituted or mono- or disubstituted by $(C_1-C_4)$-alkyl, wherein alkyl is unsubstituted or one to threefold substituted by F; or
$R^5$ and $R^6$ together with the N-atom carrying them denote
a) a 1,4-piperazinyl of the formula

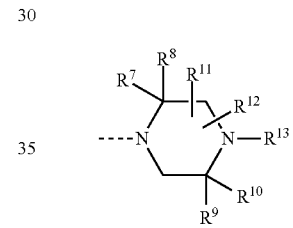

wherein
$R^7$ is H, $(C_1-C_4)$-alkyl, cyclopropyl, cyclobutyl or phenyl, wherein alkyl is unsubstituted or one to threefold substituted by F, wherein phenyl is unsubstituted or mono- or disubstituted by halogen, $CF_3$, $(C_1-C_4)$-alkyl, $O-CF_3$ or $O-(C_1-C_4)$-alkyl;
$R^8$ is H or $(C_1-C_4)$-alkyl;
or
$R^7$ and $R^8$ together with the carbon atom carrying them denote $(C_3-C_6)$-cycloalkyl;
$R^9$ is H, $(C_1-C_4)$-alkyl, cyclopropyl, cyclobutyl or phenyl, wherein alkyl is unsubstituted or one to threefold substituted by F, wherein phenyl is unsubstituted or mono- or disubstituted by halogen, $CF_3$, $(C_1-C_4)$-alkyl, $O-CF_3$ or $O-(C_1-C_4)$-alkyl;
$R^{10}$ is H or $(C_1-C_4)$-alkyl;
or
$R^9$ and $R^{10}$ together with the carbon atom carrying them denote $(C_3-C_6)$-cycloalkyl;
$R^{11}$ is H or $(C_1-C_4)$-alkyl;
$R^{12}$ is H or $(C_1-C_4)$-alkyl;
$R^{13}$ is
  i) H;
  ii) $(C_1-C_4)$-alkyl, which is unsubstituted or one to twofold substituted by
    a. $CF_3$,
    b. OH,
    c. $O-(C_1-C_4)$-alkyl, d. phenyl,
e. thienyl
f. pyridyl,
g. tetrahydrofuranyl,
h. tetrahydropyranyl,
i. 2,2'-dimethyl-1,3-dioxolanyl,
j. C(O)—O—($C_1$-$C_4$)-alkyl,
k. NH—($C_1$-$C_4$)-alkyl,
l. N(($C_1$-$C_4$)-alkyl)$_2$;
iii) C(O)—($C_1$-$C_4$)-alkyl which is unsubstituted or monosubstituted by
   a. OH,
   b. O—$CF_3$,
   c. O—($C_1$-$C_4$)-alkyl;
iv) C(O)-tetrahydrofuranyl,
v) C(O)-tetrahydropyranyl,
vi) C(O)—NH—($C_1$-$C_4$)-alkyl,
vii) C(O)—N(($C_1$-$C_4$)-alkyl)$_2$,
viii) C(O)—NH—($C_1$-$C_4$)-alkylene-COO($C_1$-$C_4$)-alkyl;
b) a morpholinyl of the formula

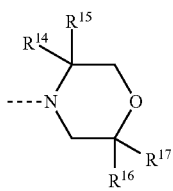

wherein
$R^{14}$ is H, ($C_1$-$C_4$)-alkyl, cyclopropyl, cyclobutyl or phenyl, wherein alkyl is unsubstituted or one to threefold substituted by F, wherein phenyl is unsubstituted or mono- or disubstituted by halogen, $CF_3$, ($C_1$-$C_4$)-alkyl, O—$CF_3$ or O—($C_1$-$C_4$)-alkyl;
$R^{15}$ is H or ($C_1$-$C_4$)-alkyl;
or
$R^{14}$ and $R^{15}$ together with the carbon atom carrying them denote ($C_3$-$C_6$)-cycloalkyl;
$R_{16}$ is H, ($C_1$-$C_4$)-alkyl, cyclopropyl, cyclobutyl or phenyl, wherein alkyl is unsubstituted or one to threefold substituted by F, wherein phenyl is unsubstituted or mono- or disubstituted by halogen, $CF_3$, ($C_1$-$C_4$)-alkyl, O—$CF_3$ or O—($C_1$-$C_4$)-alkyl;
$R^{17}$ is H or ($C_1$-$C_4$)-alkyl;
or
$R^{16}$ and $R^{17}$ together with the carbon atom carrying them denote ($C_3$-$C_6$)-cycloalkyl;
c) a ring A of the formula

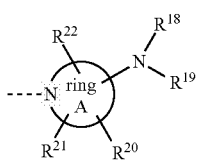

comprising one nitrogen and 3 to 6 carbon ring atoms, wherein the substituent $NR^{18}R^{19}$ is not in an adjacent position to the ring nitrogen atom and
$R^{18}$ is H, ($C_1$-$C_4$)-alkyl or C(O)—($C_1$-$C_4$)-alkylene-O—($C_1$-$C_4$)-alkyl;
$R^{19}$ is H or ($C_1$-$C_4$)-alkyl;
$R^{20}$ is H or ($C_1$-$C_4$)-alkyl;
$R^{21}$ is H or ($C_1$-$C_4$)-alkyl;
$R^{22}$ is H or ($C_1$-$C_4$)-alkyl;
d) a 1,4-diazepin of the formula

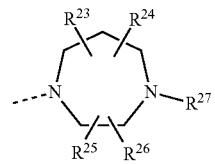

wherein
$R^{23}$ is H, ($C_1$-$C_4$)-alkyl, cyclopropyl, cyclobutyl or phenyl, wherein alkyl is unsubstituted or one to threefold substituted by F, wherein phenyl is unsubstituted or mono- or disubstituted by halogen, $CF_3$, ($C_1$-$C_4$)-alkyl, O—$CF_3$ or O—($C_1$-$C_4$)-alkyl;
$R^{24}$ is H or ($C_1$-$C_4$)-alkyl;
or
$R^{23}$ and $R^{24}$ together with the carbon atom carrying them denote ($C_3$-$C_6$)-cycloalkyl;
$R^{25}$ is H, ($C_1$-$C_4$)-alkyl, cyclopropyl, cyclobutyl or phenyl, wherein alkyl is unsubstituted or one to threefold substituted by F, wherein phenyl is unsubstituted or mono- or disubstituted by halogen, $CF_3$, ($C_1$-$C_4$)-alkyl, O—$CF_3$ or O—($C_1$-$C_4$)-alkyl;
$R^{26}$ is H or ($C_1$-$C_4$)-alkyl;
or
$R^{25}$ and $R^{26}$ together with the carbon atom carrying them denote ($C_3$-$C_6$)-cycloalkyl;
$R^{27}$ is
i) H;
ii) ($C_1$-$C_4$)-alkyl, which is unsubstituted or one to twofold substituted by
   a. $CF_3$,
   b. OH,
   c. O—($C_1$-$C_4$)-alkyl;
   d. pyridyl,
   e. tetrahydrofuranyl,
   f. tetrahydropyranyl,
   g. 2,2'-dimethyl-1,3-dioxolanyl,
   h. C(O)—O—($C_1$-$C_4$)-alkyl;
   i. NH—($C_1$-$C_4$)-alkyl;
iii) C(O)—($C_1$-$C_4$)-alkyl which is unsubstituted or monosubstituted by
   a. OH,
   b. O—($C_1$-$C_4$)-alkyl;
iv) C(O)-tetrahydrofuranyl;
v) C(O)—NH—($C_1$-$C_4$)-alkyl;
vi) C(O)—NH—($C_1$-$C_4$)-alkylen-COO($C_1$-$C_4$)-lkyl;
or a pharmaceutically acceptable salt thereof.

2. The compound of formula I as claimed in claim 1, wherein
$R^1$ is ($C_1$-$C_4$)-alkyl or cyclopropyl;
$R^2$ is H, F or Cl;
$R^3$ is H or F;
$R^4$ is H or ($C_1$-$C_4$)-alkyl;
$R^5$ is H or methyl; and
$R^6$ is 3-azetidinyl, 3-pyrrolidinyl, 3-piperidinyl, 4-piperidinyl, 3-azepanyl, and 4-azepanyl, which is unsubstituted or mono- or disubstituted by methyl or ethyl;

or $R^5$ and $R^6$ together with the N-atom carrying them denote a) a 1,4-piperazinyl of the formula

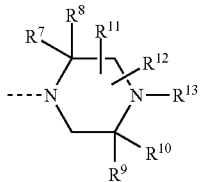

wherein $R^7$ is H, methyl, ethyl, isopropyl, cyclopropyl, $CF_3$ or $CH_2CF_3$ or phenyl, wherein phenyl is unsubstituted or mono- or disubstituted by F, $CF_3$ or isopropyl;

$R^8$ is H, methyl or ethyl;

or $R^7$ and $R^8$ together with the carbon atom carrying them denote $(C_3-C_5)$-cycloalkyl;

$R^9$ is H, $(C_1-C_4)$-alkyl, cyclopropyl or phenyl, wherein alkyl is unsubstituted or one to threefold substituted by F;

$R^{10}$ is H or $(C_1-C_4)$-alkyl;

or $R^9$ and $R^{10}$ together with the carbon atom carrying them denote cyclopentyl;

$R^{11}$ is H or $(C_1-C_4)$-alkyl;

$R^{12}$ is H;

$R^{13}$ is

H, methyl, $(CH_2)_2$—$CF_3$, $(CH_2)_2$—OH, $CH_2$—CH(OH)—$CH_2$—OH, $(CH_2)_2$—O—$CH_3$, $(CH_2)_3$—O—$CH_3$, $CH_2$-pyrid-3-yl, $CH_2$-tetrahydrofuran-2-yl, $CH_2$-tetrahydropyran-4-yl, $(CH_2)_2$-tetrahydropyran-4-yl, $CH_2$-2,2'-dimethyl-1,3-dioxolanyl, $CH_2$—C(O)—O—$CH_3$, $(CH_2)_2$—NH—$CH_3$,

C(O)$CH_3$,

C(O)—$CH_2$OH,

C(O)—$CH_2$O$CH_3$,

C(O)—$CH_2CH_2$O$CH_3$,

C(O)-tetrahydrofuran-2-yl,

C(O)—NH—$C_2H_5$ or

C(O)—NH—$CH_2$—COO$CH_3$;

b) a morpholinyl of the formula

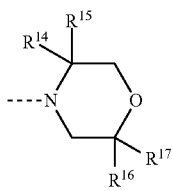

wherein $R^{14}$, $R^{15}$, $R^{16}$ and $R^{17}$ are independently of one another H or $(C_1-C_4)$-alkyl;

c) a ring A of the formula

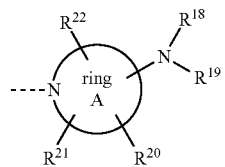

comprising one nitrogen and 4 to 5 carbon ring atoms, wherein substituent $NR^{18}R^{19}$ is not in an adjacent position to the ring nitrogen atom and $R^{18}$ is H, $(C_1-C_4)$-alkyl or C(O)—$CH_2$—O—$CH_3$;

$R^{19}$ is H;

$R^{20}$ is H or $(C_1-C_4)$-alkyl;

$R^{21}$ is H;

$R^{22}$ is H;

d) a 1,4-diazepin of the formula

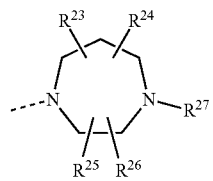

wherein $R^{23}$ is H or $(C_1-C_4)$-alkyl;

$R^{24}$ is H;

$R^{25}$ is H;

$R^{26}$ is H;

$R^{27}$ is H, C(O)—$CH_2$—$(C_1-C_4)$-alkyl or C(O)—NH—$(C_1-C_4)$-alkyl;

or a pharmaceutically acceptable salt thereof.

3. The compound of formula I as claimed in claim 1, wherein $R^1$ is methyl, ethyl or cyclopropyl;

$R^2$ is H, F or Cl;

$R^3$ is H or F;

$R^4$ is H or methyl;

$R^5$ is H or methyl;

$R^6$ is 3-azetidinyl, 3-pyrrolidinyl, 3-piperidinyl, 4-piperidinyl, 3-azepanyl, and 4-azepanyl, which is unsubstituted or mono- or disubstituted by methyl or ethyl; or $R^5$ and $R^6$ together with the N-atom carrying them denote a 1,4-piperazinyl of the formula

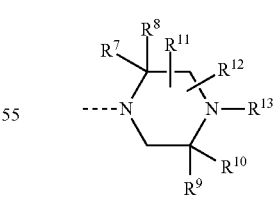

wherein $R^7$ is H, methyl, ethyl, isopropyl, cyclopropyl, $CF_3$ or $CH_2CF_3$ or phenyl, wherein phenyl is unsubstituted or mono- or disubstituted by F, $CF_3$ or isopropyl;

$R^8$ is H, methyl or ethyl;

or $R^7$ and $R^8$ together with the carbon atom carrying them denote $(C_3-C_5)$-cycloalkyl;

$R^9$ is H, $(C_1-C_4)$-alkyl, cyclopropyl or phenyl, wherein alkyl is unsubstituted or one to threefold substituted by F;
$R^{10}$ or $(C_1-C_4)$-alkyl;
or
$R^9$ and $R^{10}$ together with the carbon atom carrying them denote cyclopentyl;
$R^{11}$ is H or $(C_1-C_4)$-alkyl;
$R^{12}$ is H;
$R^{13}$ is
H, methyl,
$(CH_2)_2-CF_3$,
$(CH_2)_2-OH$,
$CH_2-CH(OH)-CH_2-OH$,
$(CH_2)_2-O-CH_3$,
$(CH_2)_3-O-CH_3$,
$CH_2$-pyrid-3-yl,
$CH_2$-tetrahydrofuran-2-yl,
$CH_2$-tetrahydropyran-4-yl,
$(CH_2)_2$-tetrahydropyran-4-yl,
$CH_2$-2,2'-dimethyl-1,3-dioxolanyl,
$CH_2-C(O)-O-CH_3$,
$(CH_2)_2-NH-CH_3$,
$C(O)CH_3$,
$C(O)-CH_2OH$,
$C(O)-CH_2OCH_3$,
$C(O)-CH_2CH_2CH_3$,
$C(O)$-tetrahydrofuran-2-yl,
$C(O)-NH-C_2H_5$ or
$C(O)-NH-CH_2-COOCH_3$; or
$R^5$ and $R^6$ together with the N-atom carrying them denote a morpholinyl of the formula

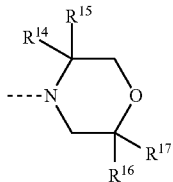

wherein
$R^{14}$ is methyl;
$R^{15}$ is methyl;
$R^{16}$ is methyl;
$R^{17}$ is methyl; or
$R^5$ and $R^6$ together with the N-atom carrying them denote a ring A of the formula

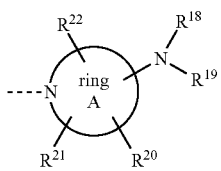

comprising one nitrogen and 4 to 5 carbon ring atoms, wherein the substituent $NR^{18}R^{19}$ is not in an adjacent position to the ring nitrogen atom and
$R^{18}$ is H, methyl or $C(O)-CH_2-O-CH_3$;
$R^{19}$ is H;
$R^{20}$ is H or methyl;

$R^{21}$ is H;
$R^{22}$ is H; or
$R^5$ and $R^6$ together with the N-atom carrying them denote a 1,4-diazepin of the formula

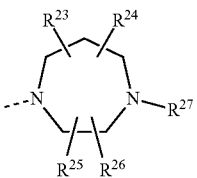

wherein
$R^{23}$ is H or methyl;
$R^{24}$ is H;
$R^{25}$ is H;
$R^{26}$ is H;
$R^{27}$ is H, $C(O)-CH_2-OCH_3$ or $C(O)-NH-(C_2H_5)$;
or a pharmaceutically acceptable salt thereof.

4. The compound of the formula I as claimed in claim 1, wherein
$R^1$ is methyl;
$R^2$ is H or F;
$R^3$ is H;
$R^4$ is H;
$R^5$ is H;
$R^6$ is 3-azetidinyl, 3-pyrrolidinyl, 3-piperidinyl, 4-piperidinyl, 3-azepanyl, and 4-azepanyl, which is unsubstituted or mono- or disubstituted by methyl or ethyl;
or
$R^5$ and $R^6$ together with the N-atom carrying them denote a 1,4-piperazinyl of the formula

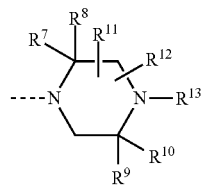

wherein
$R^7$ is H, methyl, ethyl, isopropyl, cyclopropyl, $CF_3$ or $CH_2CF_3$ or phenyl, wherein phenyl is unsubstituted or mono- or disubstituted by F, $CF_3$ or isopropyl;
$R^8$ is H, methyl or ethyl;
or
$R^7$ and $R^8$ together with the carbon atom carrying them denote $(C_3-C_5)$-cycloalkyl;
$R^9$ is H, $(C_1-C_4)$-alkyl, cyclopropyl or phenyl, wherein alkyl is unsubstituted or one to threefold substituted by F;
$R^{10}$ is H or $(C_1-C_4)$-alkyl;
or
$R^9$ and $R^{10}$ together with the carbon atom carrying them denote cyclopentyl;
$R^{11}$ is H or $(C_1-C_4)$-alkyl;
$R^{12}$ is H;
$R^{13}$ is
H, methyl,
$(CH_2)_2-CF_3$,
$(CH_2)_2-OH$,
$CH_2-CH(OH)-CH_2-OH$,
$(CH_2)_2-O-CH_3$,
$(CH_2)_3-O-CH_3$, CH$_2$-pyrid-3-yl,
CH$_2$-tetrahydrofuran-2-yl,
CH$_2$-tetrahydropyran-4-yl,
(CH$_2$)$_2$-tetrahydropyran-4-yl,
CH$_2$-2,2'-dimethyl-1,3-dioxolanyl,
CH$_2$—C(O)—O—CH$_3$,
(CH$_2$)$_2$—NH—CH$_3$,
C(O)CH$_3$,
C(O)—CH$_2$OH,
C(O)—CH$_2$OCH$_3$
C(O)—CH$_2$CH$_2$OCH$_3$,
C(O)-tetrahydrofuran-2-yl,
C(O)—NH—C$_2$H$_5$ or
C(O)—NH—CH$_2$—COOCH$_3$;
with the proviso that at least 2 radicals selected from the group consisting of R$^7$ to R$^{13}$ are H;
or
R$^5$ and R$^6$ together with the N-atom carrying them denote a ring A of the formula

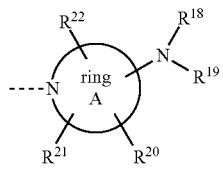

comprising one nitrogen and 4 to 5 carbon ring atoms, wherein the substituent NR$^{18}$R$^{19}$ is not in an adjacent position to the ring nitrogen atom and R$^{18}$ is H, methyl or C(O)—CH$_2$—O—CH$_3$;
R$^{19}$ is H;
R$^{20}$ is H or methyl;
R$^{21}$ is H;
R$^{22}$ is H;
or
R$^5$ and R$^6$ together with the N-atom carrying them denote a 1,4-diazepin of the formula

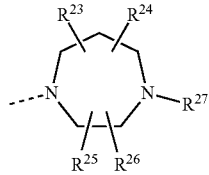

wherein
R$^{23}$ is H or methyl;
R$^{24}$ is H;
R$^{25}$ is H;
R$^{26}$ is H;
R$^{27}$ is H, C(O)—CH$_2$—OCH$_3$ or C(O)—NH—(C$_2$H$_5$));
or a pharmaceutically acceptable salt thereof.

5. The compound of the formula I as claimed in claim 1, wherein
R$^1$ is (C$_1$-C$_4$)-alkyl or cyclopropyl;
R$^2$ is H, F or Cl;
R$^3$ is H or F;
R$^4$ is H or (C$_1$-C$_4$)-alkyl;
R$^5$ is H or methyl; and
R$^6$ is 3-azetidinyl, 3-pyrrolidinyl, 3-piperidinyl, 4-piperidinyl, 3-azepanyl, and 4-azepanyl, which is unsubstituted or mono- or disubstituted by methyl or ethyl;
or
R$^5$ and R$^6$ together with the N-atom carrying them denote
e) a 1,4-piperazinyl of the formula

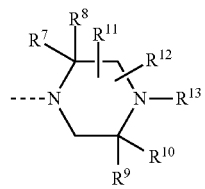

wherein
R$^7$ is H, methyl, ethyl, isopropyl, cyclopropyl, CF$_3$ or CH$_2$CF$_3$or phenyl, wherein phenyl is unsubstituted or mono- or disubstituted by F, CF$_3$ or isopropyl;
R$^8$ is H, methyl or ethyl;
or
R$^7$ and R$^8$ together with the carbon atom carrying them denote (C$_3$-C$_5$)-cycloalkyl;
R$^9$ is H, (C$_1$-C$_4$)-alkyl, cyclopropyl or phenyl, wherein alkyl is unsubstituted or one to threefold substituted by F;
R$_{10}$ is H or (C$_1$-C$_4$)-alkyl;
R$^9$ and R$^{10}$ together with the carbon atom carrying them denote cyclopentyl;
R$^{11}$ is H or (C$_1$-C$_4$)-alkyl;
R$^{12}$ is H;
R$^{13}$ is
H or methyl,
(CH$_2$)$_2$—CF$_3$,
(CH$_2$)$_2$—OH,
CH$_2$—CH(OH)—CH$_2$—OH,
(CH$_2$)$_2$—O—CH$_3$,
(CH$_2$)$_3$—O—CH$_3$,
CH$_2$-tetrahydrofuran-2-yl,
CH$_2$-tetrahydropyran-4-yl,
(CH$_2$)$_2$-tetrahydropyran-4-yl,
CH$_2$—C(O)—O—CH$_3$);
or a pharmaceutically acceptable salt thereof.

6. The compound of the formula I as claimed in claim 1 selected from the group consisting of
3-Fluoro-4-[3-methyl-4-(2-phenyl-piperazin-1-ylmethyl)-1H-pyrazolo[3,4-b]pyridin-6-yl]-phenol
3-Fluoro-4-{4-[(4-isopropyl-phenyl)-piperazin-1-ylmethyl]-3-methyl-1H-pyrazolo[3,4-b]pyridin-6-yl}-phenol
3-Fluoro-4-{3-methyl-4-[2-(4-trifluoromethyl-phenyl)-piperazin-1-ylmethyl]-1H-pyrazolo[3,4-b]pyridin-6-yl}-phenol
3-Fluoro-4-{4-[2-(4-fluoro-phenyl)-piperazin-1-ylmethyl]-3-methyl-1H-pyrazolo[3,4-b]pyridin-6-yl}-phenol
3-Fluoro-4-[3-methyl-4-(2-trifluoromethyl-piperazin-1-ylmethyl)-1H-pyrazolo[3,4-b]pyridin-6-yl]-phenol
3-Fluoro-4-{4-[2-(3-fluoro-phenyl)-piperazin-1-ylmethyl]-3-methyl-1H-pyrazolo[3,4-b]pyridin-6-yl}-phenol
4-[4-(6,9-Diaza-spiro[4.5]dec-6-ylmethyl)-3-methyl-1H-pyrazolo[3,4-b]pyridin-6-yl]-3-fluoro-phenol
3-Fluoro-4-{3-methyl-4-[2-(3-trifluoromethyl-phenyl)-piperazin-1-ylmethyl]-1H-pyrazolo[3,4-b]pyridin-6-yl}-phenol
4-{4-[2-(3,5-Difluoro-phenyl)piperazin-1-ylmethyl]-3-methyl-1H-pyrazolo[3,4-b]pyridin-6-yl}-3-fluoro-phenol 3-Fluoro-4-{4-[2-(2-fluoro-phenyl)-piperazin-1-ylmethyl]-3-methyl-1H-pyrazolo[3,4-b]pyridin-6-yl}-phenol
3-Fluoro-4-[3-methyl-4-(2,2,5-trirnethyl-piperazin-1-ylmethyl)-1H-pyrazolo[3,4-b]pyridin-6-yl]-phenol
3-Fluoro-4-[3-methyl-4-(2-methyl-2-phenyl-piperazin-1-ylmethyl)-1H-pyrazolo[3,4-b]pyridin-6-yl]-phenol
3-Fluoro-4-(3-methyl-4-piperazin-1-ylmethyl-1H-pyrazolo[3,4-b]pyridin-6-yl)-phenol
4-[4-(4,7-Diaza-spiro[2.5]oct-4-ylmethyl)-3-methyl-1H-pyrazolo[3,4-b]pyridin-6-yl]-3-fluoro-phenol
4-[4-(8,8-Dimethyl-6,9-diaza-spiro[4.5]dec-6-ylmethyl)-3-methyl-1H-pyrazolo[3,4-b]pyridin-6-yl]-3-fluoro-phenol
3-Fluoro-4-[3-methyl-4-(8-methyl-6,9-diaza-spiro[4.5]dec-6-ylmethyl)-1H-pyrazolo[3,4-b]pyridin-6-yl]-phenol
4-[4-(5,8-Diaza-spiro[3.5]non-5-ylmethyl)-3-methyl-1H-pyrazolo[3,4-b]pyridin-6-yl]-3-fluoro-phenol
4-[4-(2,2-Diethyl-piperazin-1-ylmethyl)-3-methyl-1H-pyrazolo[3,4-b]pyridin-6-yl]-3-fluoro-phenol
3-Fluoro-4-[3-methyl-4-(5-methyl-2-trifluoromethyl-piperazin-1-ylmethyl)-1H-pyrazolo[3,4-b]pyridin-6-yl]-phenol
3-Fluoro-4-[4-(5-isopropyl-2,2-dimethyl-piperazin-1-ylmethyl)-3-methyl-1H-pyrazolo[3,4-b]pyridin-6-yl]-phenol
4-[4-(5-Ethyl-2,2,5-trimethyl-piperazin-1-ylmethyl)-3-methyl-1H-pyrazolo[3,4-b]pyridin-6-yl]-3-fluoro-phenol
4-[4-(5,5-Diethyl-2,2-dimethyl-piperazin-1-ylmethyl)-3-methyl-1H-pyrazolo[3,4-b]pyridin-6-yl]-3-fluoro-phenol
4-[4-(5-Cyclopropyl-2,2,5-trimethyl-piperazin-1-ylmethyl)-3-methyl-1H-pyrazolo[3,4-b]pyridin-6-yl]-3-fluoro-phenol
4-[4-(3-Amino-3-methyl-piperidin-1-ylmethyl)-3-methyl-1H-pyrazolo[3,4-b]pyridin-6-yl]-3-fluoro-phenol
3-Fluoro-4-[3-methyl-4-(3-methyl-[1,4]diazepan-1-ylmethyl)-1H-pyrazolo[3,4-b]pyridin-6-yl]-phenol
4-[4-(2,2-Dimethyl-piperazin-1-ylmethyl)-3-methyl-1H-pyrazolo[3,4-b]pyridin-6-yl]-3-fluoro-phenol
4-[4-((2S,5R)-2,5-Dimethyl-piperazin-1-ylmethyl)-3-methyl-1H-pyrazolo[3,4-b]pyridin-6-yl]-3-fluoro-phenol
3-Fluoro-4-[3-methyl-4-(2,2,5,5-tetramethyl-piperazin-1-ylmethyl)-1H-pyrazolo[3,4-b]pyridin-6-yl]-phenol
3-Fluoro-4-[3-methyl-4-(trans-2-methyl-5-phenyl-piperazin-1-ylmethyl)-1H-pyrazolo[3,4-b]pyridin-6-yl]-phenol
4-[4-((2S,5R)-5-Ethyl-2-methyl-piperazin-1-ylmethyl)-3-methyl-1H-pyrazolo[3,4-b]pyridin-6-yl]-3-fluoro-phenol
4-[4-(2-Ethyl-2,5,5-trimethyl-piperazin-1-ylmethyl)-3-methyl-1H-pyrazolo[3,4-b]pyridin-6-yl]-3-fluoro-phenol
4-[4-(2,2-Diethyl-5,5-dimethyl-piperazin-1-ylmethyl)-3-methyl-1H-pyrazolo[3,4-b]pyridin-6-yl]-3-fluoro-phenol
4-[3-Methyl-4-(8-methyl-6,9-diaza-spiro[4.5]dec-9-ylmethyl)-1H-pyrazolo[3,4-b]pyridin-6-yl]-phenol
4-[4-(2-Cyclopropyl-2,5,5-trimethyl-piperazin-1-ylmethyl)-3-methyl-1H-pyrazolo[3,4-b]pyridin-6-yl]-3-fluoro-phenol
3-Fluoro-4-[3-methyl-4-(8-methyl-6,9-diaza-spiro[4.5]dec-9-ylmethyl)-1H-pyrazolo[3,4-b]pyridin-6-yl]-phenol
4-[4-(8,8-Dimethyl-6,9-diaza-spiro[4.5]dec-9-ylmethyl)-3-methyl-1H-pyrazolo[3,4-b]pyridin-6-yl]-3-fluoro-phenol
3-Fluoro-4-[4-(2-isopropyl-5,5-dimethyl-piperazin-1-ylmethyl)-3-methyl-1H-pyrazolo[3,4-b]pyridin-6-yl]-phenol
3-Fluoro-4-[3-methyl-4-(2,5,5-trimethyl-piperazin-1-ylmethyl)-1H-pyrazolo[3,4-b]pyridin-6-yl]-phenol
4-[4-(2-Ethyl-5,5-dimethyl-piperazin-1-ylmethyl)-3-methyl-1H-pyrazolo[3,4-b]pyridin-6-yl]-3-fluoro-phenol
4-[4-(4,7-Diaza-spiro[2.5]oct-4-ylmethyl)-3-methyl-1H-pyrazolo[3,4-b]pyridin-6-yl]-phenol
4-[3-Methyl-4-(2-phenyl-piperazin-1-ylmethyl)-1H-pyrazolo[3,4-b]pyridin-6-yl]-phenol
4-{4-[2-(4-Fluoro-phenyl)-piperazin-1-ylmethyl]-3-methyl-1H-pyrazolo[3,4-b]pyridin-6-yl}-phenol
4-[3-Methyl-4-(trans-5-methyl-2-phenyl-piperazin-1-ylmethyl)-1H-pyrazolo[3,4-b]pyridin-6-yl]-phenol
4-{3-Methyl-4-[2-(4-trifluoromethyl-phenyl)-piperazin-1-ylmethyl]-1H-pyrazolo[3,4-b]pyridin-6-yl}-phenol
4-{4-[2-(4-Isopropyl-phenyl)-piperazin-1-ylmethyl]-3-methyl-1H-pyrazolo[3,4-b]pyridin-6-yl}-phenol
4-{4-[(3-Ethyl-piperidin-3-ylamino)-methyl]-3-methyl-1H-pyrazolo[3,4-b]pyridin-6-yl}-phenol
4-[4-(6,9-Diaza-spiro[4.5]dec-6-ylmethyl)-3-methyl-1H-pyrazolo[3,4-b]pyridin-6-yl]-phenol
4-[3-Methyl-4-(2,2,5-trimethyl-piperazin-1-ylmethyl)-1H-pyrazolo[3,4-b]pyridin-6-yl]-phenol
4-[3-Methyl-4-(2,2,5,5-tetramethyl-piperazin-1-ylmethyl)-1H-pyrazolo[3,4-b]pyridin-6-yl]-phenol
4-[4-(2-Ethyl-2,5,5-trimethyl-piperazin-1-ylmethyl)-3-methyl-1H-pyrazolo[3,4-b]pyridin-6-yl]-phenol
4-[4-(2,2-Diethyl-5,5-dimethyl-piperazin-1-ylmethyl)-3-methyl-1H-pyrazolo[3,4-b]pyridin-6-yl]-phenol
4-[3-Methyl-4-(2,5,5-trimethyl-piperazin-1-ylmethyl)-1H-pyrazolo[3,4-b]pyridin-6-yl]-phenol
4-[4-(2-Ethyl-5,5-dimethyl-piperazin-1-ylmethyl)-3-methyl-1H-pyrazolo[3,4-b]pyridin-6-yl]-phenol
4-[4-((2S,5R)-2,5-Dimethyl-piperazin-1-ylmethyl)-3-methyl-1H-pyrazolo[3,4-b]pyridin-6-yl]-phenol
4-[4-(3,3-Dimethyl-piperazin-1-ylmethyl)-3-methyl-1H-pyrazolo[3,4-b]pyridin-6-yl]-3-fluoro-phenol
3-Fluoro-4-[3-methyl-4-(2,2,5,5-tetramethyl-morpholin-4-ylmethyl)-1H-pyrazolo[3,4-b]pyridin-6-yl]-phenol
4-[4-(5-Ethyl-2,2,5-trimethyl-piperazin-1-ylmethyl)-3-methyl-1H-pyrazolo[3,4-b]pyridin-6-yl]-phenol
4-[4-(5,5-Diethyl-2,2-dimethyl-piperazin-1-ylmethyl)-3-methyl-1H-pyrazolo[3,4-b]pyridin-6-yl]-2-fluoro-phenol
3-Chloro-4-[4-(5,5-diethyl-2,2-dimethyl-piperazin-1-ylmethyl)-3-methyl-1H-pyrazolo[3,4-b]pyridin-6-yl]-phenol
4-{4-[(3,3-Dimethyl-piperidin-4-ylamino)-methyl]-3-methyl-1H-pyrazolo[3,4-b]pyridin-6-yl}-phenol
4-[3-Methyl-4-(2,2,5-trimethyl-4-pyridin-3-ylmethyl-piperazin-1-ylmethyl)-1H-pyrazolo[3,4-b]pyridin-6-yl]-phenol
4-{3-Methyl-4-[2,2,5-trimethyl-4-(tetrahydro-furan-2-ylmethyl)-piperazin-1-ylmethyl]-1H-pyrazolo[3,4-b]pyridin-6-yl}phenol
4-{4-[4-(2-Methoxy-ethyl)-2,2,5-trirnethyl-piperazin-1-ylmethyl]-3-methyl-1H-pyrazolo[3,4-b]pyridin-6-yl}-phenol
4-{4-[4-(3-Methoxy-propyl)-2,2,5-trimethyl-piperazin-1-ylmethyl]-3-methyl-1H-pyrazolo[3,4-b]pyridin-6-yl}-phenol 3-Fluoro-4-{3-methyl-4-[2,2,5,5-tetramethyl-4-(3,3,3-trifluoro-propyl)-piperazin-1-ylmethyl]-1H-pyrazolo[3,4-b]pyridin-6-yl}phenol 3-Fluoro-4-[3-methyl-4-(2,2,4,5,5-pentamethyl-piperazin-1-ylmethyl)-1H-pyrazolo[3,4-b]pyridin-6-yl]-phenol 3-Fluoro-4-{4-[4-(3-methoxy-propyl)-2,2,5,5-tetramethyl-piperazin-1-ylmethyl]-3-methyl-1H-pyrazolo[3,4-b]pyridin-6-yl}-phenol 3-Fluoro-4-(3-methyl-4-{2,2,5,5-tetramethyl-4-[2-(tetrahydro-pyran-4-yl)-ethyl]-piperazin-1-ylmethyl}-1H-pyrazolo[3,4-b]pyridin-6-yl)-phenol 4-{4-[4-((S)-2,2-Dimethyl-[1,3]dioxolan-4-ylmethyl]-2,2,5,5-tetramethyl-piperazin-1-ylmethyl]-3-methyl-1H-pyrazolo[3,4-b]pyridin-6-yl}-3-fluoro-phenol 3-Fluoro-4-{3-methyl-4-[2,2,5,5-tetramethyl-4-(tetrahydro-pyran-4-ylmethyl)-piperazin-1-ylmethyl]-1H-pyrazolo[3,4-b]pyridin-6-yl}-phenol 3-Fluoro-4-[3-methyl-4-(6,8,8-trimethyl-6,9-diaza-spiro[4.5]dec-9-ylmethyl)-1H-pyrazolo[3,4-b]pyridin-6-yl]-phenol 3-Fluoro-4-{4-[4-(2-hydroxy-ethyl)-2,2,5,5-tetramethyl-piperazin-1-ylmethyl]-3-methyl-1H-pyrazolo[3,4-b]pyridin-6-yl}-phenol (S)-3-{4-[6-(2-Fluoro-4-hydroxy-phenyl)-3-methyl-1H-pyrazolo[3,4-b]pyridin-4-ylmethyl]-2,2,5,5-tetramethyl-piperazin-1-yl}-propane-1,2-diol {4-[6-(2-Fluoro-4-hydroxy-phenyl)-3-methyl-1H-pyrazolo[3,4-b]pyridin-4-ylmethyl]-2,2,5,5-tetramethyl-piperazin-1-yl}-acetic acid methyl ester 1-{4-[6-(2-Fluoro-4-hydroxy-phenyl)-3-methyl-1H-pyrazolo[3,4-b]pyridin-4-ylmethyl]-2,2,5,5-tetramethyl-piperazin-1-yl}-2-methoxy-ethanone 1-{4-[6-(2-Fluoro-4-hydroxy-phenyl)-3-methyl-1H-pyrazolo[3,4-b]pyridin-4-ylmethyl]-2,2,5,5-tetramethyl-piperazin-1-yl}-3-methoxy-propan-1-one {4-[6-(2-Fluoro-4-hydroxy-phenyl)-3-methyl-1H-pyrazolo[3,4-b]pyridin-4-ylmethyl]-2,2,5,5-tetramethyl-piperazin-1-yl}-(tetrahydro-furan-3-yl)-methanone 1-{4-[6-(2-Fluoro-4-hydroxy-phenyl)-3-methyl-1H-pyrazolo[3,4-b]pyridin-4-ylmethyl]-2,2,5,5-tetramethyl-piperazin-1-yl}-ethanone 1-{4-[6-(2-Fluoro-4-hydroxy-phenyl)-3-methyl-1H-pyrazolo[3,4-b]pyridin-4-ylmethyl]-2-methyl-[1,4]diazepan-1-yl}-2-methoxy-ethanone 1-{4-[6-(2-Fluoro-4-hydroxy-phenyl)-3-methyl-1H-pyrazolo[3,4-b]pyridin-4-ylmethyl]-2,2,5,5-tetramethyl-piperazin-1-yl}-2-hydroxy-ethanone N-{1-[6-(2-Fluoro-4-hydroxy-phenyl)-3-methyl-1H-pyrazolo[3,4-b]pyridin-4-ylmethyl]-3-methyl-piperidin-3-yl}-2-methoxy-acetamide 1-{9-[6-(4-Hydroxy-phenyl)-3-methyl-1H-pyrazolo[3,4-b]pyridin-4-ylmethyl]-8-methyl-6,9-diaza-spiro[4.5]dec-6-yl}-2-methoxy-ethanone 4-{3-Methyl-4-[2,2,5,5-tetramethyl-4-(3,3,3-trifluoro-propyl)-piperazin-1-ylmethyl]-1H-pyrazolo[3,4-b]pyridin-6-yl}-phenol 4-[3-Methyl-4-(2,2,4,5,5-pentamethyl-piperazin-1-ylmethyl)-1H-pyrazolo[3,4-b]pyridin-6-yl]-phenol 4-{3-Methyl-4-[2,2,5,5-tetramethyl-4-(2-methylamino-ethyl)-piperazin-1-ylmethyl]-1H-pyrazolo[3,4-b]pyridin-6-yl}-phenol {4-[6-(4-Hydroxy-phenyl)-3-methyl-1H-pyrazolo[3,4-b]pyridin-4-ylmethyl]-2,2,5,5-tetramethyl-piperazin-1-yl}-acetic acid methyl ester ({4-[6-(4-Hydroxy-phenyl)-3-methyl-1H-pyrazolo[3,4-b]pyridin-4-ylmethy]-2,2,5,5tetramethyl-piperazine-1-carbonyl}-amino)-acetic acid methyl ester 4-[6-(4-Hydroxy-phenyl)-3-methyl-1H-pyrazolo[3,4-b]pyridin-4-ylmethy]-2,2,5,5tetramethyl-piperazine-1-carboxylic acid ethylamide 4-[6-(2-Fluoro-4-hydroxy-phenyl)-3-methyl-1H-pyrazolo[3,4-b]pyridin-4-ylmethyl]-2methyl-[1,4]diazepane-1-carboxylic acid ethylamide 1-{4-[6-(2-Fluoro-4-hydroxy-phenyl)-3-methyl-1H-pyrazolo[3,4-b]pyridin-4-ylmethyl]-2,2,5,5-tetramethyl-piperazin-1-yl}-2-methoxy-ethanone 4-{3-Methyl-4-[(R)-3-(2,2,2-trifluoro-ethyl)-piperazin-1-ylmethyl]-1H-pyrazolo[3,4-b]pyridin-6-yl}-phenol 4-{3-Methyl-4-[(R)-2-(2,2,2-trifluoro-ethyl)-piperazin-1-ylmethyl]-1H-pyrazolo[3,4-b]pyridin-6-yl}-phenol 4-[3-Methyl-4-(3-methylamino-pyrrolidin-1-ylmethyl)-1H-pyrazolo[3,4-b]pyridin-6-yl]-phenol 4-{3-Methyl-4-[(methyl-pyrrolidin-3-yl-amino)-methyl]-1H-pyrazolo[3,4-b]pyridin-6-yl}-phenol 4-(3-Cyclopropyl-4-piperazin-1-ylmethyl-1H-pyrazolo[3,4-b]pyridin-6-yl)-phenol 4-(3-Ethyl-4-piperazin-1-ylmethyl-1H-pyrazolo[3,4-b]pyridin-6-yl)-phenol 3-Fluoro-4-[3-methyl-4-(1-piperazin-1-yl-ethyl)-1H-pyrazolo[3,4-b]pyridin-6-yl]-phenol 4-{4-[1-((3S,5R)-3,5-Dimethyl-piperazin-1-yl)-ethyl]-3-methyl-1H-pyrazolo[3,4-b]pyridin-6-yl}-3-fluoro-phenol 3-Fluoro-4-[3-methyl-4-((2S,5R)-2-methyl-5-phenyl-piperazin-1-ylmethyl)-1H-pyrazolo[3,4-b]pyridin-6-yl]-phenol 3-Fluoro-4-[3-methyl-4-((2R,5S)-2-methyl-5-phenyl-piperazin-1-ylmethyl)-1H-pyrazolo[3,4-b]pyridin-6-yl]-phenol 3-Fluoro-4-{4-[(S)-2-(4-isopropyl-phenyl)-piperazin-1-ylmethyl]-3-methyl-1H-pyrazolo[3,4-1H]pyridin-6-yl}-phenol 3-Fluoro-4-{4-[(R)-2-(4-isopropyl-phenyl)-piperazin-1-ylmethyl]-3-methyl-1H-pyrazolo[3,4-1H]pyridin-6-yl}-phenol 3-Fluoro-4-{3-methyl-4-[(S)-2-(4-trifluoromethyl-phenyl)-piperazin-1-ylmethyl]-1H-pyrazolo[3,4-b]pyridin-6-yl}-phenol 3-Fluoro-4-{3-methyl-4-[(R)-2-(4-trifluoromethyl-phenyl)-piperazin-1-ylmethyl]-1H-pyrazolo[3,4-b]pyridin-6-yl}-phenol 3-Fluoro-4-{4-[(S)-2-(4-fluoro-phenyl)-piperazin-1-ylmethyl]-3-methyl-1H-pyrazolo[3,4-1H]pyridin-6-yl}-phenol 3-Fluoro-4-{4-[(R)-2-(4-fluoro-phenyl)-piperazin-1-ylmethyl]-3-methyl-1H-pyrazolo[3,4-1H]pyridin-6-yl}-phenol 3-Fluoro-4-[3-methyl-4-((R)-2-trifluoromethyl-piperazin-1-ylmethyl)-1H-pyrazolo[3,4-b]pyridin-6-yl]-phenol 3-Fluoro-4-[3-methyl-4-((S)-2-trifluoromethyl-piperazin-1-ylmethyl)-1H-pyrazolo[3,4-b]pyridin-6-yl]-phenol 3-Fluoro4[3-methyl-4-((S)-2-phenyl-piperazin-1-ylmethyl)-1H-pyrazolo[3,4-b]pyridin-6-yl]-phenol 3-Fluoro4[3-methyl-4-((R)-2-phenyl-piperazin-1-ylmethyl)-1H-pyrazolo[3,4-b]pyridin-6-yl]-phenol 4-[3-Methyl-4-((2R,5S)-5-methyl-2-phenyl-piperazin-1-ylmethyl)-1H-pyrazolo[3,4-b]pyridin-6-yl]-phenol 4-{3-Methyl-4-[(S)-2-(4-trifluoromethyl-phenyl)-piperazin-1-ylmethyl]-1H-pyrazolo[3,4-b]pyridin-6-yl}-phenol 4-{3-Methyl-4-[(R)-2-(4-trifluoromethyl-phenyl)-piperazin-1-ylmethyl]-1H-pyrazolo[3,4-b]pyridin-6-yl}-phenol
3-Fluoro-4-[3-methyl-4-((S)-2,2,5-trimethyl-piperazin-1-ylmethyl)-1H-pyrazolo[3,4-b]pyridin-6-yl]-phenol
3-Fluoro-4-[3-methyl-4-((R)-2,2,5-trimethyl-piperazin-1-ylmethyl)-1H-pyrazolo[3,4-1H]pyridin-6-yl]-phenol
3-Fluoro-4-[3-methyl-4-((S)-2-methyl-2-phenyl-piperazin-1-ylmethyl)-1H-pyrazolo[3,4-1H]pyridin-6-yl]-phenol
3-Fluoro-4-[3-methyl-4-((R)-2-methyl-2-phenyl-piperazin-1-ylmethyl)-1H-pyrazolo[3,4-1H]pyridin-6-yl]-phenol
3-Fluoro-4-{4-[(S)-2-(3-fluoro-phenyl)-piperazin-1-ylmethyl]-3-methyl-1H-pyrazolo[3,4-1H]pyridin-6-yl}-phenol
3-Fluoro-4-{4-[(R)-2-(3-fluoro-phenyl)-piperazin-1-ylmethyl]-3-methyl-1H-pyrazolo[3,4-1H]pyridin-6-yl}-phenol
4-[4-((R)-2-Ethyl-2,5,5-thmethyl-piperazin-1-ylmethyl)-3-methyl-1H-pyrazolo[3,4-b]pyridin-6-yl]-3-fluoro-phenol
4-[4-((S)-2-Ethyl-2,5,5-trimethyl-piperazin-1-ylmethyl)-3-methyl-1H-pyrazolo[3,4-b]pyridin-6-yl]-3-fluoro-phenol
3-Fluoro-4-[3-methyl-4-((R)-2,5,5-trimethyl-piperazin-1-ylmethyl)-1H-pyrazolo[3,4-1H]pyridin-6-yl]-phenol
3-Fluoro-4-[3-methyl-4-((S)-2,5,5-thmethyl-piperazin-1-ylmethyl)-1H-pyrazolo[3,4-b]pyridin-6-yl]-phenol
4-[4-((S)-2-Cyclopropyl-2,5,5-thmethyl-piperazin-1-ylmethyl)-3-methyl-1H-pyrazolo[3,4-1H]pyridin-6-yl]-3-fluoro-phenol
4-[4-((R)-2-Cyclopropyl-2,5,5-trimethyl-piperazin-1-ylmethyl)-3-methyl-1H-pyrazolo[3,4-1H]pyridin-6-yl]-3-fluoro-phenol
3-Fluoro-4-[3-methyl-4-((S)-8-methyl-6,9-diaza-spiro[4.5]clec-6-ylmethyl)-1H-pyrazolo[3,4-1H]pyridin-6-yl]-phenol
3-Fluoro-4-[3-methyl-4-((R)-8-methyl-6,9-diaza-spiro[4.5]clec-6-ylmethyl)-1H-pyrazolo[3,4-1H]pyridin-6-yl]-phenol
3-Fluoro-4-[44(S)-5-isopropyl-2,2-dimethyl-piperazin-1-ylmethyl)-3-methyl-1H-pyrazolo[3,4-1H]pyridin-6-yl]-phenol
3-Fluoro-4-[44(R)-5-isopropyl-2,2-dimethyl-piperazin-1-ylmethyl)-3-methyl-1H-pyrazolo[3,4-1H]pyridin-6-yl]-phenol
4-[3-Methyl-4-((S)-2,2,5-thmethyl-piperazin-1-ylmethyl)-1H-pyrazolo[3,4-b]pyridin-6-yl]-phenol
4[3-Methyl-4-((R)-2,2,5-thmethyl-piperazin-1-ylmethyl)-1H-pyrazolo[3,4-b]pyridin-6-yl]-phenol
3-Fluoro-4-[4-((S)-2-isopropyl-5,5-dimethyl-piperazin-1-ylmethyl)-3-methyl-1H-pyrazolo[3,4-1H]pyridin-6-yl]-phenol
3-Fluoro-4-[4-((R)-2-isopropyl-5,5-dimethyl-piperazin-1-ylmethyl)-3-methyl-1H-pyrazolo[3,4-1H]pyridin-6-yl]-phenol
4-[4-((R)-5-Ethyl-2,2,5-thmethyl-piperazin-1-ylmethyl)-3-methyl-1H-pyrazolo[3,4-b]pyridin-6-yl]-3-fluoro-phenol
4-[4-((S)-5-Ethyl-2,2,5-thmethyl-piperazin-1-ylmethyl)-3-methyl-1H-pyrazolo[3,4-b]pyridin-6-yl]-3-fluoro-phenol
3-Fluoro-4-[3-methyl-4-((S)-8-methyl-6,9-diaza-spiro[4.5]clec-9-ylmethyl)-1H-pyrazolo[3,4-1H]pyridin-6-yl]-phenol
3-Fluoro-4-[3-methyl-4-((R)-8-methyl-6,9-diaza-spiro[4.5]clec-9-ylmethyl)-1H-pyrazolo[3,4-1H]pyridin-6-yl]-phenol
4-[3-Methyl-4-((S)-2,5,5-thmethyl-piperazin-1-ylmethyl)-1H-pyrazolo[3,4-b]pyridin-6-yl]-phenol
4-[3-Methyl-4-((R)-2,5,5-thmethyl-piperazin-1-ylmethyl)-1H-pyrazolo[3,4-b]pyridin-6-yl]-phenol
4-[4-((R)-2-Ethyl-2,5,5-thmethyl-piperazin-1-ylmethyl)-3-methyl-1H-pyrazolo[3,4-b]pyridin-6-yl]-phenol
4-[4-((S)-2-Ethyl-2,5,5-thmethyl-piperazin-1-ylmethyl)-3-methyl-1H-pyrazolo[3,4-b]pyridin-6-yl]-phenol
4-[4-((S)-2-Ethyl-5,5-dimethyl-piperazin-1-ylmethyl)-3-methyl-1H-pyrazolo[3,4-b]pyridin-6-yl]-3-fluoro-phenol
4-[4-((R)-2-Ethyl-5,5-dimethyl-piperazin-1-ylmethyl)-3-methyl-1H-pyrazolo[3,4-b]pyridin-6-yl]-3-fluoro-phenol
4-[4-((S)-2-Ethyl-5,5-dimethyl-piperazin-1-ylmethyl)-3-methyl-1H-pyrazolo[3,4-b]pyridin-6-yl]-phenol
4-[4-((R)-2-Ethyl-5,5-dimethyl-piperazin-1-ylmethyl)-3-methyl-1H-pyrazolo[3,4-b]pyridin-6-yl]-phenol
-[4-((S)-3-Amino-3-methyl-piperidin-1-ylmethyl)-3-methyl-1H-pyrazolo[3,4-b]pyridin-6-yl]-3-fluoro-phenol
4-[4-((R)-3-Amino-3-methyl-piperidin-1-ylmethyl)-3-methyl-1H-pyrazolo[3,4-b]pyridin-6-yl]-3-fluoro-phenol
4-[4-((R)-5-Cyclopropyl-2,2,5-trimethyl-piperazin-1-ylmethyl)-3-methyl-1H-pyrazolo[3,4-b]pyridin-6-yl]-3-fluoro-phenol
4-[4-((S)-5-Cyclopropyl-2,2,5-trimethyl-piperazin-1-ylmethyl)-3-methyl-1H-pyrazolo[3,4-b]pyridin-6-yl]-3-fluoro-phenol
3-Fluoro-4-[3-methyl-4-((2R,5S)-5-methyl-2-trifluoromethyl-piperazin-1-ylmethyl)-1H-pyrazolo[3,4-b]pyridin-6-yl]-phenol
3-Fluoro-4-[3-methyl-4-((2R,5R)-5-methyl-2-trifluoromethyl-piperazin-1-ylmethyl)-1H-pyrazolo[3,4-b]pyridin-6-yl]-phenol
3-Fluoro-4-[3-methyl-4-((2S,5R)-5-methyl-2-trifluoromethyl-piperazin-1-ylmethyl)-1H-pyrazolo[3,4-b]pyridin-6-yl]-phenol and
3-Fluoro-4-[3-methyl-4-((2S,5S)-5-methyl-2-trifluoromethyl-piperazin-1-ylmethyl)-1H-pyrazolo[3,4-b]pyridin-6-yl]-phenol.

7. A pharmaceutical composition comprising at least one compound of formula I

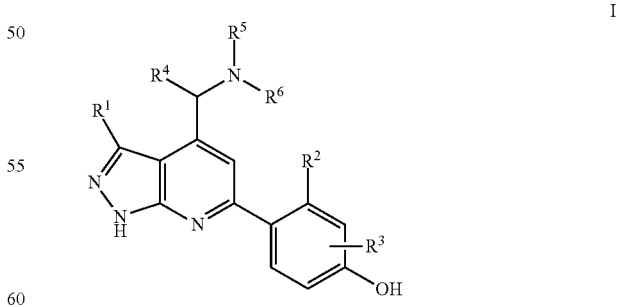

wherein
$R^1$ is $(C_1-C_4)$-alkyl, $CF_3$, cyclopropyl or cyclobutyl;
$R^2$ is H, halogen, methyl or $CF_3$;
$R^3$ is H, halogen, methyl or $CF_3$;
$R^4$ is H, $(C_1-C_4)$-alkyl or $CF_3$;
$R^5$ is H or $(C_1-C_4)$-alkyl;

$R^6$ is a 4- to 8-membered monocyclic heterocycle comprising a ring nitrogen, which is unsubstituted or mono- or disubstituted by $(C_1-C_4)$-alkyl, wherein alkyl is unsubstituted or one to threefold substituted by F; or $R^5$ and $R^6$ together with the N-atom carrying them denote a) a 1,4-piperazinyl of the formula

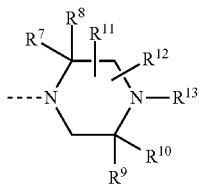

wherein $R^7$ is H, $(C_1-C_4)$-alkyl, cyclopropyl, cyclobutyl or phenyl, wherein alkyl is unsubstituted or one to threefold substituted by F, wherein phenyl is unsubstituted or mono- or disubstituted by halogen, $CF_3$, $(C_1-C_4)$-alkyl, -O—$CF_3$ or O—$(C_1-C_4)$-alkyl;

$R^8$ is H or $(C_1-C_4)$-alkyl;

or $R^7$ and $R^8$ together with the carbon atom carrying them denote $(C_3-C_6)$-cycloalkyl;

$R^9$ is H, $(C_1-C_4)$-alkyl, cyclopropyl, cyclobutyl or phenyl, wherein alkyl is unsubstituted or one to threefold substituted by F, wherein phenyl is unsubstituted or mono- or disubstituted by halogen, $CF_3$, $(C_1-C_4)$-alkyl, O—$CF_3$ or O—$(C_1-C_4)$-alkyl;

$R^{10}$ is H or $(C_1-C_4)$-alkyl;

or $R^9$ and $R^{10}$ together with the carbon atom carrying them denote $(C_3-C_6)$-cycloalkyl;

$R^{11}$ is H or $(C_1-C_4)$-alkyl;

$R^{12}$ is H or $(C_1-C_4)$-alkyl;

$R^{13}$ is i) H;

ii) $(C_1-C_4)$-alkyl, which is unsubstituted or one to twofold substituted by a. $CF_3$,
  b. OH,
  c. O—$(C_1-C_4)$-alkyl,
  d. phenyl,
  e. thienyl
  f. pyridyl,
  g. tetrahydrofuranyl,
  h. tetrahydropyranyl,
  i. 2,2'-dimethyl-1,3-dioxolanyl,
  j. C(O)—O—$(C_1-C_4)$-alkyl,
  k. NH—$(C_1-C_4)$-alkyl,
  l. N$((C_1-C_4)$-alkyl$)_2$;

iii) C(O)—$(C_1-C_4)$-alkyl which is unsubstituted or monosubstituted by a. OH,
  b. O—$CF_3$,
  c. O—$(C_1-C_4)$-alkyl, iv) C(O)-tetrahydrofuranyl, v) C(O)-tetrahydropyranyl, vi) C(O)—NH—$(C_1-C_4)$-alkyl, vii) C(O)—N$((C_1-C_4)$-alkyl$)_2$, viii) C(O)—NH—$(C_1-C_4)$-alkylene-COO$(C_1-C_4)$-alkyl;

b) a morpholinyl of the formula

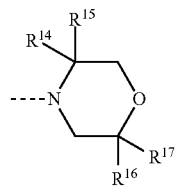

wherein $R^{14}$ is H, $(C_1-C_4)$-alkyl, cyclopropyl, cyclobutyl or phenyl, wherein alkyl is unsubstituted or one to threefold substituted by F, wherein phenyl is unsubstituted or mono- or disubstituted by halogen, $CF_3$, $(C_1-C_4)$-alkyl, O—$CF_3$ or O—$(C_1-C_4)$-alkyl;

$R^{15}$ is H or $(C_1-C_4)$-alkyl;

or $R^{14}$ and $R^{15}$ together with the carbon atom carrying them denote $(C_3-C_6)$-cycloalkyl;

$R^{16}$ is H, $(C_1-C_4)$-alkyl, cyclopropyl, cyclobutyl or phenyl, wherein alkyl is unsubstituted or one to threefold substituted by F, wherein phenyl is unsubstituted or mono- or disubstituted by halogen, $CF_3$, $(C_1-C_4)$-alkyl, O—$CF_3$ or O—$(C_1-C_4)$-alkyl;

$R^{17}$ is H or $(C_1-C_4)$-alkyl;

or $R^{16}$ and $R^{17}$ together with the carbon atom carrying them denote $(C_3-C_6)$-cycloalkyl;

c) a ring A of the formula

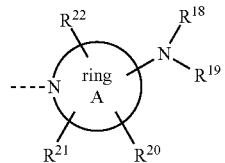

comprising one nitrogen and 3 to 6 carbon ring atoms, wherein the substituent $NR^{18}R^{19}$ is not in an adjacent position to the ring nitrogen atom and $R^{18}$ is H, $(C_1-C_4)$-alkyl or C(O)—$(C_1-C_4)$-alkylene-O—$(C_1-C_4)$-alkyl;

$R^{19}$ is H or $(C_1-C_4)$-alkyl;

$R^{20}$ is H or $(C_1-C_4)$-alkyl;

$R^{21}$ is H or $(C_1-C_4)$-alkyl;

$R^{22}$ is H or $(C_1-C_4)$-alkyl;

d) a 1,4-diazepin of the formula

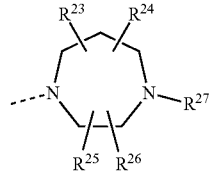

wherein $R^{23}$ is H, $(C_1-C_4)$-alkyl, cyclopropyl, cyclobutyl or phenyl, wherein alkyl is unsubstituted or one to threefold substituted by F, wherein phenyl is unsubstituted or mono- or disubstituted by halogen, $CF_3$, $(C_1-C_4)$-alkyl, O—$CF_3$ or O—$(C_1-C_4)$-alkyl;

$R^{24}$ is H or $(C_1\text{-}C_4)$-alkyl;
or
$R^{23}$ and $R^{24}$ together with the carbon atom carrying them denote $(C_3\text{-}C_6)$-cycloalkyl;
$R^{25}$ is H, $(C_1\text{-}C_4)$-alkyl, cyclopropyl, cyclobutyl or phenyl, wherein alkyl is unsubstituted or one to threefold substituted by F, wherein phenyl is unsubstituted or mono- or disubstituted by halogen, $CF_3$, $(C_1\text{-}C_4)$-alkyl, $O\text{--}CF_3$ or $O\text{--}(C_1\text{-}C_4)$-alkyl;
$R^{26}$ is H or $(C_1\text{-}C_4)$-alkyl;
or
$R^{25}$ and $R^{26}$ together with the carbon atom carrying them denote $(C_3\text{-}C_6)$-cycloalkyl;
$R^{27}$ is
  i) H;
  ii) $(C_1\text{-}C_4)$-alkyl, which is unsubstituted or one to twofold substituted by
    a. $CF_3$,
    b. OH,
    c. $O\text{--}(C_1\text{-}C_4)$-alkyl;
    d. pyridyl,
    e. tetrahydrofuranyl,
    f. tetrahydropyranyl,
    g. 2,2'-dimethyl-1,3-dioxolanyl,
    h. $C(O)\text{--}O\text{--}(C_1\text{-}C_4)$-alkyl;
    i. $NH\text{--}(C_1\text{-}C_4)$-alkyl;
  iii) $C(O)\text{--}(C_1\text{-}C_4)$-alkyl which is unsubstituted or monosubstituted by
    a. OH,
    b. $O\text{--}(C_1\text{-}C_4)$-alkyl;
  iv) $C(O)$-tetrahydrofuranyl;
  v) $C(O)\text{--}NH\text{--}(C_1\text{-}C_4)$-alkyl;
  vi) $C(O)\text{--}NH\text{--}(C_1\text{-}C_4)$-alkylen-$COO(C_1\text{-}C_4)$-alkyl;
or a pharmaceutically acceptable salt thereof.

8. A pharmaceutical composition comprising a compound of formula I as claimed in claim 1, or a pharmaceutically acceptable salt thereof.

\* \* \* \* \*